United States Patent
Gao et al.

(10) Patent No.: US 11,780,831 B2
(45) Date of Patent: Oct. 10, 2023

(54) COMPOUND, DISPLAY PANEL AND DISPLAY APPARATUS

(71) Applicants: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Lei Zhang, Shanghai (CN); Wenpeng Dai, Shanghai (CN); Quan Ran, Shanghai (CN); Lu Zhai, Shanghai (CN); Wenjing Xiao, Shanghai (CN); Jinghua Niu, Shanghai (CN)

(73) Assignees: SHANGHAI TIANMA AM-OLED CO., LTD., Shanghai (CN); WUHAN TIANMA MICRO-ELECTRONICS CO., LTD, Shanghai (CN)

( * ) Notice: Subject to any disclaimer, the term of this patent is extended or adjusted under 35 U.S.C. 154(b) by 615 days.

(21) Appl. No.: 17/035,952

(22) Filed: Sep. 29, 2020

(65) Prior Publication Data

US 2021/0024511 A1 Jan. 28, 2021

(51) Int. Cl.
*C07D 409/14* (2006.01)
*C07D 519/00* (2006.01)
(Continued)

(52) U.S. Cl.
CPC ......... *C07D 409/14* (2013.01); *C07D 519/00* (2013.01); *H10K 85/40* (2023.02);
(Continued)

(58) Field of Classification Search
None
See application file for complete search history.

(56) References Cited

U.S. PATENT DOCUMENTS

2013/0082209 A1* 4/2013 Stoessel ............... H10K 85/342
252/301.16

FOREIGN PATENT DOCUMENTS

| CN | 107382994 A | 11/2017 |
|---|---|---|
| KR | 20160041021 A | 4/2016 |

* cited by examiner

Primary Examiner — Gregory D Clark
(74) Attorney, Agent, or Firm — TAROLLI, SUNDHEIM, COVELL & TUMMINO L.L.P.

(57) ABSTRACT

Provided is a compound represented by formula 1, and a display panel and a display apparatus including the compound. In formula 1, $L_1$ and $L_2$ are each independently selected from the group consisting of a single bond, C6-C30 aryl, and C4-C30 heteroaryl; a and b are each independently selected from 0, 1, 2, 3, or 4; $D_1$ and $D_2$ are each independently a nitrogen-containing electron donor unit selected from the group consisting of carbazolyl and derivative groups thereof, acridinyl and derivative groups thereof, diarylamino and derivative groups thereof, and triarylamino and derivative groups thereof; and c and d are each independently selected from 0, 1, 2, 3, or 4, and $c+d \geq 1$.

formula 1

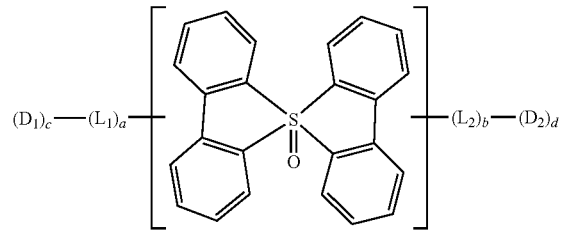

17 Claims, 2 Drawing Sheets

(51) Int. Cl.
    *H10K 85/40*         (2023.01)
    *H10K 85/60*         (2023.01)
    *H10K 50/15*         (2023.01)
    *H10K 50/16*         (2023.01)
    *H10K 50/18*         (2023.01)
    *H10K 50/17*         (2023.01)

(52) U.S. Cl.
    CPC ......... *H10K 85/631* (2023.02); *H10K 85/653* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

COMPOUND, DISPLAY PANEL AND DISPLAY APPARATUS

CROSS-REFERENCE TO RELATED APPLICATIONS

The present application claims priority to Chinese Patent Application No. 202010758299.2, filed on Jul. 31, 2020, the content of which is incorporated herein by reference in its entirety.

TECHNICAL FIELD

The present application relates to the technical field of organic electroluminescence materials, and particularly, to a compound used as a bipolar host material, and a display panel and a display apparatus including the compound.

BACKGROUND

With the development of electronic display technology, Organic Light-Emitting Diodes (OLEDs) are widely used in various display apparatuses. Especially in recent years, the demand for the OLEDs in the smartphone industry has been increasing, and thus the research and application of the light-emitting materials of the OLEDs also has increased.

Based on the light-emitting mechanism, materials for a light-emitting layer of an OLED can be generally divided into four types: (1) fluorescent materials; (2) phosphorescent materials; (3) triplet-triplet annihilation (TTA) materials; (4) thermally activated delayed fluorescence (TADF) materials.

Regarding the fluorescent materials, according to spin-statistics, a ratio of singlet excitons to triplet excitons is 1:3, and thus the maximum internal quantum yield of the fluorescent materials does not exceed 25%. According to the Lambertian luminescence mode, the light extraction efficiency is about 20%, and thus an external quantum efficiency (EQE) of an OLED based on the fluorescent material does not exceed 5%.

With respect to the phosphorescent materials, an intersystem crossing of molecules can be enhanced by spin coupling due to a heavy atom effect of the phosphorescent materials, and 75% of triplet excitons can be directly utilized to complete emission involving both S1 and T1 at room temperature, where a theoretical maximum internal quantum yield can reach 100%. According to the Lambertian luminescence mode, a light extraction efficiency is about 20%, and thus the EQE of an OLED based on the phosphorescent materials can reach 20%. However, the phosphorescent materials are conventionally complexes of heavy metals, such as Ir, Pt, Os, Re, Ru, etc., and are unsuitable for a large-scale production due to the high production costs. Under a high electric current density, a substantial efficiency roll-off can be observed in the phosphorescent materials, which lead to a deterioration of the stability of the phosphorescent devices.

Regarding the TAA materials, two adjacent triplet excitons are combined to form a singlet excited state molecule with a higher energy level and a ground state molecule. However, since two triplet excitons merely produce one singlet state exciton, the theoretical maximum internal quantum yield can only reach 62.5%. In order to prevent a substantial roll-off of efficiency, a concentration of triplet excitons should be regulated during this process.

For the TADF materials, when an energy level difference between the singlet excited state and the triplet excited state is relatively small, a reverse intersystem crossing (RISC) may occur in the molecules, and the excitons are converted from T1 state to S1 state by absorbing the ambient heat, so that 75% of triplet excitons and 25% of singlet excitons can be utilized at the same time. In this way, the theoretical maximum internal quantum yield can reach 100%. The TADF materials are mainly organic compounds and require no rare metal elements, so that the production cost is relatively low. The TADF materials can be chemically modified by various methods. The TADF materials have many advantages over the conventional OLED light-emitting materials. However, there are few TADF materials that have been discovered so far, and it is urgent to develop new TADF materials applicable in the OLEDs.

SUMMARY

In view of the problems in the related art, a purpose of the present disclosure is to provide a compound, having a structure represented by formula 1:

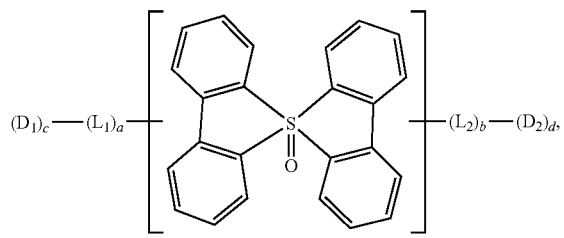

formula 1 wherein $L_1$ and $L_2$ are each independently selected from the group consisting of a single bond, a substituted or unsubstituted C6-C30 aryl, and a C4-C30 heteroaryl;

a and b are each independently selected from 0, 1, 2, 3, or 4;

$D_1$ and $D_2$ are each independently a nitrogen-containing electron donor unit selected from the group consisting of carbazolyl and derivative groups thereof, acridinyl and derivative groups thereof, diarylamino and derivative groups thereof, and triarylamino and derivative groups thereof; and c and d are each independently selected from 0, 1, 2, 3, or 4, and c+d≥1.

In the compound of the present disclosure, by introducing an S═O double bond, the compound has a stronger electron withdrawing ability, and the core unit has characteristics of an electron acceptor. Moreover, the S═O double bond is located at the connection point of the spiro ring, where the LUMO presents sp3 hybridization characteristics, presenting a regular tetrahedral spatial structure, which makes the LUMO energy level more evenly dispersed, and providing a bipolar host material or TADF luminescent material with excellent performance when matched with an electron donor.

The present disclosure also provides a display panel including an organic light-emitting device, the organic light-emitting device includes an anode; a cathode; and a light-emitting layer disposed between the anode and the cathode, and a light-emitting material of the light-emitting layer includes one or more of compounds of the present disclosure.

The present disclosure also provides a display apparatus including the above-mentioned display panel.

DESCRIPTION OF EMBODIMENTS

Figure 1:
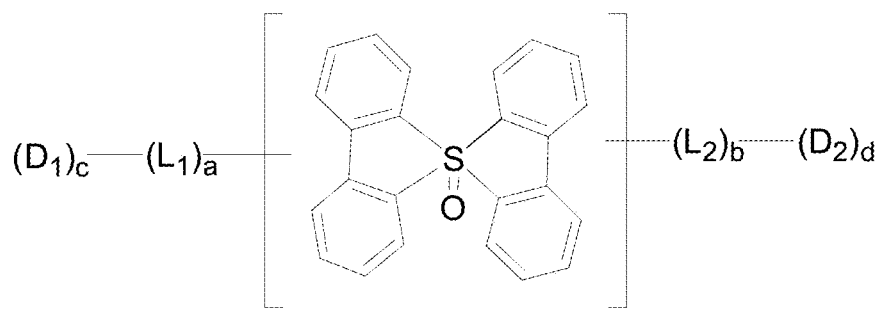
FIG. 1 is a chemical formula of a compound according to the present disclosure.

The present disclosure is described in detail in combination with examples and comparative examples. These embodiments are only used to illustrate the present disclosure, but not intended to limit the scope of the present disclosure. Without departing from the scope of the present disclosure, any modification or equivalent replacement with respect to the technical solutions of the present disclosure shall fall into the scope of protection of the present disclosure.

In a first aspect, the present disclosure provides a compound, having a structure represented by formula 1:

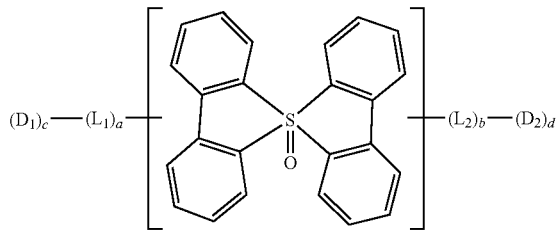

formula 1 wherein $L_1$ and $L_2$ are each independently selected from the group consisting of a single bond, a substituted or unsubstituted C6-C30 aryl, and a C4-C30 heteroaryl;

a and b are each independently selected from 0, 1, 2, 3, or 4;

$D_1$ and $D_2$ are each independently a nitrogen-containing electron donor unit selected from the group consisting of carbazolyl and derivative groups thereof, acridinyl and derivative groups thereof, diarylamino and derivative groups thereof, and triarylamino and derivative groups thereof; and c and d are each independently selected from 0, 1, 2, 3, or 4, and c+d≥1.

In the compound of the present disclosure, by introducing an S=O double bond, the compound has a stronger electron withdrawing ability, and the core unit has characteristics of an electron acceptor. Moreover, the S=O double bond is located at the connection point of the spiro ring, where the LUMO presents sp3 hybridization characteristics, presenting a regular tetrahedral spatial structure, which makes the LUMO energy level more evenly dispersed, and providing a bipolar host material or TADF luminescent material with excellent performance when matched with an electron donor. The present disclosure also provides a display panel and a display apparatus including the compound of the present disclosure.

In addition, in the compound represented by formula 1, group $(D_1)_c$-$(L_1)_a$ and group $(L_2)_a$-$(D_2)_c$ can be bonded to ortho positions, which increases a dihedral angle between the D unit and the core unit. Thus, the D unit and the electron accepting unit (i.e., the core unit) have a greater steric hindrance there between, which effectively inhibits the phenomenon of fluorescence quenching caused by accumulation of molecules. Moreover, the ortho-position connection of group $(D_1)_c$-$(L_1)_a$ and group $(L_2)_a$-$(D_2)_c$ allows the molecule to have a greater rigid structure, which limits the movement inside the molecules and the structural relaxation of the excited state molecules, thereby reducing the non-radiation transition rate of the excited state molecules, increasing the radiation transition rate, and improving the light-emitting efficiency. The ortho-position connection of group $(D_1)_c$-$(L_1)_a$ and group $(L_2)_a$-$(D_2)_c$ increases the space restriction in the molecule, the vibration relaxation in the molecule is thus reduced, and the luminescence color purity of the molecules can be improved to achieve lower half-width. The ortho-position connection also allows a high degree of molecular distortion, which can effectively reduce the conjugation length to obtain a higher triplet energy level, so that the compound is more suitable as a blue light-emitting material and a phosphorescent host material.

When $L_1$ and $L_2$ are single bonds, the core unit is directly bonded to $D_1$ and $D_2$, which leads to a strong intramolecular charge transfer interaction between the unit D and the unit A. In this way, HOMO and LUMO are less overlapped, and thus can be better spatially separated. Thus, lower $\Delta E_{ST}$ can be achieved, which can effectively improve the physical process of reverse intersystem crossing, achieving better TADF effect and improving the light-emitting efficiency.

When $L_1$ and $L_2$ are not single bonds, the degree of orbital overlapping between the core unit and the unit D can be further increased, enhancing increase an oscilator strength, increasing the transition dipole moment, and improving the light-emitting efficiency.

The group $(D_1)_c$-$(L_1)_a$ and the group $(L_2)_a$-$(D_2)_c$ can be exactly the same to form a symmetrical structure, so that it is simpler to synthesize the compound. The core of the molecule itself has a spatially orthogonal non-planar molecular structure. The substitution at symmetrical positions of the core can enhance the rigidity of the molecule, extend the conjugation of the molecule, increase the molecular oscillator strength and transition dipole moment, and improve the light-emitting efficiency of the molecules.

The group $(D_1)_c$-$(L_1)_a$ and the group $(L_2)_a$-$(D_2)_c$ may not be completely the same. In this case, the compound has an asymmetric molecular structure, which can reduce the crystallinity of the molecule. Thus, it is easier to obtain an amorphous film during the vapor-deposition process, which is beneficial to prolong the stability and reliability of the device in a long-term operation.

In an embodiment of the compound according to the present disclosure, the compound has a structure represented by formula 1-1 or formula 1-2:

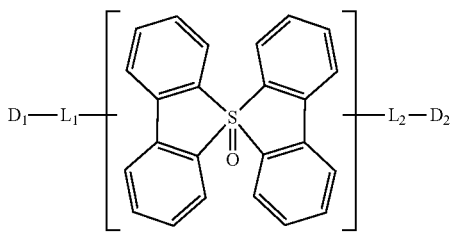

formula 1-1 formula 1-2

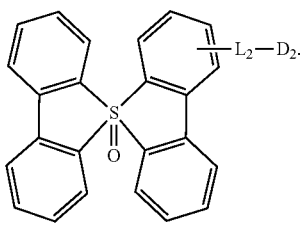

In the compound represented by formula 1-2, an L2-D2 substituent only exists on one side. The compound has a small molecular weight, is easy to be evaporated, and has low energy consumption. In addition, the one-sided substitution leads to an asymmetric molecular structure, which can reduce the crystallinity of the molecule, and it is easier to obtain an amorphous film during the vapor-deposition process, which is beneficial to prolong the stability and reliability of the device in a long-term operation.

In an embodiment of the compound according to the present disclosure, $L_1$ and $L_2$ are each independently selected from the group consisting of phenyl, biphenyl, naphthyl, anthracyl, phenanthryl, acenaphthylenyl, pyrenyl, perylenyl, fluorenyl, spirodifluorenyl, chrysenyl, benzophenanthryl, and benzanthracyl.

In an embodiment of the compound according to the present disclosure, $D_1$ and $D_2$ are each independently selected from the group consisting of:

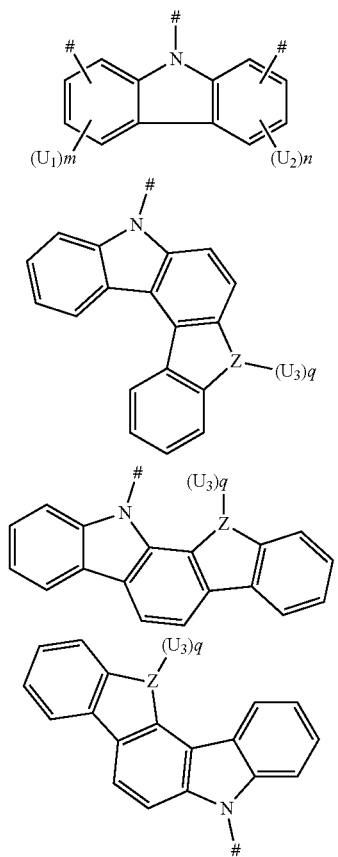

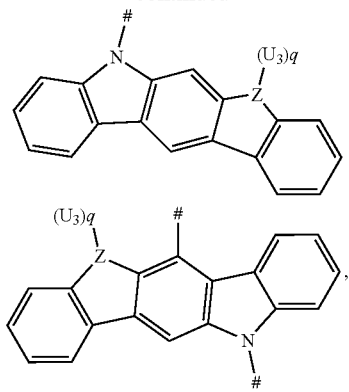

wherein Z is selected from the group consisting of a carbon atom, a nitrogen atom, an oxygen atom, and a sulfur atom;

q is 0, 1 or 2;

$U_1$, $U_2$, and $U_3$ are each independently selected from the group consisting of a hydrogen atom, C1-C6 alkyl, C1-C6 alkoxy, and C6-C12 aryl;

when Z is an oxygen atom or a sulfur atom, q is 0; and # indicates a bonding position.

In an embodiment of the compound according to the present disclosure, $D_1$ and $D_2$ are each independently selected from the group consisting of the following groups:

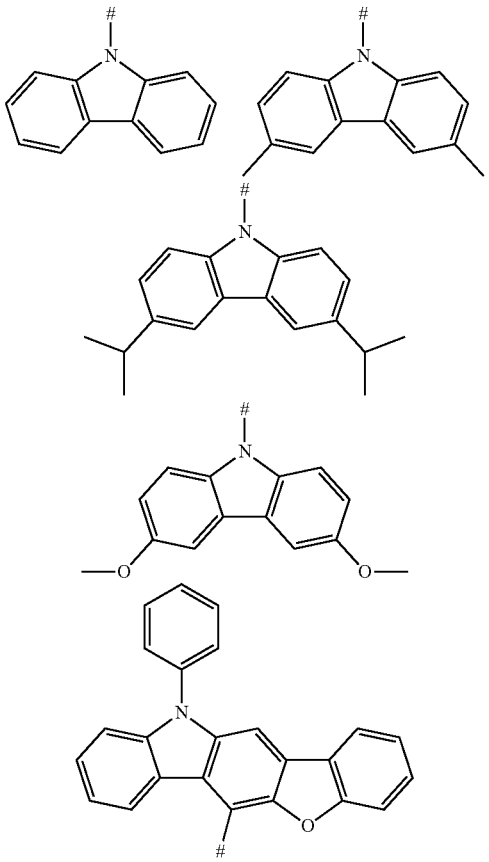

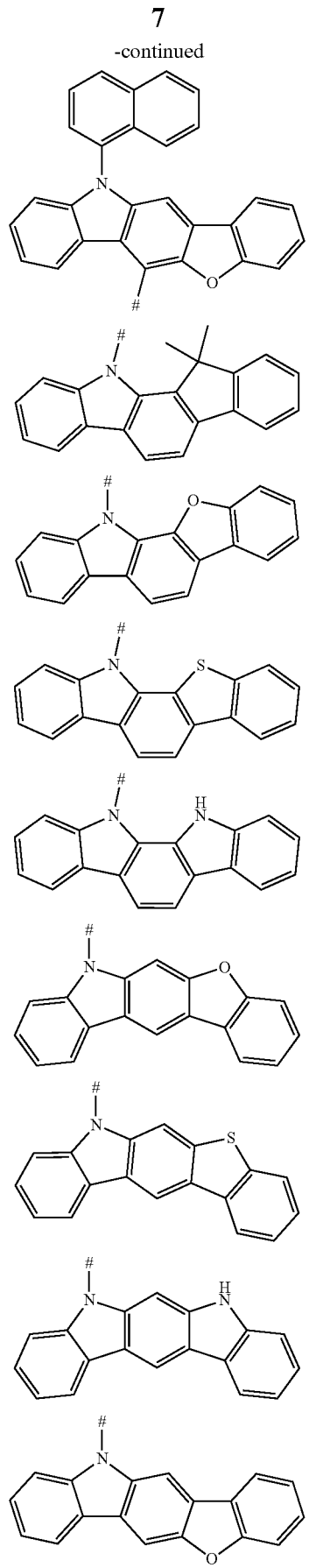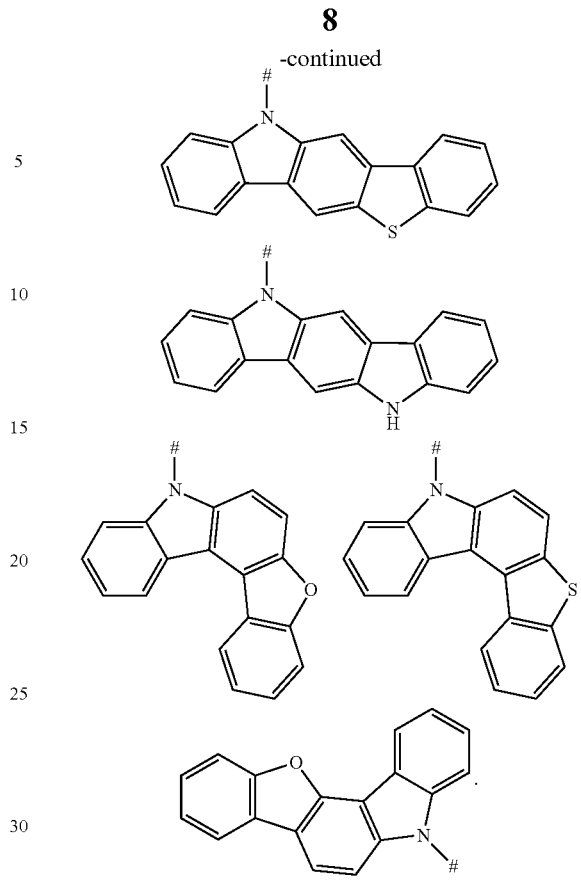

When the electron donor D is carbazolyl or a derivative group thereof, it has the following advantages: (1) the raw material is cheap and the cost is low; (2) molecular performances can be modified without changing the main skeleton structure of the molecule; (3) nitrogen atom can be easily functionally modified; (4) multiple connection positions on the carbazolyl are available for bonding to other molecular structures; (5) the molecule has good thermal and chemical stability; (6) the molecule has high triplet energy level; and (7) the molecule has excellent electron-donating ability, excellent light-emitting performance, and excellent hole transmission characteristics.

In an embodiment of the compound according to the present disclosure, $D_1$ and $D_2$ are each independently selected from the group consisting of the following groups:

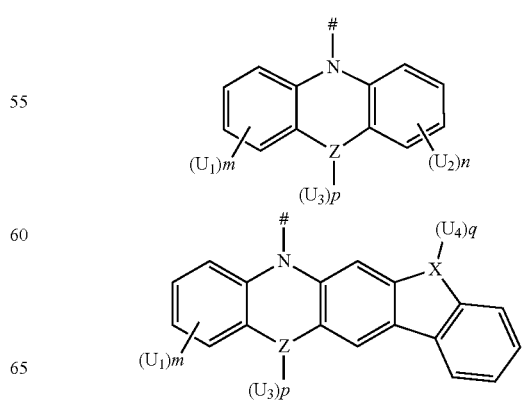

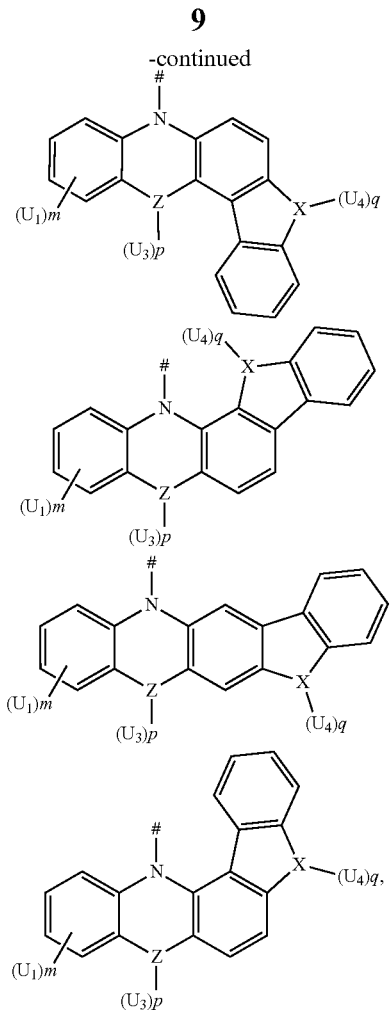

wherein Z is selected from the group consisting of a carbon atom, a nitrogen atom, an oxygen atom, a sulfur atom and a silicon atom;

X is selected from the group consisting of a carbon atom, a nitrogen atom, an oxygen atom, a sulfur atom and a silicon atom;

m, n, p and q are each independently selected from 0, 1 or 2;

$U_1$, $U_2$, $U_3$ and $U_4$ are each independently selected from the group consisting of a hydrogen atom, C1-C6 alkyl, C3-C6 cycloalkyl, C1-C6 alkoxy, C6-C12 aryl, and C12-C20 substituted or unsubstituted diphenylamino;

when Z is an oxygen atom or a sulfur atom, p is 0;

when X is an oxygen atom or a sulfur atom, q is 0; and # indicates a bonding position.

In an embodiment of the compound according to the present disclosure, $D_1$ and $D_2$ are each independently selected from the group consisting of the following groups:

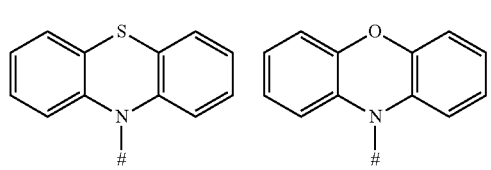

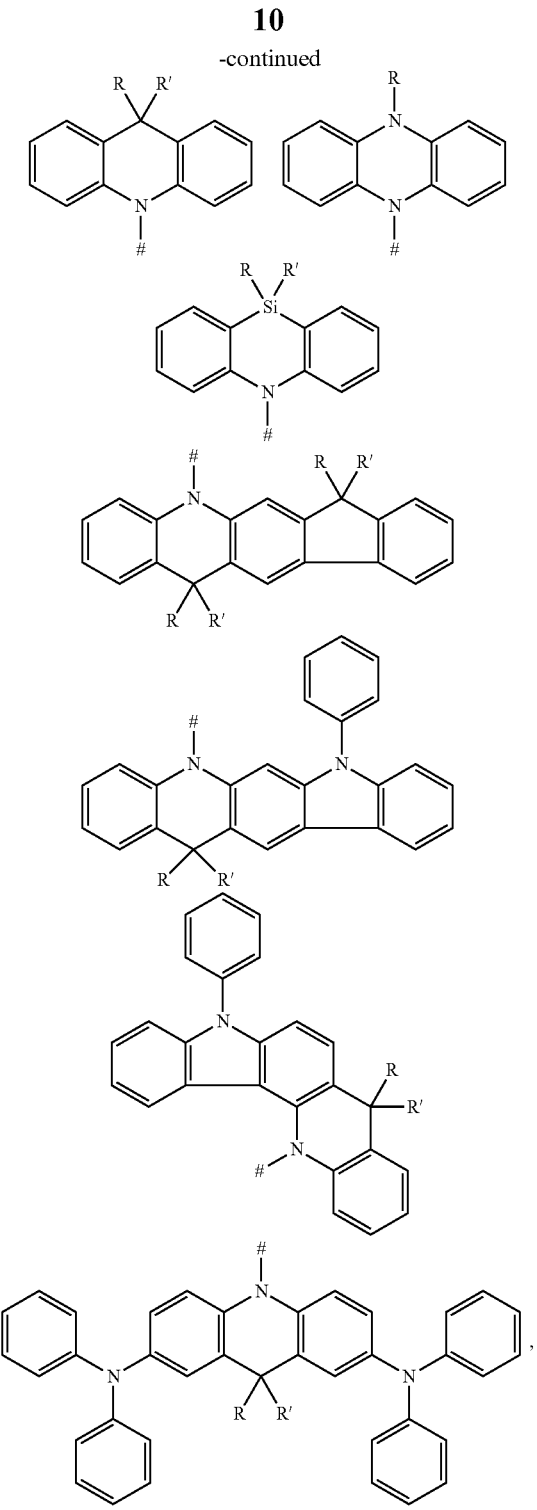

wherein R and R' are each independently selected from the group consisting of a hydrogen atom, C1-C6 alkyl, C1-C6 alkoxy, C1-C6 cycloalkyl, C6-C12 aryl, and C4-C12 heteroaryl.

When the electron donor D is acridinyl or a derivative group thereof or a structurally similar group, it has the following advantages: (1) very strong electron-donating ability and shorter delayed fluorescence lifetime; (2) better separated HOMO and LUMO; (3) rigid molecular structure, which can effectively reduce the non-radiation attenuation of the excited state; (4) the rigid molecular structure reducing the free rotational vibration in the molecule, which is beneficial to improve a monochromaticity of the material and reduce full width at half maximum (FWHW) of the luminescence peak of the material; and (5) high triplet energy level.

In an embodiment of the compound according to the present disclosure, $D_1$ and $D_2$ are each independently selected from the group consisting of the following groups:

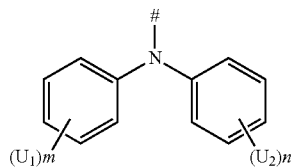

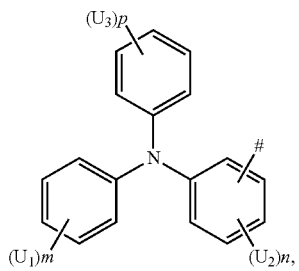

wherein $U_1$, $U_2$ and $U_3$ are each independently selected from the group consisting of a hydrogen atom, C1-C6 alkyl, and C1-C6 alkoxy;

m, n, and p are each independently selected from 0, 1 or 2; and # indicates a bonding position.

In an embodiment of the compound according to the present disclosure, $D_1$ and $D_2$ are each independently selected from the group consisting of the following groups:

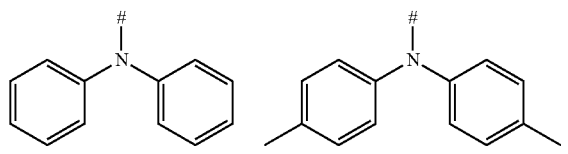

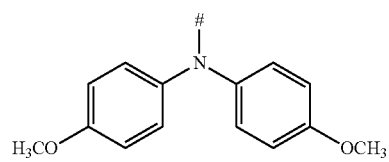

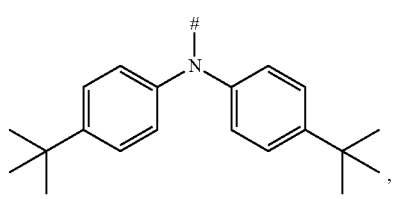

wherein # indicates a bonding position.

In this embodiment of the compound according to the present disclosure, when the electron donor D is diphenylamino or a derivative group thereof, it has the following advantages: (1) moderate electron-donating properties, good hole transmission capacity; and (2) good thermal and chemical stability, wide sources of raw materials, low cost, easy chemical modification, achieving effective spatial separation of HOMO and LUMO achieved when combined with an electron acceptor.

In an embodiment of the compound according to the present disclosure, $D_1$ and $D_2$ are each independently selected from the group consisting of the following groups:

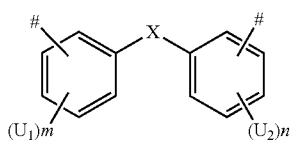

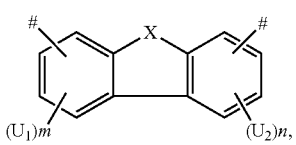

wherein X is an oxygen atom or a sulfur atom;

m and n are each independently selected from 0, 1 or 2;

$U_1$ and $U_2$ are each independently selected from the group consisting of a hydrogen atom, C1-C6 alkyl, C3-C6 cycloalkyl, and C1-C6 alkoxy; and # indicates a bonding position.

In an embodiment of the compound according to the present disclosure, the compound is selected from the following compounds:

P001
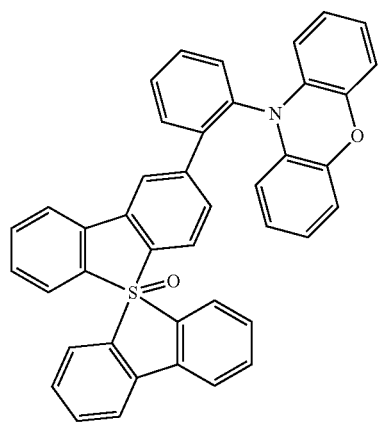
P002
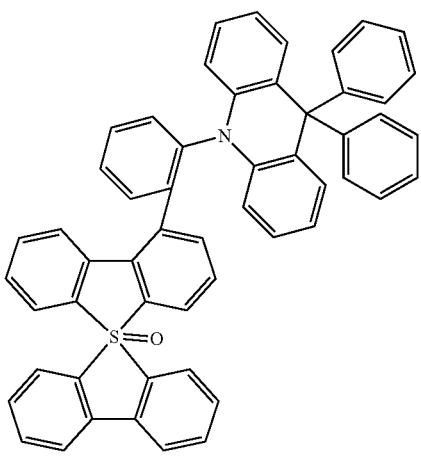
P003
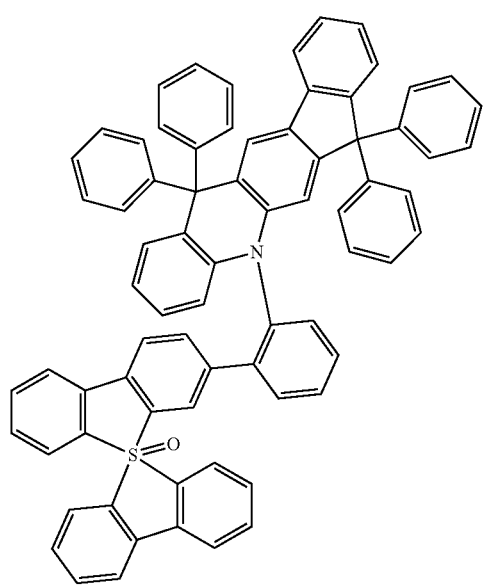
P004
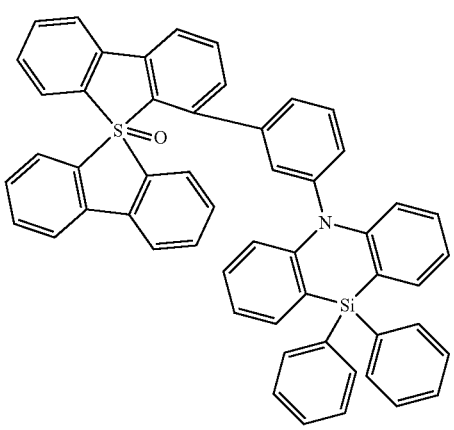
P005
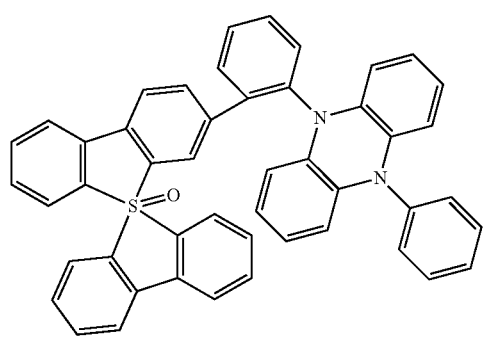
P006
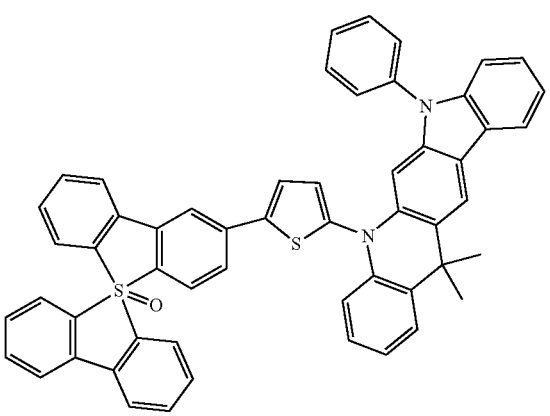

-continued
P007
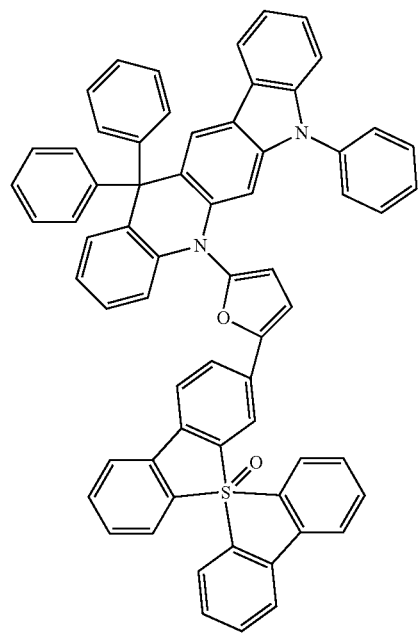
P008
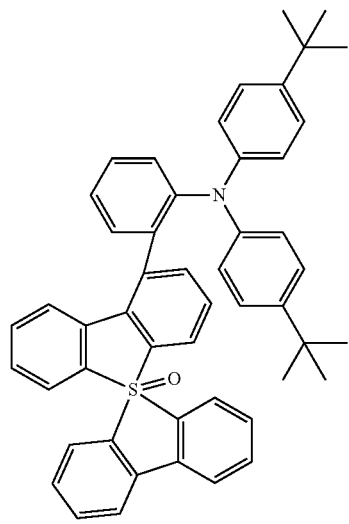
P009
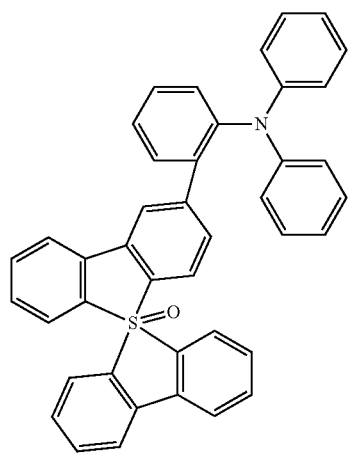
P010
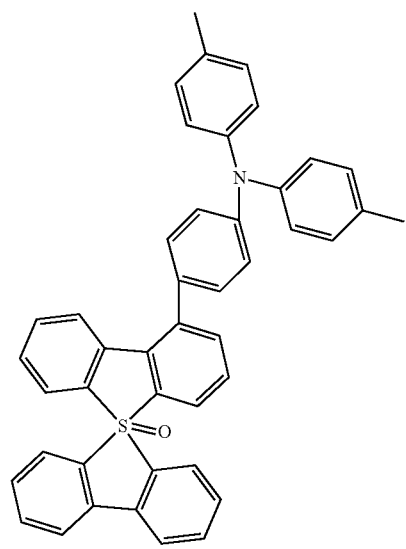

-continued
P011
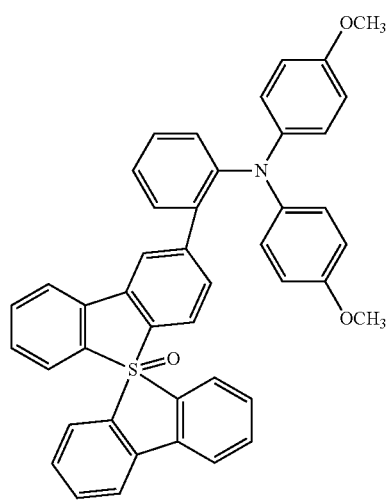
P012
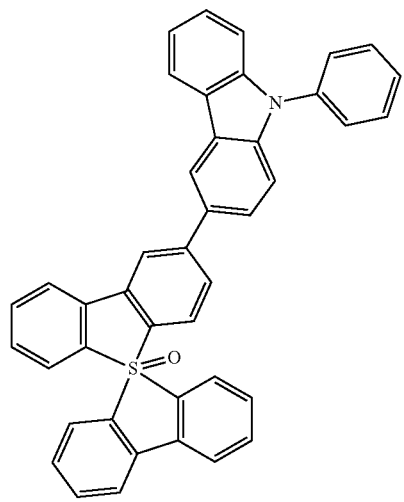
P013
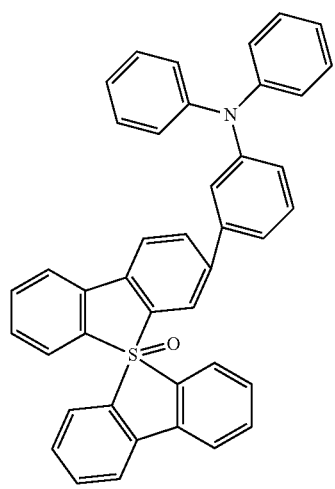
P014
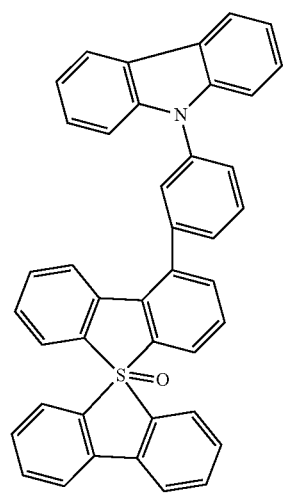
P015
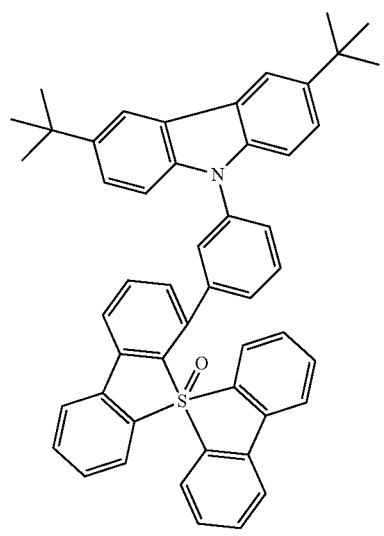
P016
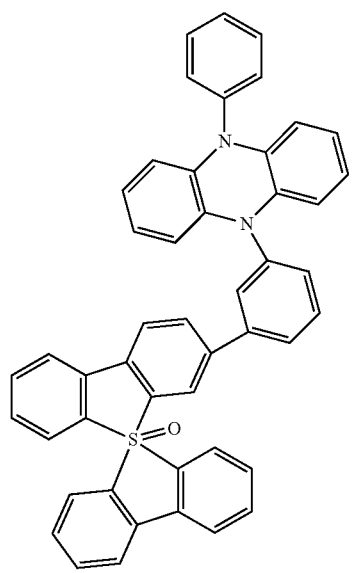

-continued
P017
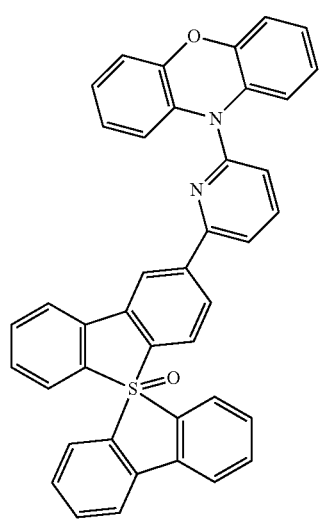
P018
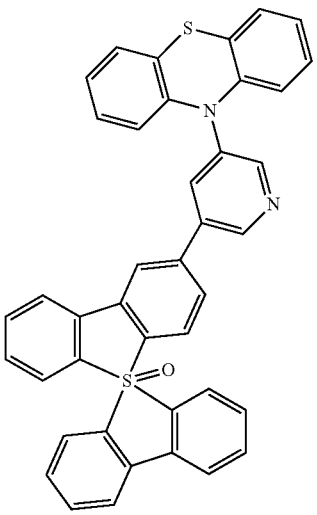
P019
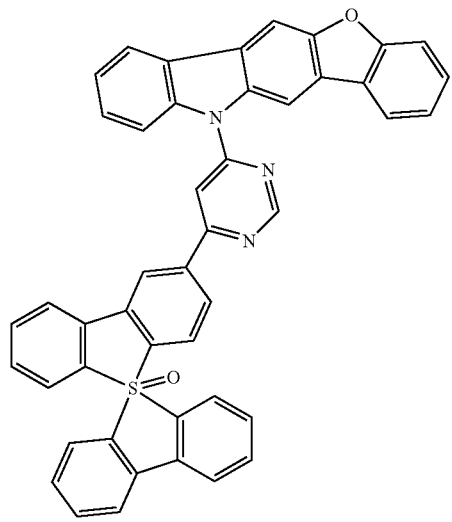
P020
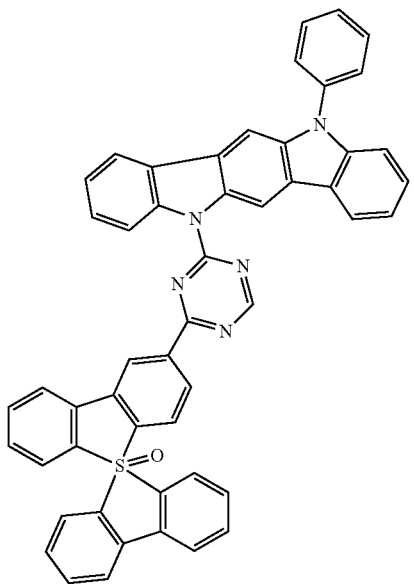
P021
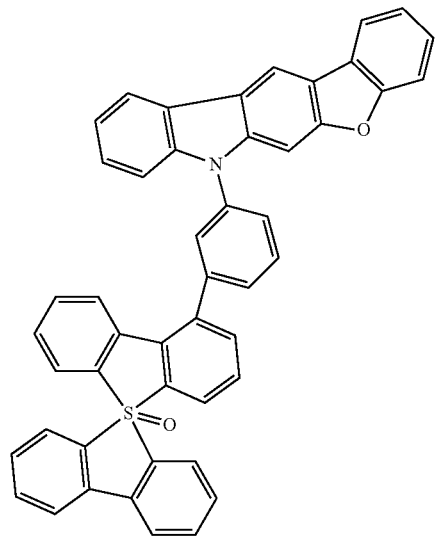
P022
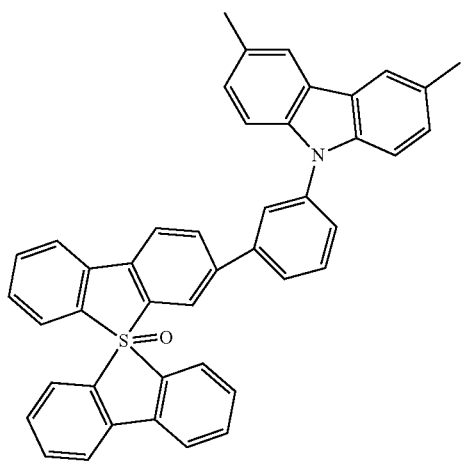

-continued
P023
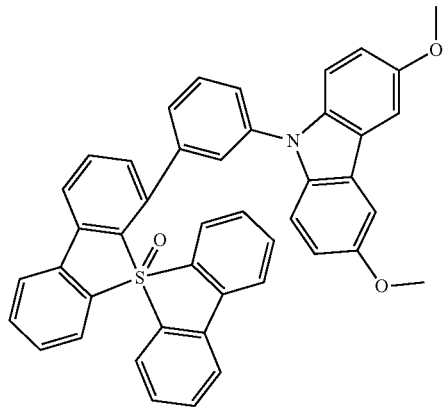
P024
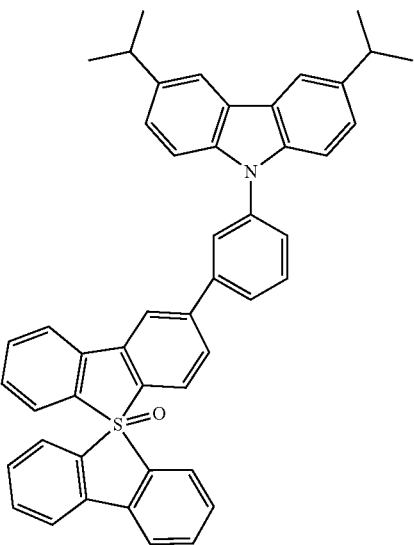
P025
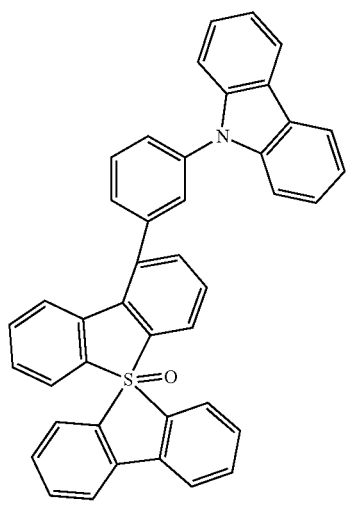
P026
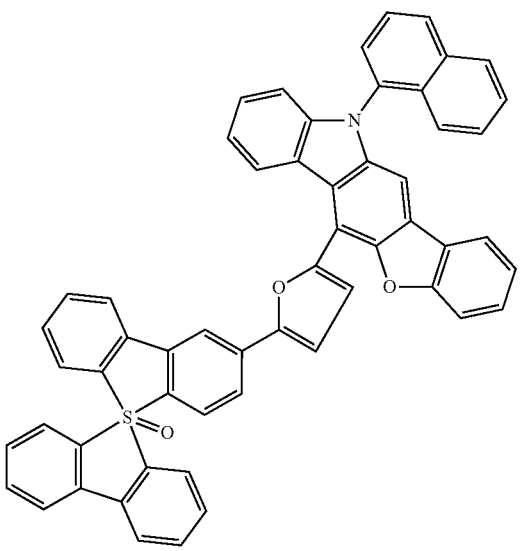

-continued
P027
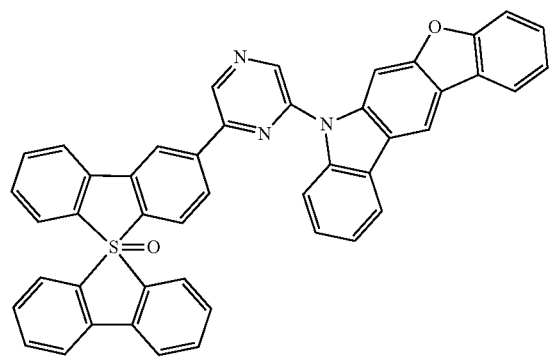
P028
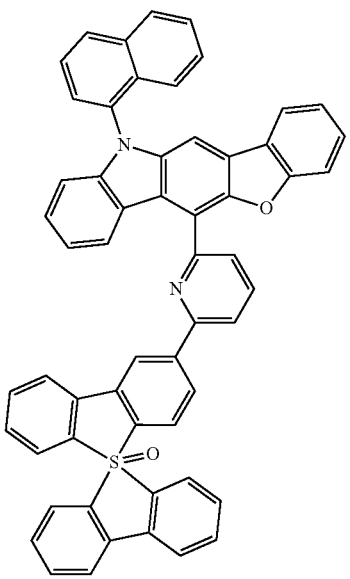
P029
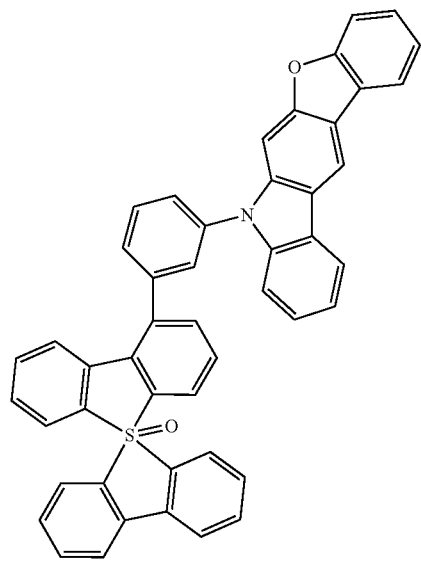
P030
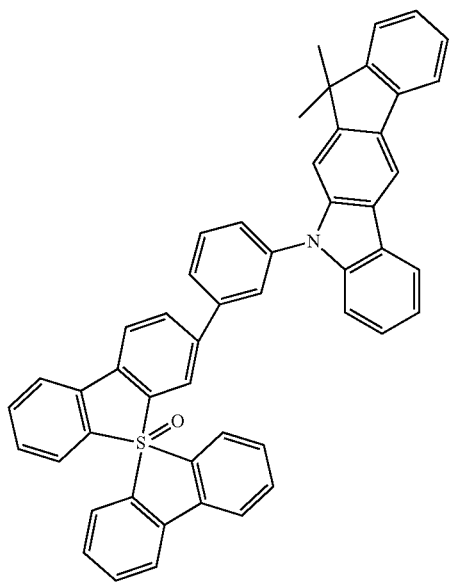

-continued
P031
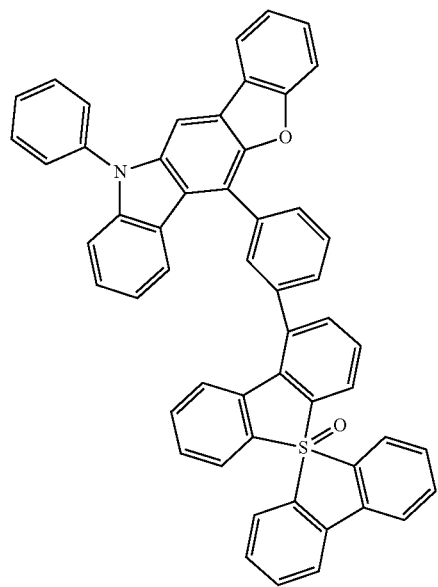
P032
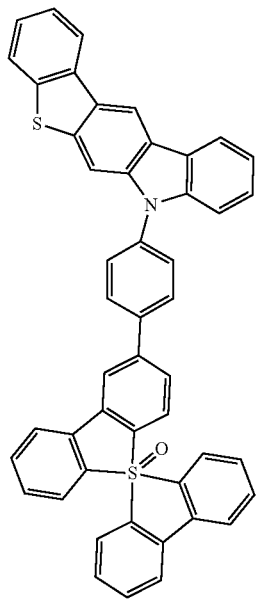
P033
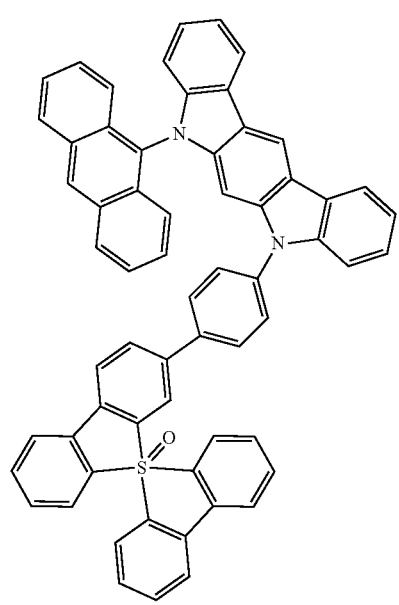
P034
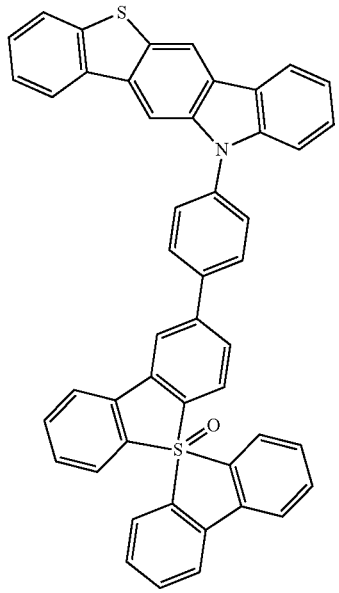

-continued
P035 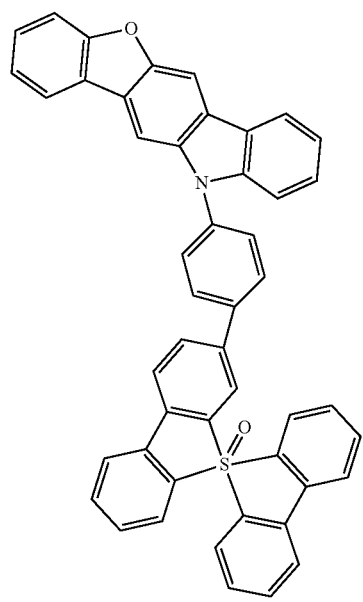
P036 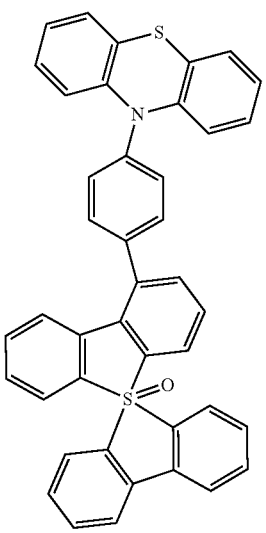
P037 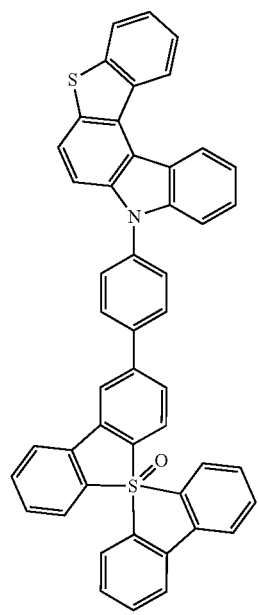
P038 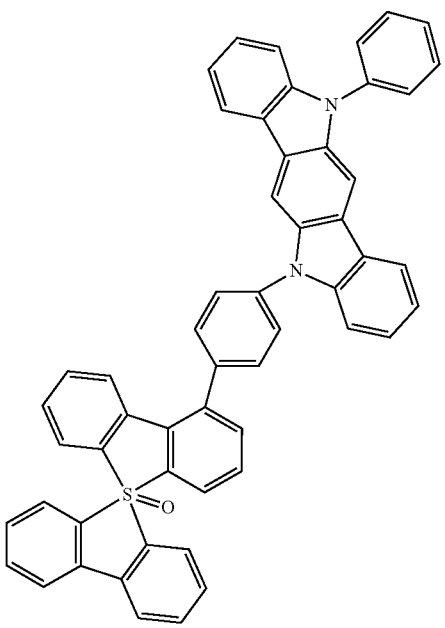

-continued
P039
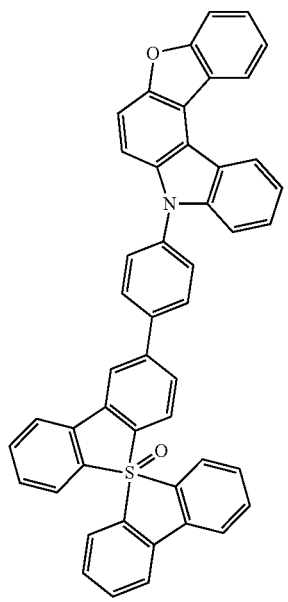
P040
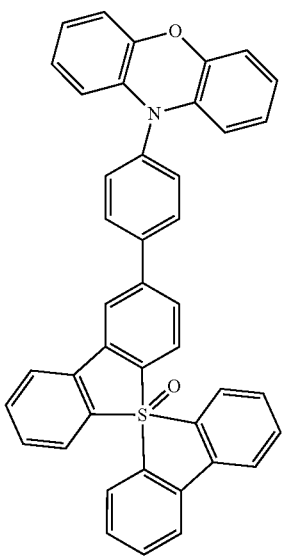
P041
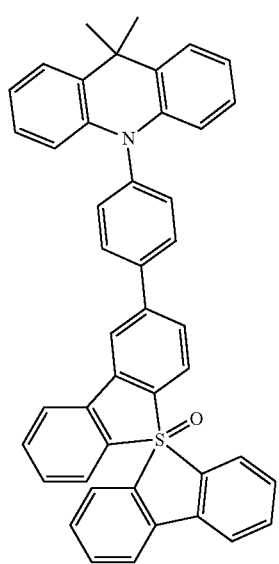
P042
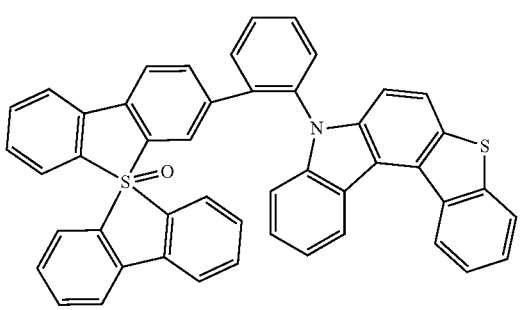

-continued
P043
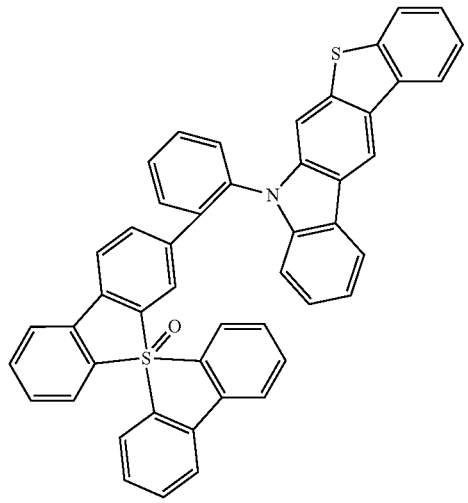
P044
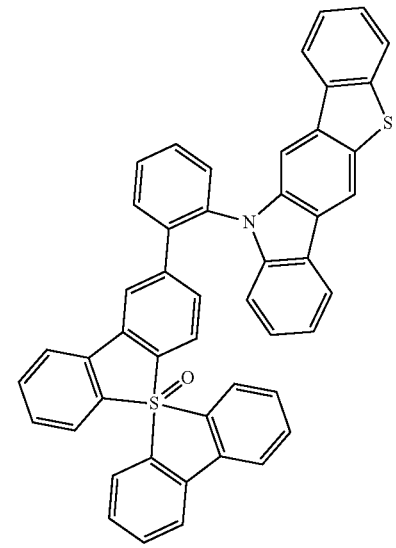
P045
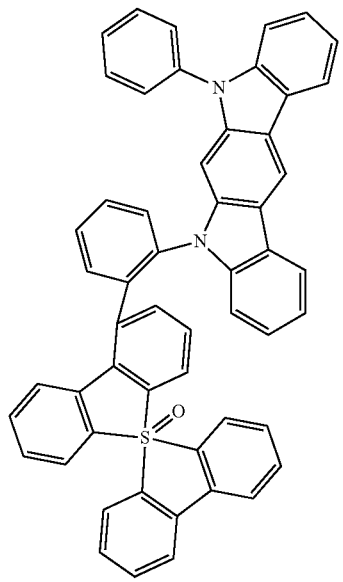
P046
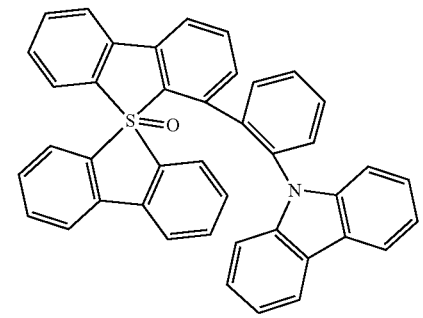
P047
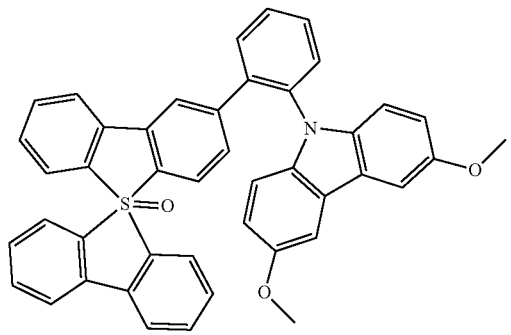
P048
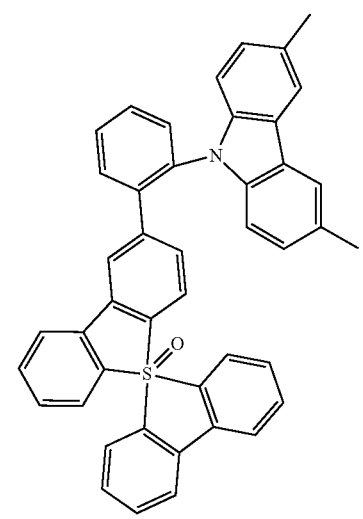

-continued
P049
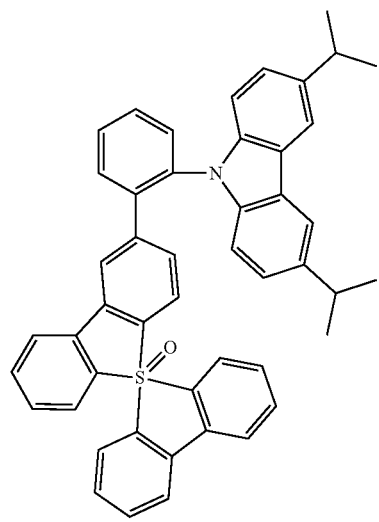
P050
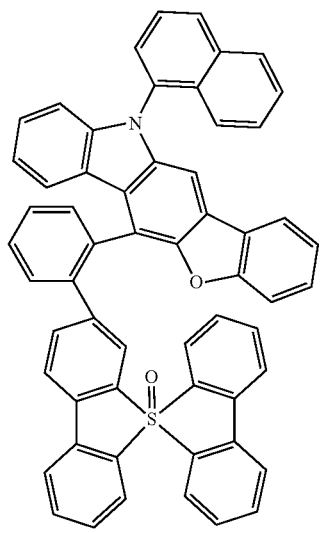
P051
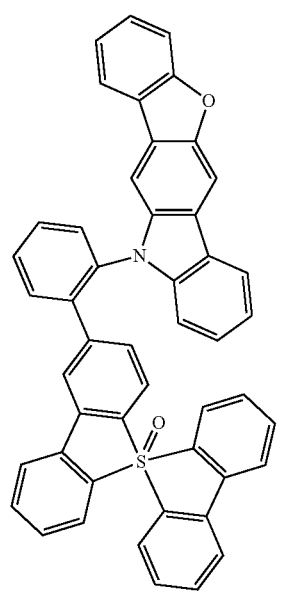
P052
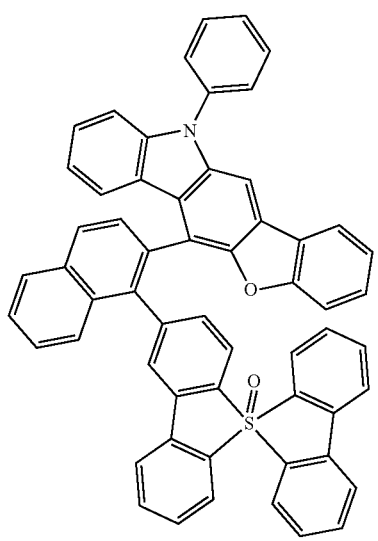

-continued
P053
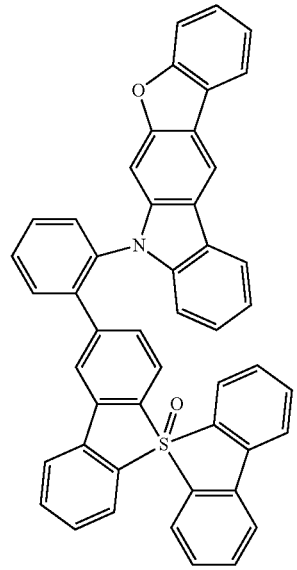
P054
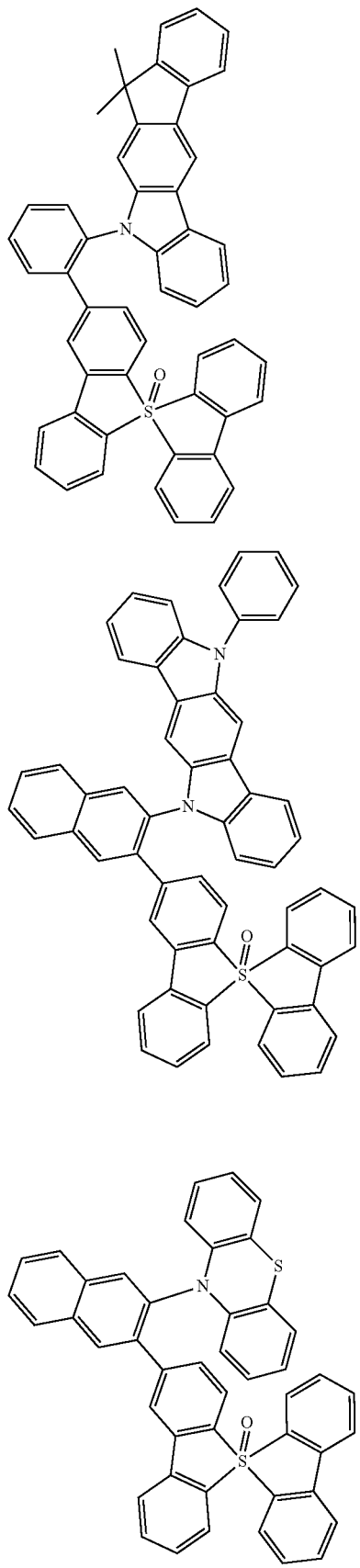
P055
P056
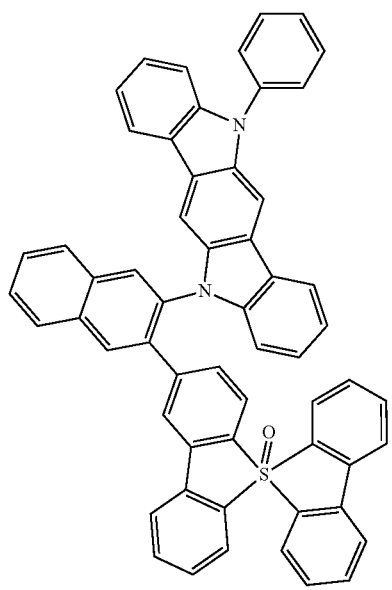
P057
P058
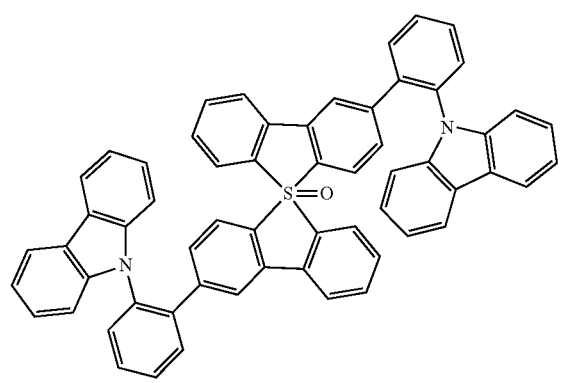

-continued
P059
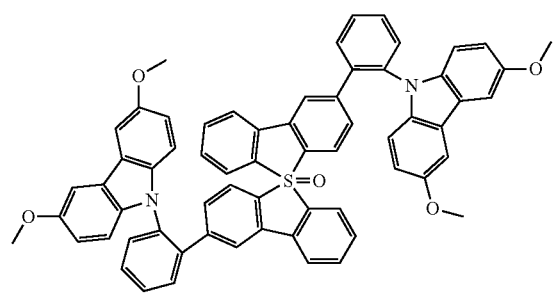
P060
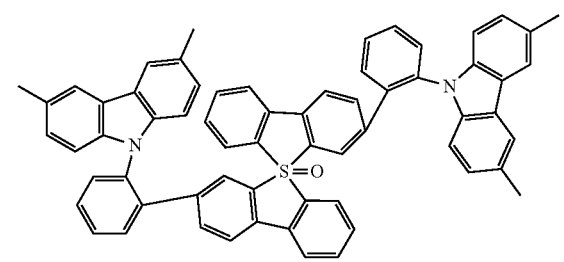
P061
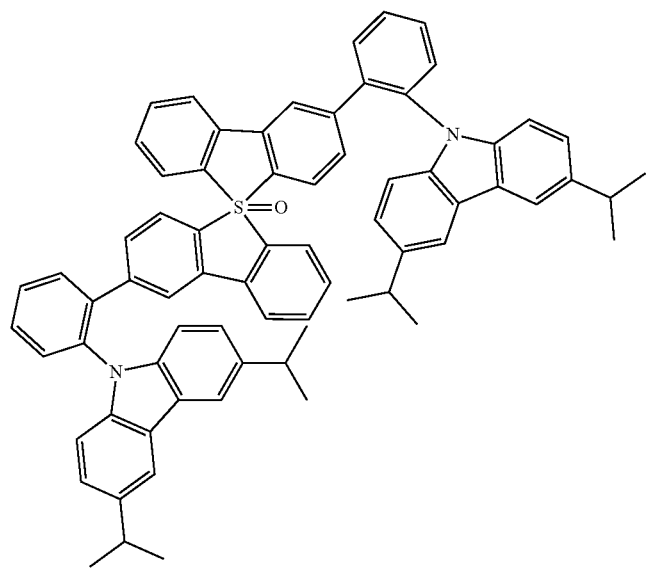
P062
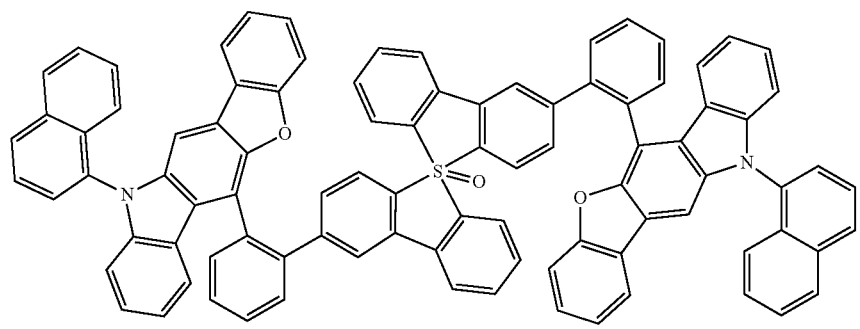

-continued
P063
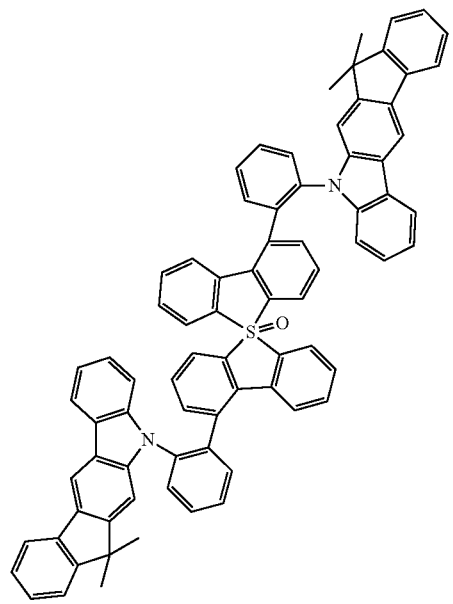
P064
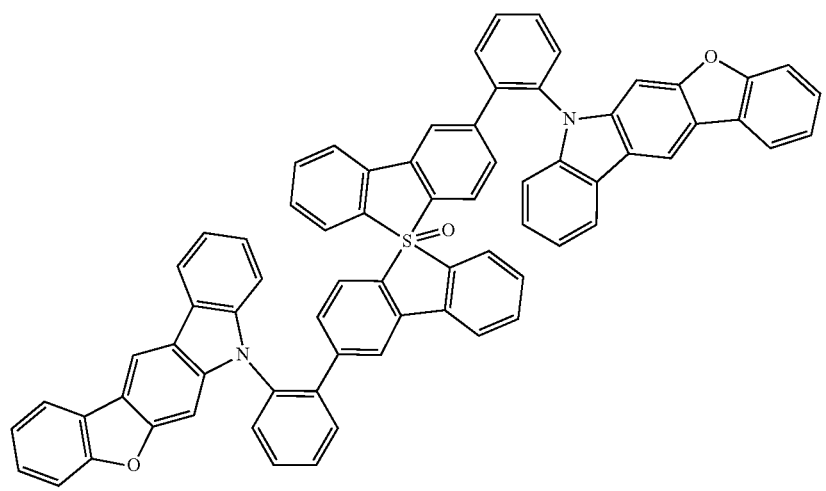
P065
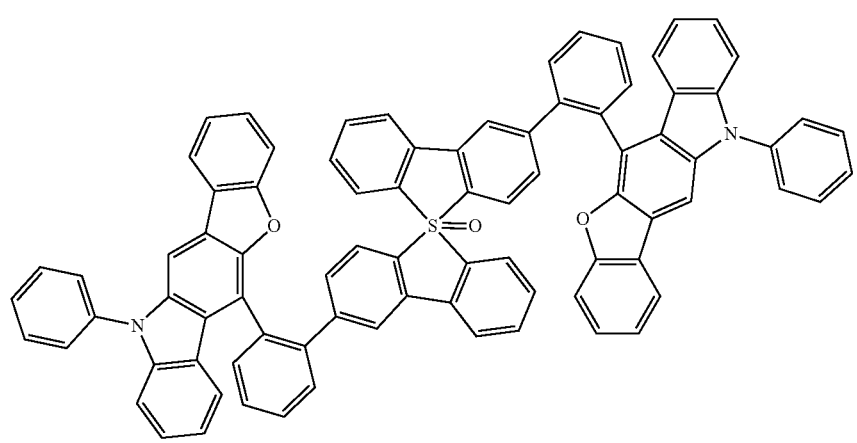

-continued
P066
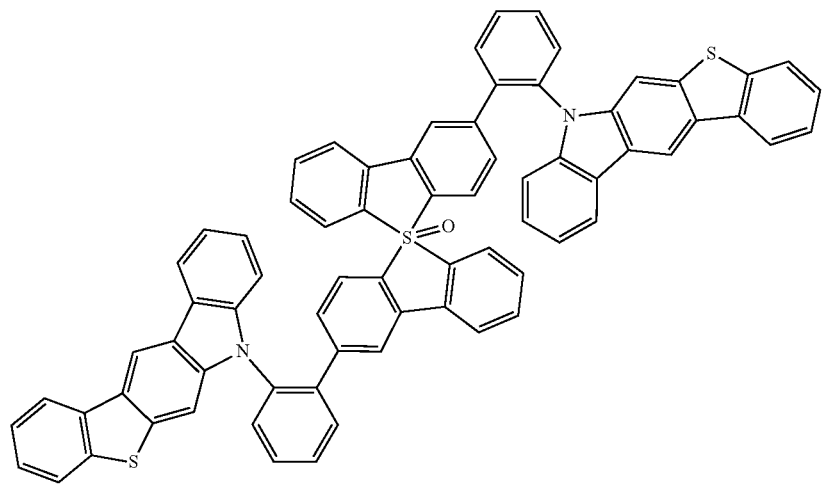
P067
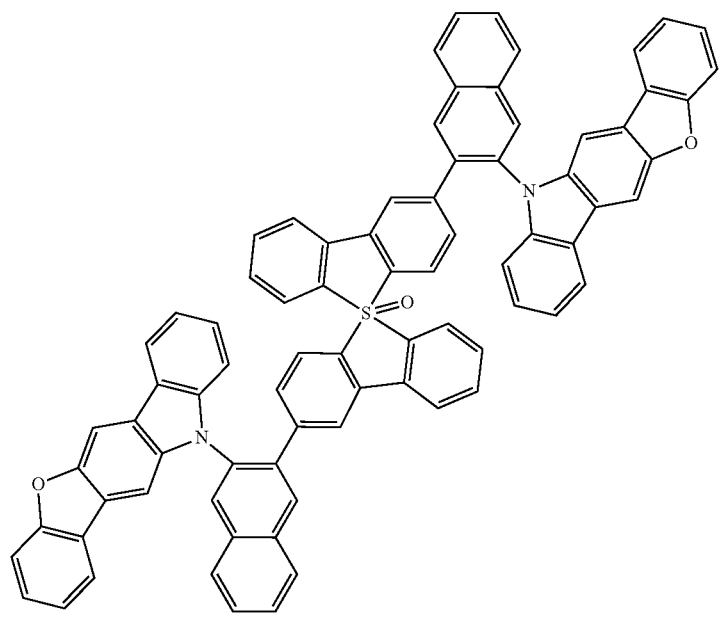
P068
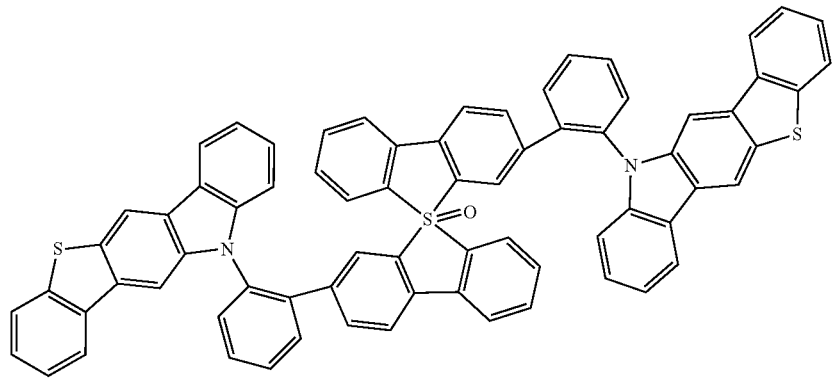

-continued
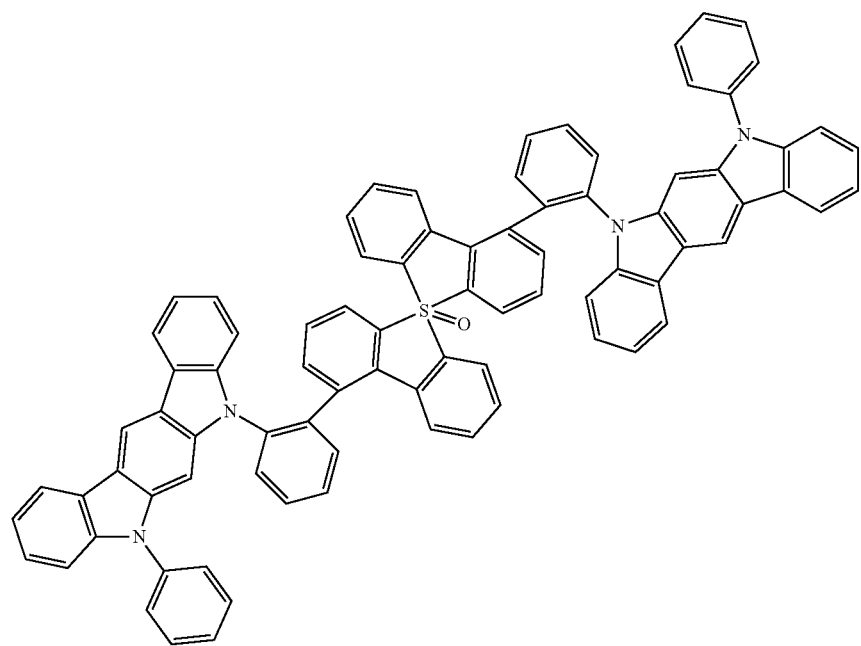
P069
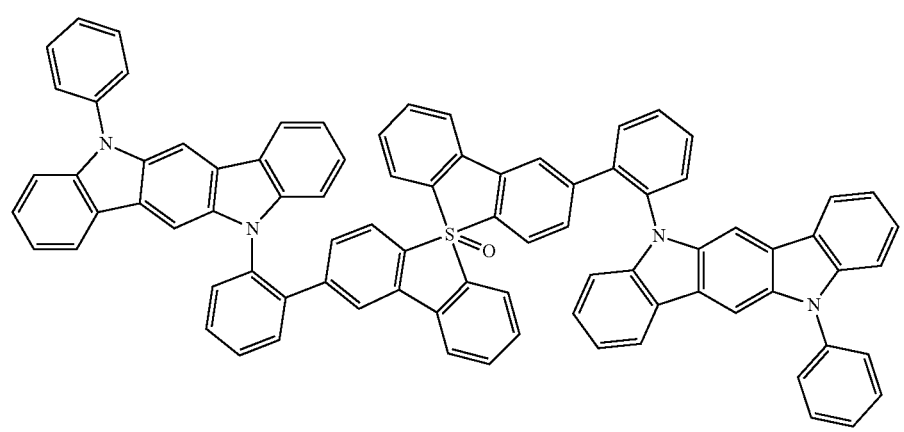
P070

P071
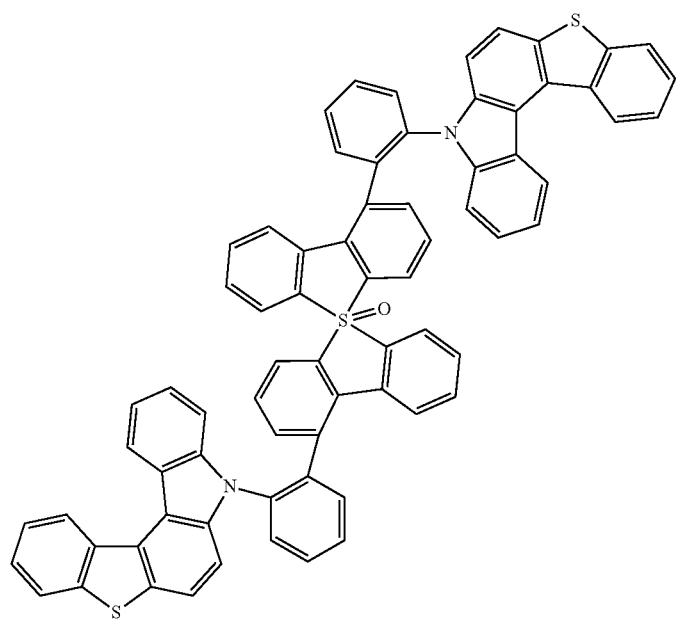
P072
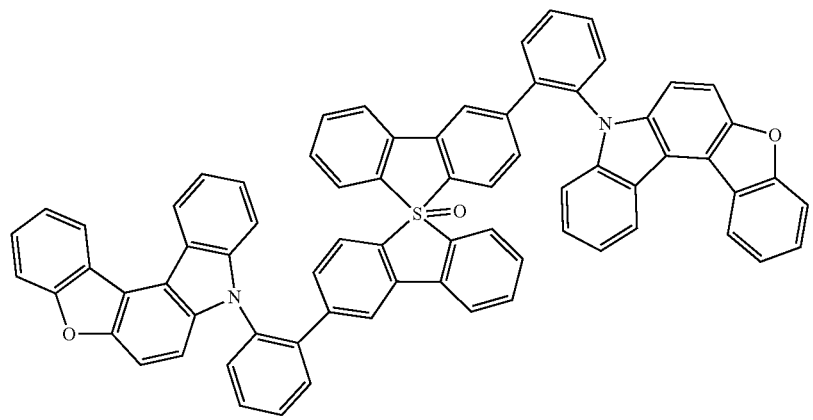
P073
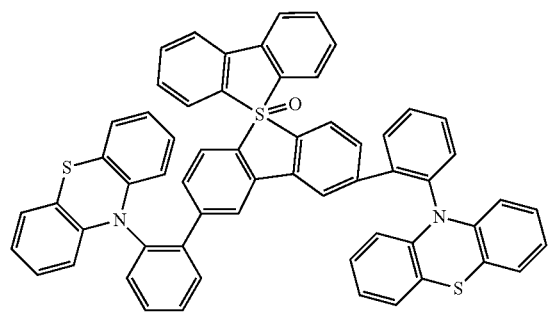
P074
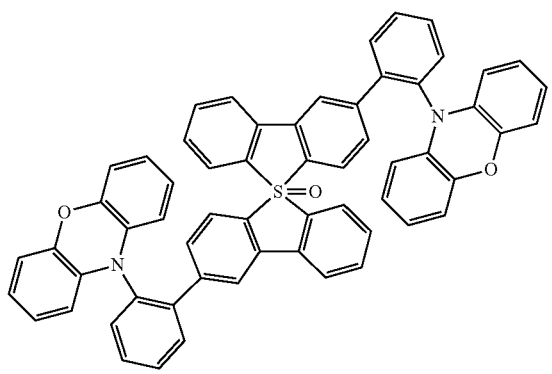

-continued
P075
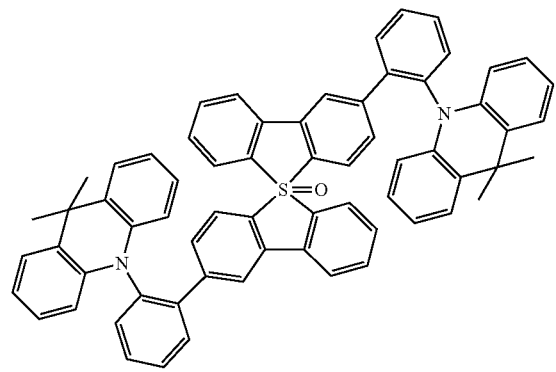
P076
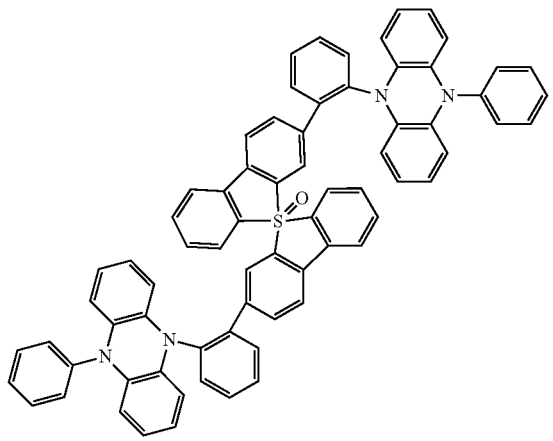
P077
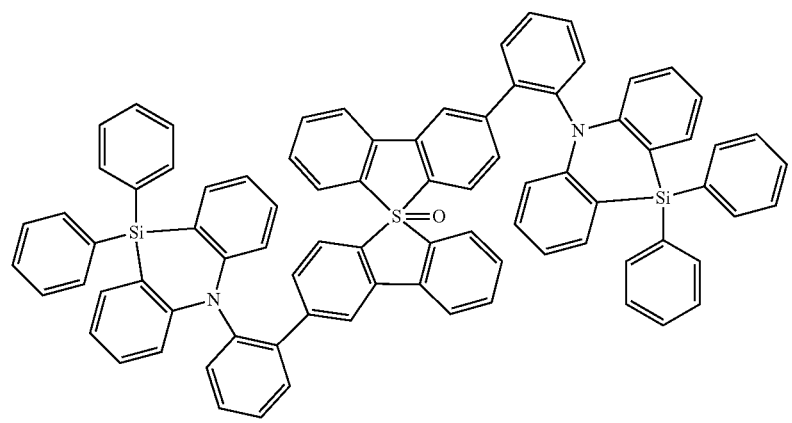
P078
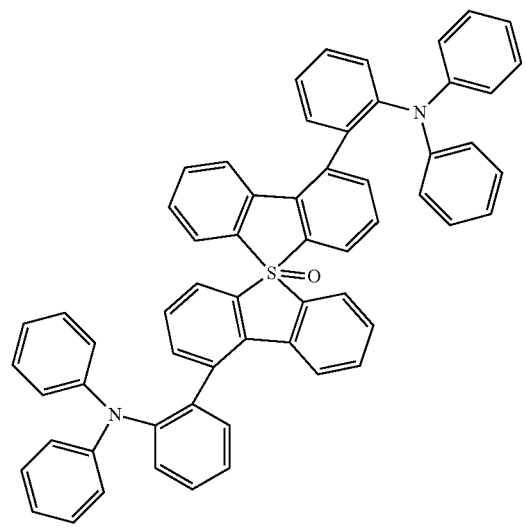

-continued
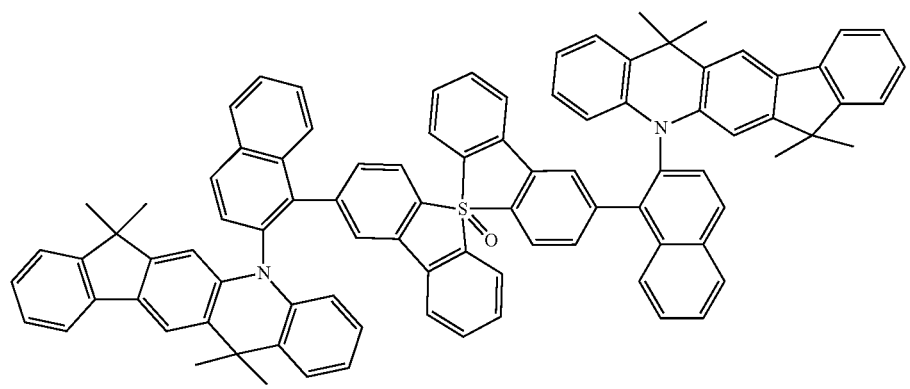
P079
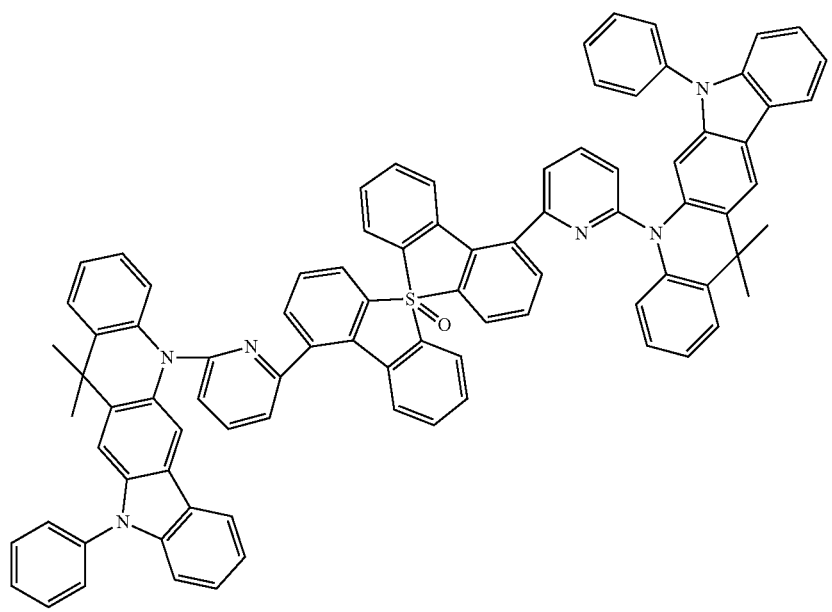
P080
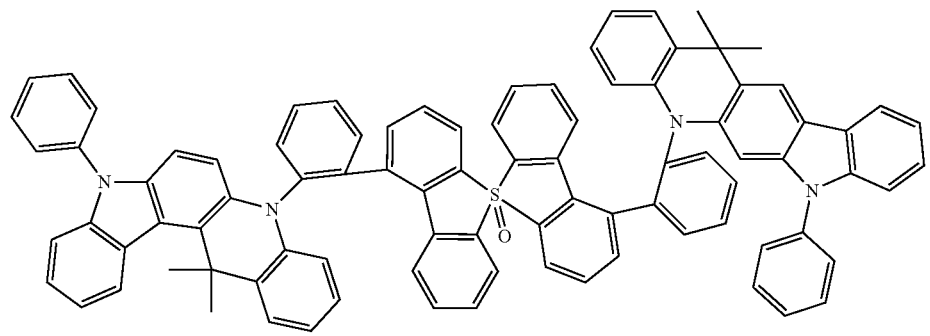
P081

-continued
P082
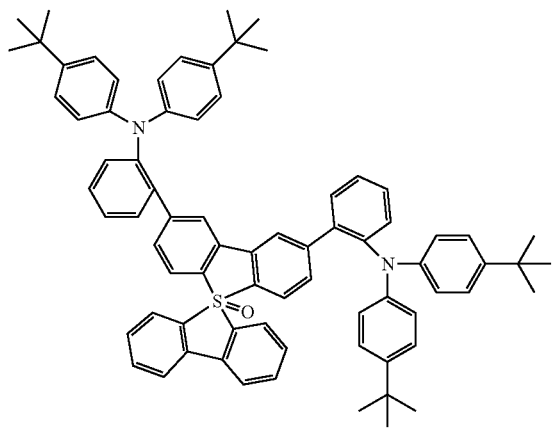
P083
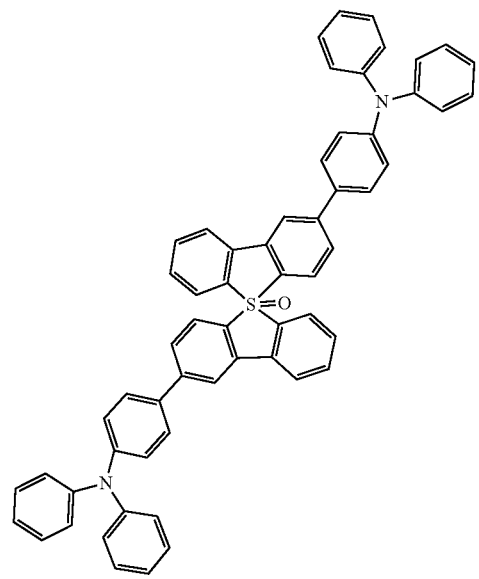
P084
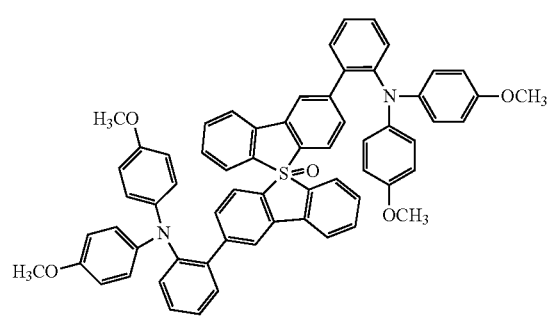
P085
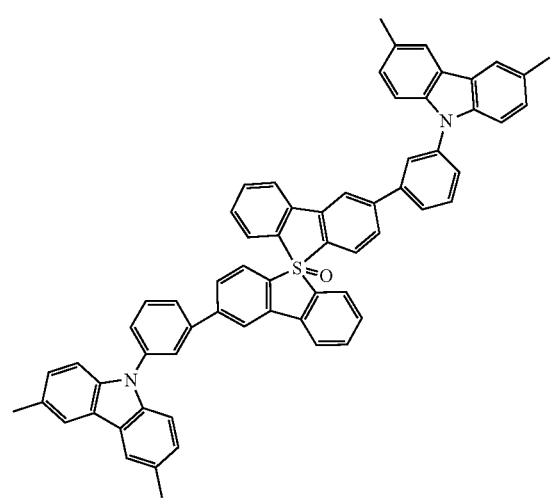

-continued
P086
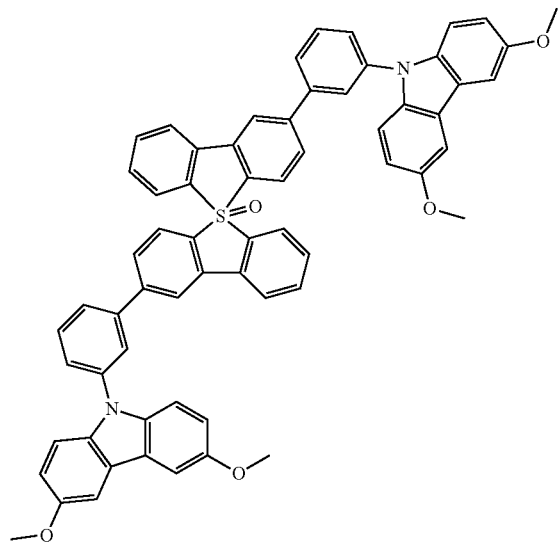
P087
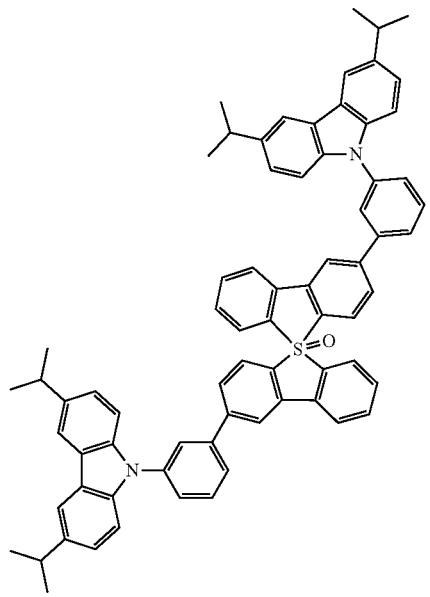
P088
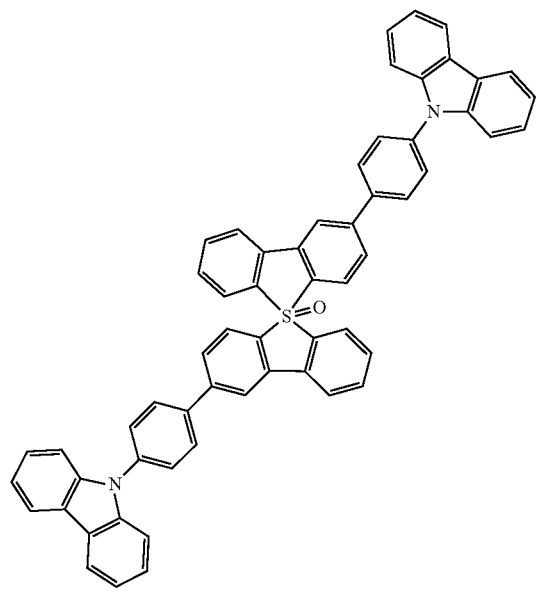

P089
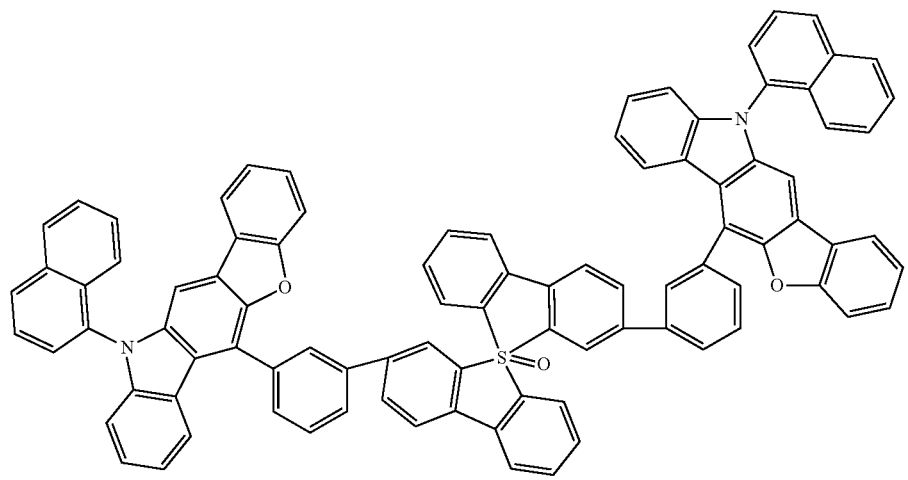
P090
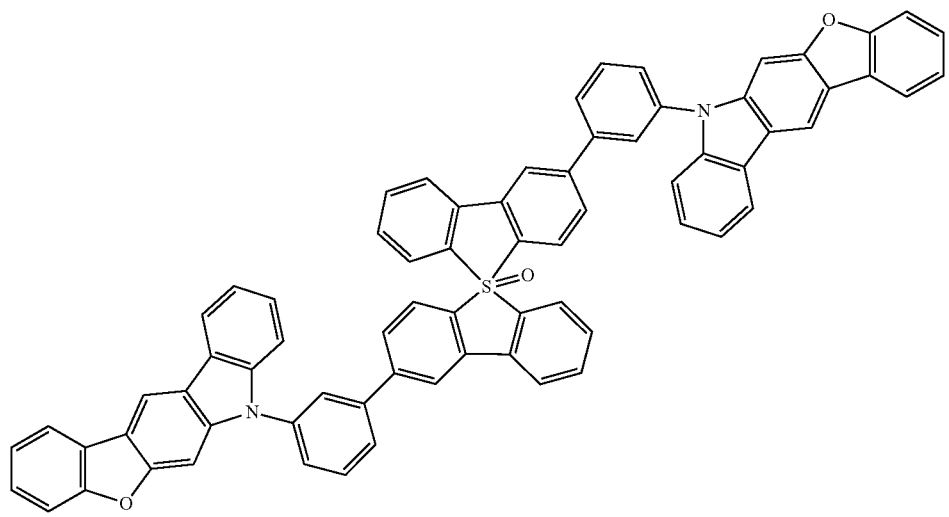
P091
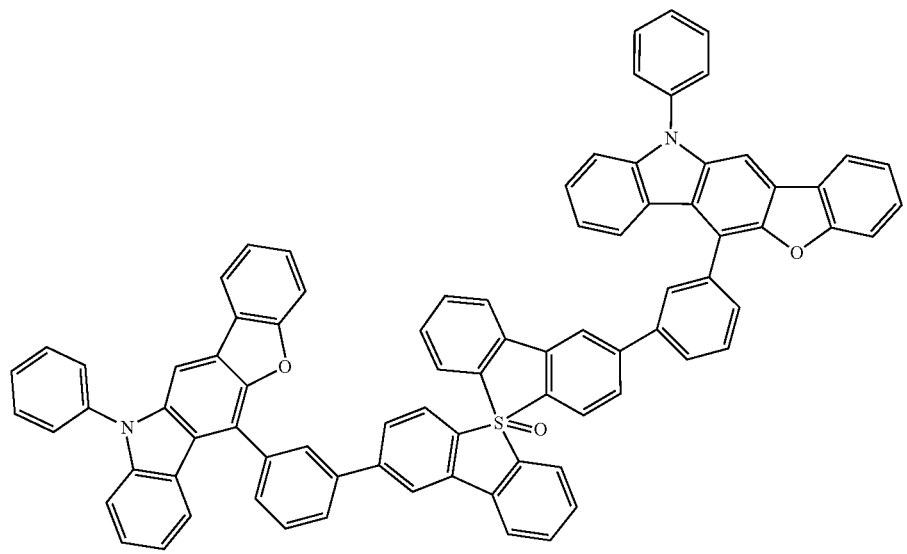

-continued
P092
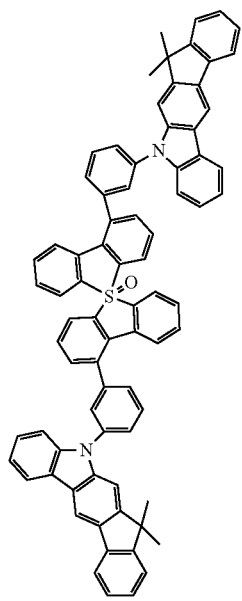
P093
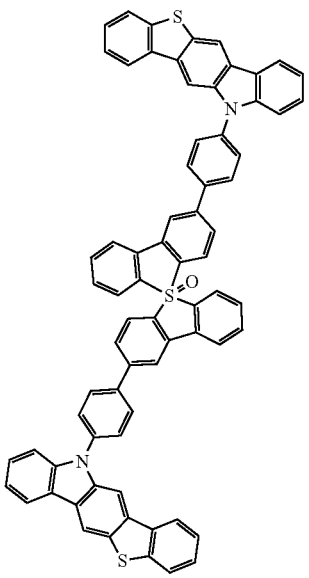
P094
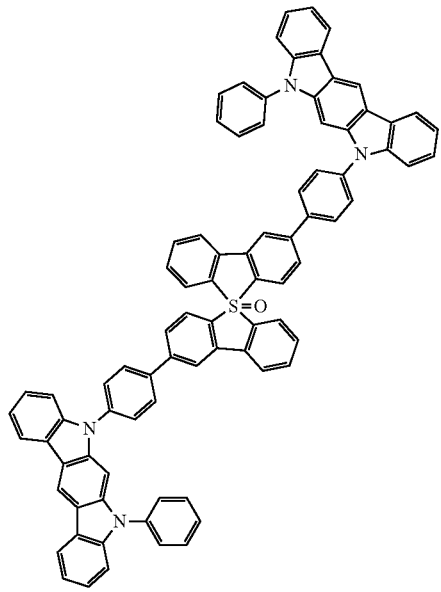
P095
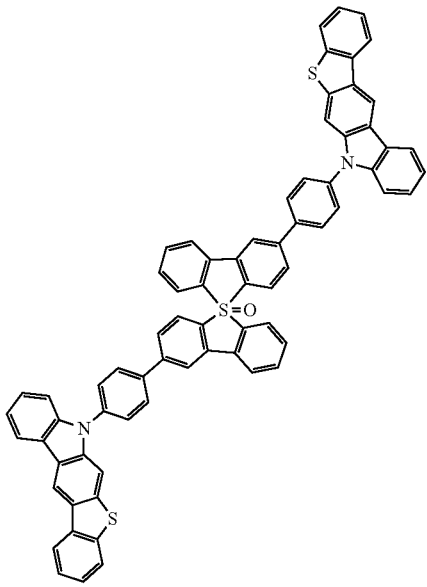

-continued
P096
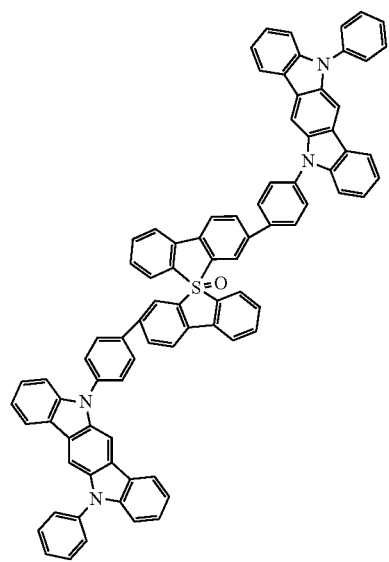
P097
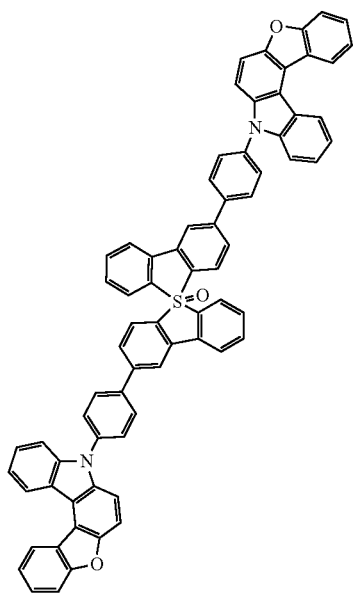
P098
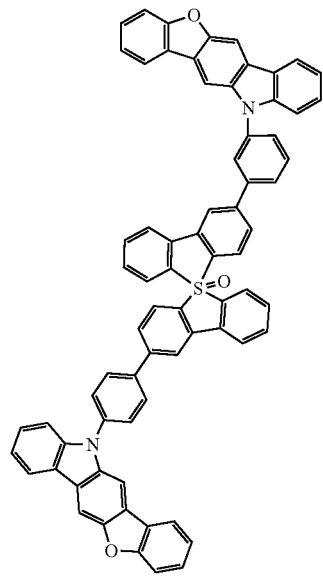
P099
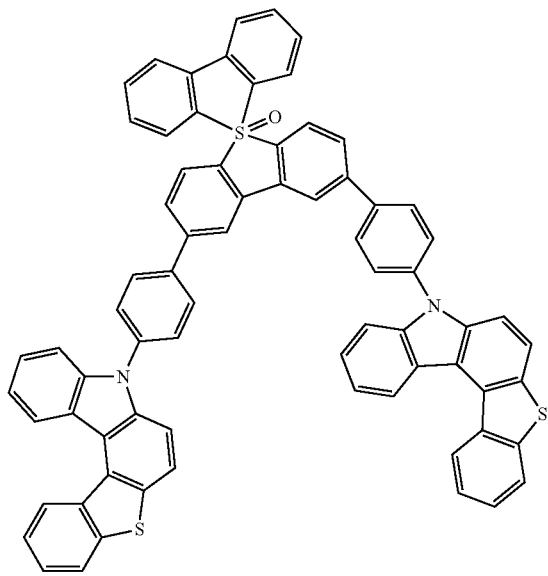

-continued
P100
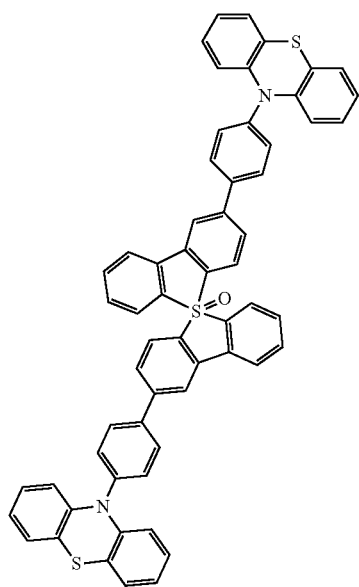
P101
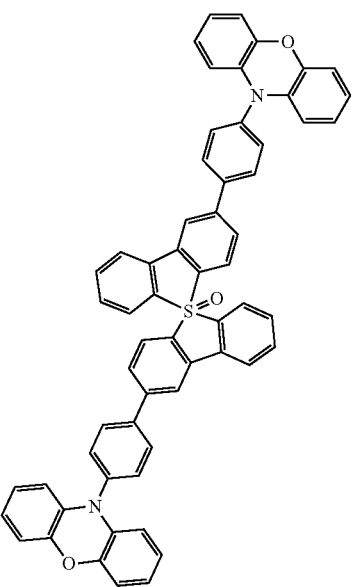
P102
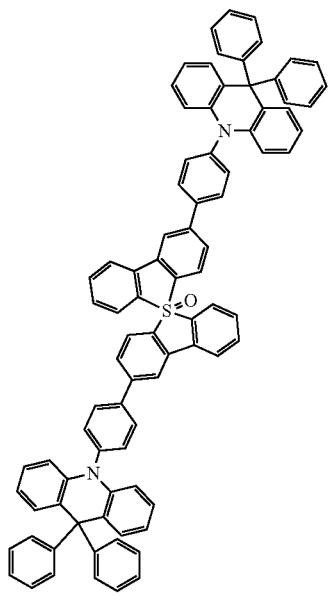

-continued
P103
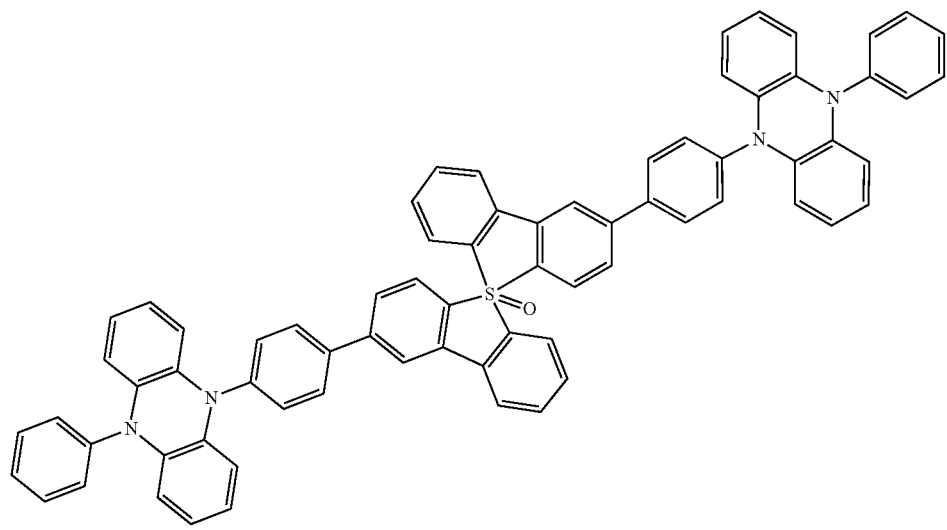
P104
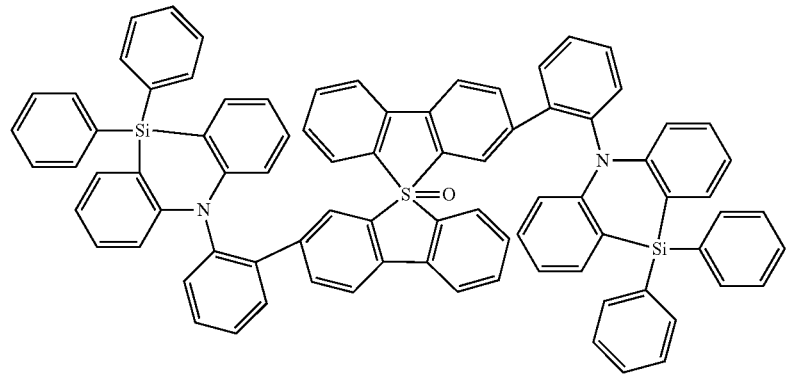
P105
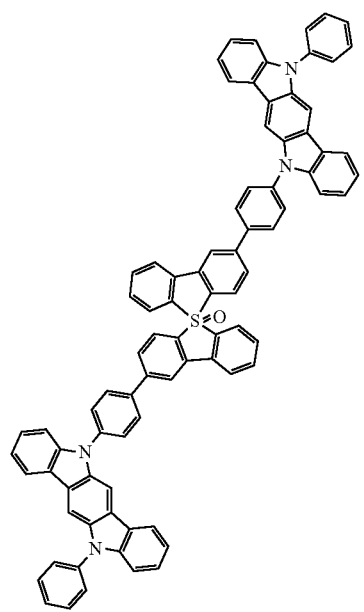
P106
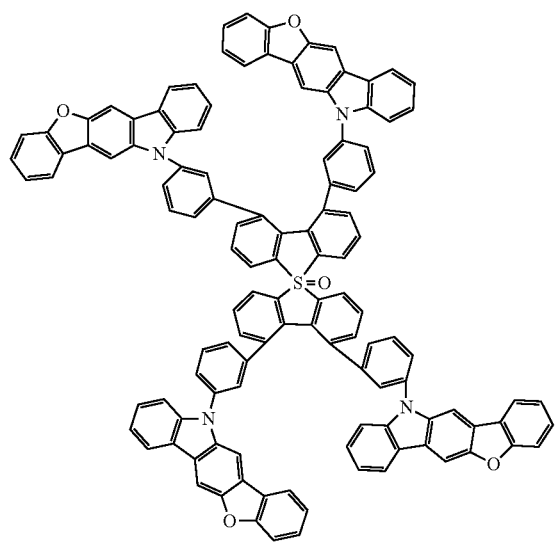

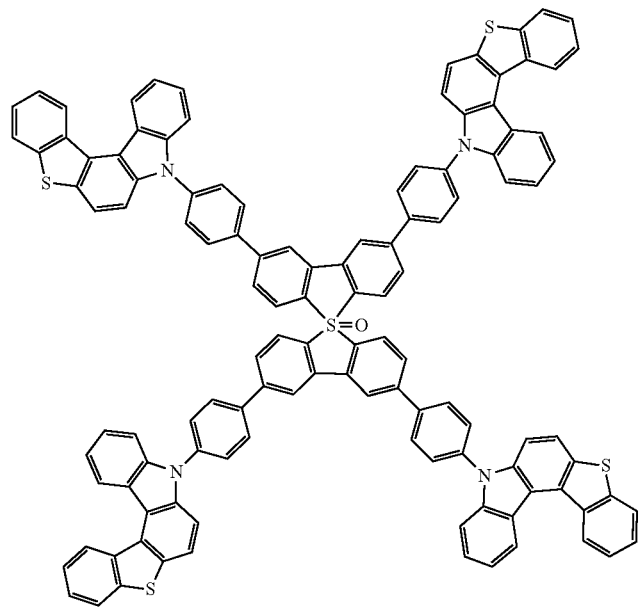
P107
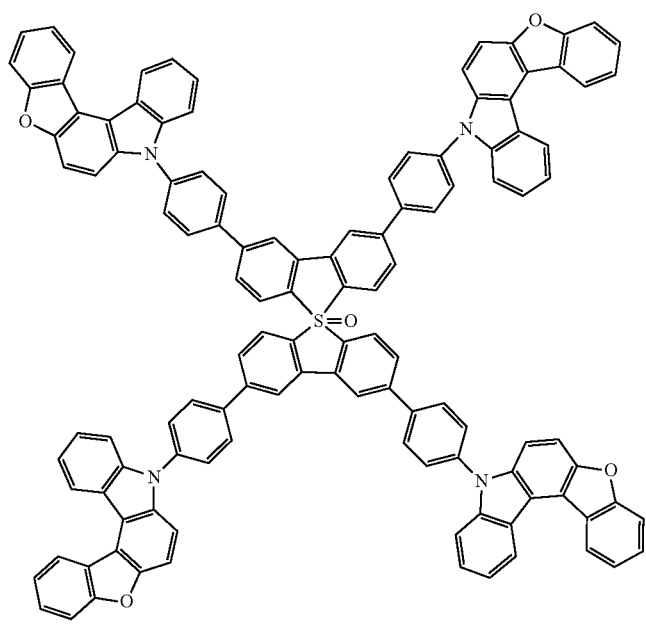
P108

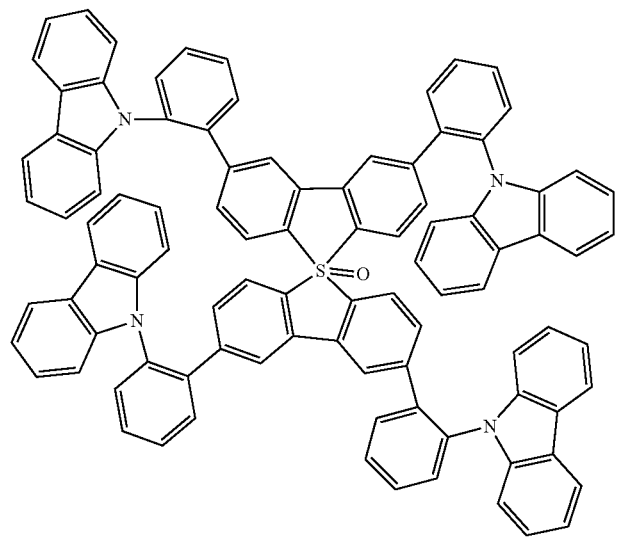
P109
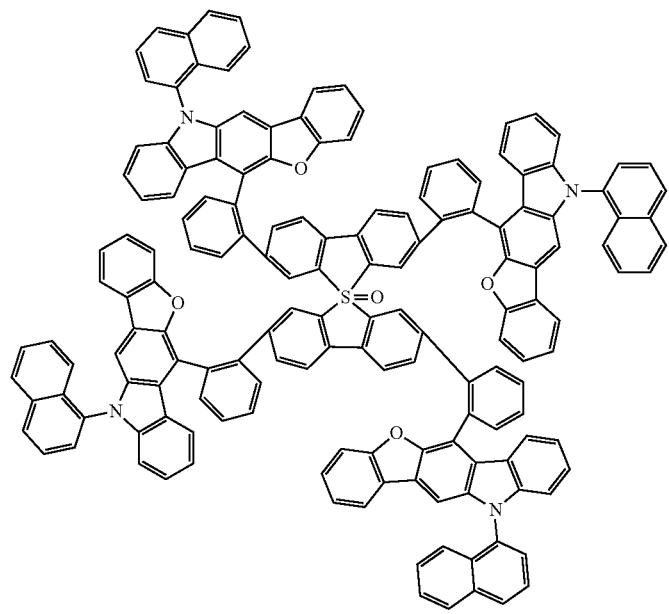
P110

-continued
P111
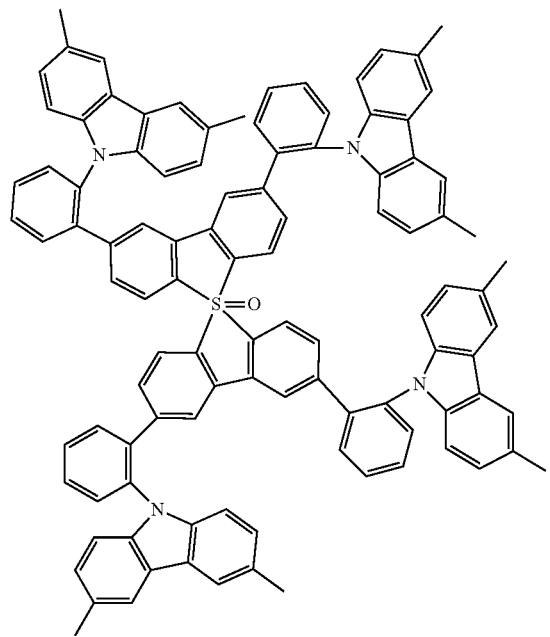
P112
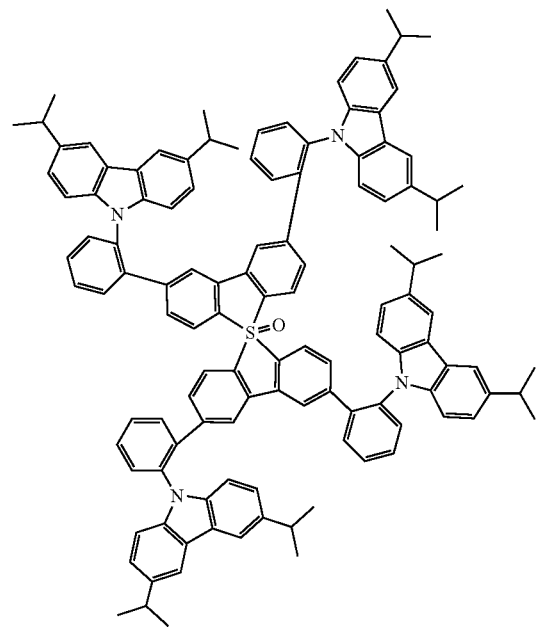
P113
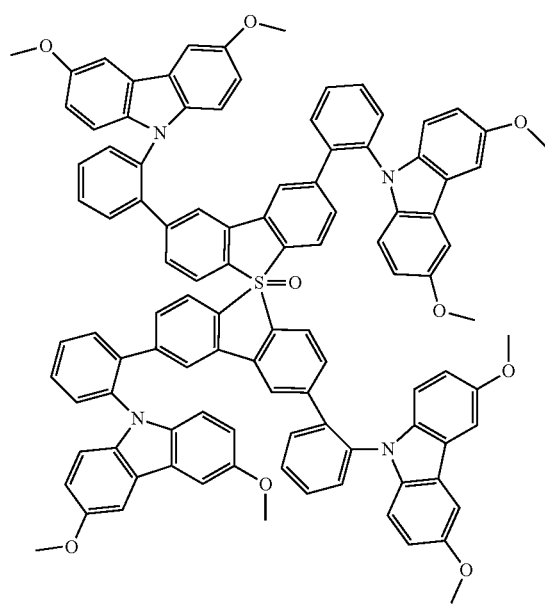
P114
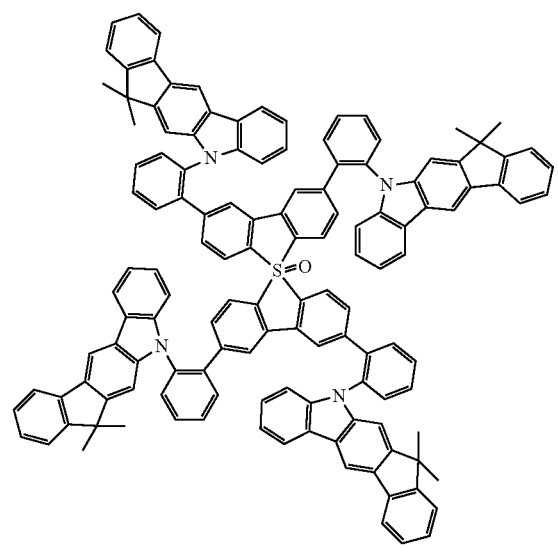

-continued
P115
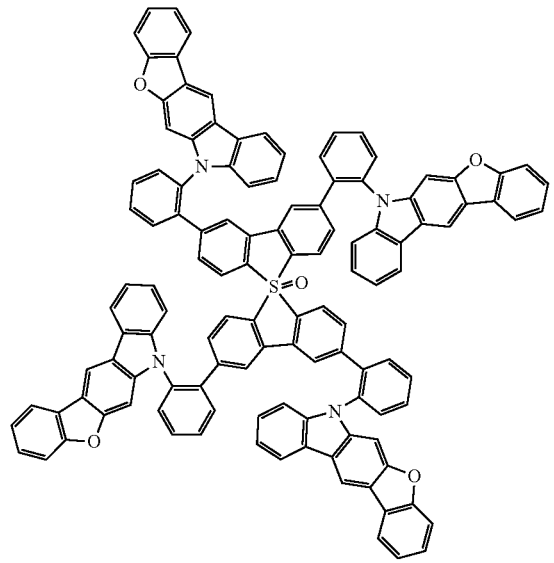
P116
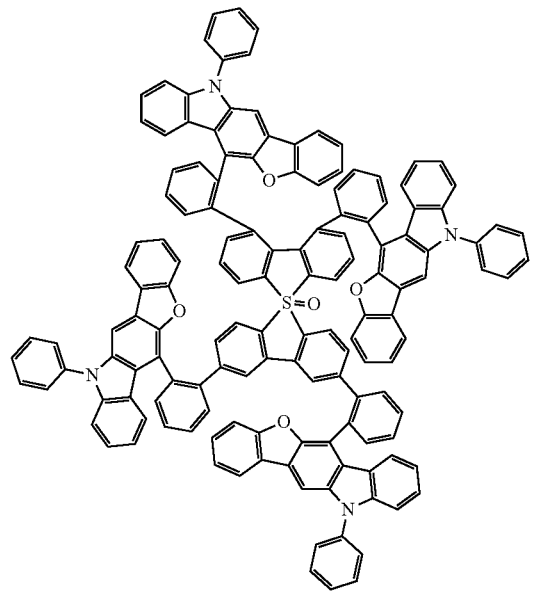
P117
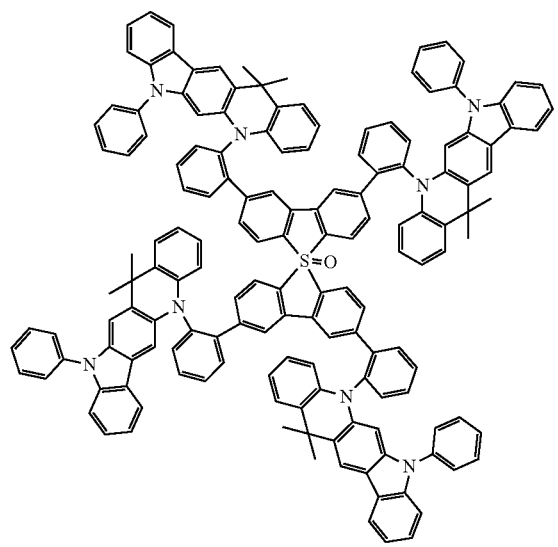
P118
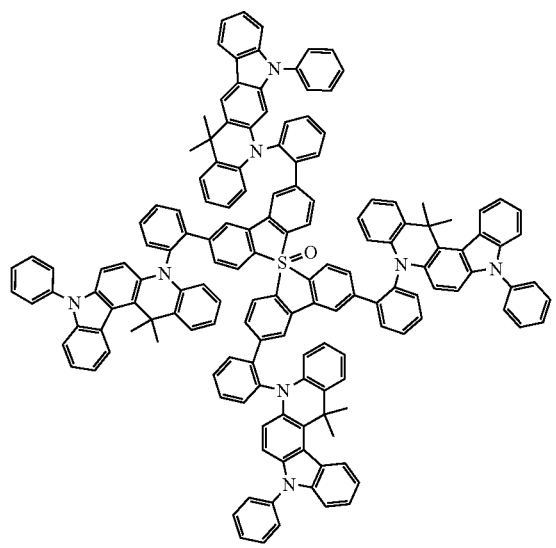

-continued
P119
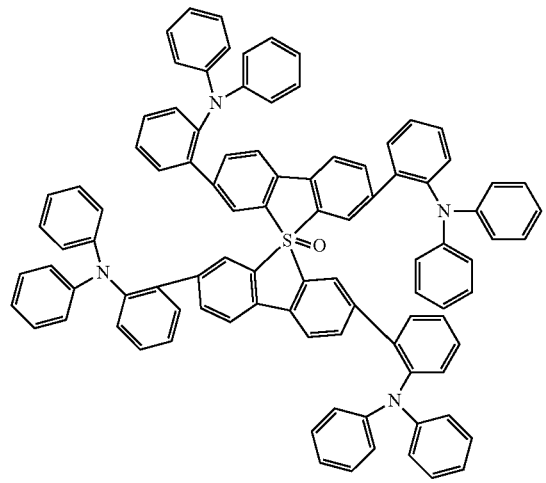
P120
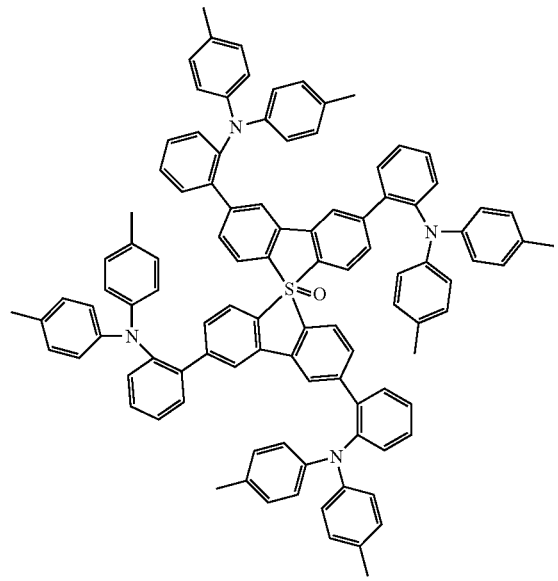
P121
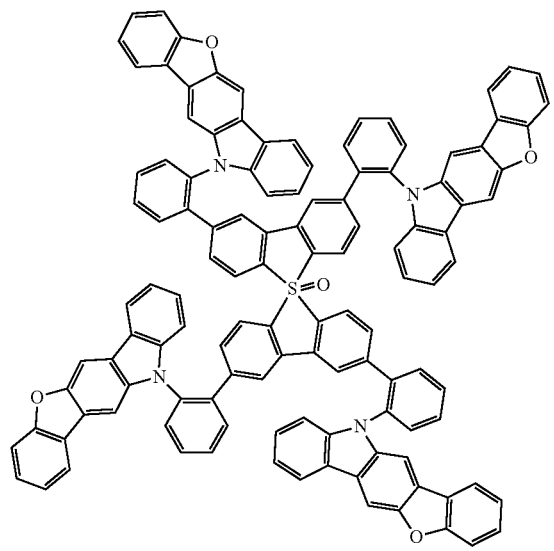
P122
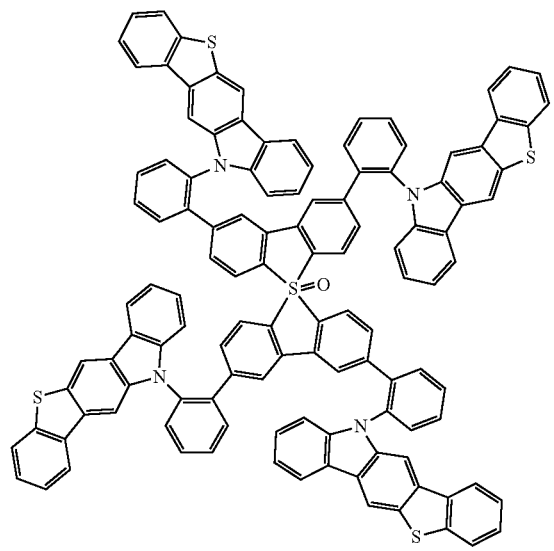

-continued
P123
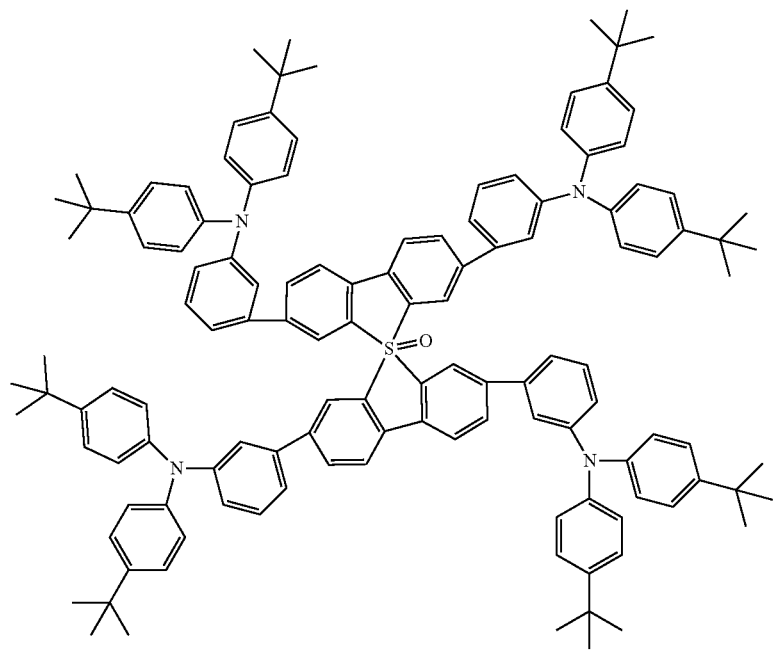
P124
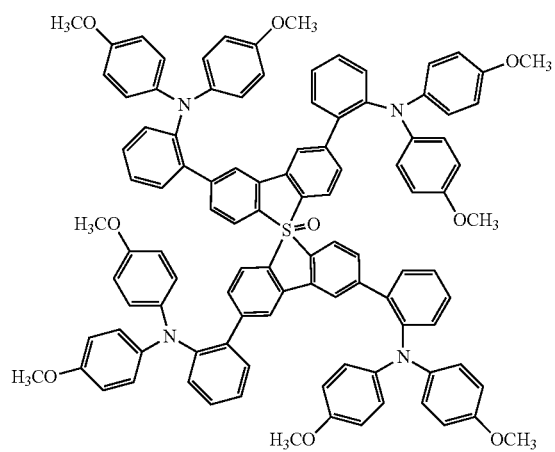
P125
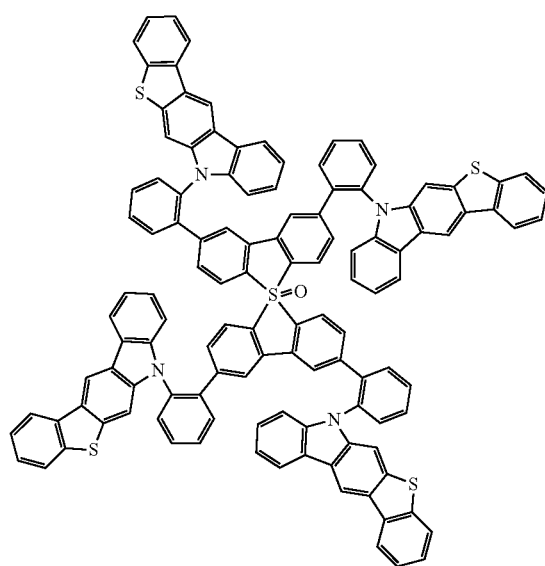

P126
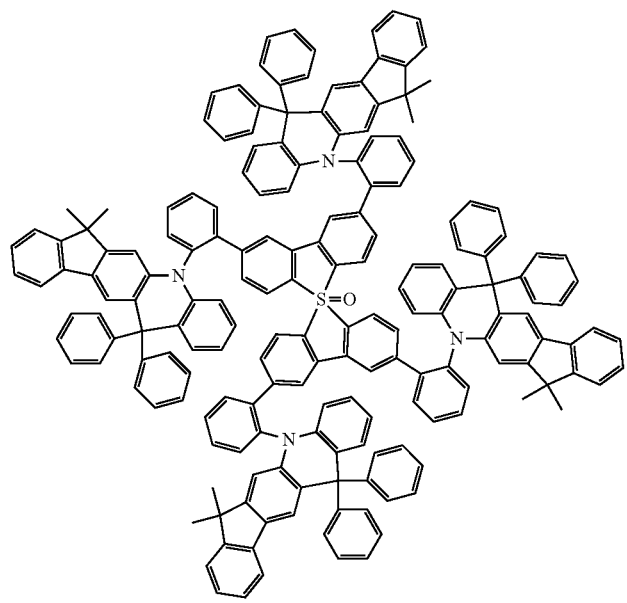
P127
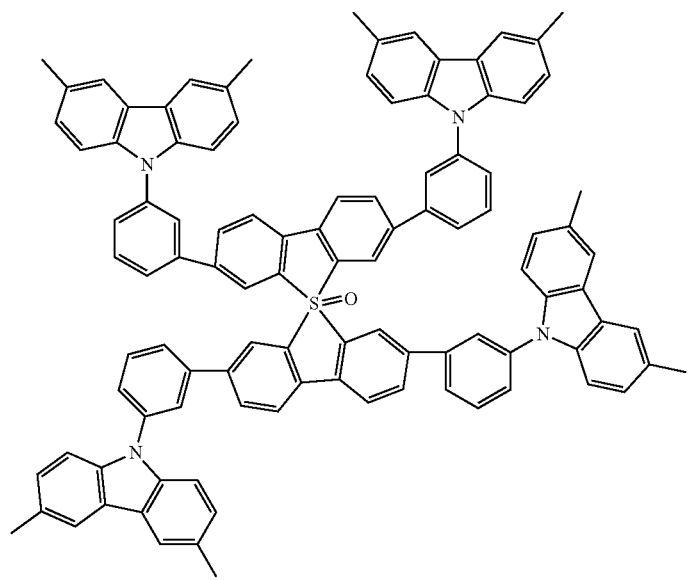

-continued
P128
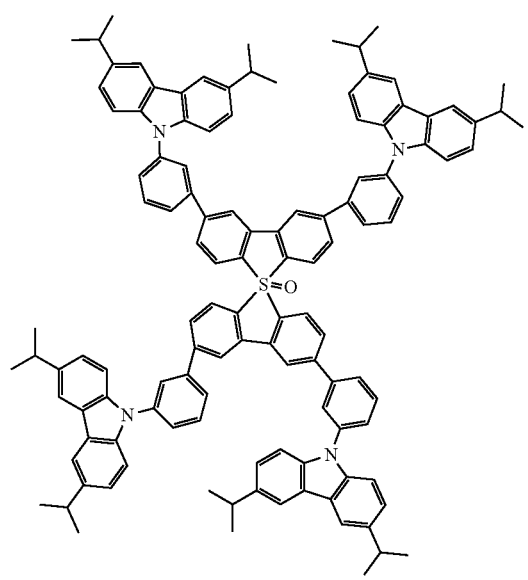
P129
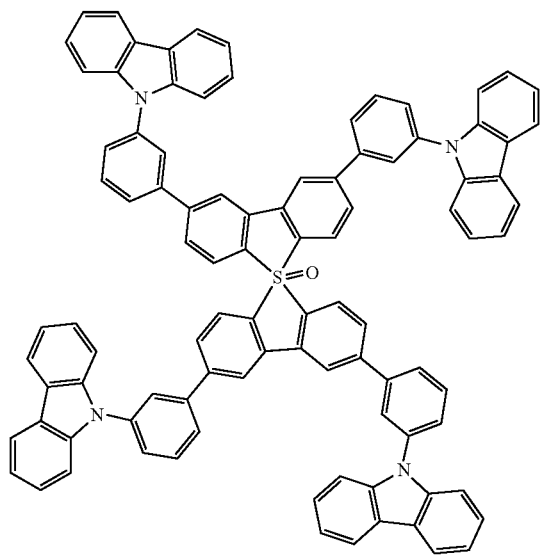
P130
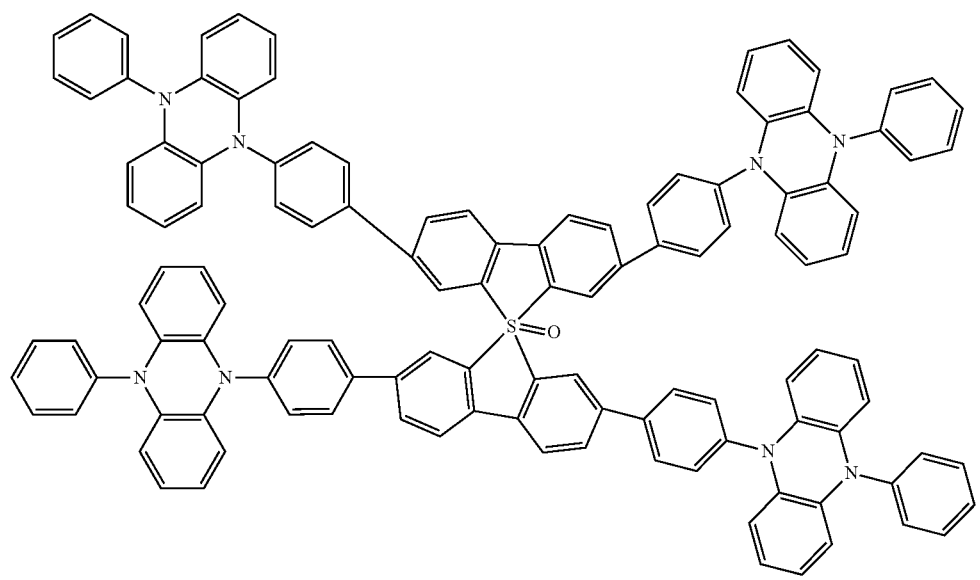

-continued
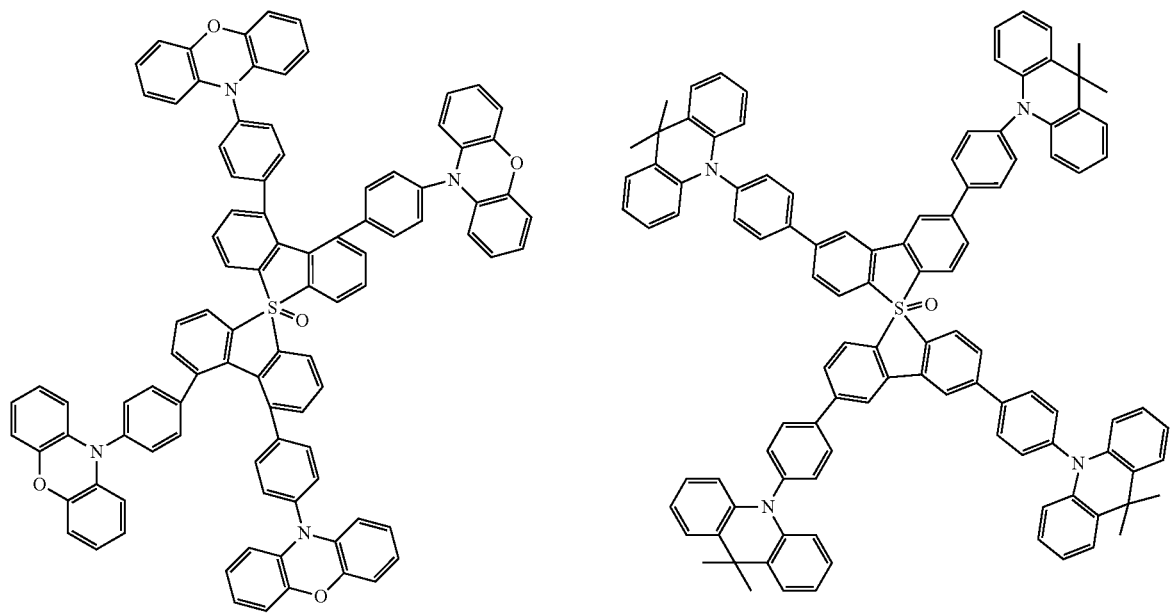
P131
P132
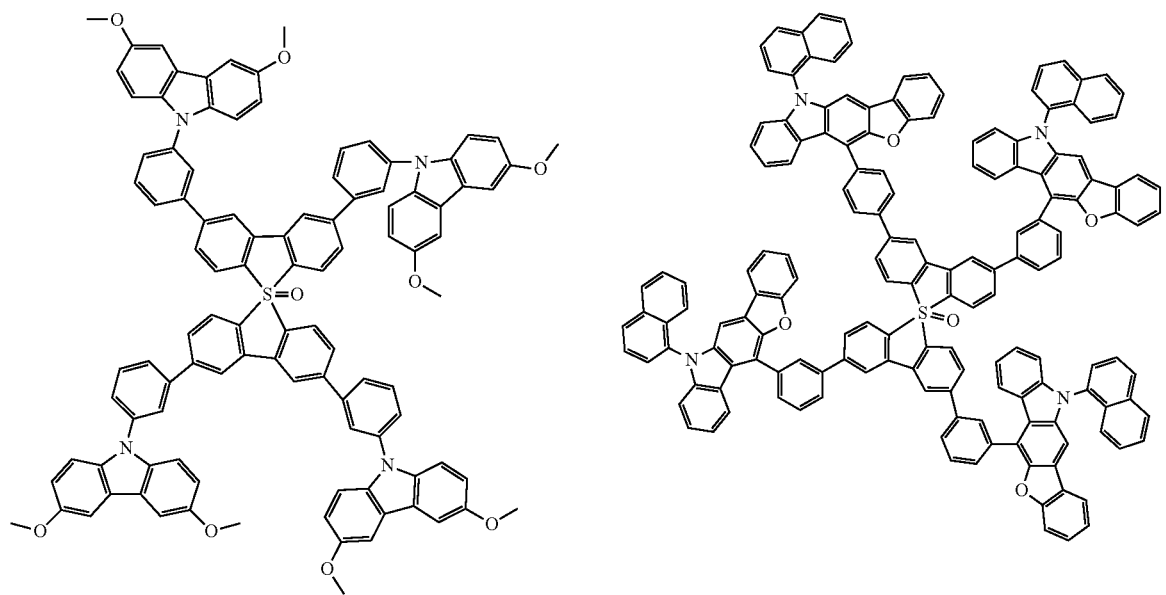
P133
P134

P135
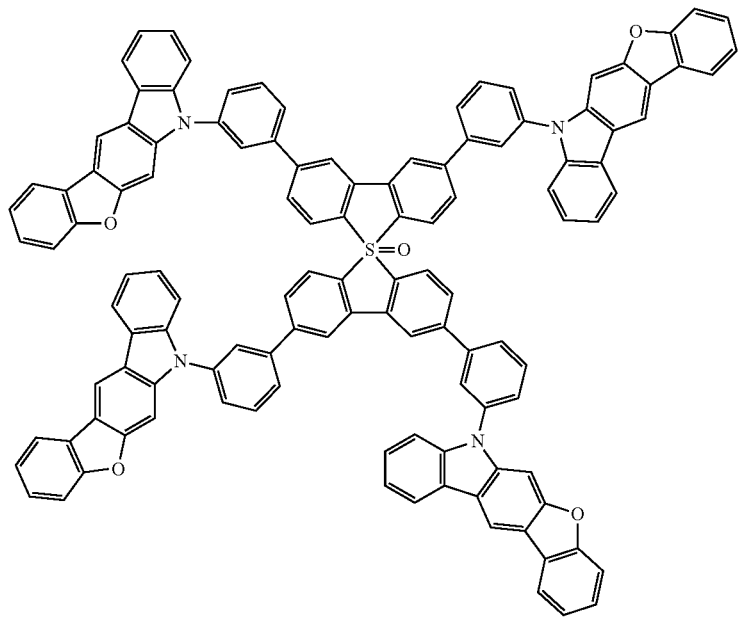
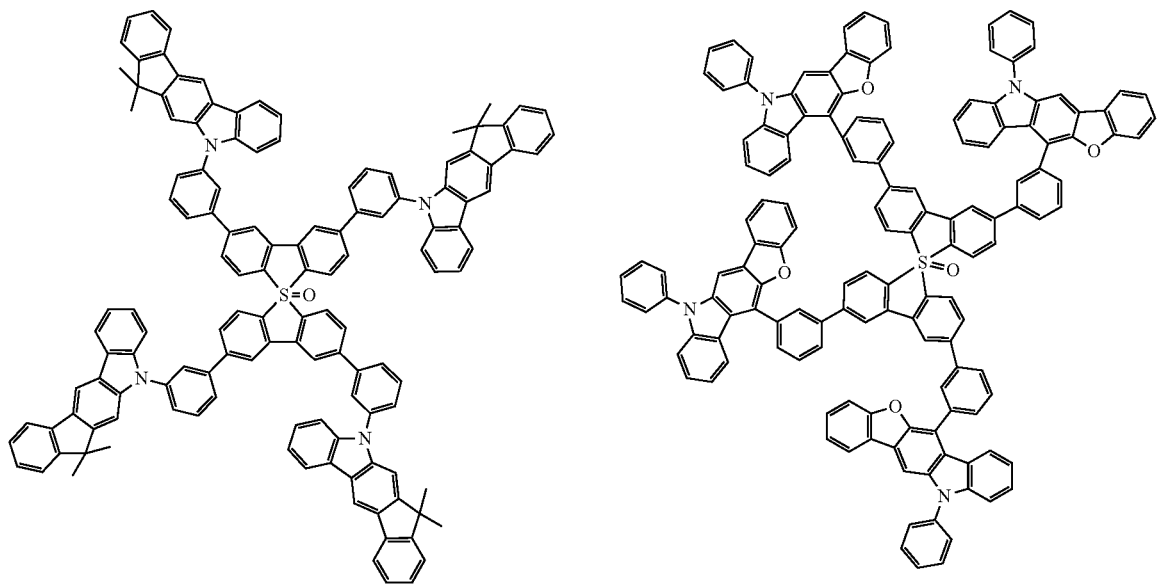
136
P137

P138
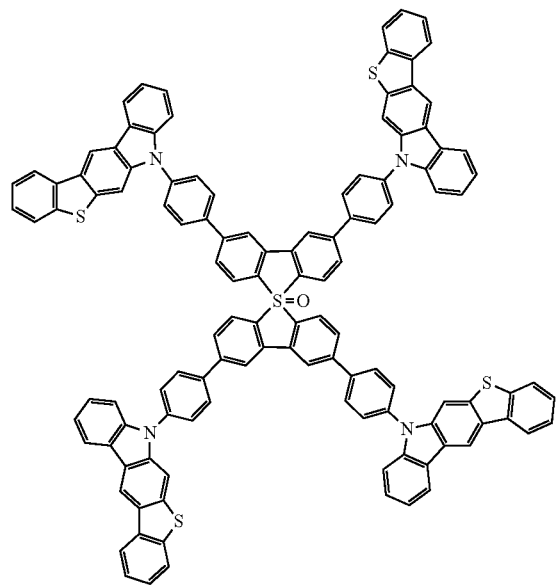
P139
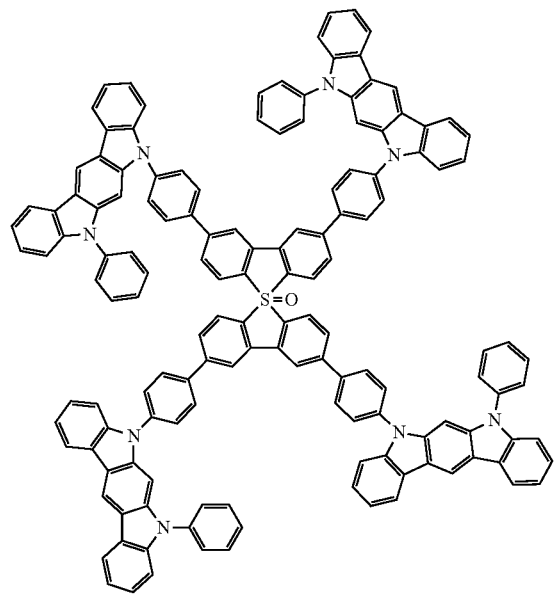
P140
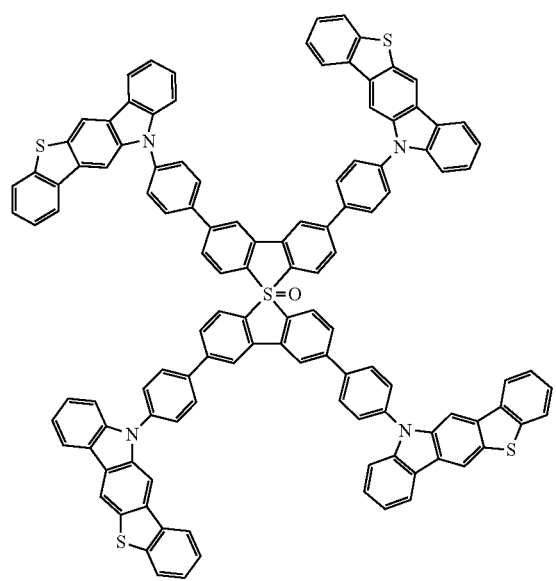
P141
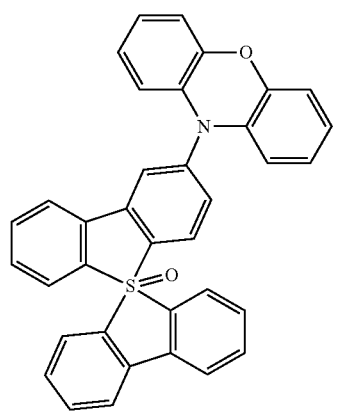

-continued
P142
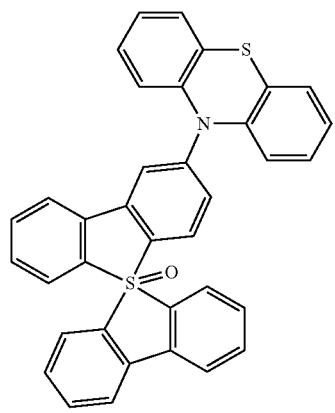
P143
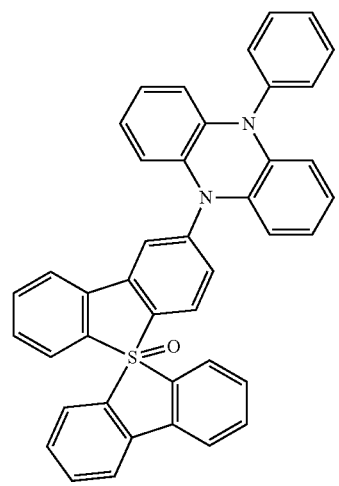
P144
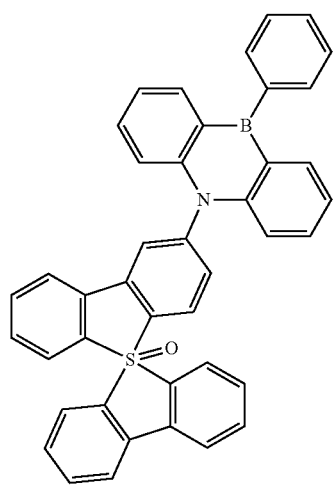
P145
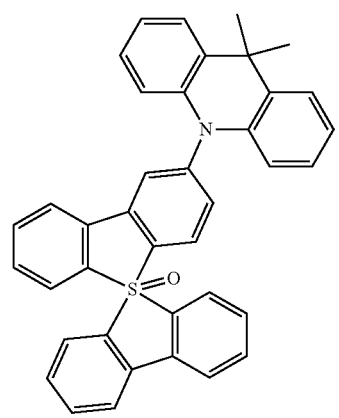
P146
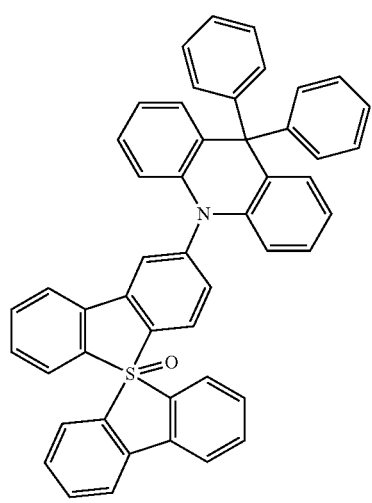
P147
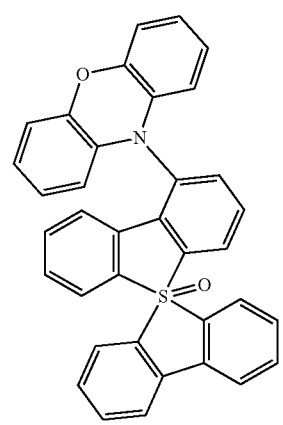

-continued
P148
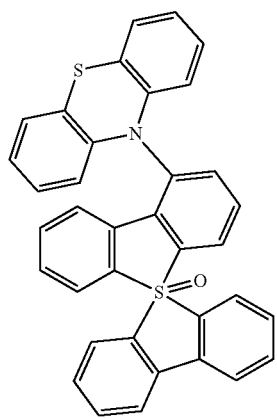
P149
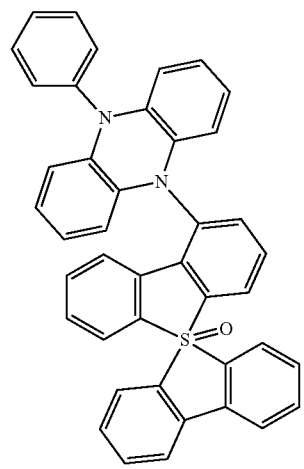
P150
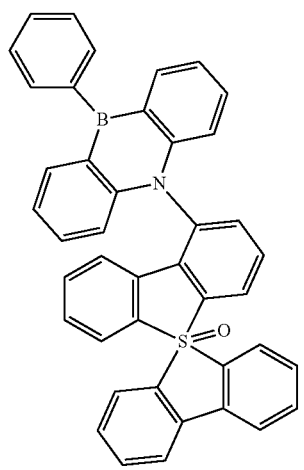
P151
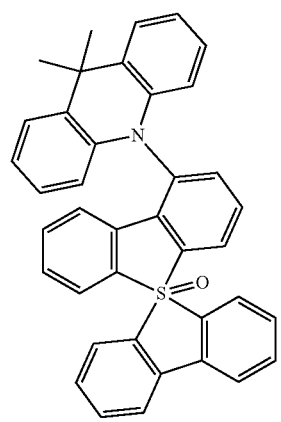
P152
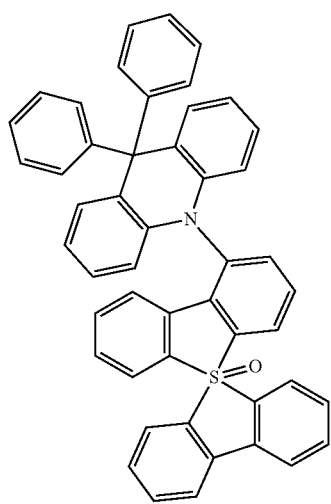
P153
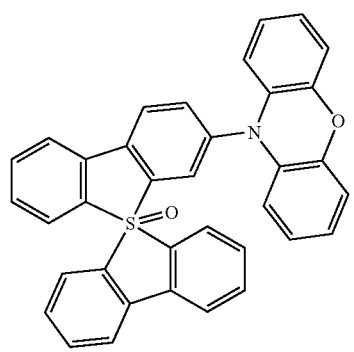

-continued
P154 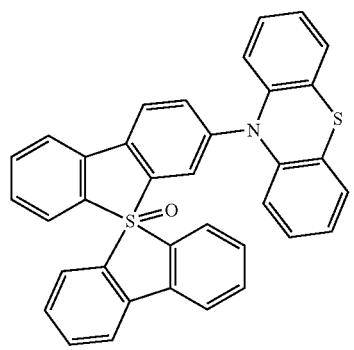
P155 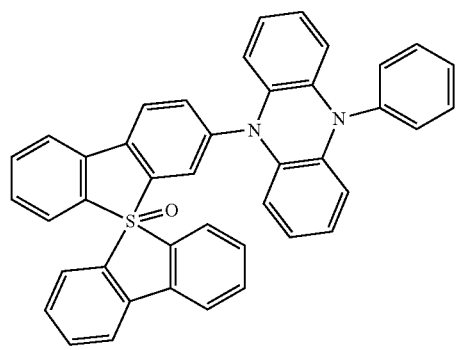
P156 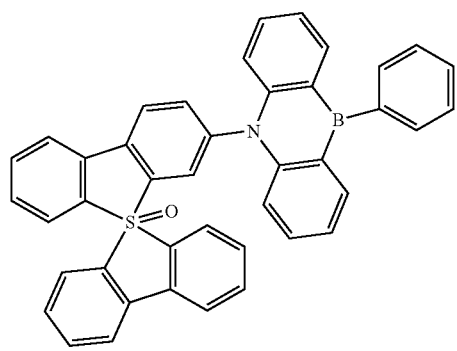
P157 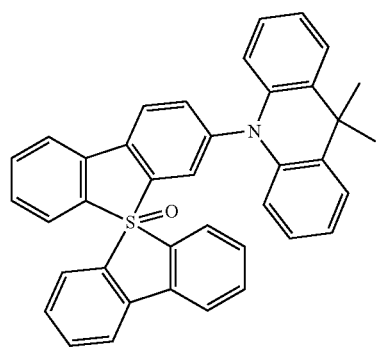
P158 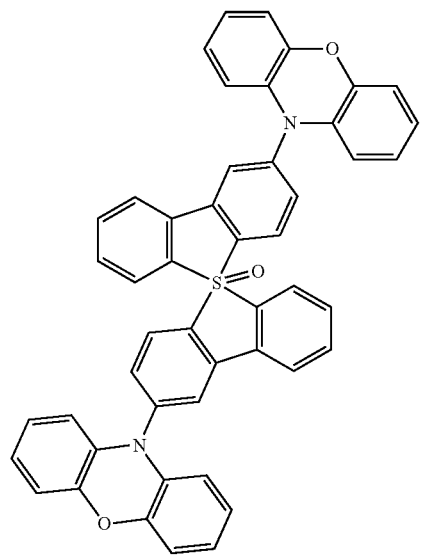
P159 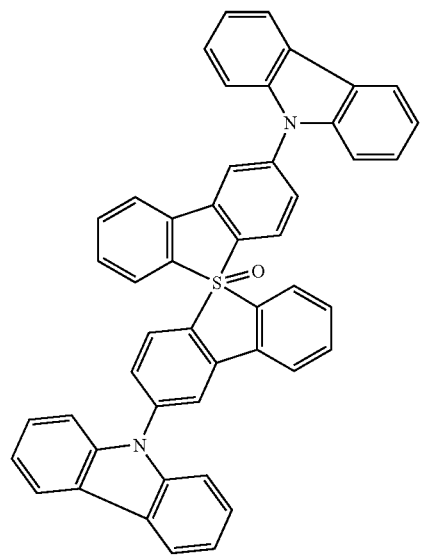

-continued
P160
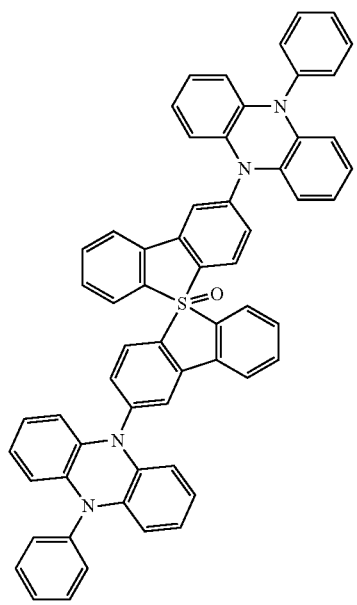
P161
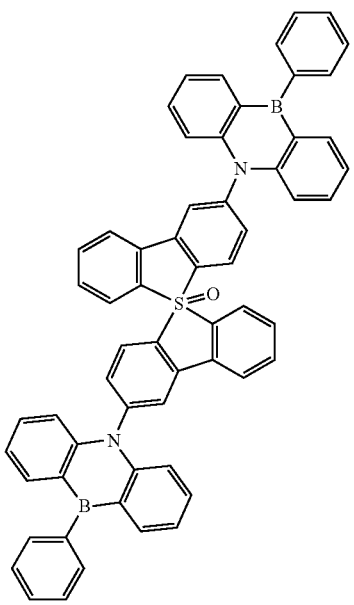
P162
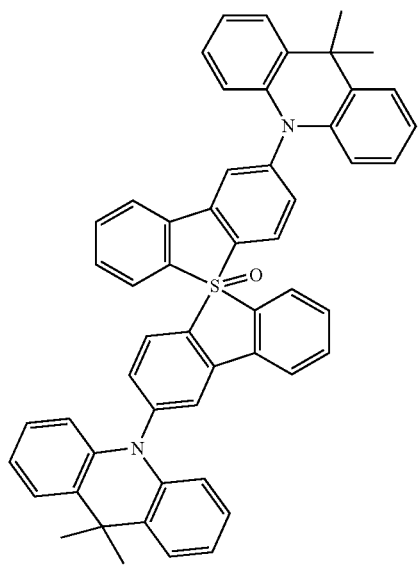
P163
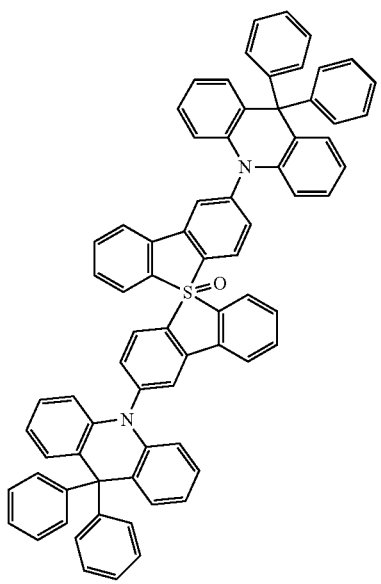

-continued
P164
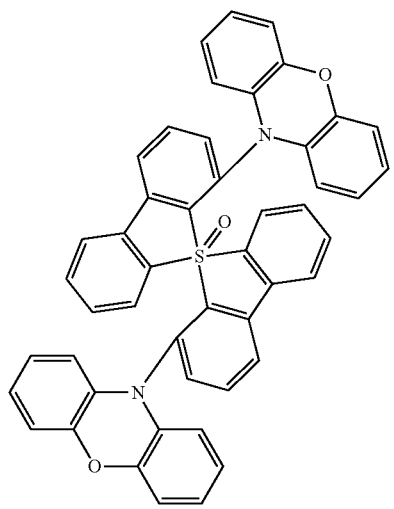
P165
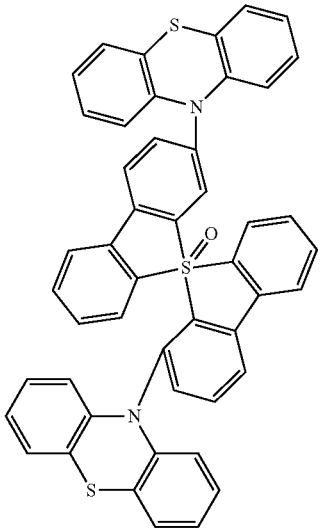
P166
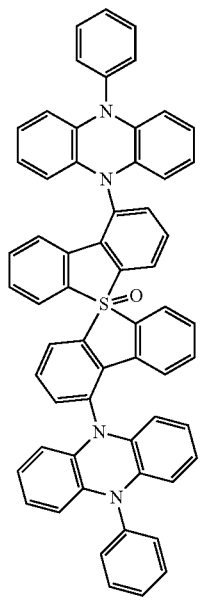
P167
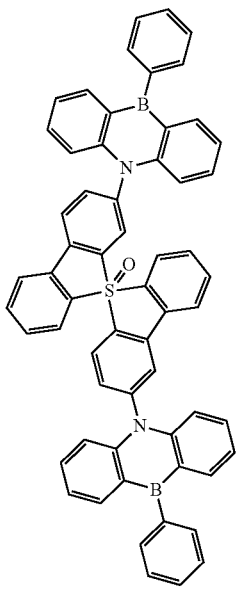
P168
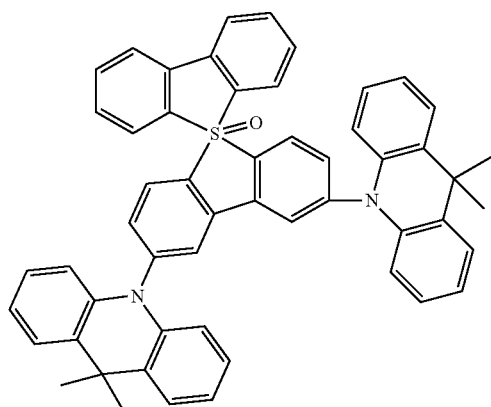
P169
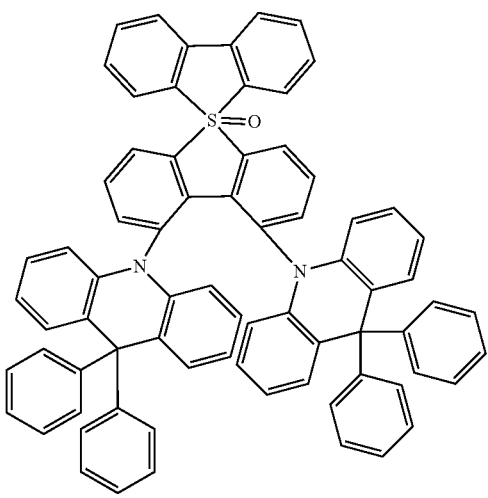

-continued
P170
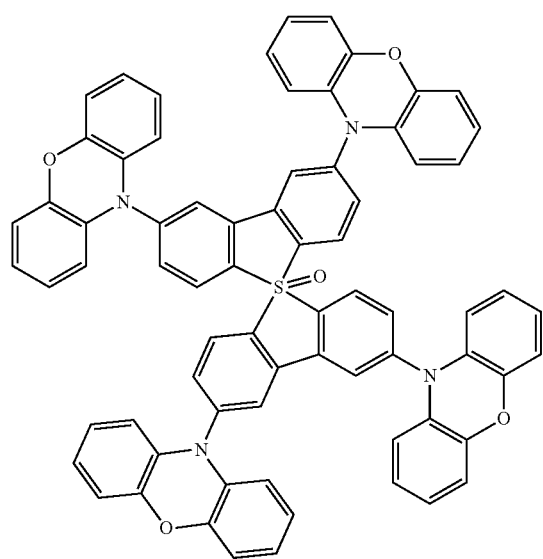
P171
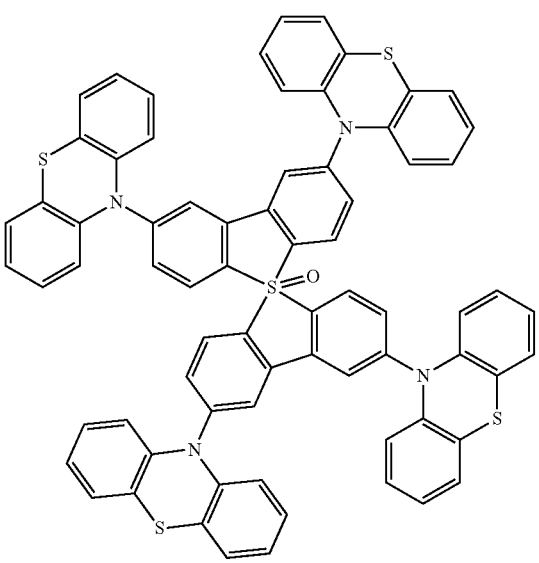
P172
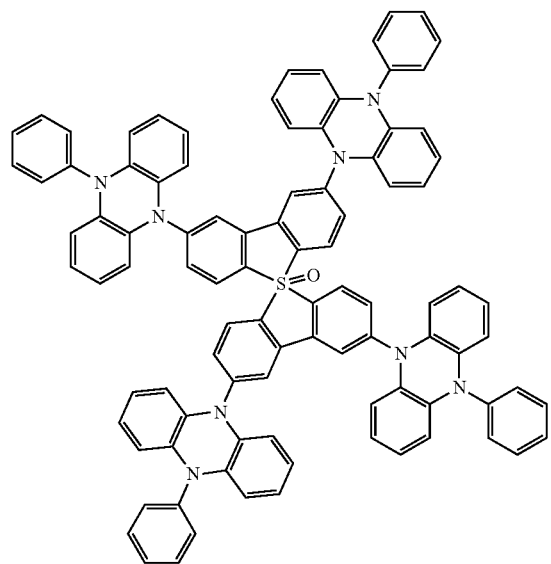
P173
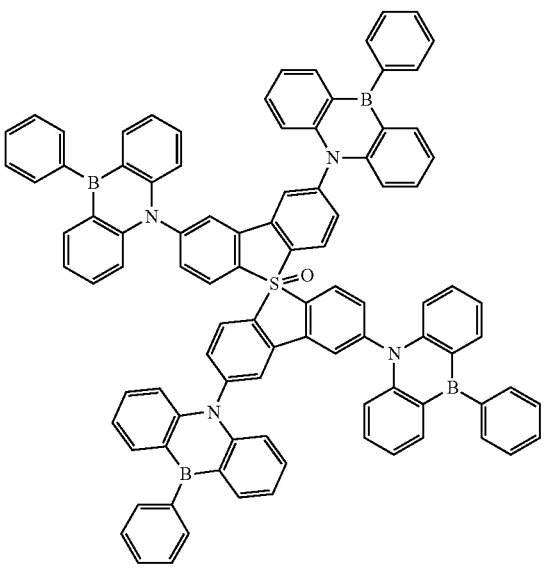

-continued
P174
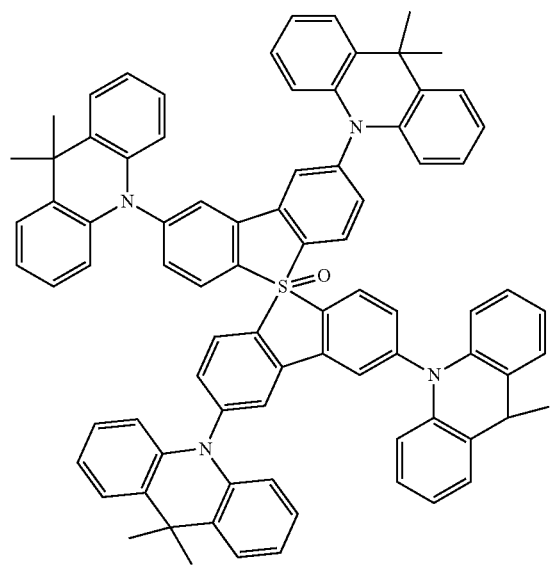
P175
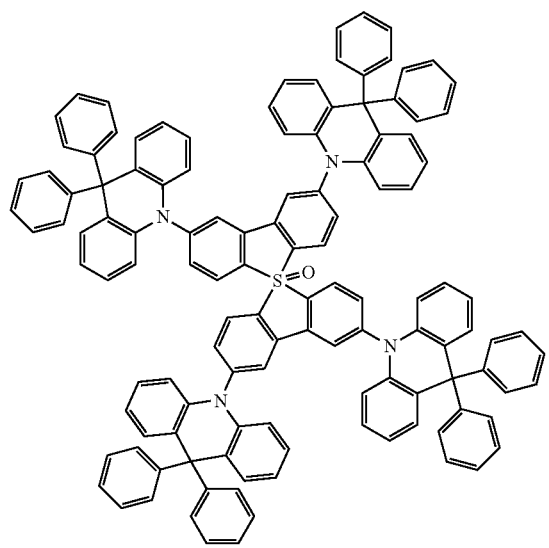
P176
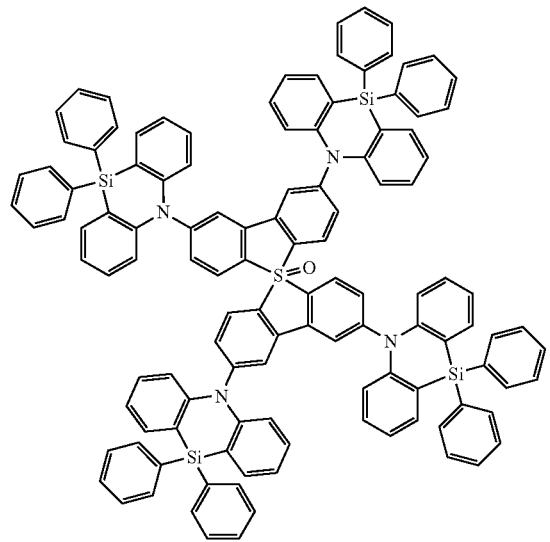
P177
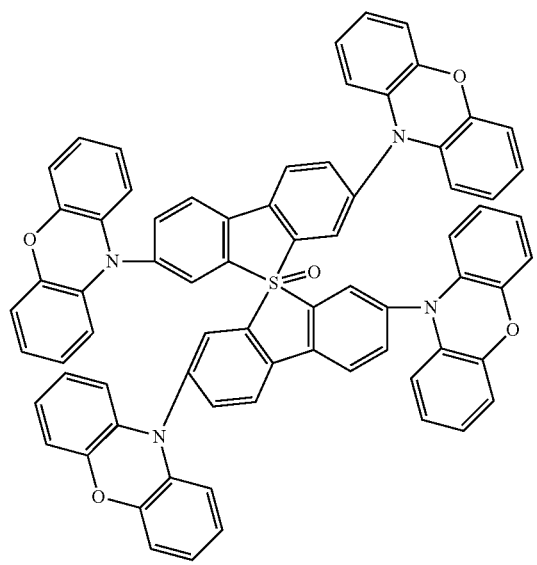

-continued
P178
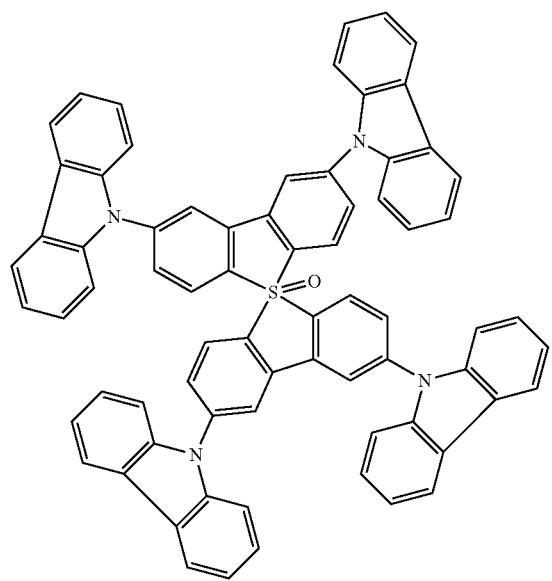
P179
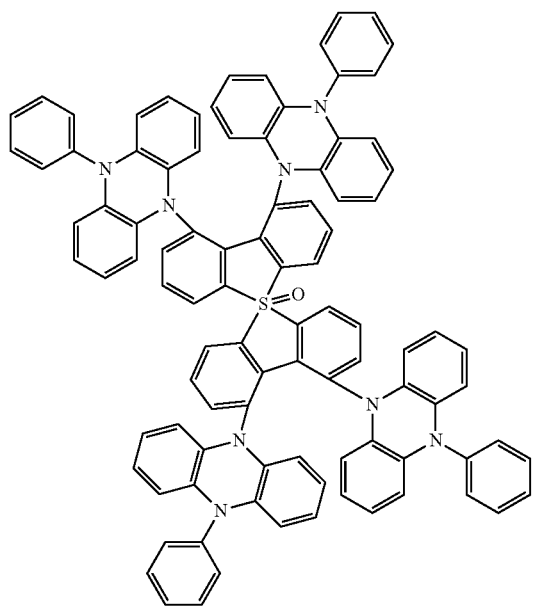
P180
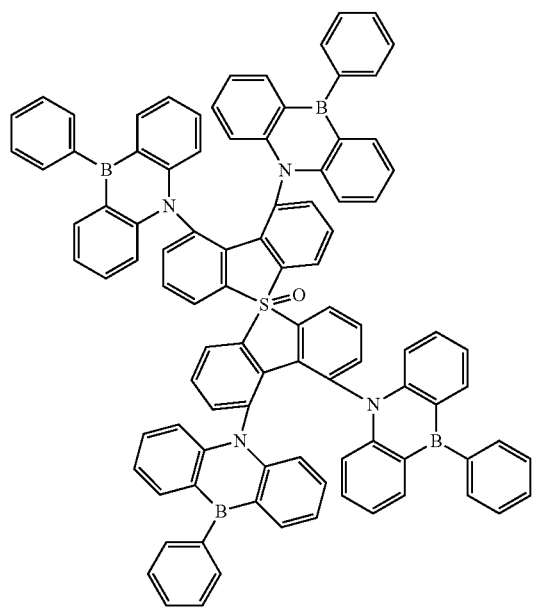
P181
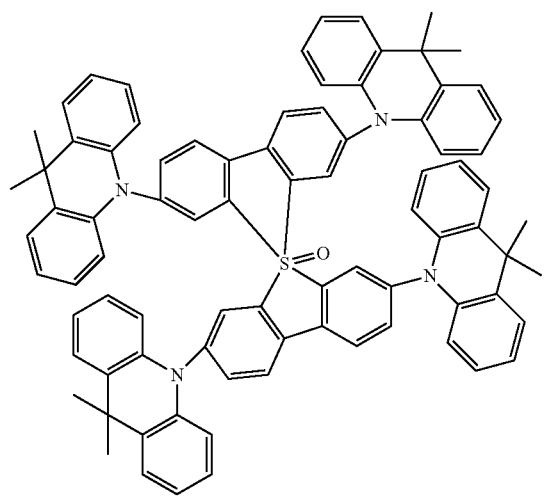

-continued
P182
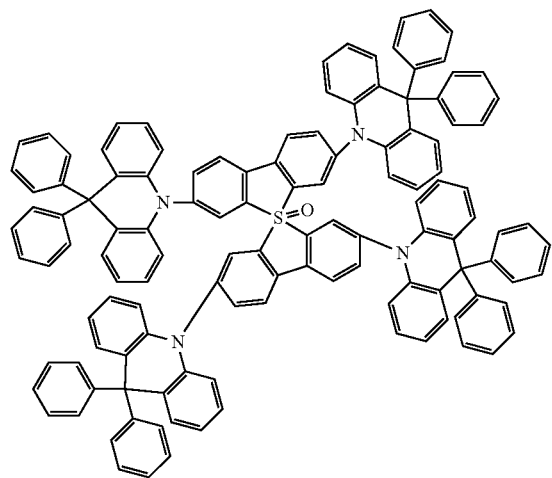
P183
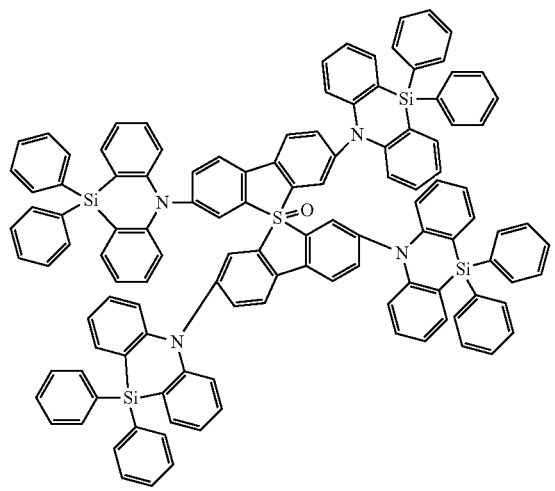
P184
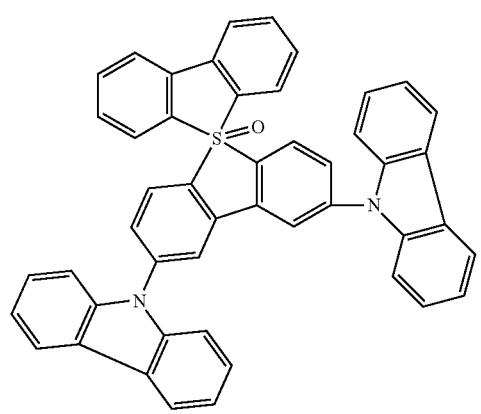
P185
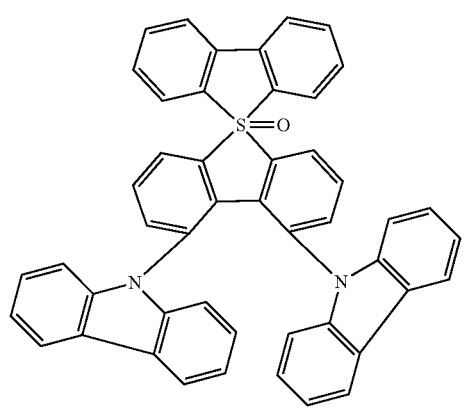
P186
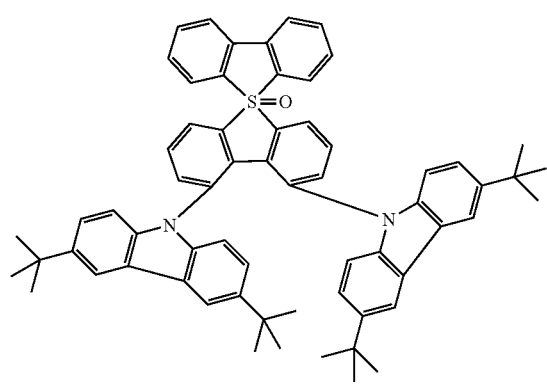
P187
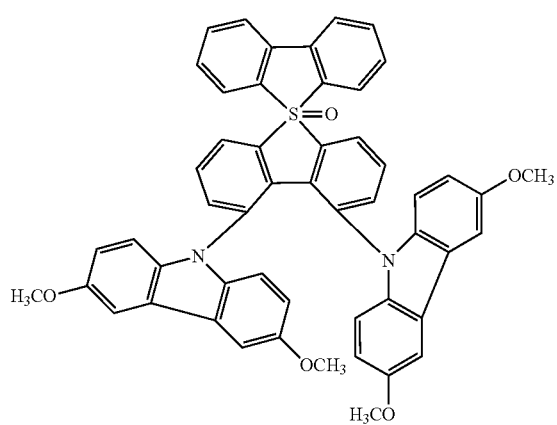

-continued
P188
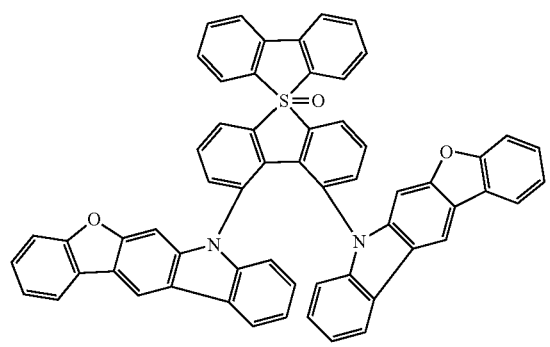
P189
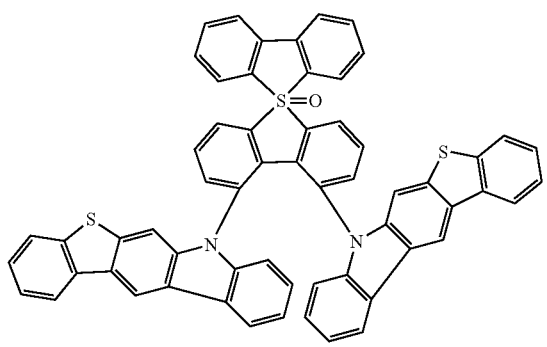
P190
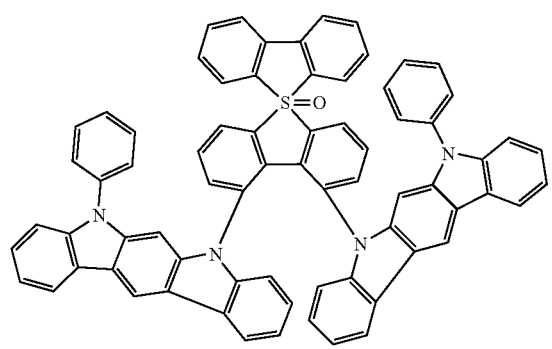
P191
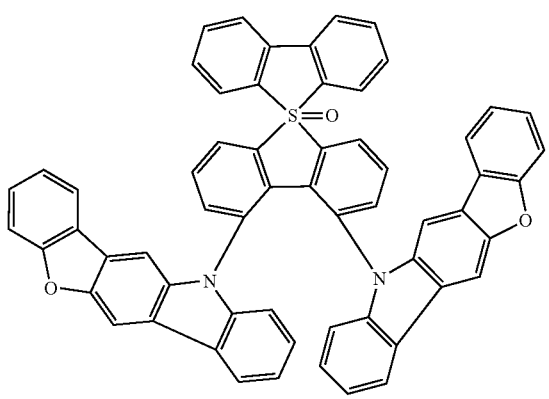
P192
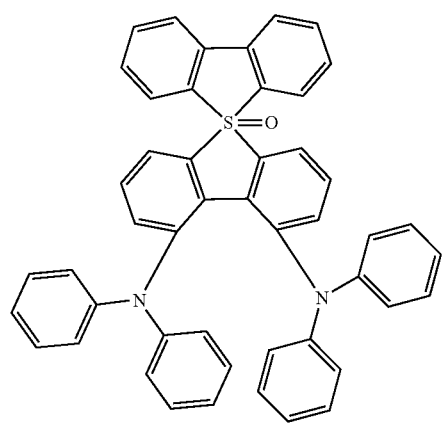
P193
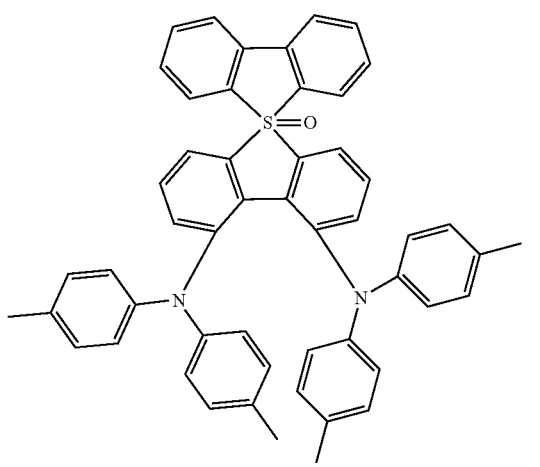

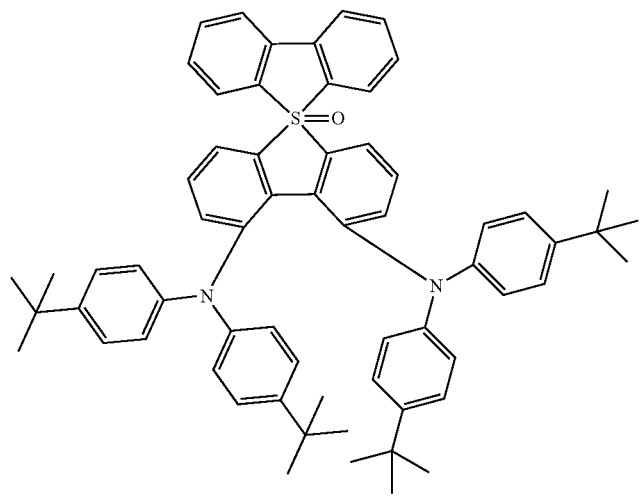

P194

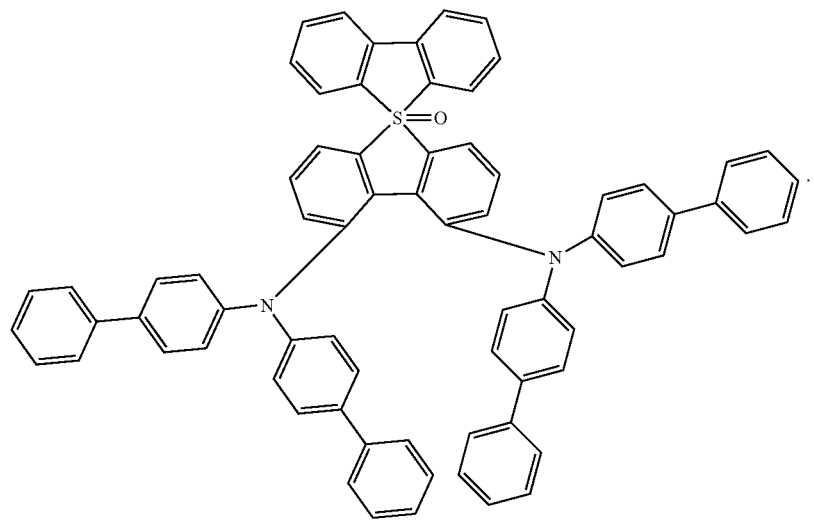

P195

Some of the compounds provided by the present disclosure have an energy level difference smaller than 0.3 eV between singlet and triplet states, which effectively achieves conversion from triplet excitons to singlet excitons through reverse intersystem crossing, improving the utilization efficiency of excitons. Therefore, some of the compounds provided by the present disclosure can also be used as a thermally activated delayed fluorescence (TADF) material to achieve high the light-emitting efficiency.

In another aspect, the present disclosure provides methods for preparing the exemplary compounds P041, P074, P165, P185, and P130, as described in the Examples 1-5 below.

Example 1

Synthesis of Compound P041

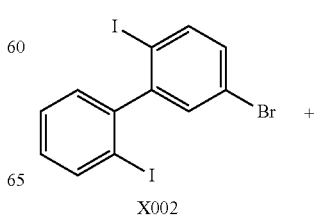

X002

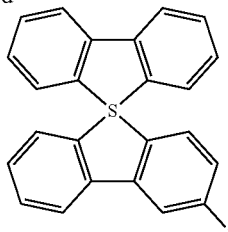

X001

X003

Under nitrogen atmosphere, compound X002 (10.0 mmol) was weighed and placed in a 50 mL flask, and dissolved with diethyl ether (10 mL). The solution was cooled to −78° C., added with n-BuLi (20 mmol), and stirred evenly.

Under the protection of nitrogen atmosphere, compound X001 (10.0 mmol) was dissolved in anhydrous tetrahydrofuran (THF, 150 mL), the temperature of the reaction system was lowered to −78° C., trimethylsilyl trifluoromethanesulfonate (13.0 mmol) was added, followed by stirring for 1 h. The reaction system was slowly warmed to room temperature, and then further stirred for 1 h, and the temperature was lowered to −78° C. again. The diethyl ether solution of X002 (10 ml, 10 mmol) prepared in the previous step was added, and stirred for 1 h. The reaction system was slowly warmed to room temperature, and then further stirred for 2 h. The reaction system was poured into water to quench the reaction, the volatile solvent was removed by distillation under reduced pressure, and the crude product was washed with anhydrous diethyl ether and extracted with dichloromethane. The organic phase was collected, dried over anhydrous Na$_2$SO$_4$ and then filtered to obtain an organic phase, and the solvent is removed by distillation under reduced pressure to obtain a crude product. The crude product was recrystallized using THF at −20° C. to obtain intermediate X003 (8.8 mmol, 88%).

MALDI-TOF MS: C$_{24}$H$_{15}$BrS, m/z calculated: 414.0; measured: 414.2.

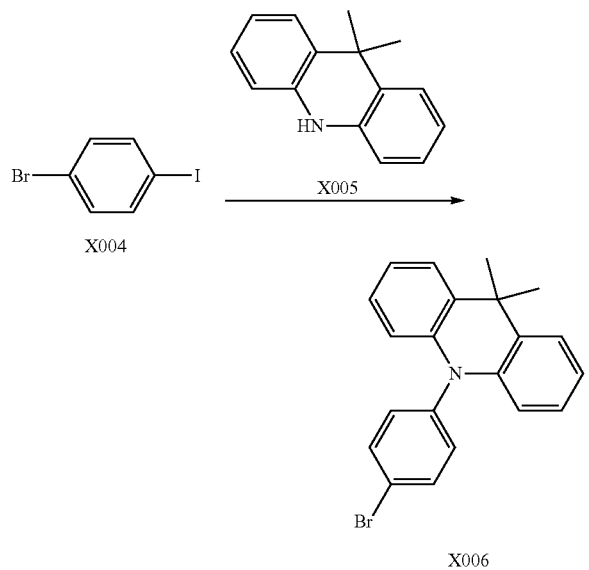

X004

X005

X006

Compound X004 (2.5 mmol), compound X005 (2.6 mmol), (dibenzylideneacetone)dipalladium (0) (0.25 mmol), sodium tert-butoxide (4 mmol), and tri-tert-butylphosphine tetrafluoroborate (0.5 mmol) were first added into a 100 mL three-necked flask, degassing and nitrogen replacement were repeated 3 times quickly under stirring, and 60 mL of toluene was added through a syringe. Under nitrogen flow, the mixture was heated and refluxed for 3 h. After the reaction was finished, the reaction solution was left to cool to room temperature, added with water, extracted with dichloromethane, and washed with saturated brine. The organic phase was dried over anhydrous sodium sulfate, and after distilling the solvent, it was purified with the column chromatography to obtain intermediate X006 (2.0 mmol, 80%).

MALDI-TOF MS: C$_{21}$H$_{18}$BrN, m/z calculated: 363.1; measured: 363.2.

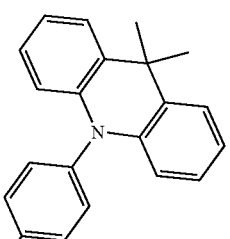

X006

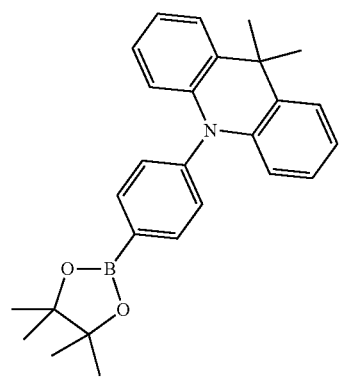

X007

In a 100 mL three-necked flask, the intermediate X006 (2 mmol), bis(pinacolato)diboron (2.2 mmol), [1,1'-bis(diphenylphosphino)ferrocene]dichloropalladium(II) (0.1 mmol) and potassium acetate (12 mmol) were first added individually, degassing and nitrogen replacement were repeated 3 times quickly under stirring, and 10 mL of tetrahydrofuran was added through a syringe. Under stirring at a constant speed, the obtained mixed solution reacted at a reaction temperature of 80° C. and refluxed under heating for 5 h. After the reaction was finished, the mixed solution was cooled to room temperature, added with 10 mL of water, and extracted with diethyl ether. The obtained organic phase was dried over anhydrous sodium sulfate, and after distilling the solvent, it was purified with the column chromatography to obtain intermediate X007 (1.7 mmol, 85%).

MALDI-TOF MS: C$_{27}$H$_{30}$BNO$_2$, m/z calculated: 411.2; measured: 411.3.

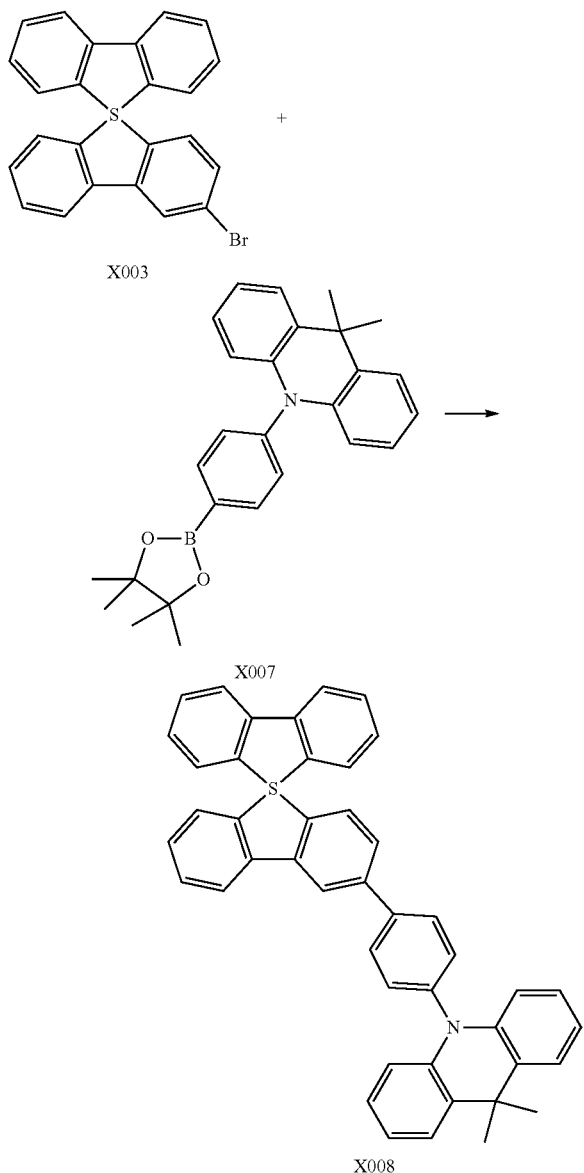

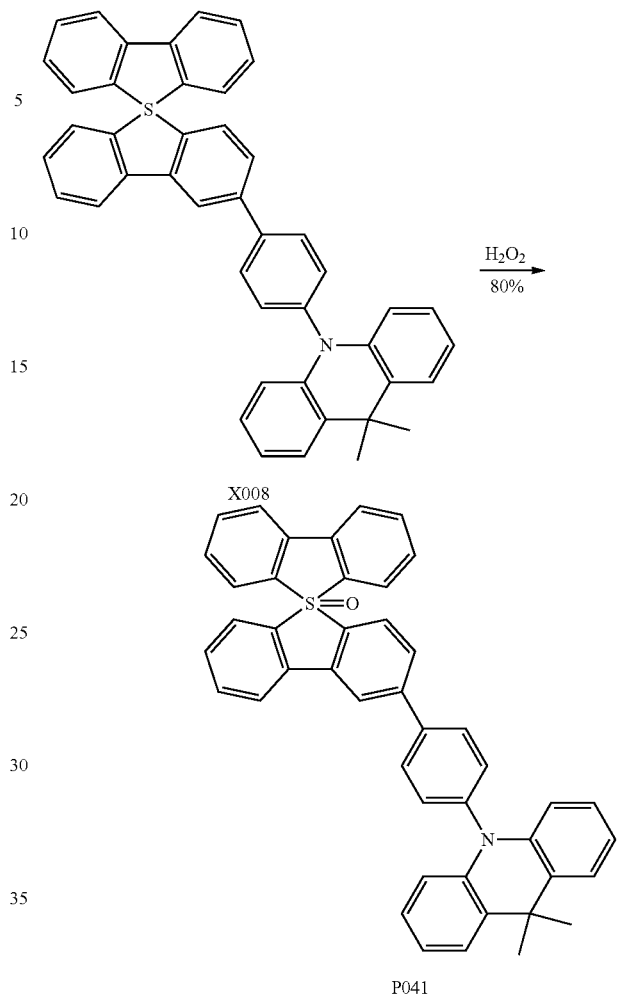

Under the protection of nitrogen, compound X003 (4.5 mmol), compound X007 (4.6 mmol), [Pd$_2$(dba)$_3$]·CHCl$_3$ (0.18 mmol) and HP(t-Bu)$_3$·BF$_4$ (0.36 mmol) were weighed and added into a 500 mL two-necked flask. 100 mL of toluene was poured into the two-necked flask, in which gaseous N$_2$ was introduced for 15 min in advance to remove oxygen, then 10 mL of an aqueous solution of 1M K$_2$CO$_3$ (in which gaseous N$_2$ was introduced for 15 min in advance to remove oxygen) was added dropwise, and the mixture was stirred overnight at room temperature. After the reaction was finished, 30 mL of deionized water was added, and then a few drops of 2M HCl was added. The mixture was extracted with dichloromethane, and the organic phase was collected and dried over anhydrous Na$_2$SO$_4$. The dried solution was filtered, and the solvent was removed with a rotary evaporator to obtain a crude product. The crude product was purified by silica gel column chromatography to obtain solid X008 (3.7 mmol, 82%).

MALDI-TOF MS: C$_{45}$H$_{33}$NS, m/z calculated: 619.2; measured: 619.3.

At room temperature, 40 mL of glacial acetic acid and 20 mL of dichloromethane were added into a 250 mL single-necked flask, then the raw material intermediate X008 (3.0 mmol) and 5 times the equivalent amount of 30% hydrogen peroxide were added, and the mixture were stirred at 55-60° C. for 24 h. Then, the mixture was cooled to room temperature, extracted with dichloromethane, and purified with column chromatography to obtain compound P041 (2.3 mmol, 77%).

MALDI-TOF MS: m/z calculated: C$_{45}$H$_{33}$NOS: 635.2; measured: 635.4.

Elemental analysis of compound P110: calculated: C, 85.01; H, 5.23; N, 2.20; measured: C, 85.06; H, 5.20; N, 2.18.

Example 2

Synthesis of Compound P074

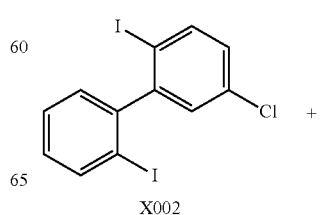

X002

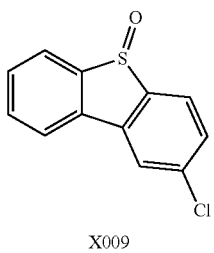

X009

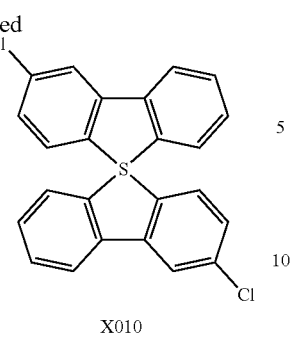

X010

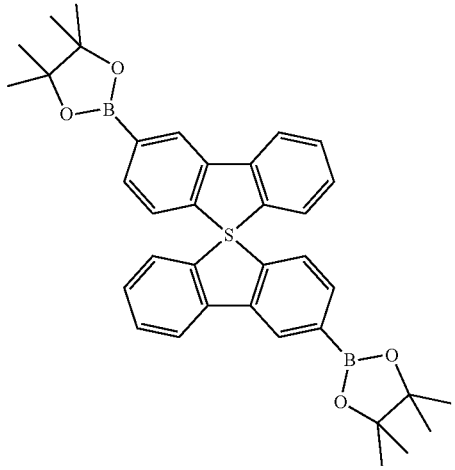

X011

Under nitrogen atmosphere, compound X002 (5.0 mmol) was weighed and placed in a 50 mL flask, and dissolved with diethyl ether (5 mL). The solution was cooled to −78° C., added with n-BuLi (10 mmol), and stirred evenly.

Under the protection of nitrogen atmosphere, compound X009 (5.0 mmol) was dissolved in anhydrous tetrahydrofuran (THF, 80 mL), the temperature of the reaction system was lowered to −78° C., trimethylsilyl trifluoromethanesulfonate (7.0 mmol) was added, followed by stirring for 1 h. The reaction system was slowly warmed to room temperature, and then further stirred for 1 h, and the temperature was lowered to −78° C. again. The diethyl ether solution of X002 (5 ml, 5 mmol) prepared in the previous step was added, and stirred for 1 h. The reaction system was slowly warmed to room temperature, and then further stirred for 2 h. The reaction system was poured into water to quench the reaction, the volatile solvent was removed by distillation under reduced pressure, the crude product was washed with anhydrous diethyl ether and extracted with dichloromethane. The organic phase was collected, dried over anhydrous $Na_2SO_4$ and then filtered to obtain an organic phase, and the solvent is removed by distillation under reduced pressure to obtain a crude product. The crude product was recrystallized using THF at −20° C. to obtain intermediate X010 (4.1 mmol, 82%).

MALDI-TOF MS: $C_{24}H_{14}Cl_2S$, m/z calculated: 404.0; measured: 404.3.

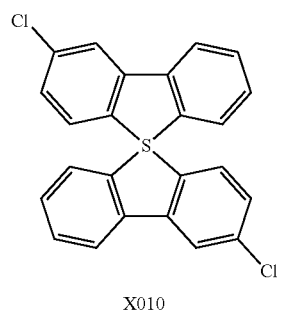

X010

In a 250 mL three-necked flask, the intermediate X010 (2 mmol), bis(pinacolato)diboron (4.4 mmol), [1,1'-bis(diphenylphosphino)ferrocene]dichloropalladium(II) (0.2 mmol) and potassium acetate (24 mmol) were first added individually, the degassing and nitrogen replacement were repeated 3 times quickly under stirring, and 50 mL of tetrahydrofuran was added through a syringe. Under stirring at a constant speed, the obtained mixed solution reacted at a reaction temperature of 80° C. and refluxed under heating for 12 h. After the reaction was finished, the mixed solution was cooled to room temperature, added with 20 mL of water, and extracted with diethyl ether. The obtained organic phase was dried over anhydrous sodium sulfate, and after distilling the solvent, it was purified with the column chromatography to obtain intermediate X011 (1.6 mmol, 80%).

MALDI-TOF MS: $C_{36}H_{38}B_2O_4S$, m/z calculated: 588.3; measured: 588.5.

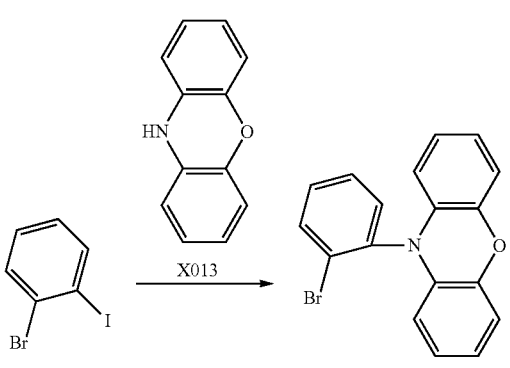

X012    X013    X014

Compound X012 (3.2 mmol), compound X013 (3.4 mmol), (dibenzylideneacetone)dipalladium (0) (0.30 mmol), sodium tert-butoxide (4.5 mmol), and tri-tert-butylphosphine tetrafluoroborate (0.6 mmol) were first added into a 250 mL three-necked flask, the degassing and nitrogen replacement were repeated 3 times quickly under stirring, and 80 mL of toluene was added through a syringe. Under nitrogen flow, the mixture was heated and refluxed for 3 h. After the reaction was finished, the reaction solution was left to cool to room temperature, added with water, extracted with dichloromethane, and washed with saturated brine. The organic phase was dried over anhydrous sodium sulfate, and after distilling the solvent, it was purified with the column chromatography to obtain intermediate X014 (2.5 mmol, 78%).

MALDI-TOF MS: $C_{18}H_{12}BrNO$, m/z calculated: 337.0; measured: 337.2.

was extracted with dichloromethane, and the organic phase was collected and dried over anhydrous $Na_2SO_4$. The dried solution was filtered, and the solvent was removed with a rotary evaporator to obtain a crude product. The crude product was purified by silica gel column chromatography to obtain solid X015 (3.8 mmol, 84%).

MALDI-TOF MS: $C_{60}H_{38}N_2O_2S$, m/z calculated: 850.3; measured: 850.5.

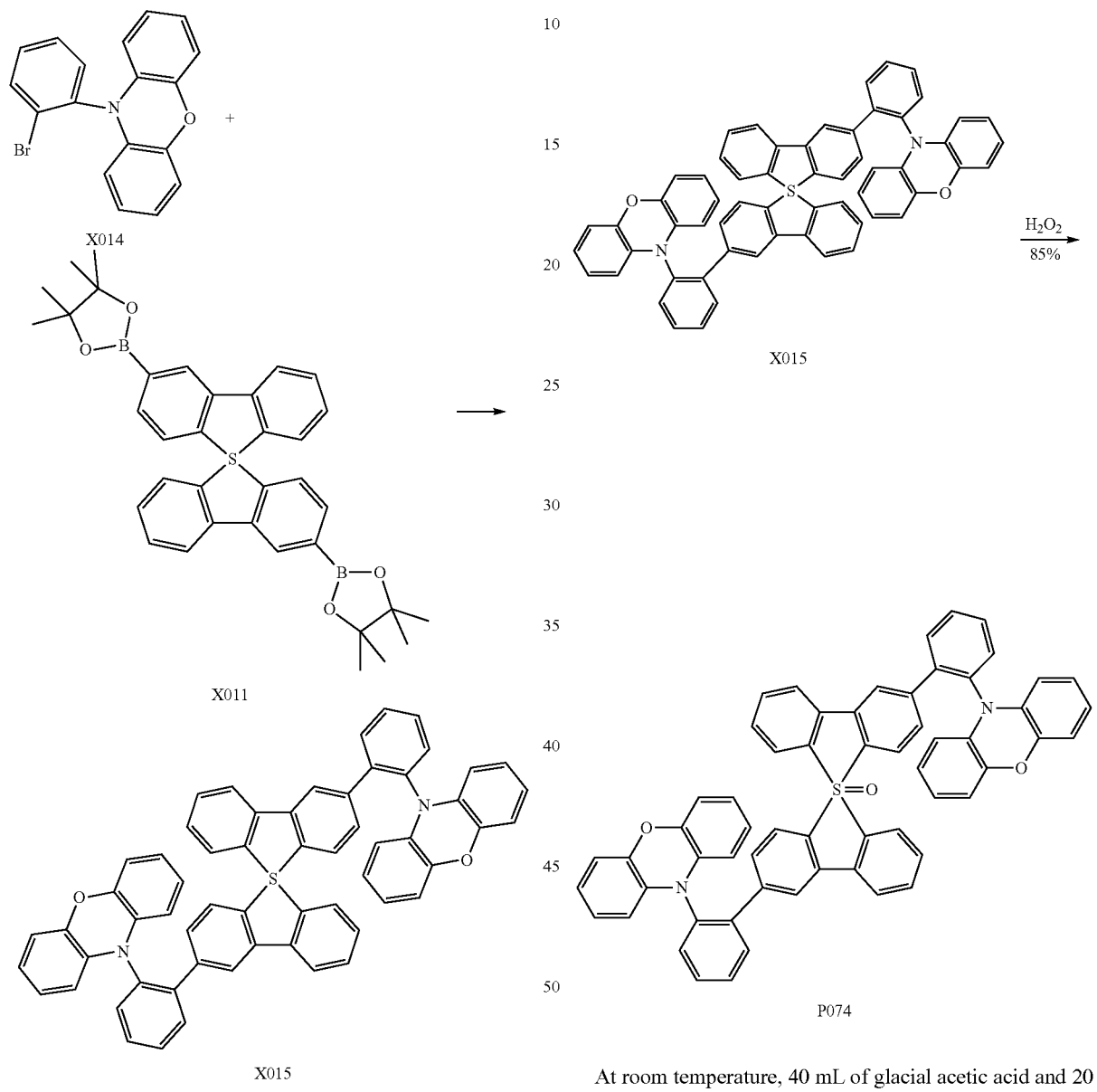

Under the protection of nitrogen, compound X011 (4.5 mmol), compound X014 (9.6 mmol), $[Pd_2(dba)_3]\cdot CHCl_3$ (0.36 mmol) and $HP(t-Bu)_3\cdot BF_4$ (0.72 mmol) were weighed and added into a 500 mL two-necked flask. 100 mL of toluene was poured into the two-necked flask, in which gaseous $N_2$ was introduced for 15 min in advance to remove oxygen, and then 10 mL of an aqueous solution of 1M $K_2CO_3$ (in which gaseous $N_2$ was introduced for 15 min in advance to remove oxygen) was added dropwise, and the mixture was stirred overnight at room temperature. After the reaction was finished, 25 mL of deionized water was added, and then a few drops of 2M HCl was added. The mixture At room temperature, 40 mL of glacial acetic acid and 20 mL of dichloromethane were added into a 250 mL single-necked flask, then the raw material intermediate X015 (2.0 mmol) and 5 times the equivalent amount of 30% hydrogen peroxide were added, and stirred at 60° C. for 24 h. Then, the mixture was cooled to room temperature, extracted with dichloromethane, and purified with column chromatography to obtain compound P074 (1.7 mmol, 85%).

MALDI-TOF MS: m/z calculated: $C_{60}H_{38}N_2O_3S$: 866.3; measured: 866.4.

Elemental analysis of compound P074: calculated: C, 83.12; H, 4.42; N, 3.23; measured: C, 83.18; H, 4.40; N, 3.20.

Example 3

Synthesis of Compound P165

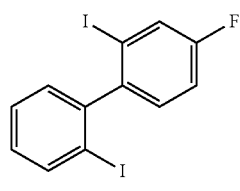

X016

+

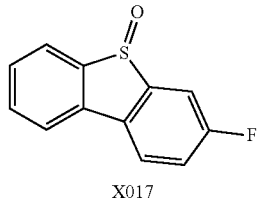

X017

→

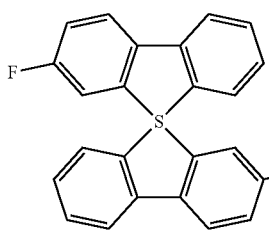

X018

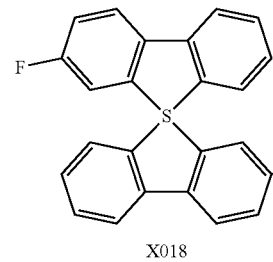

X018

+

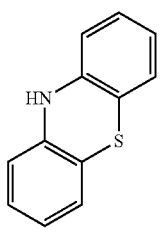

X019

→

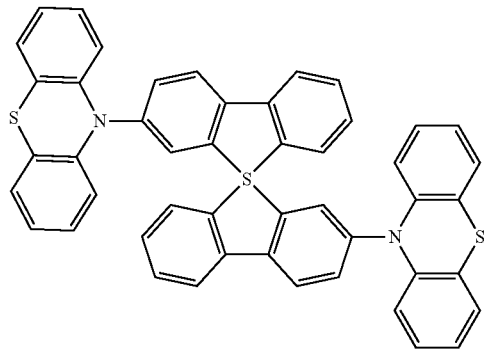

X020

Under nitrogen atmosphere, compound X016 (10.0 mmol) was weighed and placed in a 50 mL flask, and dissolved with diethyl ether (10 mL). The solution was cooled to −78° C., added with n-BuLi (20 mmol), and stirred evenly.

Under the protection of nitrogen atmosphere, compound X017 (10.0 mmol) was dissolved in anhydrous THF (80 mL), the temperature of the reaction system was lowered to −78° C., trimethylsilyl trifluoromethanesulfonate (7.0 mmol) was added, followed by stirring for 1 h. The reaction system was slowly warmed to room temperature, and then further stirred for 1 h, and the temperature was lowered to −78° C. again. The diethyl ether solution of X016 (5 ml, 5 mmol) prepared in the previous step was added, and stirred for 1 h. The reaction system was slowly warmed to room temperature, and then further stirred for 2 h. The reaction system was poured into water to quench the reaction, the volatile solvent was removed by distillation under reduced pressure, the crude product was washed with anhydrous diethyl ether and extracted with dichloromethane. The organic phase was collected, dried over anhydrous $Na_2SO_4$ and then filtered to obtain an organic phase, and the solvent is removed by distillation under reduced pressure to obtain a crude product. The crude product was recrystallized using THF at −20° C. to obtain intermediate X018 (3.8 mmol, 76%).

MALDI-TOF MS: $C_{24}H_{14}F_2S$, m/z calculated: 372.1; measured: 372.3.

In a 250 ml round bottom flask, compound X019 (8.6 mmol), NaH (9.8 mmol) and tetrahydrofuran (60 mL) were mixed and then stirred at 0° C. under nitrogen flow for 2 h. the intermediate X018 (3.5 mmol) dissolved in tetrahydrofuran (60 mL) was added to the above round bottom flask, and then stirred at 0° C. for 2 hours. The mixture was slowly warmed to room temperature and then stirred for 12 h. The reaction was quenched with ice water, and extracted with dichloromethane/water, and the organic phase was collected. After the organic layer was dried over anhydrous sodium sulfate, and then after removing the organic solvent by distillation under reduced pressure, purified with the column chromatography to obtain a solid X020 (2.3 mmol, yield 66%).

MALDI-TOF MS: $C_{48}H_{30}N_2S_3$, m/z calculated: 730.2: measured: 730.3.

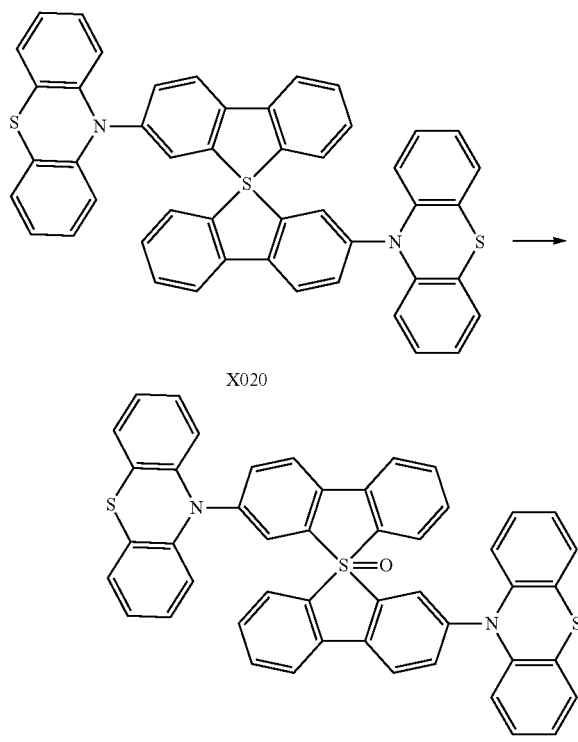

X020

P165

At room temperature, 30 mL of glacial acetic acid and 20 mL of dichloromethane were added into a 250 mL single-necked flask, then the raw material intermediate X020 (2.0 mmol) and 5 times the equivalent amount of 30% hydrogen peroxide were added, and stirred at 60° C. for 24 h. Then, the mixture was cooled to room temperature, extracted with dichloromethane, and purified with column chromatography to obtain compound P165 (1.55 mmol, 78%).

MALDI-TOF MS: $C_{48}H_{30}N_2OS_3$, m/z calculated: 746.2; measured: 746.5.

Elemental analysis of compound P165: calculated: C, 77.18; H, 4.05; N, 3.75; measured: C, 77.25; H, 4.02; N, 3.71.

Example 4

Synthesis of Compound P185

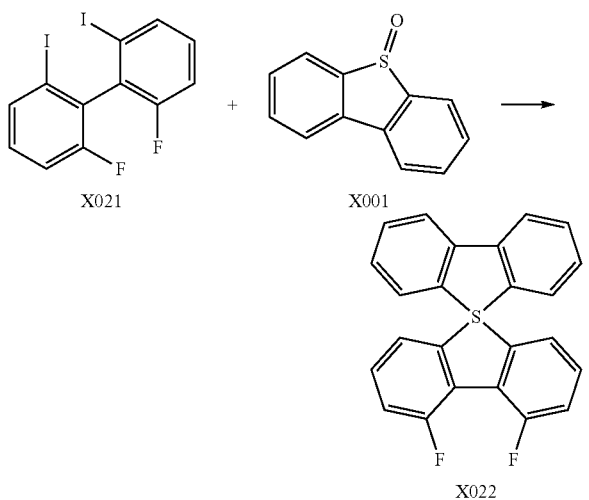

X021

X001

X022

Under nitrogen atmosphere, compound X021 (10.0 mmol) was weighed and placed in a 50 mL flask, and dissolved with diethyl ether (10 mL). The solution was cooled to −78° C., added with n-BuLi (20 mmol), and stirred evenly.

Under the protection of nitrogen atmosphere, compound X001 (5.0 mmol) was dissolved in anhydrous THF (80 mL), the temperature of the reaction system was lowered to −78° C., trimethylsilyl trifluoromethanesulfonate (7.0 mmol) was added, followed by stirring for 1 h. The reaction system was slowly warmed to room temperature, and then further stirred for 1 h, and the temperature was lowered to −78° C. again. The diethyl ether solution of X021 (5 mL, 5 mmol) prepared in the previous step was added, and stirred for 1 h. The reaction system was slowly warmed to room temperature, and then further stirred for 2 h. The reaction system was poured into water to quench the reaction, the volatile solvent was removed by distillation under reduced pressure, and the crude product was washed with anhydrous diethyl ether and extracted with dichloromethane. The organic phase was collected, dried over anhydrous $Na_2SO_4$ and then filtered to obtain an organic phase, and the solvent is distilled under reduced pressure to obtain a crude product. The crude product was recrystallized using THF at −20° C. to obtain intermediate X022 (3.25 mmol, 65%).

MALDI-TOF MS: $C_{24}H_{14}F_2S$, m/z calculated: 372.1; measured: 372.2.

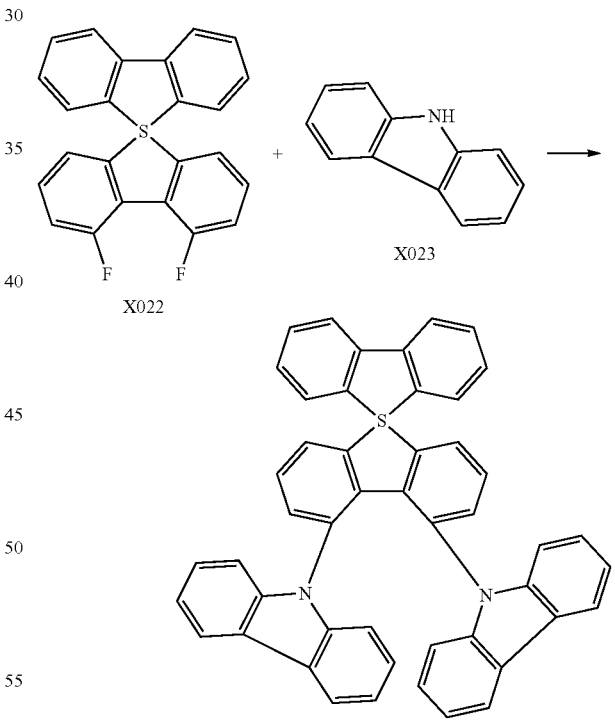

X022

X023

X024

In a 250 ml round bottom flask, compound X023 (4.0 mmol), NaH (4.6 mmol) and tetrahydrofuran (40 mL) were mixed and then stirred at 0° C. under nitrogen flow for 2 h. The intermediate X022 (1.6 mmol) dissolved in tetrahydrofuran (40 mL) was added to the above round bottom flask, and then stirred at 0° C. for 2 hours. The mixture was slowly warmed to room temperature and then stirred for 12 h. The reaction was quenched with ice water, and extracted with dichloromethane/water, and the organic phase was collected. After the organic layer was dried over anhydrous sodium sulfate, then distillated under reduced pressure, and then purified with the column chromatography to obtain a solid X024 (0.88 mmol, yield 55%).

MALDI-TOF MS: $C_{48}H_{30}N_2S$, m/z calculated: 666.2; measured: 666.4.

Example 5

Synthesis of Compound P130

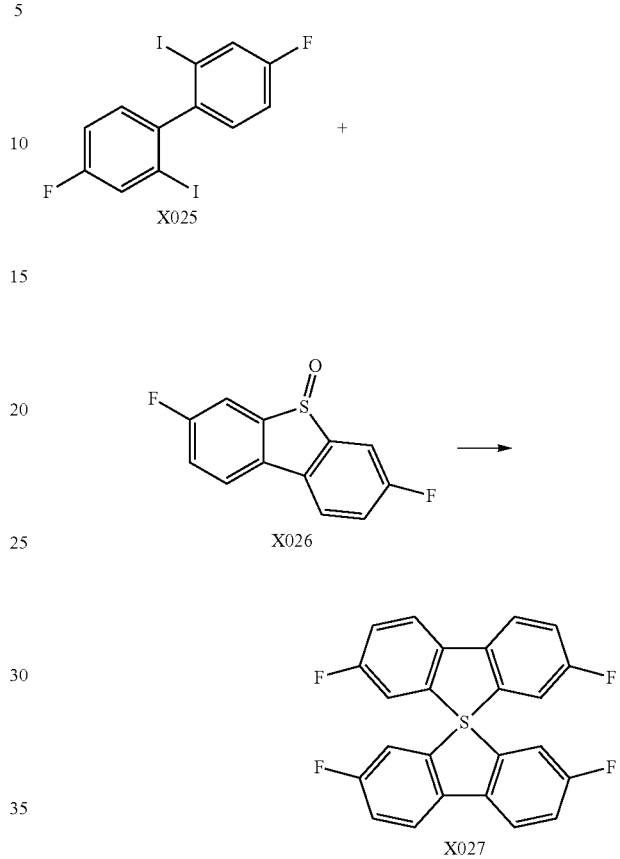

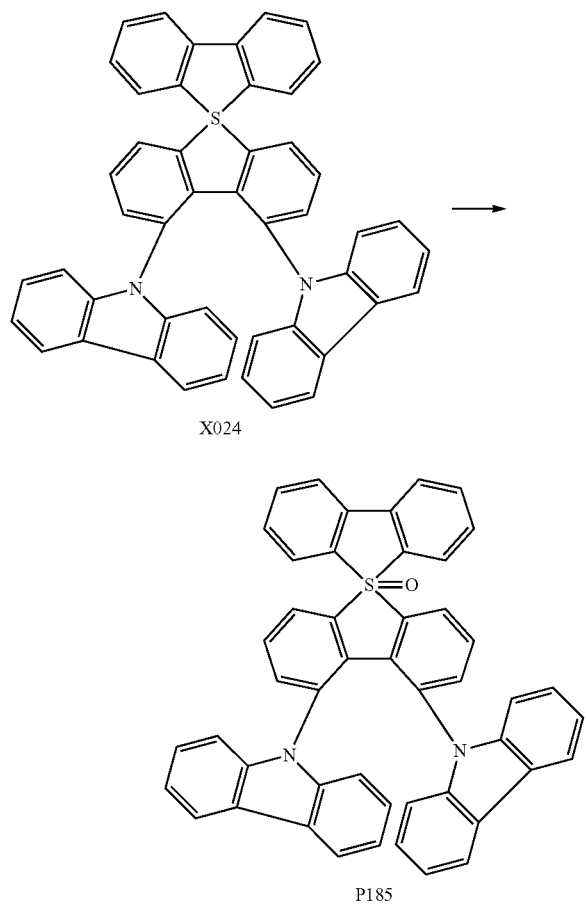

At room temperature, 30 mL of glacial acetic acid and 15 mL of dichloromethane were added into a 100 mL single-necked flask, and then the raw material intermediate X024 (1.0 mmol) and 5 times the equivalent amount of 30% hydrogen peroxide were added, and stirred at 60° C. for 24 h. Then, the mixture was cooled to room temperature, extracted with dichloromethane, and purified with column chromatography to obtain compound P185 (0.8 mmol, 80%).

MALDI-TOF MS: $C_{48}H_{30}N_2OS$, m/z calculated: 682.2; measured: 682.5.

Elemental analysis of compound P185: calculated: C, 84.43; H, 4.43; N, 4.10; measured: C, 84.48; H, 4.40; N, 4.07.

Under nitrogen atmosphere, compound X025 (10.0 mmol) was weighed and placed in a 50 mL flask, and dissolved with diethyl ether (10 mL). The solution was cooled to −78° C., added with n-BuLi (20 mmol), and stirred evenly.

Under the protection of nitrogen atmosphere, compound X026 (5.0 mmol) was dissolved in anhydrous THF (80 mL), the temperature of the reaction system was lowered to −78° C., trimethylsilyl trifluoromethanesulfonate (7.0 mmol) was added, followed by stirring for 1 h. The reaction system was slowly warmed to room temperature, and then further stirred for 1 h, and the temperature was lowered to −78° C. again. The diethyl ether solution of X025 (5 mL, 5 mmol) prepared in the previous step was added, and stirred for 1 h. The reaction system was slowly warmed to room temperature, and then further stirred for 2 h. The reaction system was poured into water to quench the reaction, the volatile solvent was removed by distillation under reduced pressure, and the crude product was washed with anhydrous diethyl ether and extracted with dichloromethane. The organic phase was collected, dried over anhydrous $Na_2SO_4$ and then filtered to obtain an organic phase, and the solvent is removed by distillation under reduced pressure to obtain a crude product. The crude product was recrystallized using THF at −20° C. to obtain intermediate X027 (3.4 mmol, 68%).

MALDI-TOF MS: $C_{24}H_{12}F_4S$, m/z calculated: 408.1; measured: 408.2.

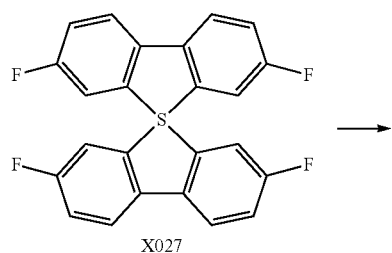

X027

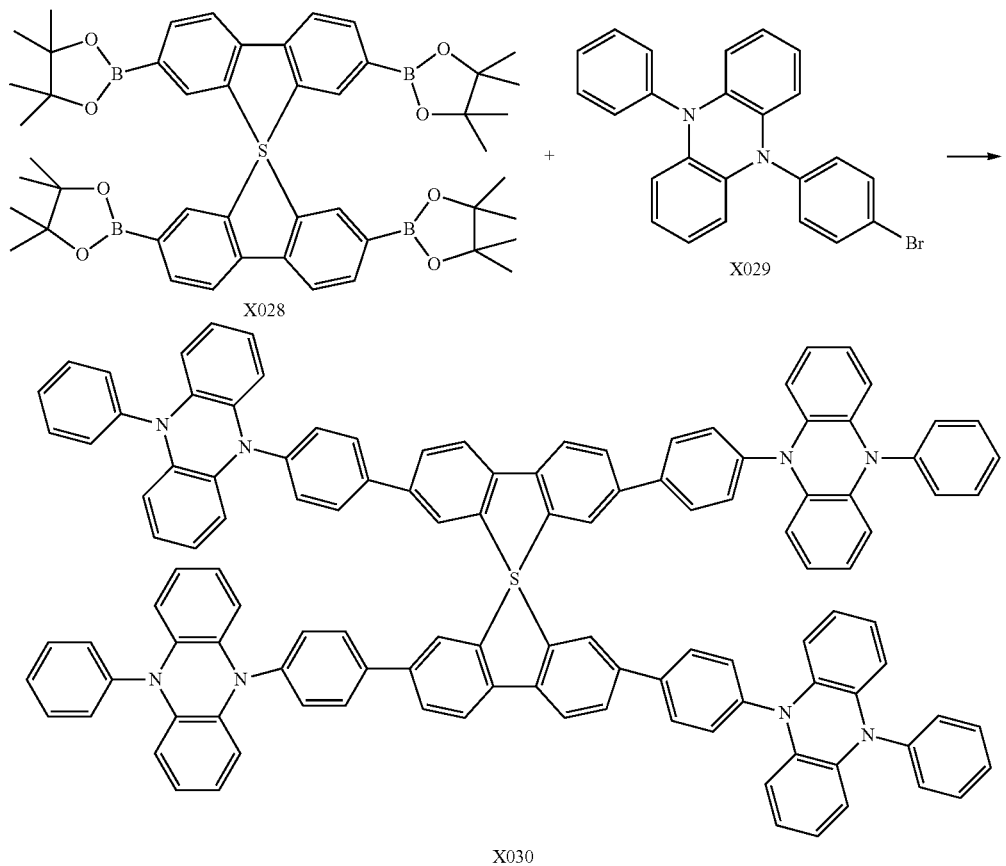

ally, degassing and nitrogen replacement were repeated 3 times quickly under stirring, and 100 mL of tetrahydrofuran was added through a syringe. Under stirring at a constant speed, the obtained mixed solution reacted at a reaction temperature of 80° C. and refluxed under heating for 12 h. After the reaction was finished, the mixed solution was cooled to room temperature, added with 30 mL of water, and extracted with diethyl ether. The obtained organic phase was dried over anhydrous sodium sulfate, distilled to remove the solvent, and purified with the column chromatography to obtain intermediate X028 (1.52 mmol, 76%).

MALDI-TOF MS: $C_{48}H_{60}B_4O_8S$, m/z calculated: 840.4; measured: 840.5.

-continued

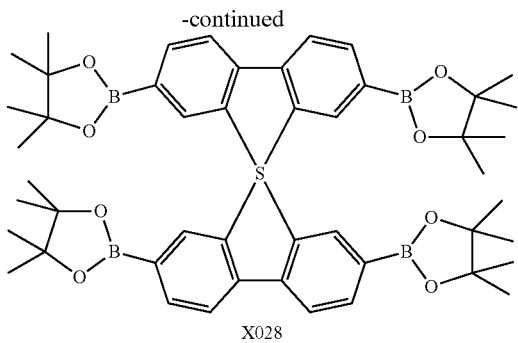

X028

In a 250 ml three-necked flask, the intermediate X027 (2 mmol), bis(pinacolato)diboron (9.6 mmol), [1,1'-bis(diphenylphosphino)ferrocene]dichloropalladium(II) (0.4 mmol) and potassium acetate (48 mmol) were first added individu- Under the protection of nitrogen, compound X011 (2 mmol), compound X014 (9.6 mmol), $[Pd_2(dba)_3]\cdot CHCl_3$ (0.64 mmol) and $HP(t-Bu)_3\cdot BF_4$ (1.28 mmol) were weighed and added into a 500 mL two-necked flask. 150 mL of toluene was poured into the two-necked flask, in which gaseous $N_2$ was introduced for 15 min in advance to remove oxygen, and then 15 mL of an aqueous solution of 1M $K_2CO_3$ (in which gaseous $N_2$ was introduced for 15 min in advance to remove oxygen) was added dropwise, and the mixture was stirred overnight at room temperature. After the reaction was finished, 25 mL of deionized water was added, and then a few drops of 2M HCl was added. The mixture was extracted with dichloromethane, and the organic phase was collected and dried over anhydrous $Na_2SO_4$. The dried solution was filtered, and the solvent was removed with a rotary evaporator to obtain a crude product. The crude product was purified by silica gel chromatography to obtain solid X030 (1.44 mmol, 72%).

MALDI-TOF MS: $C_{120}H_{80}N_8S$, m/z calculated: 1664.6; measured: 1664.8.

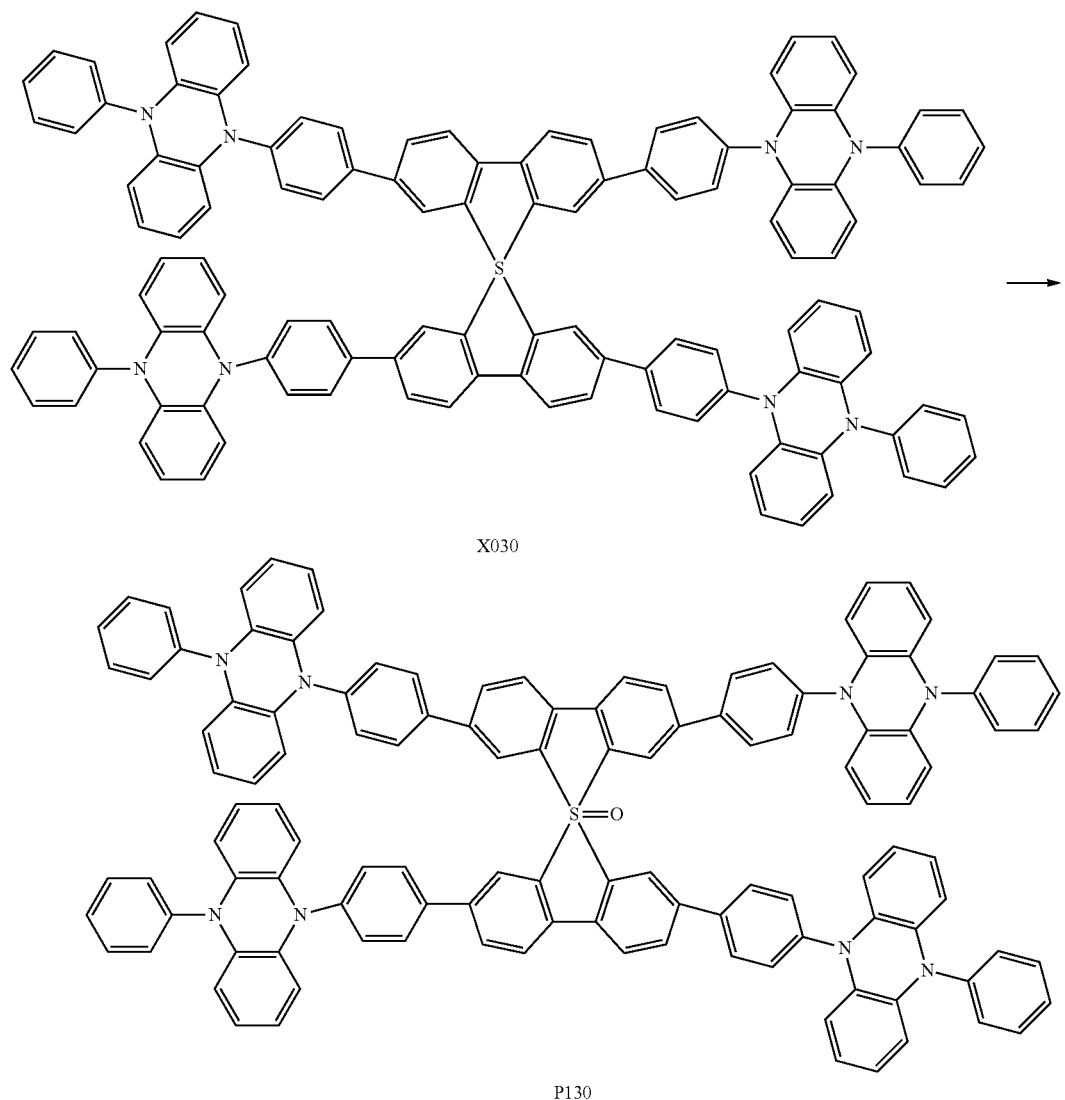

X030

P130

At room temperature, 50 mL of glacial acetic acid and 25 mL of dichloromethane were added into a 100 mL single-necked flask, then the raw material intermediate X030 (2.0 mmol) and 5 times the equivalent amount of 30% hydrogen peroxide were added, and stirred at 60° C. for 24 h. Then, the mixture was cooled to room temperature, extracted with dichloromethane, and purified with column chromatography to obtain compound P130 (1.4 mmol, 70%).

MALDI-TOF MS: $C_{120}H_{80}N_8OS$, m/z calculated: 1680.6; measured: 1680.8.

Elemental analysis of compound P165: calculated: C, 85.69; H, 4.79; N, 6.66; measured: C, 85.75; H, 4.76; N, 6.63.

Tests of Performances of Compounds (1) Simulation Calculation of Compounds:

With respect to compounds of the present disclosure, the distributions of the molecular frontier orbitals HOMO and LUMO were optimized and calculated by applying a density functional theory (DFT) and using a Gaussian 09 software pack under B3LYP/6-31G calculation level. Meanwhile, the singlet energy level $S_1$ and the triplet energy level $T_1$ were simulated and calculated based on a time-dependent density functional theory (TDDFT). The results are shown in Table 1.

TABLE 1

| | Compound | HOMO (eV) | LUMO (eV) | $S_1$ (eV) | $T_1$ (eV) | $E_g$ (eV) |
|---|---|---|---|---|---|---|
| Example 1 | P005 | −4.19 | −1.45 | 2.32 | 2.31 | 0.01 |
| Example 2 | P041 | −4.06 | −1.56 | 2.209 | 2.208 | 0.001 |
| Example 3 | P058 | −5.32 | −1.44 | 3.40 | 2.79 | 0.61 |
| Example 4 | P074 | −4.65 | −1.43 | 2.73 | 2.70 | 0.03 |
| Example 5 | P083 | −4.91 | −1.55 | 3.02 | 2.63 | 0.39 |
| Example 6 | P088 | −5.32 | −1.78 | 3.21 | 2.76 | 0.45 |
| Example 7 | P101 | −4.63 | −1.87 | 2.446 | 2.439 | 0.007 |
| Example 8 | P103 | −4.07 | −1.76 | 2.019 | 2.015 | 0.004 |
| Example 9 | P130 | −4.04 | −1.89 | 1.860 | 1.858 | 0.002 |
| Example 10 | P158 | −4.65 | −1.89 | 2.35 | 2.34 | 0.01 |
| Example 11 | P159 | −5.34 | −1.77 | 3.30 | 2.73 | 0.57 |
| Example 12 | P162 | −5.01 | −1.79 | 2.79 | 2.78 | 0.01 |
| Example 13 | P165 | −4.98 | −1.88 | 2.70 | 2.69 | 0.01 |

TABLE 1-continued

| | Compound | HOMO (eV) | LUMO (eV) | $S_1$ (eV) | $T_1$ (eV) | $E_g$ (eV) |
|---|---|---|---|---|---|---|
| Example 14 | P178 | −5.40 | −1.99 | 3.13 | 2.65 | 0.48 |
| Example 15 | P185 | −5.16 | −1.65 | 2.96 | 2.79 | 0.17 |
| Example 16 | P186 | −5.00 | −1.60 | 2.86 | 2.73 | 0.13 |

It can be seen from Table 1 that the $\Delta E_{ST}$ of each of the compounds P005, P041, P074, P101, P103, P130, P158, P162, P165, P185 and P186 is less than 0.3 ev, achieving a smaller singlet-triplet energy level difference. Thus, the conversion from triplet excitons to singlet excitons can be efficiently realized through the reverse intersystem crossing, and the utilization efficiency of excitons is improved. In view of the results of $\Delta E_{ST}$, these compound of the present disclosure can be used as the TADF materials, and can be used as a guest material of the organic light-emitting layer. In addition, the compounds P058, P083, P088, P159 and P178 all have appropriate HOMO and LUMO energy levels, bipolar molecular characteristics, good hole and electron transmission characteristics, and high triplet energy levels, and thus can be used as phosphorescent host materials.

The present disclosure also provides a display panel including an organic light-emitting device. The organic light-emitting device includes an anode, a cathode, and a light-emitting layer disposed between the anode and the cathode. A host or guest material of the light-emitting layer is one or more of the compounds provided in the present disclosure.

In an embodiment of the display panel according to the present disclosure, the light-emitting layer includes a host material and a guest material. The host material is one or more of the compounds provided in the present disclosure, the guest material is a red phosphorescent material and/or a green phosphorescent material. For example, the guest material is PtOEP and/or Ir(ppy)$_3$.

According to an embodiment of the display panel of the present disclosure, the organic light-emitting device further includes one or more of a hole injection layer (HIL), a hole transport layer (HTL), an electron blocking layer (EBL), a hole blocking layer (HBL), an electron transport layer (ETL), or an electron injection layer (EIL).

The hole injection layer, the hole transport layer, and the electron blocking layer can be made of a material selected from, but not limited to, 2,2'-dimethyl-N,N'-di-1-naphthyl-N,N'-diphenyl [1,1'-biphenyl]-4,4'-diamine (α-NPD), 4,4',4''-tris(carbazol-9-yl)triphenylamine (TCTA), 1,3-bis(N-dicarbazolyl)benzene (mCP), 4,4'-bis(N-carbazolyl)-1,1'-biphenyl (CBP), 3,3'-bis(N-carbazolyl)-1,1'-biphenyl (mCBP), 2,3,6,7,10,11-hexacyano-1,4,5,8,9,12-hexaazatriphenylene (HATCN), 4,4'-cyclohexyldi[N, N-bis(4-methylphenyl)aniline (TAPC), N,N'-bis-(1-naphthalenyl)-N,N'-bis-phenyl-(1,1'-biphenyl)-4,4'-di amine (α-NPB), N,N'-bis(naphthalene-2-yl)-N,N'-bis(phenyl)benzidine (NPB), poly(3,4-ethyl enedioxythiophene)-poly(styrenesulfonate) (PEDOT:PSS), polyvinylcarbazole (PVK), 9-phenyl-3,9-bicarbazole (CCP), molybdenum trioxide (MoO$_3$), or the like.

The hole blocking layer, the electron transport layer, and the electron injection layer can be made of a material selected from, but not limited to, 2,8-bis(diphenylphosphoryl)dib enzothiophene (PPT), TSPO1, 1,3,5-tris(1-phenyl-1H-benzimidazol-2-yl)benzene (TPBi), 2,8-bis(diphenylphosphoryl) dibenzofuran (PPF), bis[2-diphenylphosphino)phenyl]ether oxide (DPEPO), lithium fluoride (LiF), 4,6-bis(3,5-di(pyridin-3-yl)phenyl)-2-methylpyrimidine (B3PYMPM), 4,7-diphenyl-1, 10-phenanthroline (Bphen), 1,3,5-tris[(pyridin-3-yl)-3-phenyl]benzene (TmPyBP), tris[2,4,6-trimethyl-3-(pyridin-3-yl)phenyl]borane (3TPYMB), 1,3-bis(3,5-di(pyridin-3-yl)phenyl)benzene (B3PYPB), 1,3-bis[3,5-di(pyridin-3-yl)phenyl]benzene (BMPYPHB), 2,4,6-tris(biphenyl-3-yl)-1,3,5-triazine (T2T), diphenyl bis[4-(pyridin-3-yl)phenyl]silane (DPPS), cesium carbonate (Cs2O3), bis(2-methyl-8-quinolinolato-N1,O8)-(1,1'-biphenyl-4-olato)aluminum (BAlq), 8-hydroxyquinolinolato-lithium (Liq), tris(8-hydroxyquinoline) aluminum (Alq3), or the like.

In an embodiment of the display panel provided by the present disclosure, the light-emitting layer includes a host material and a guest material. The host material is selected from the group consisting of 2,8-bis(diphenylphosphoryl) dibenzothiophene, 4,4'-bis(N-carbazolyl)-1,1'-biphenyl, 3,3'-bis(N-carbazolyl)-1,1'-biphenyl, 2,8-bis(diphenylphosphoryl)dibenzofuran, bis(4-(9H-carbazolyl-9-yl)phenyl)diphenylsilane, 9-(4-tert-butylphenyl)-3,6-bis(triphenylsilyl)-9H-carbazole, bis[2-diphenylphosphino)phenyl]ether, 1,3-bis[3,5-di(pyridin-3-yl)phenyl]benzene, 4,6-bis(3,5-di (pyridin-3-yl)phenyl)-2-methylpyrimidine, 9-(3-(9H-carbazolyl-9-yl)phenyl)-9H-carbazole-3-carbonitrile, 9-phenyl-9-[4-(triphenylsilyl)phenyl]-9H-fluorene, 1,3,5-tris(1-phenyl-1H-benzimidazol-2-yl)benzene, diphenyl [4-(triphenylsilyl)phenyl]phosphine oxide, 4,4',4''-tris(carbazol-9-yl)triphenyl amine, 2,6-dicarbazole-1,5-pyridine, polyvinylcarbazole, polyfluorene, and combinations thereof. The guest material may be selected from the group consisting of a fluorescent material, a phosphorescent material, a thermally activated delayed fluorescent material, an aggregation-induced luminescence material, and combinations thereof.

In the display panel provided by the present disclosure, the anode of the organic light-emitting device can be made of a metal, for example, copper, gold, silver, iron, chromium, nickel, manganese, palladium, platinum, and alloys thereof. In an embodiment, the anode can be made of a metal oxide, such as indium oxide, zinc oxide, indium tin oxide (ITO), indium zinc oxide (IZO), etc. In an embodiment, the anode can be made of a conductive polymer, such as polyaniline, polypyrrole, poly(3-methylthiophene) and the like. In addition to the anode material mentioned above, the anode also can be made of any suitable materials known in the related art and combinations thereof, as long as the material of the anode is conductive to injecting holes.

In the display panel provided by the present disclosure, the cathode of the organic light-emitting device can be made of metal, such as aluminum, magnesium, silver, indium, tin, titanium, and alloys thereof. In an embodiment, the cathode can be made of a multiple-layer metal material, such as LiF/Al, LiO$_2$/Al, BaF$_2$/Al, etc. In addition to the cathode materials listed above, the cathode also can be made of any suitable materials known in the related art and combinations thereof, as long as the material of the cathode is conductive to injecting electrons.

The organic light-emitting device can be manufactured according to methods well known in the art, which will not be described in detail herein. In the present disclosure, the organic light-emitting display device can be manufactured by: forming an anode on a transparent or opaque smooth substrate, forming an organic thin layer on the anode, and further forming a cathode on the organic thin layer. The organic thin layer can be formed by a known method such as vapor deposition, sputtering, spin coating, dipping, ion plating, and the like.

The following illustrative examples are provided to explain the actual applications of the compound according to the present disclosure in the organic light-emitting display panels.

(2) Test of Performances of Devices

Application Example 1

Figure 2:
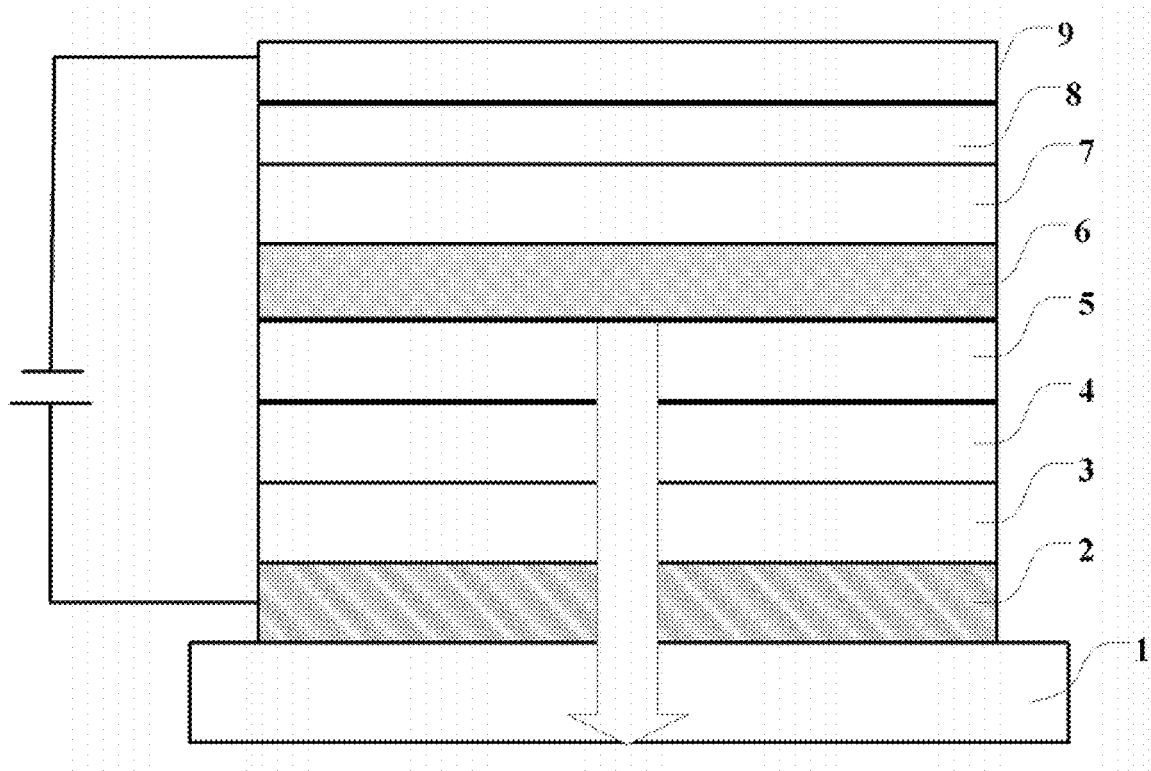
FIG. 2 is a structural schematic diagram of an OLED according to the present disclosure.

The present example provides an OLED device, as shown in FIG. 2. The OLED device includes: a substrate 1, an ITO anode 2, a hole injection layer 3, a first hole transport layer 4, a second hole transport layer 5, a light-emitting layer 6, a first electron transport layer 7, a second electron transport layer 8, and a cathode 9. The arrow in FIG. 2 represents a light extraction direction of the device.

The OLED device is manufactured with the following method.

1) the glass substrate 1 was cut into a size of 50 mm×50 mm×0.7 mm, ultrasonically cleaned in acetone, isopropyl alcohol and deionized water for 30 minutes, respectively, and then cleaned under UV ozone for 30 minutes; the obtained glass substrate with an indium tin oxide (ITO) anode layer 2 formed by physical vapor deposition or sputtering thereon was mounted on a vacuum deposition apparatus;

2) the compound a, as a hole injection material, was vacuum evaporated on the ITO anode layer 2 to form the hole injection layer 3, having a thickness of 10 nm;

3) the compound b, as a hole transport material, was vacuum evaporated on the hole injection layer 3 to form the first hole transport layer 4, having a thickness of 100 nm;

4) the compound c, as a hole transport material, was vacuum evaporated on the first hole transport layer 4 to form the second hole transport layer 5, having a thickness of 10 nm;

5) a light-emitting layer 6 having a thickness of 30 nm was formed on the second hole transport layer 5 by vacuum evaporation, where the compound d (mCBP) was used as a host material, and compound P005 according to the present disclosure was used as a dopant (a guest material) with a doping ratio of 10% (mass ratio);

6) compound e, as an electron transport material, was vacuum evaporated on the light-emitting layer 6 to form the first electron transport layer 7, having a thickness of 10 nm;

7) compound f and compound g (in a mass ratio of 1:1), as electron transmission materials, were vacuum evaporated on the first electron transport layer 7 to form the second electron transport layer 8, having a thickness of 30 nm; and 8) the silver electrode was vacuum evaporated on the second electron transport layer 8 to form the cathode 9 having a thickness of 15 nm.

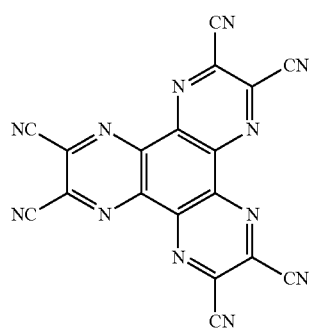

compound a

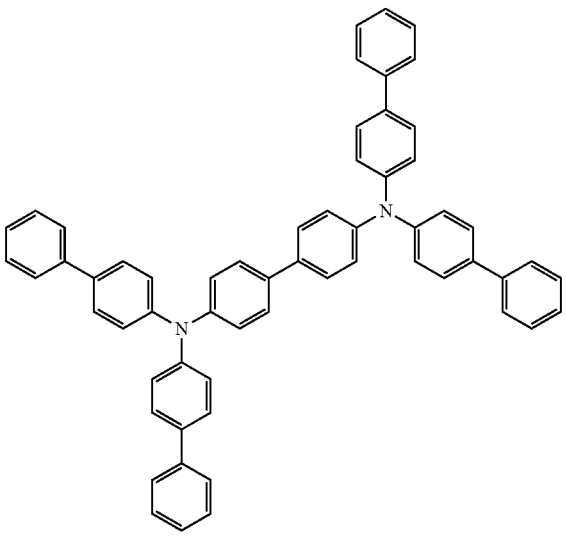

compound b

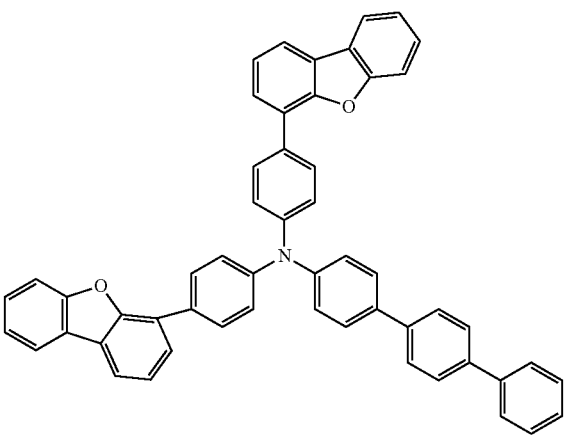

compound c compound d

-continued
compound e
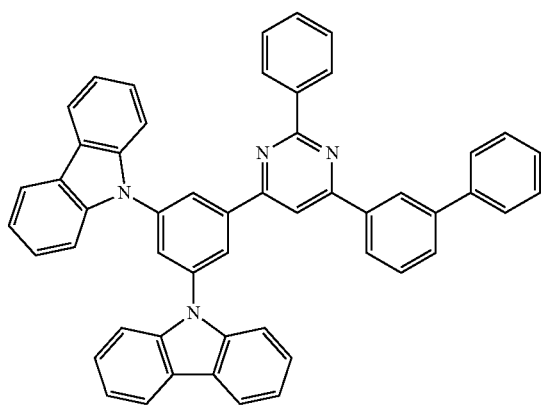
compound f
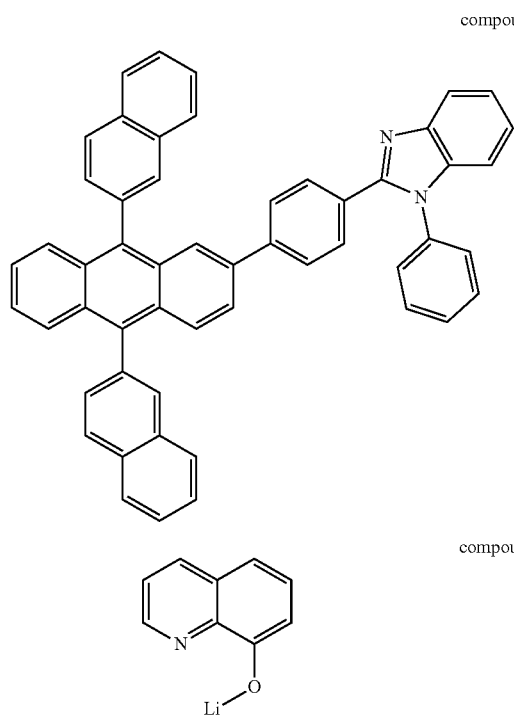
compound g
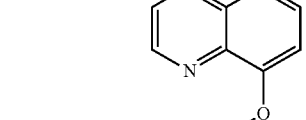
comparative compound 1
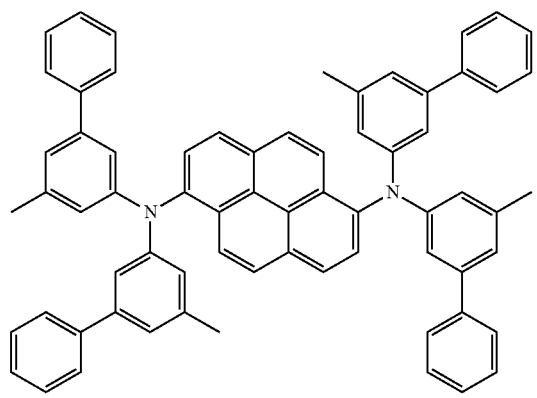
comparative compound 2
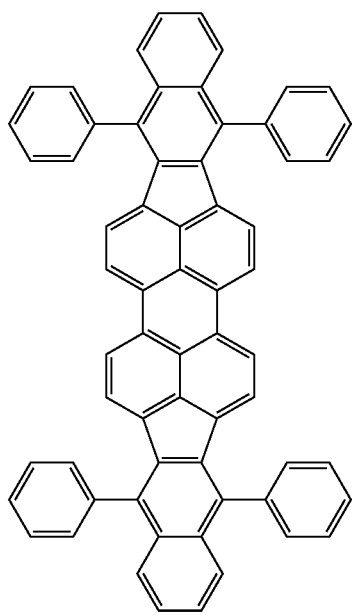
comparative compound 3
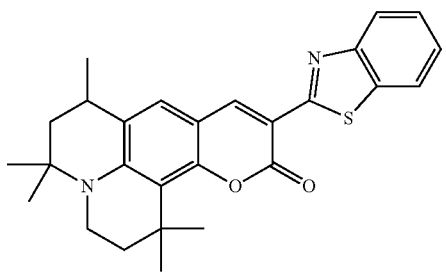
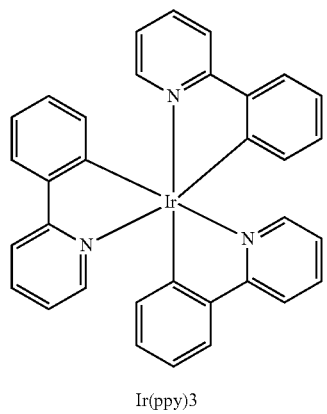
Ir(ppy)3

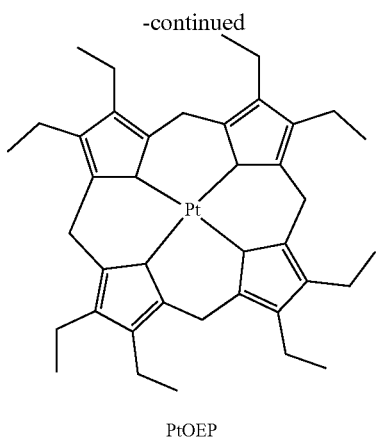

PtOEP

Application Example 2

This Application Example differs from Application Example 1 in that compound P005 in step 5) was replaced by compound P041. The other manufacturing steps are the same.

Application Example 3

This Application Example differs from Application Example 1 in that compound P005 in step 5) was replaced by compound P074. The other manufacturing steps are the same.

Application Example 4

This Application Example differs from Application Example 1 in that compound P005 in step 5) was replaced by compound P101. The other manufacturing steps are the same.

Application Example 5

This Application Example differs from Application Example 1 in that compound P005 in step 5) was replaced by compound P103. The other manufacturing steps are the same.

Application Example 6

This Application Example differs from Application Example 1 in that compound P005 in step 5) was replaced by compound P130. The other manufacturing steps are the same.

Application Example 7

This Application Example differs from Application Example 1 in that compound P005 in step 5) was replaced by compound P158. The other manufacturing steps are the same.

Application Example 8

This Application Example differs from Application Example 1 in that compound P005 in step 5) was replaced by compound P162. The other manufacturing steps are the same.

Application Example 9

This Application Example differs from Application Example 1 in that compound P005 in step 5) was replaced by compound P165. The other manufacturing steps are the same.

Application Example 10

This Application Example differs from Application Example 1 in that compound P005 in step 5) was replaced by compound P185. The other manufacturing steps are the same.

Application Example 11

This Application Example differs from Application Example 1 in that compound P005 in step 5) was replaced by compound P186. The other manufacturing steps are the same.

Application Example 12

This Application Example differs from Application Example 1 in that in step 5), compound mCBP was replaced by compound P058, compound P005 was replaced by Ir(ppy)$_3$, and the doping ratio was 5%. The other manufacturing steps are the same.

Application Example 13

This Application Example differs from Application Example 1 in that in step 5), compound mCBP was replaced by compound P083, compound P005 was replaced by Ir(ppy)$_3$, and the doping ratio was 5%. The other manufacturing steps are the same.

Application Example 14

This Application Example differs from Application Example 1 in that in step 5), compound mCBP was replaced by compound P088, compound P005 was replaced by Ir(ppy)$_3$, and the doping ratio was 5%. The other manufacturing steps are the same.

Application Example 15

This Application Example differs from Application Example 1 in that in step 5), compound mCBP was replaced by compound P159, compound P005 was replaced by Ir(ppy)$_3$, and the doping ratio was 5%. The other manufacturing steps are the same.

Application Example 16

This Application Example differs from Application Example 1 in that in step 5), compound mCBP was replaced by compound P178, compound P005 was replaced by Ir(ppy)$_3$, and the doping ratio was 5%. The other manufacturing steps are the same.

Application Example 17

This Application Example differs from Application Example 1 in that in step 5), compound mCBP was replaced by compound P101, compound P005 was replaced by PtOEP, and the doping ratio was 5%. The other manufacturing steps are the same.

Comparative Example 1

The Comparative Example 1 differs from Application Example 1 in that in step 5), compound P005 was replaced by a comparative compound 1, and the doping ratio of the comparative compound 1 was 2%. The other manufacturing steps are the same.

Comparative Example 2

The Comparative Example 1 differs from Application Example 1 in that in step 5), compound P005 was replaced by a comparative compound 2, and the doping ratio of the comparative compound 2 was 2%. The other manufacturing steps are the same.

Comparative Example 3

The Comparative Example 1 differs from Application Example 1 in that in step 5), compound P005 was replaced by a comparative compound 3, and the doping ratio of the comparative compound 3 was 2%. The other manufacturing steps are the same.

Comparative Example 4

The Comparative Example 1 differs from Application Example 1 in that in step 5), compound mCBP was replaced by a comparative compound 4, compound P005 was replaced by Ir(ppy)₃, and the doping ratio was 5%. The other manufacturing steps are the same.

comparative compound 4

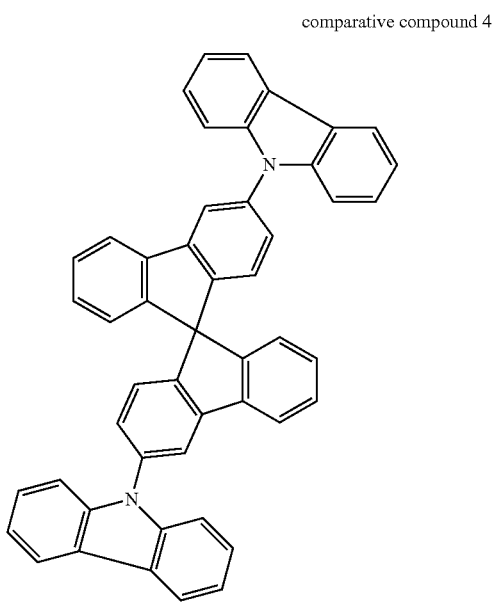 [SMILES: c1ccc2c(c1)-c1cc(-n3c4ccccc4c4ccccc43)ccc1C21c2ccccc2-c2cc(-n3c4ccccc4c4ccccc43)ccc21]

Currents under different voltages of the OLED devices were tested with a Keithley 2365A digital nanovoltmeter, and then the currents were divided by a light-emitting area to calculate current densities of the OLED devices at different voltages. Brightness and radiant energy flow densities of the OLED devices at different voltages were tested using a Konicaminolta CS-2000 spectroradiometer. According to the current density and brightness of the OLED device at different voltages, an operating voltage $V_{on}$ and a current efficiency $CE_{(10mAkm^2)}$ (in an unit of cd/A) at the same current density (10 mA/cm²) were obtained.

DC voltage was applied to the manufactured organic light-emitting devices. The measurement results of the luminous performance of the devices were summarized in Table 2.

TABLE 2

| | Host material | Guest material | $V_{on}$ (V) | $CE_{(10\ mA/cm^2)}$ (cd A⁻¹) | Color |
|---|---|---|---|---|---|
| Application Example 1 | mCBP | P005 | 3.95 | 56.3 | green light |
| Application Example 2 | mCBP | P041 | 4.01 | 58.8 | green light |
| Application Example 3 | mCBP | P074 | 3.98 | 56.0 | green light |
| Application Example 4 | mCBP | P101 | 3.96 | 57.4 | green light |
| Application Example 5 | mCBP | P103 | 3.68 | 25.8 | red light |
| Application Example 6 | mCBP | P130 | 3.70 | 26.3 | red light |
| Application Example 7 | mCBP | P158 | 3.94 | 56.7 | green light |
| Application Example 8 | mCBP | P162 | 4.02 | 25.0 | blue light |
| Application Example 9 | mCBP | P165 | 3.99 | 24.9 | blue light |
| Application Example 10 | mCBP | P185 | 4.04 | 21.6 | blue light |
| Application Example 11 | mCBP | P186 | 4.05 | 22.1 | blue light |
| Application Example 12 | P058 | Ir(ppy)3 | 4.05 | 52.7 | green light |
| Application Example 13 | P083 | Ir(ppy)3 | 4.04 | 53.6 | green light |
| Application Example 14 | P088 | Ir(ppy)3 | 4.02 | 55.2 | green light |
| Application Example 15 | P159 | Ir(ppy)3 | 3.98 | 56.3 | green light |
| Application Example 16 | P178 | Ir(ppy)3 | 4.01 | 54.6 | green light |
| Application Example 17 | P101 | PtOEP | 3.79 | 19.8 | red light |
| Comparative Example 1 | mCBP | Comparative compound 1 | 4.15 | 7.0 | blue light |
| Comparative Example 2 | mCBP | Comparative compound 2 | 4.08 | 10.4 | red light |
| Comparative Example 3 | mCBP | Comparative compound 3 | 4.72 | 12.4 | green light |
| Comparative Example 4 | Comparative compound 4 | Ir(ppy)3 | 4.35 | 43.8 | green light |

It can be known from Table 2 that, compared with the comparative device using the classic blue light-emitting material comparative compound 1 as the fluorescent dopant, the current efficiency CE of each of the OLED devices using compounds P162, P165, P185, and P186 as the dopants is significantly higher than the current efficiency CE of the comparative OLED device, which is mainly attributed to the TADF characteristics of the organic compounds P162, P165, P185, and P186. The triplet excitons, transition of which is forbidden for conventional fluorescent molecules, can be utilized to emit light, thereby improving the efficiency of OLED devices and reducing the driving voltage.

In view of TABLE 2, it is also known that, compared with the comparative devices respectively using the classic red light-emitting material comparative compound 2 or the classic green light-emitting material comparative compound 3 as the fluorescent dopant, the current efficiency CE of each of the OLED devices using compounds P005, P041, P074, P101, P103, P130 and P158 as the dopant is significantly higher than the current efficiency CE of the comparative OLED devices, which is mainly attributed to the TADF characteristics of the organic compounds P005, P041, P074, P101, P103, P130 and P158, The triplet excitons, transition of which is forbidden for conventional fluorescent molecules, can be utilized to emit light, improving the efficiency of OLED device and reducing the driving voltage.

Compared with the comparative compound 4, the OLED devices, in which the compounds P058, P083, P088, P159 and P178 of the present disclosure were used as the phosphorescent host material and Ir(ppy)3 was used as the green light dopant material, can have current efficiency CE reaching 52.7-56.3 cd/A, excellent light-emitting performance. It indicates that the organic compounds of the present disclosure can be used as the phosphorescent host material of the light-emitting layer, which is mainly attributed to the bipolar carrier transmission characteristics of the compounds of the present disclosure that can effectively broaden the carrier recombination area, improving the light-emitting efficiency. Moreover, the compounds of the present disclosure have high triplet energy levels, which can effectively confine excitons inside the light-emitting layer and thus reduces the non-radiation transition attenuation caused by the diffusion of excitons to the outside of the light-emitting layer.

In another aspect, the present disclosure provides a display apparatus including the display panel as described above.

Figure 3:
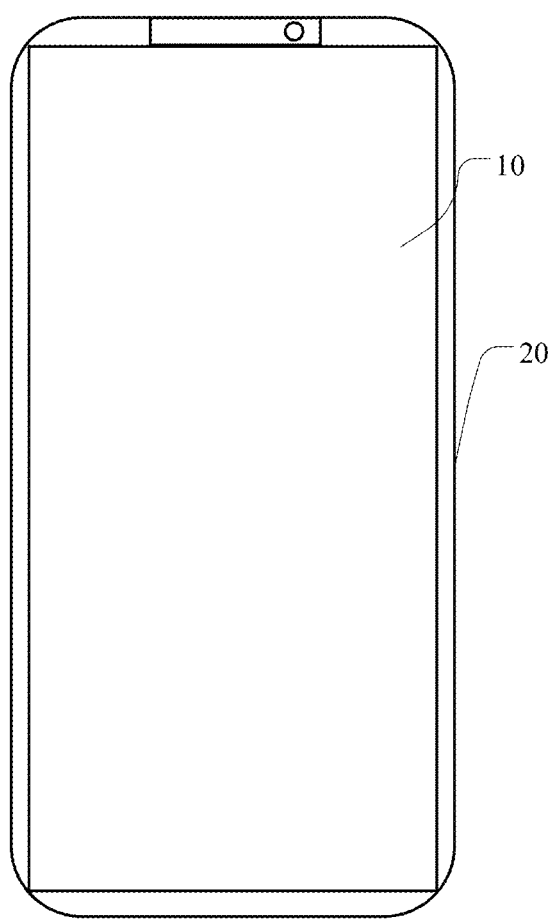
FIG. 3 is a schematic diagram of a display apparatus according to an embodiment of the present disclosure.

In the present disclosure, the display apparatus may be a display screen of mobile phone, computer, television, smart watch, smart car, VR or AR helmet, or any other smart apparatuses. FIG. 3 is a schematic diagram of a display apparatus according to an embodiment of the present disclosure. In FIG. 3, a mobile phone display panel is denoted with reference sign 10, and a display apparatus is denoted with reference sign 20.

The above embodiments of the present disclosure are several preferred embodiments, but not intended to limit the scope of the claims. Any change and modification can be made by those skilled in the art without departing from the scope of the present application. The scope of protection is defined by the claims.

What is claimed is:

1. A compound, having a structure represented by formula 1:

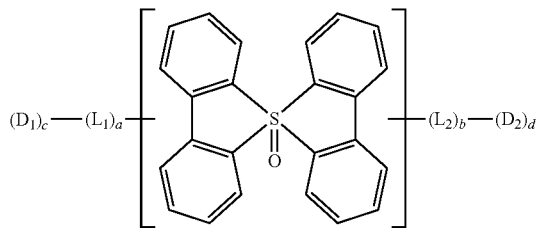

formula 1 wherein $L_1$ and $L_2$ are each independently selected from the group consisting of a single bond, a substituted or unsubstituted C6-C30 aryl, and a C4-C30 heteroaryl; a and b are each independently selected from 0, 1, 2, 3, or 4;

$D_1$ and $D_2$ are each independently a nitrogen-containing electron donor unit selected from the group consisting of carbazolyl and derivative groups thereof, acridinyl and derivative groups thereof, diarylamino and derivative groups thereof, and triarylamino and derivative groups thereof; and c and d are each independently selected from 0, 1, 2, 3, or 4, and c+d≥1.

2. The compound according to claim 1, wherein the compound has a structure represented by formula 1-1 or formula 1-2:

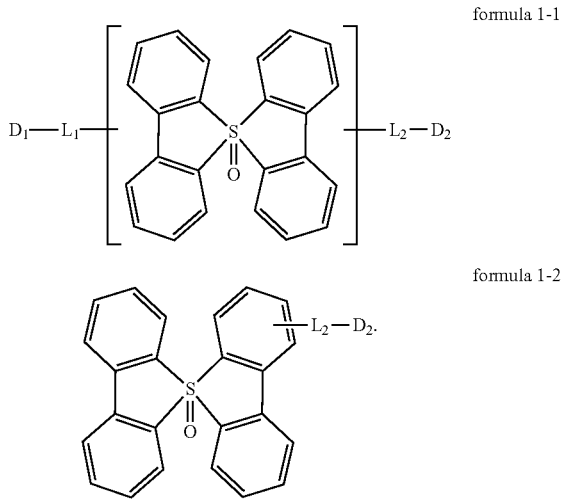

3. The compound according to claim 1, wherein $L_1$ and $L_2$ are each independently selected from the group consisting of phenyl, biphenyl, naphthyl, anthracyl, phenanthryl, acenaphthylenyl, pyrenyl, perylenyl, fluorenyl, spirodifluorenyl, chrysenyl, benzophenanthryl, and benzanthracyl.

4. The compound according to claim 1, wherein $D_1$ and $D_2$ are each independently selected from the group consisting of:

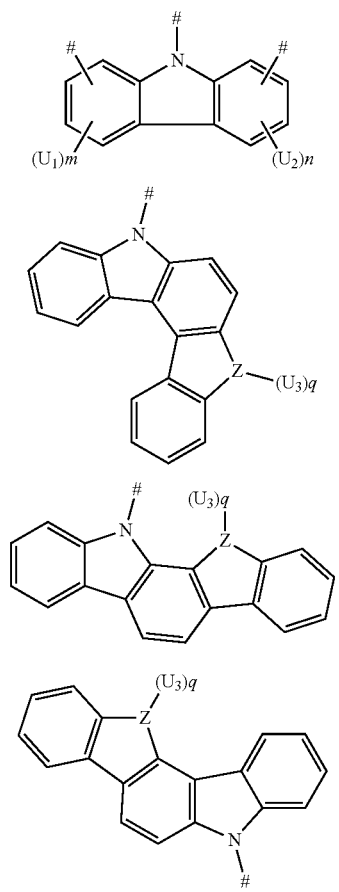

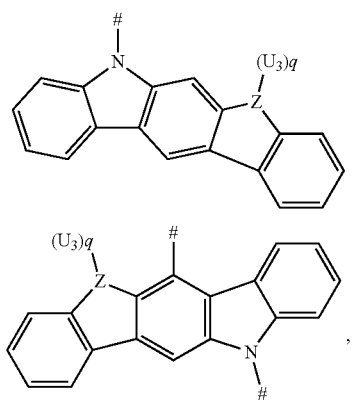

wherein Z is selected from the group consisting of a carbon atom, a nitrogen atom, an oxygen atom, and a sulfur atom;

q is 0, 1 or 2;

$U_1$, $U_2$, and $U_3$ are each independently selected from the group consisting of a hydrogen atom, C1-C6 alkyl, C1-C6 alkoxy, and C6-C12 aryl;

when Z is an oxygen atom or a sulfur atom, q is 0; and # indicates a bonding position.

5. The compound according to claim 4, wherein $D_1$ and $D_2$ are each independently selected from the group consisting of:

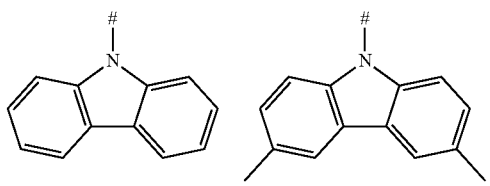

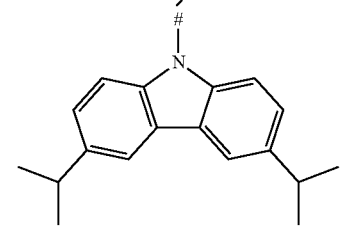

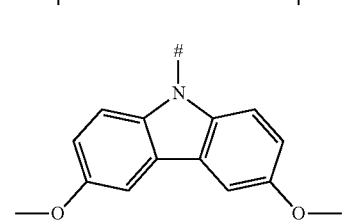

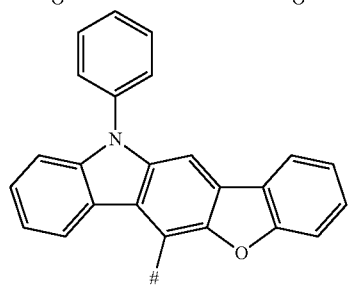

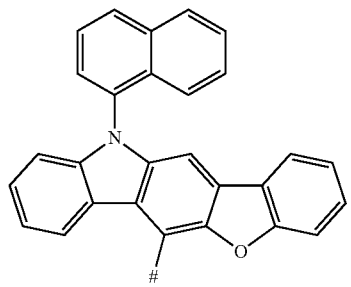

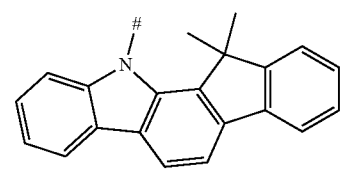

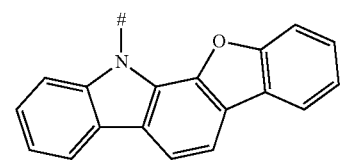

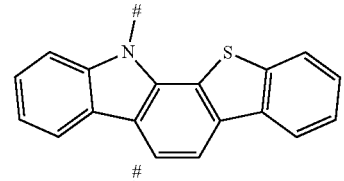

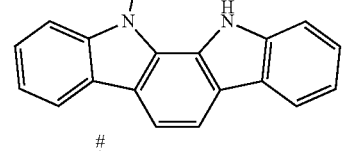

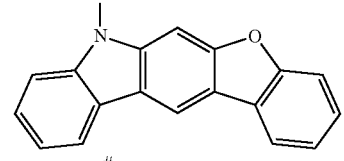

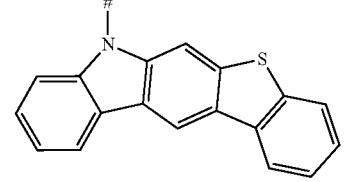

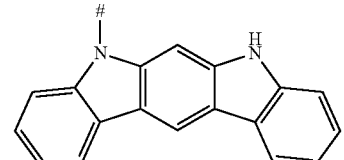

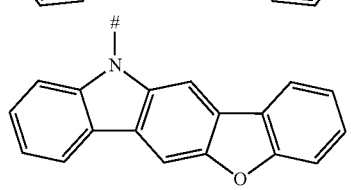

-continued

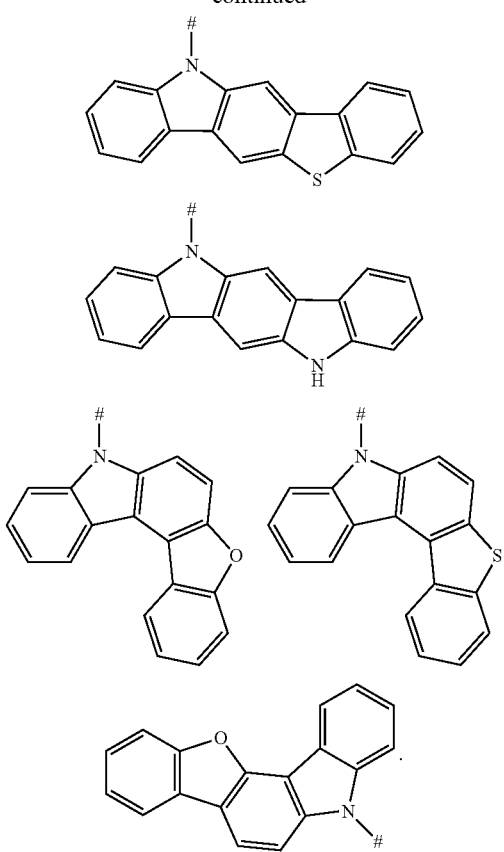

6. The compound according to claim 1, wherein $D_1$ and $D_2$ are each independently selected from the group consisting of:

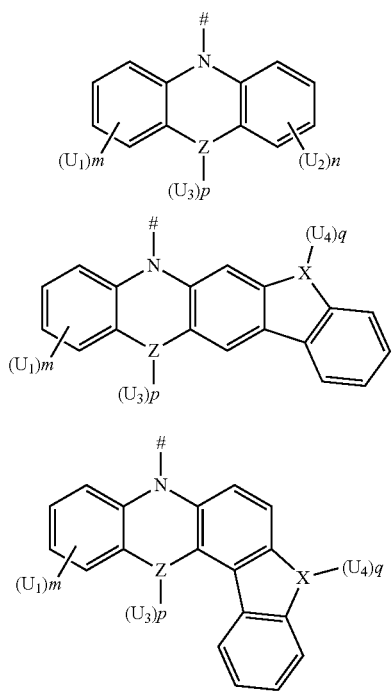

-continued

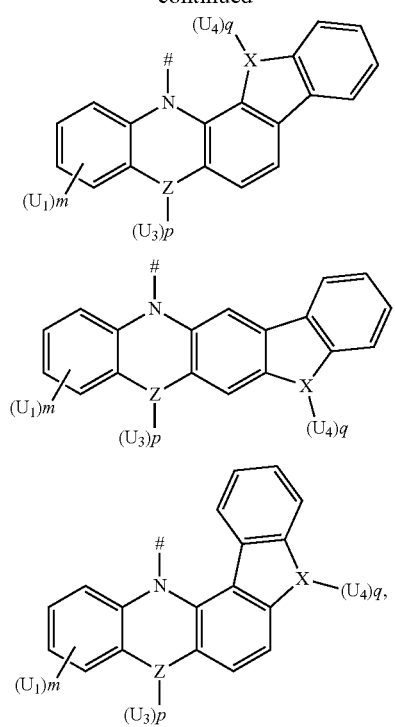

wherein Z is selected from the group consisting of a carbon atom, a nitrogen atom, an oxygen atom, a sulfur atom, and a silicon atom;

X is selected from the group consisting of a carbon atom, a nitrogen atom, an oxygen atom, a sulfur atom, and a silicon atom;

m, n, p and q are each independently selected from 0, 1 or 2;

$U_1$, $U_2$, $U_3$ and $U_4$ are each independently selected from the group consisting of a hydrogen atom, C1-C6 alkyl, C3-C6 cycloalkyl, C1-C6 alkoxy, C6-C12 aryl, and C12-C20 substituted or unsubstituted diphenylamino;

when Z is an oxygen atom or a sulfur atom, p is 0;

when X is an oxygen atom or a sulfur atom, q is 0; and # indicates a bonding position.

7. The compound according to claim 6, wherein $D_1$ and $D_2$ are each independently selected from the group consisting of:

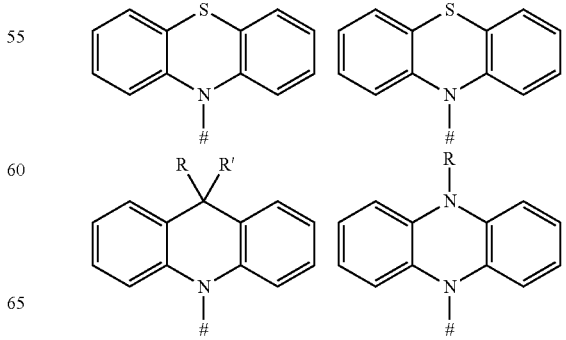

-continued

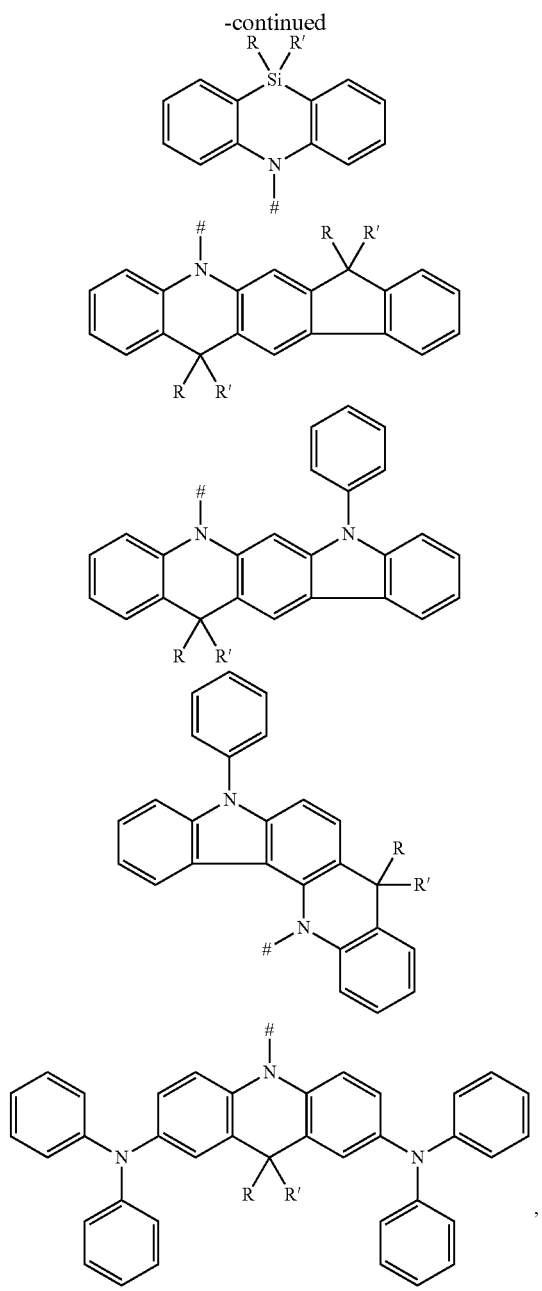

wherein R and R' are each independently selected from the group consisting of a hydrogen atom, C1-C6 alkyl, C1-C6 alkoxy, C1-C6 cycloalkyl, C6-C12 aryl, and C4-C12 heteroaryl.

8. The compound according to claim 1, wherein $D_1$ and $D_2$ are each independently selected from the group consisting of:

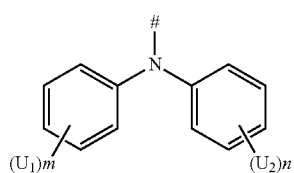

-continued

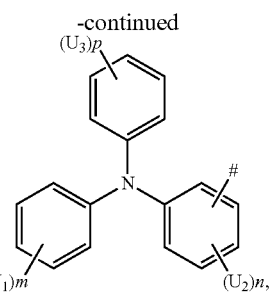

wherein $U_1$, $U_2$ and $U_3$ are each independently selected from the group consisting of a hydrogen atom, C1-C6 alkyl, and C1-C6 alkoxy;
m, n, and p are each independently selected from 0, 1 or 2; and
# indicates a bonding position.

9. The compound according to claim 8, wherein $D_1$ and $D_2$ are each independently selected from the group consisting of:

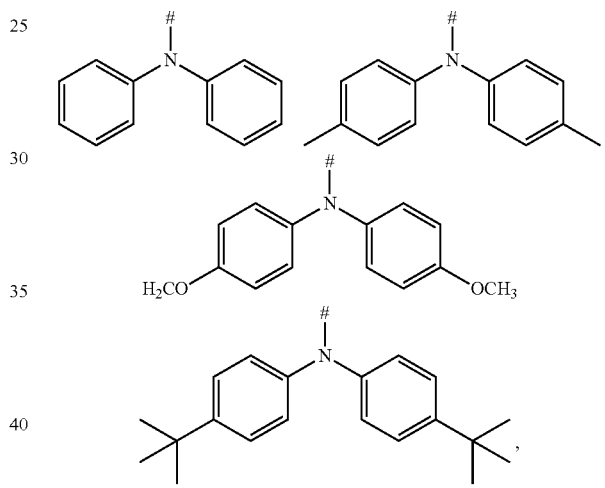

wherein # indicates a bonding position.

10. The compound according to claim 1, wherein $D_1$ and $D_2$ are each independently selected from the group consisting of:

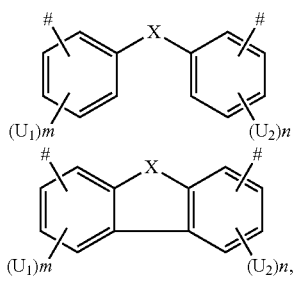

wherein X is an oxygen atom or a sulfur atom;
m and n are each independently selected from 0, 1 or 2;
$U_1$ and $U_2$ are each independently selected from the group consisting of a hydrogen atom, C1-C6 alkyl, C3-C6 cycloalkyl, and C1-C6 alkoxy; and
# indicates a bonding position.

11. The compound according to claim 1, wherein the compound is selected from the following compounds:
P001
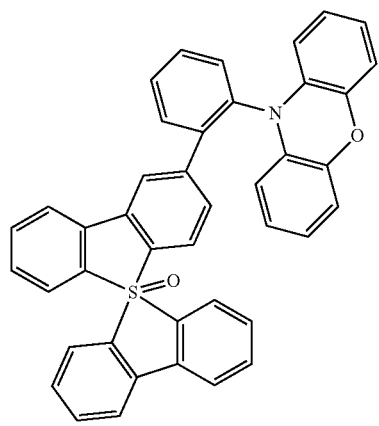
P002
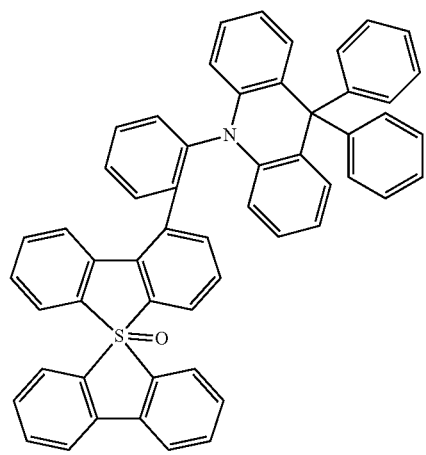
P003
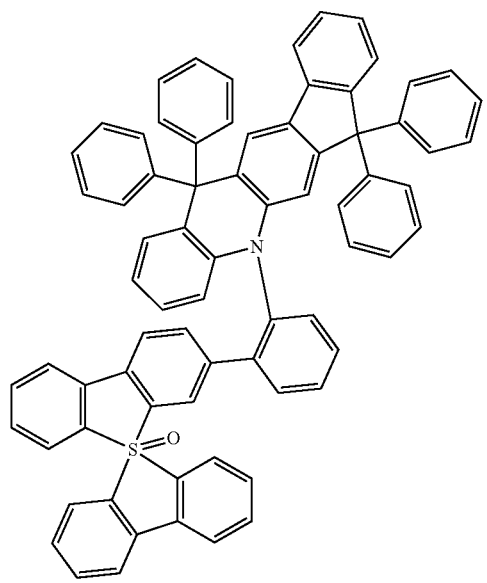
P004
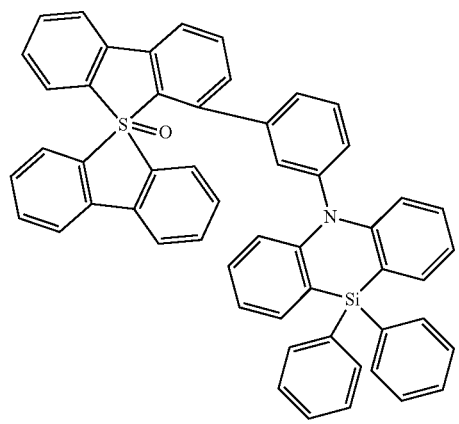
P005
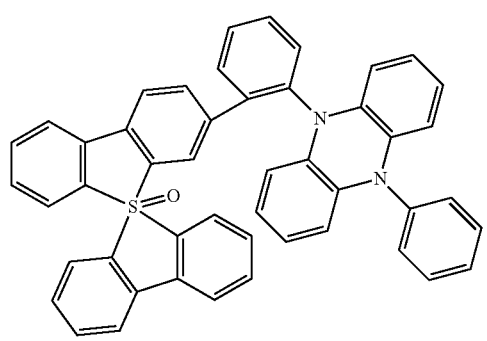
P006
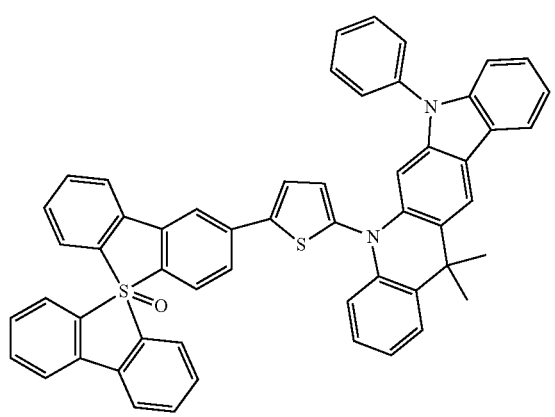

-continued
P007
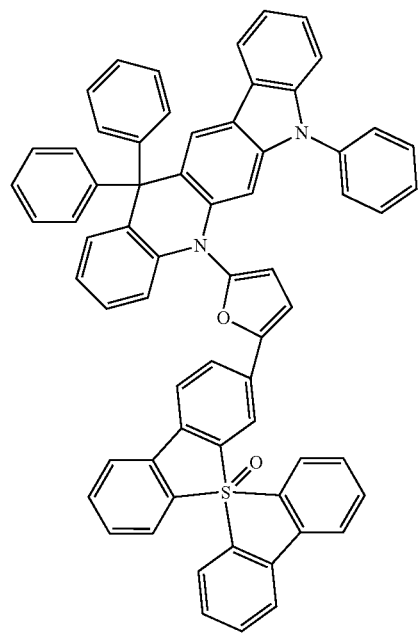
P008
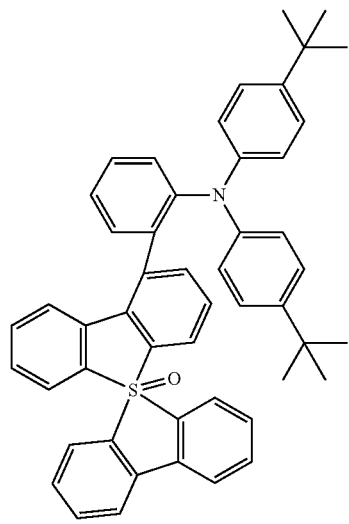
P009
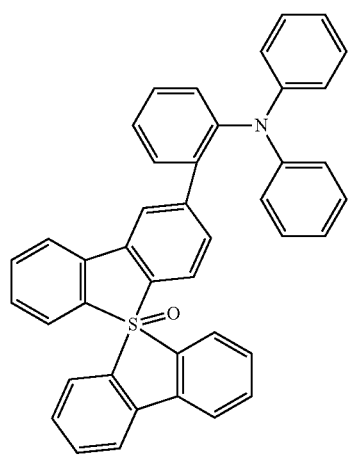
P010
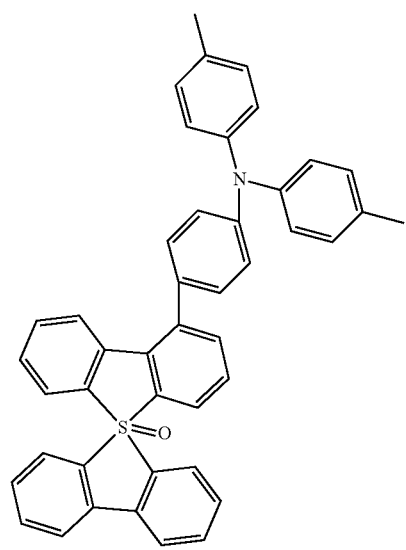

-continued
P011
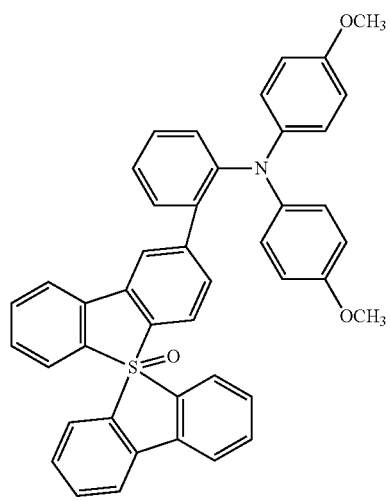
P012
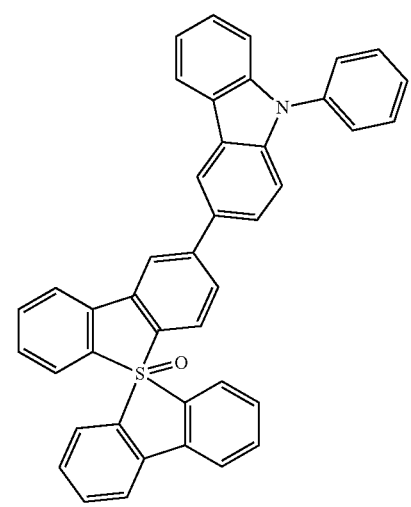
P013
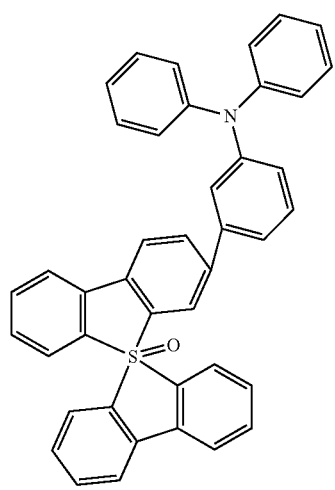
P014
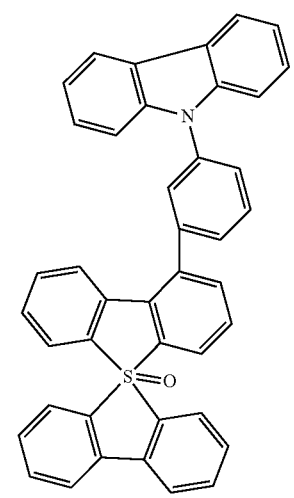
P015
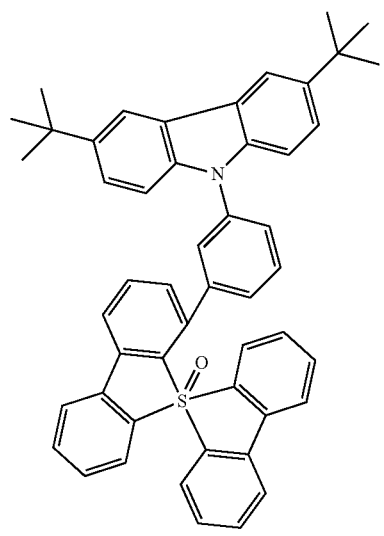
P016
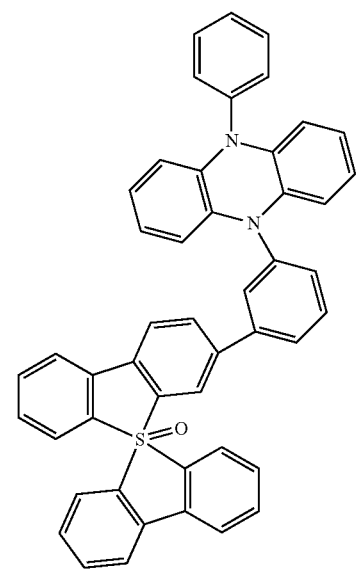

-continued
P017
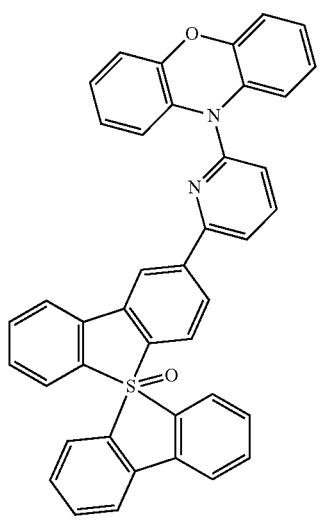
P018
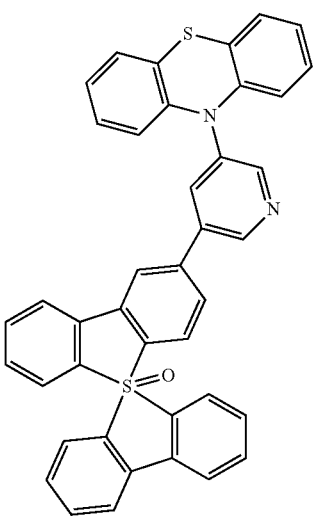
P019
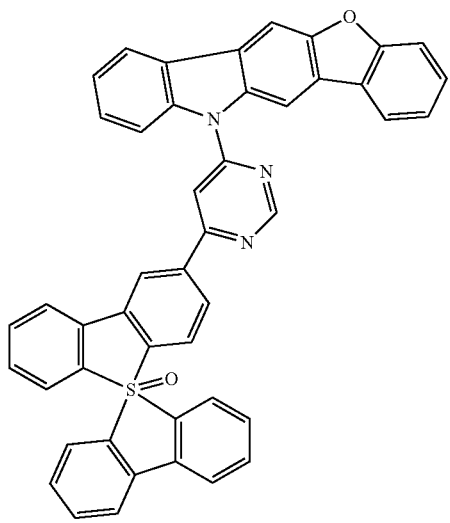
P020
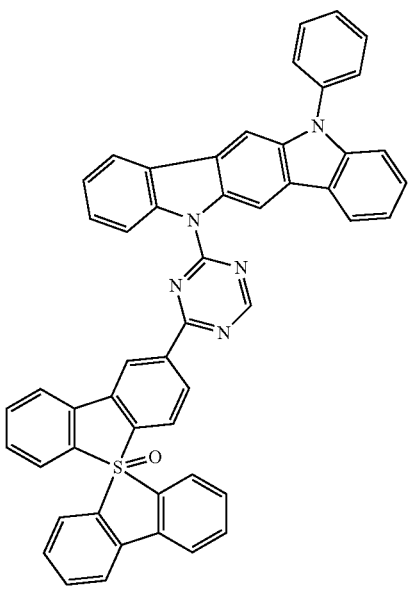
P021
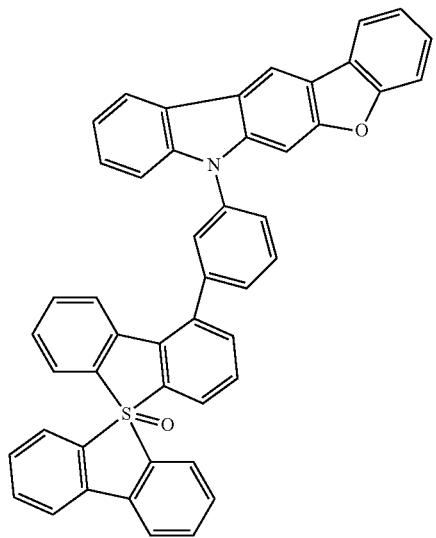
P022
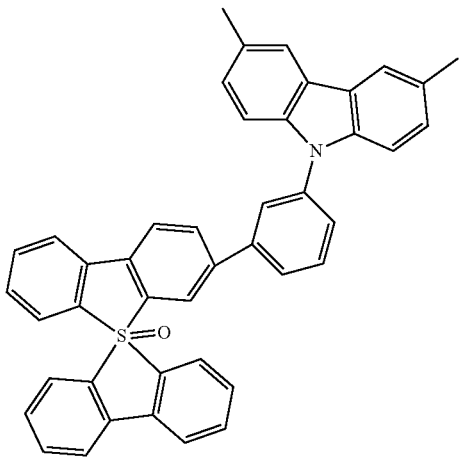

-continued
P023
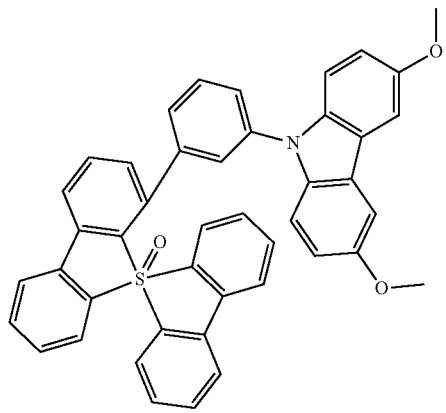
P024
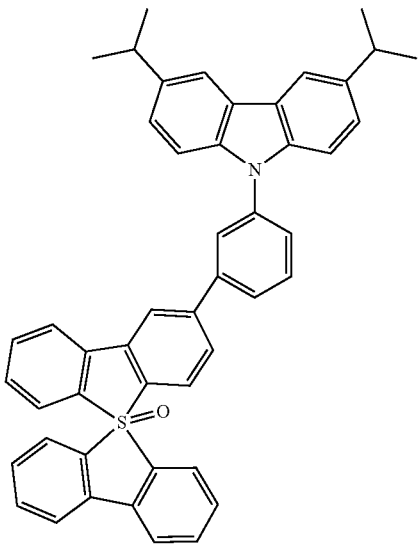
P025
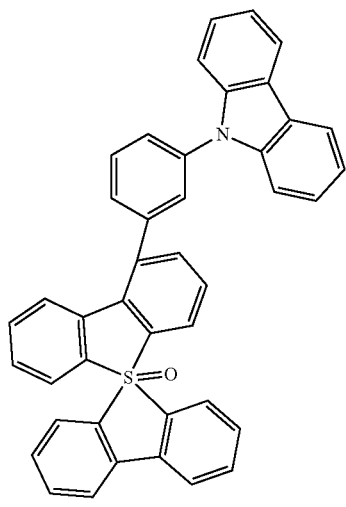
P026
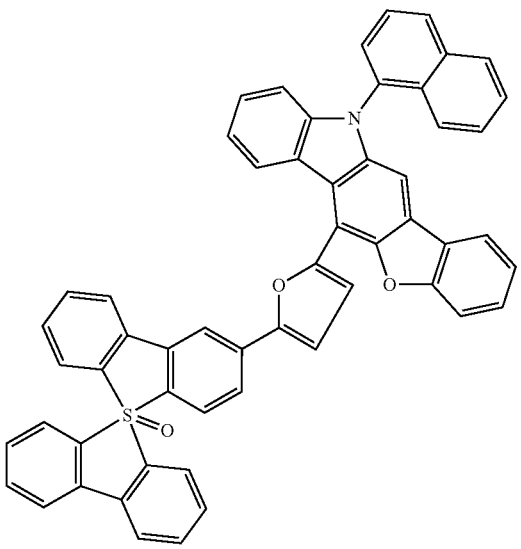

-continued
P027
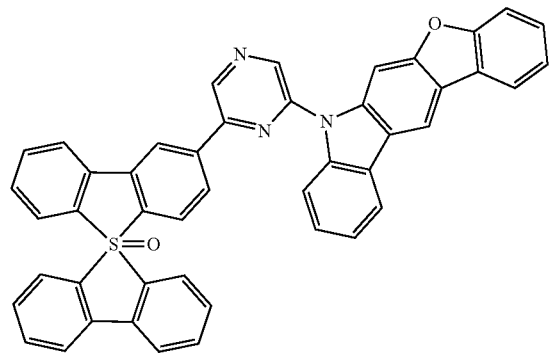
P028
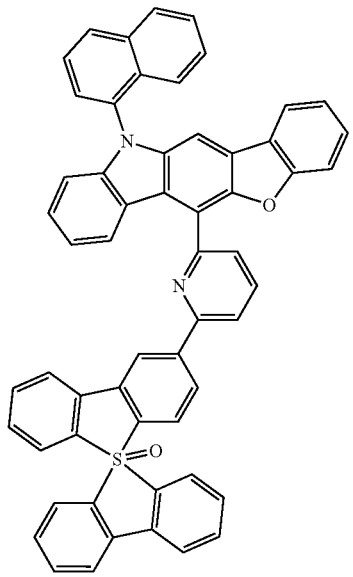
P029
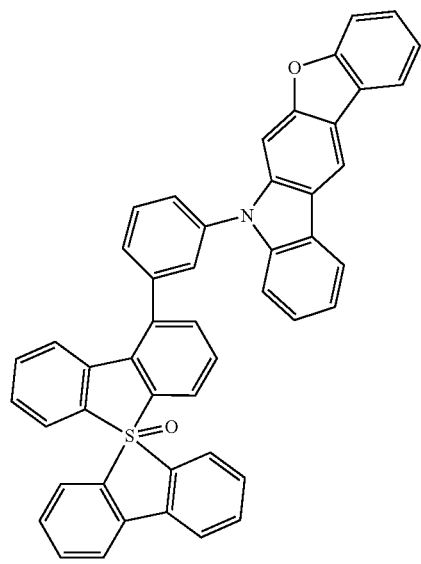
P030
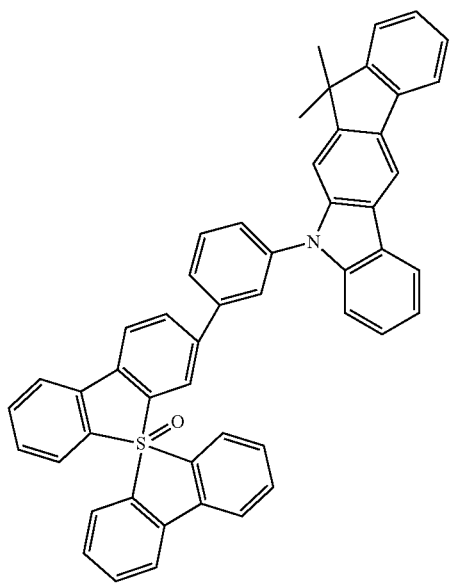

-continued
P031
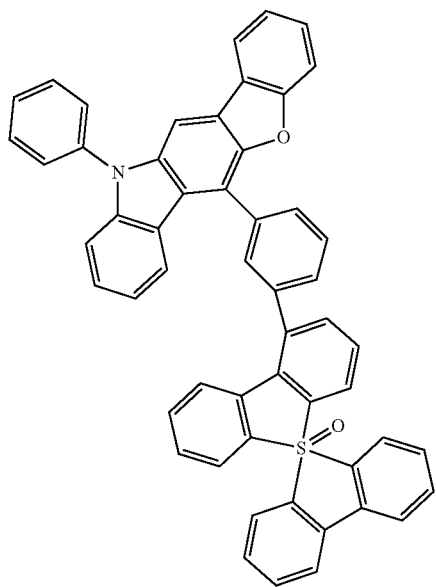
P032
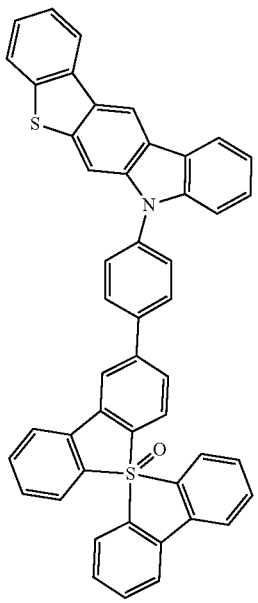
P033
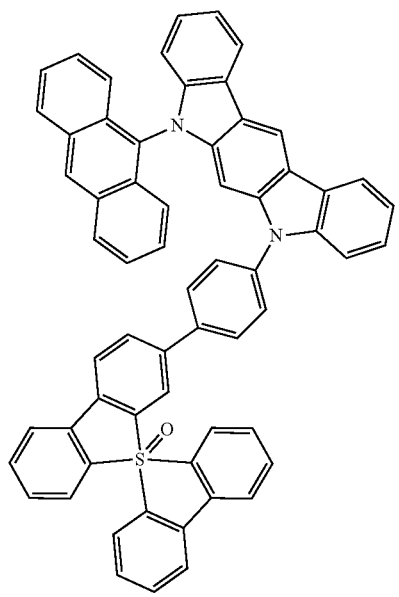
P034
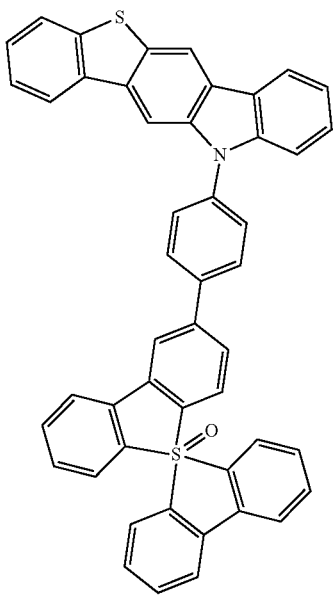

-continued
P035
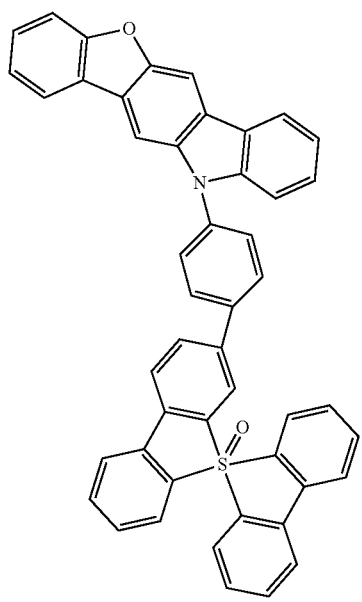
P036
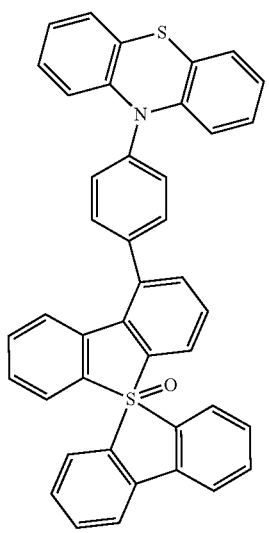
P037
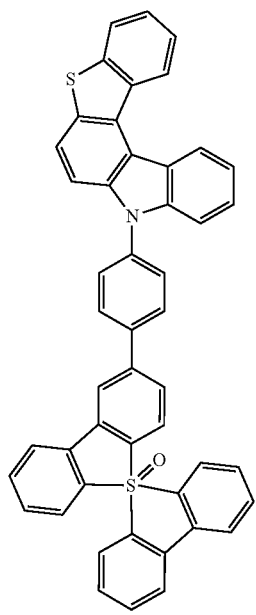
P038
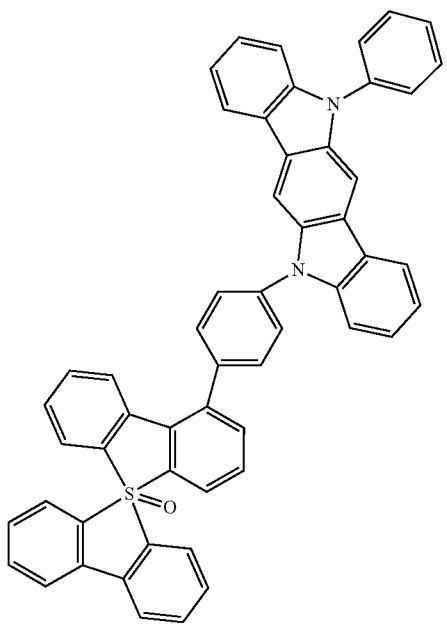

-continued
P039
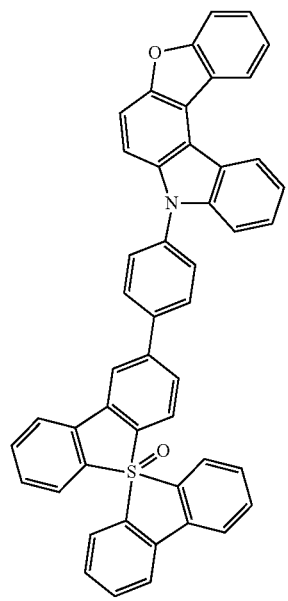
P040
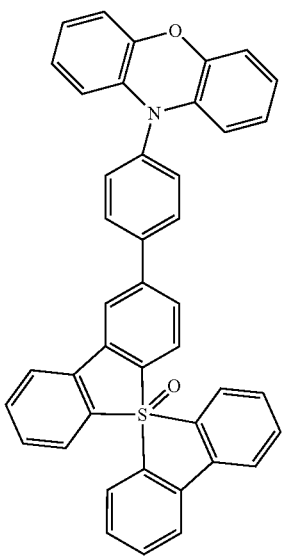
P041
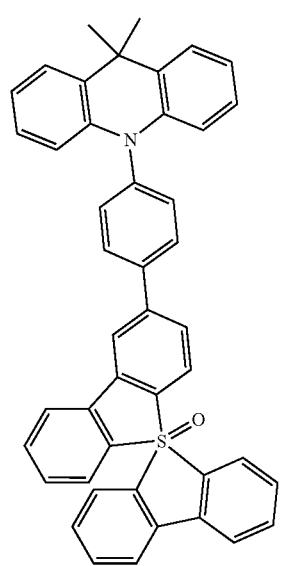
P042
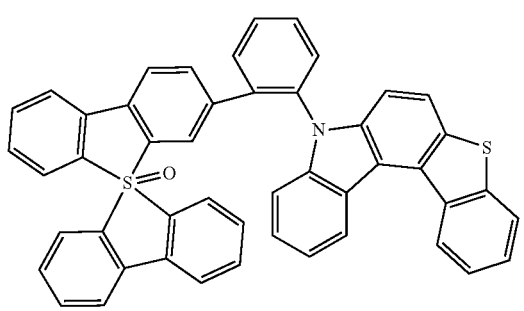

-continued
P043
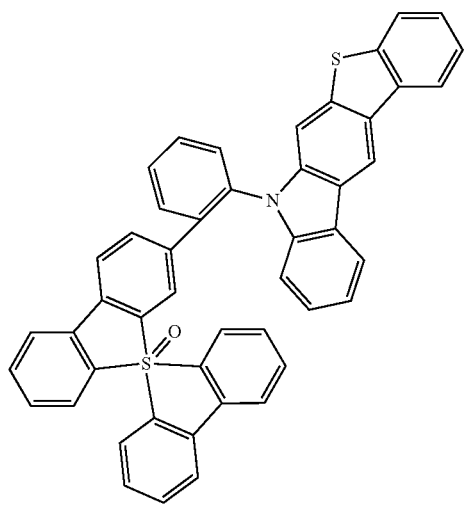
P044
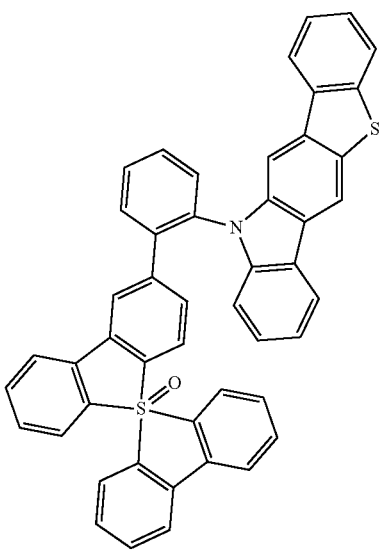
P045
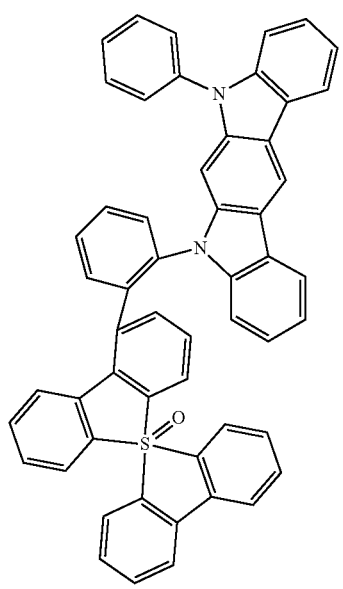
P046
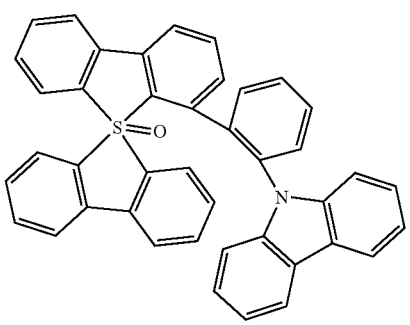
P047
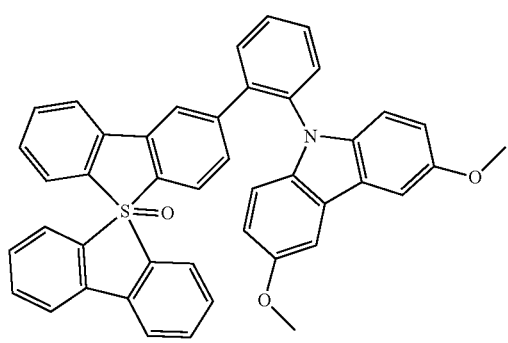
P048
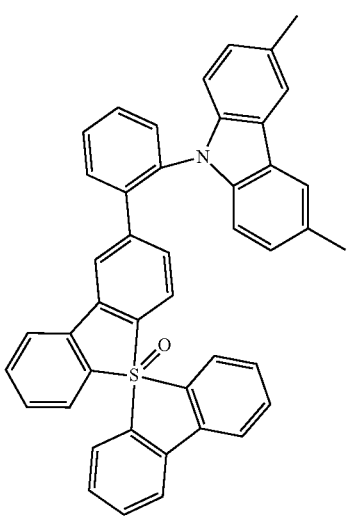

-continued
P049
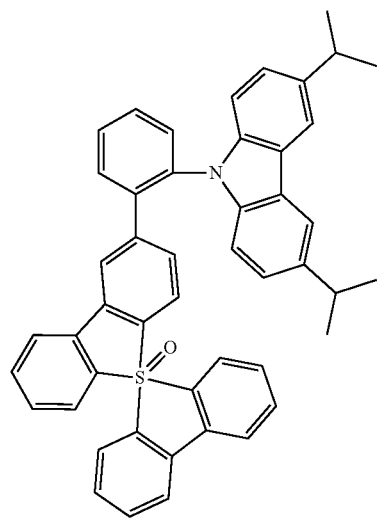
P050
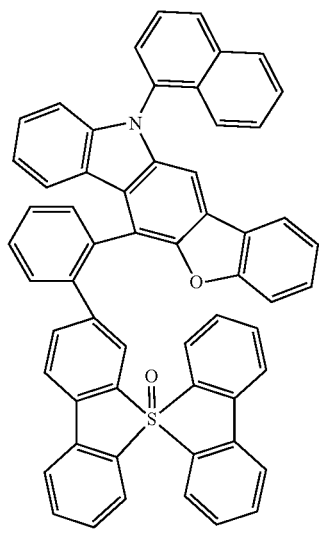
P051
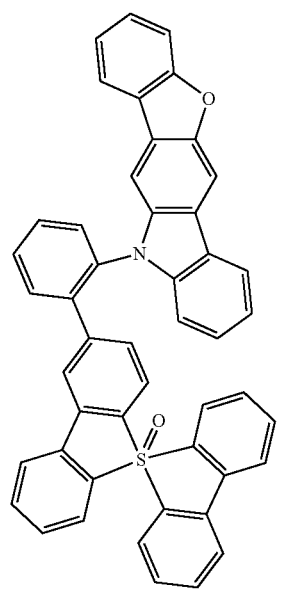
P052
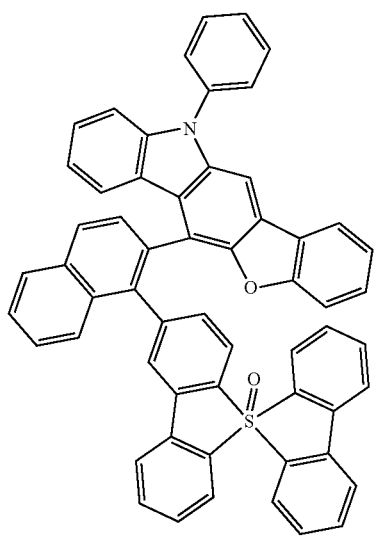

-continued
P053
P054
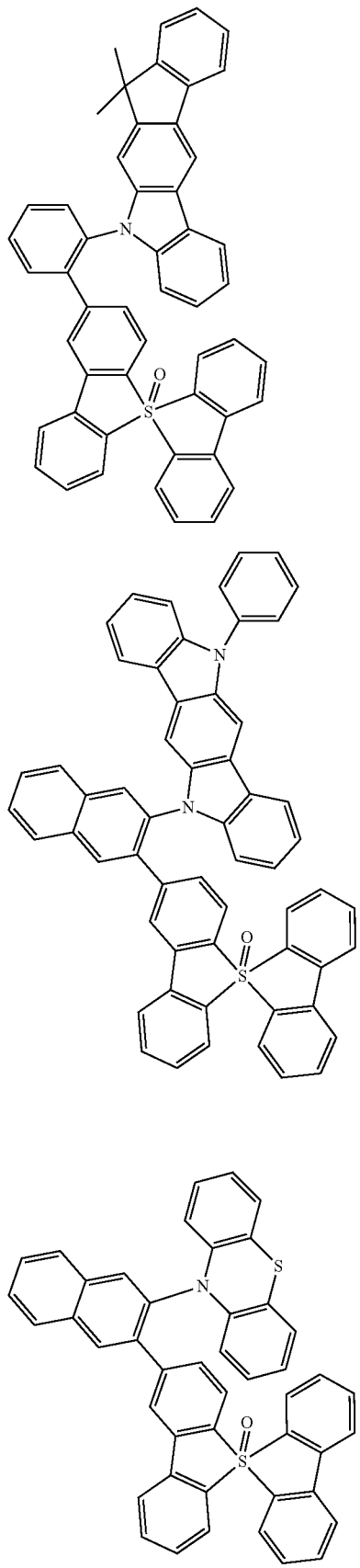
P055
P056
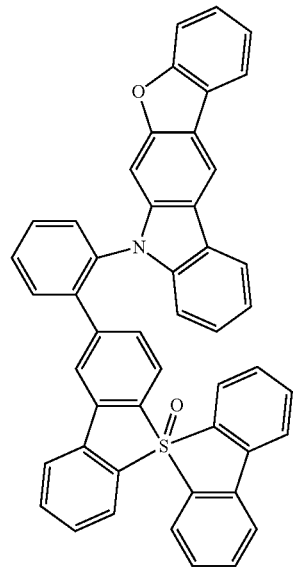
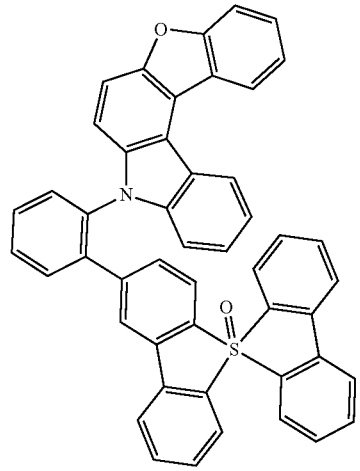
P057
P058
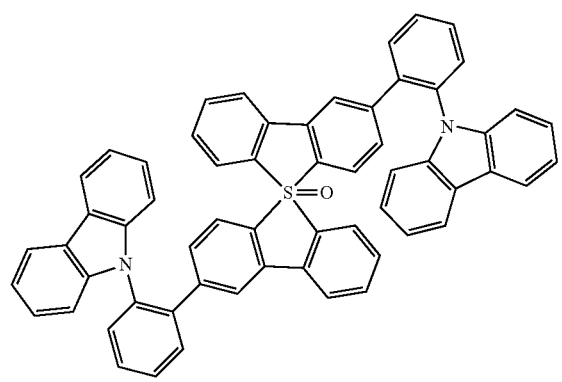

-continued
P059
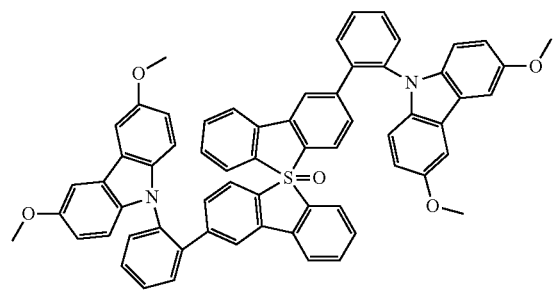
P060
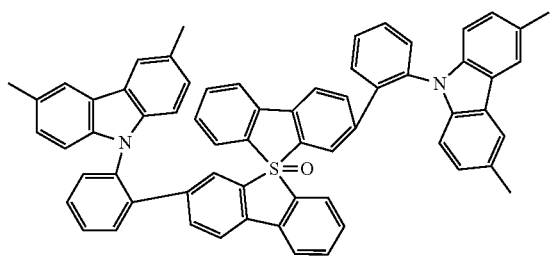
P061
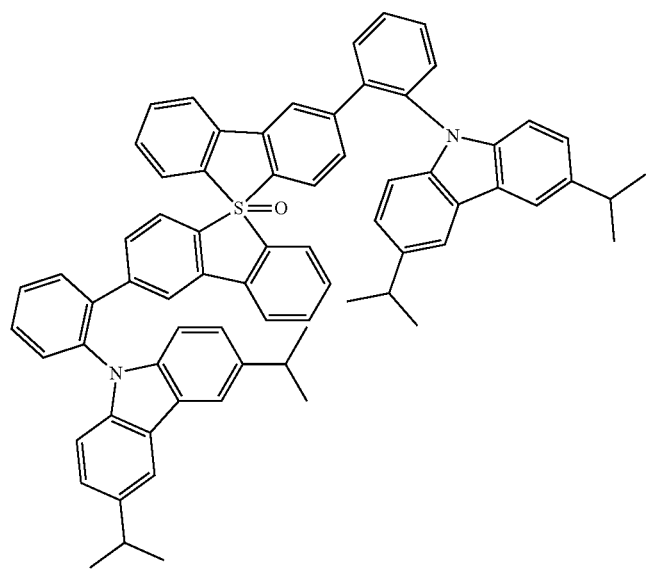
P062
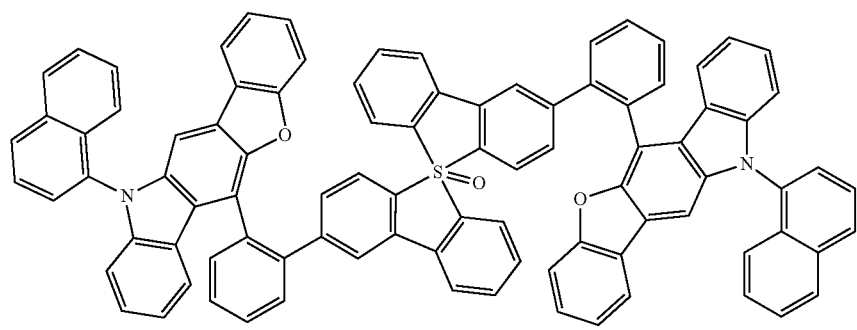

-continued
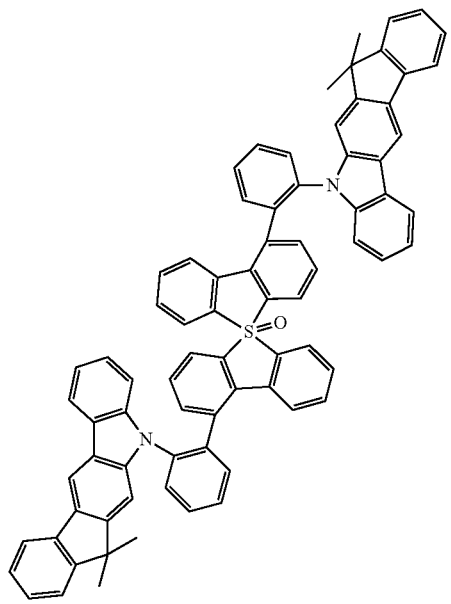
P063
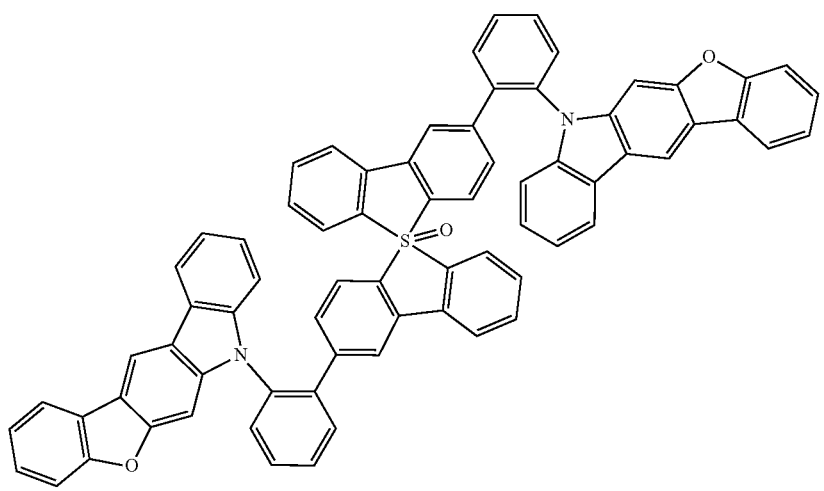
P064
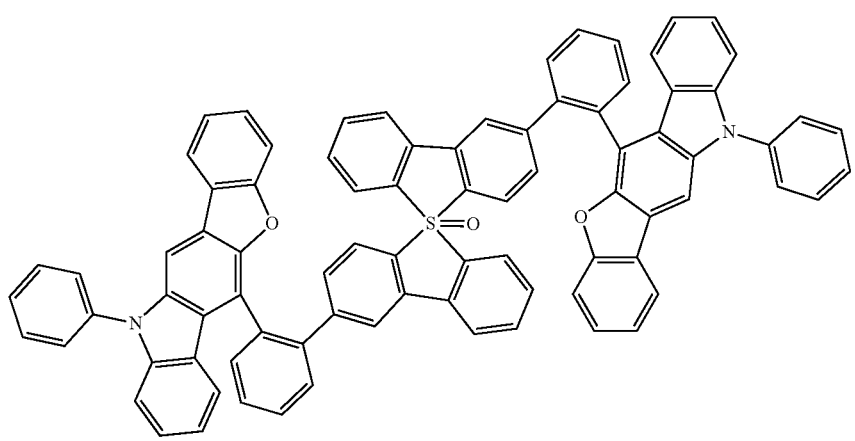
P065

-continued
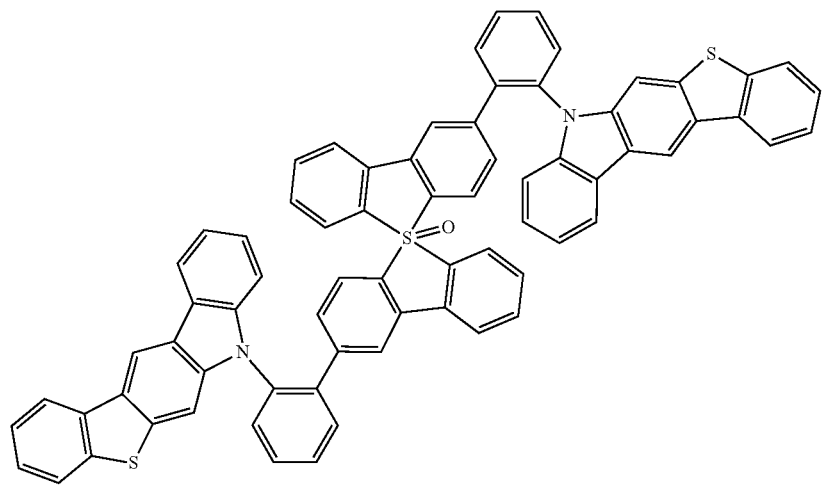
P066
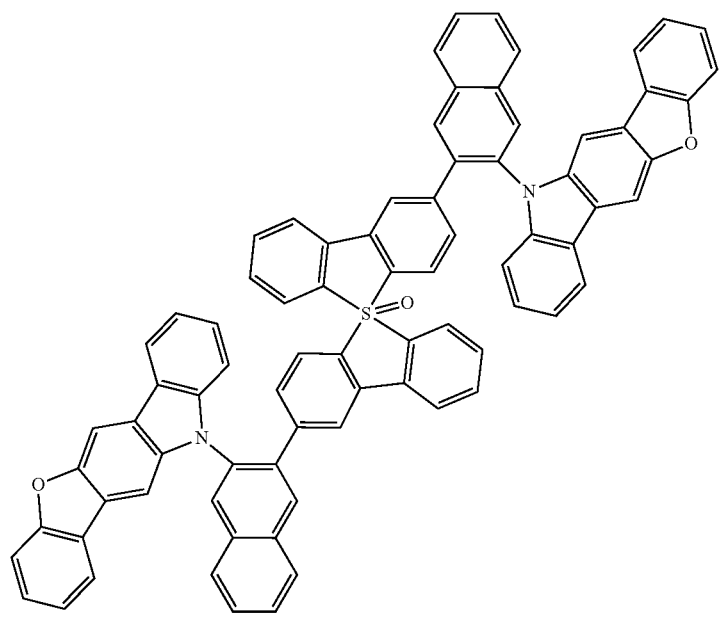
P067
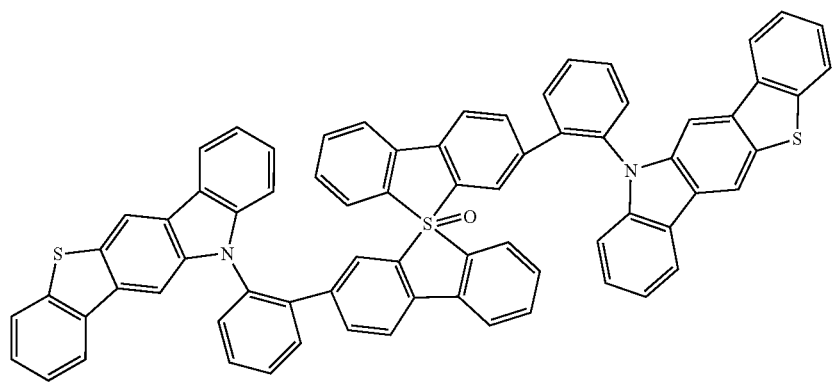
P068

-continued
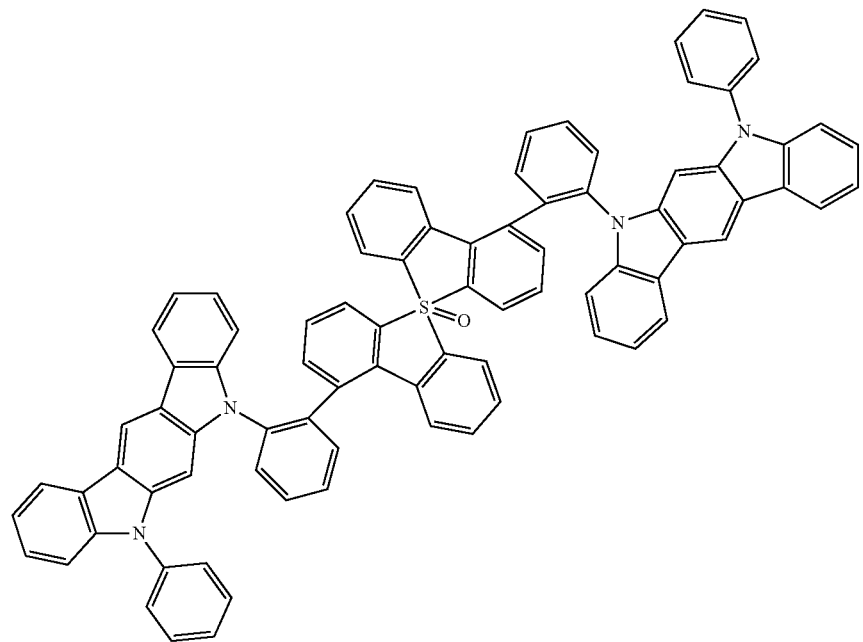
P069
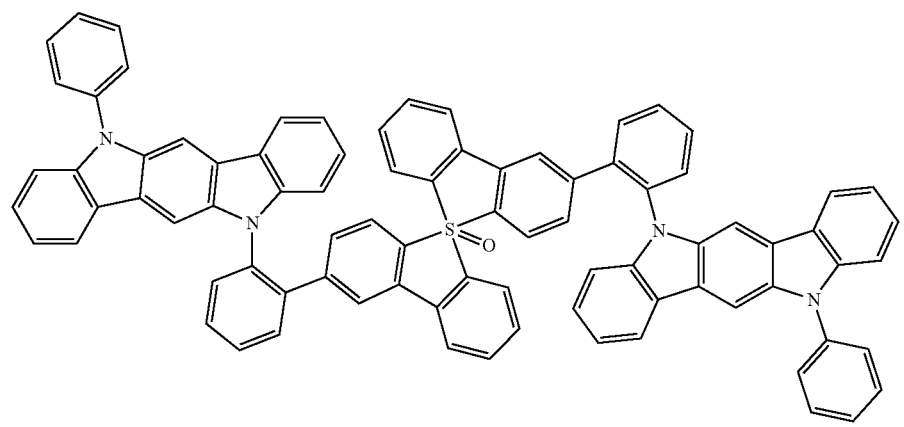
P070

-continued
P071
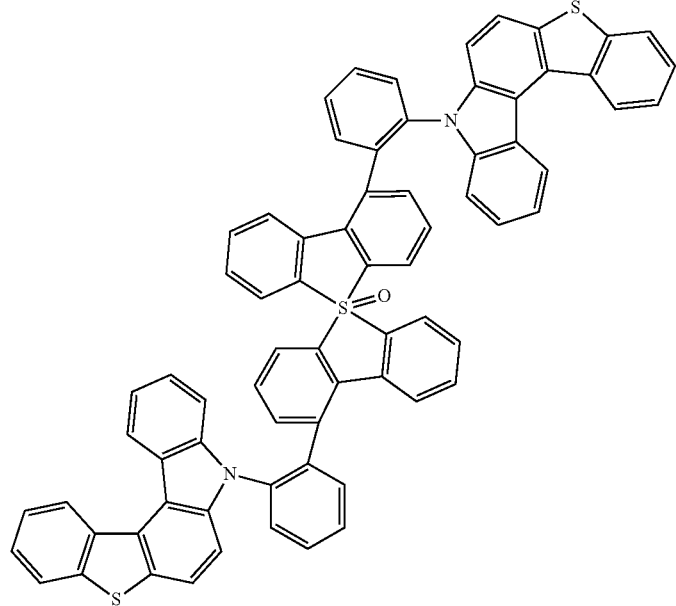
P072
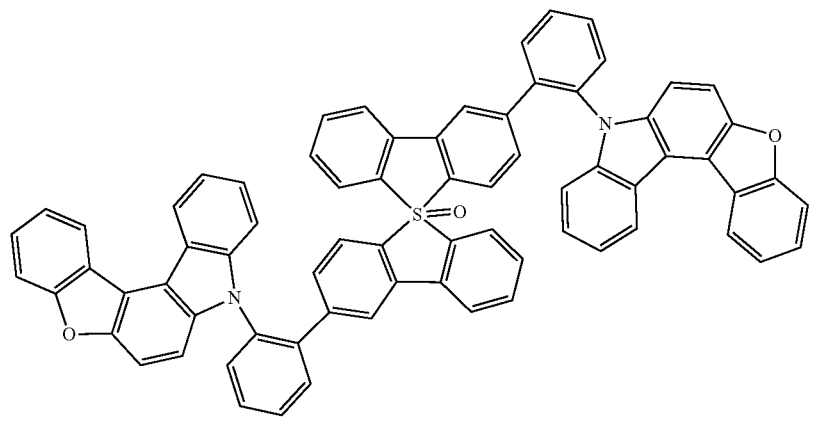
P073
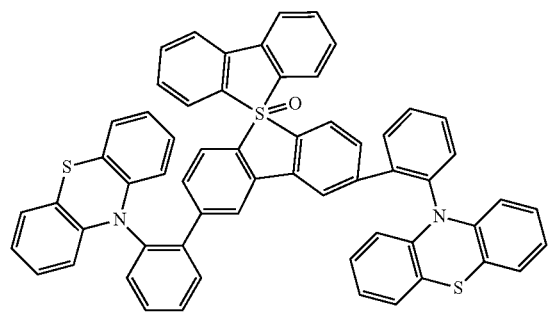
P074
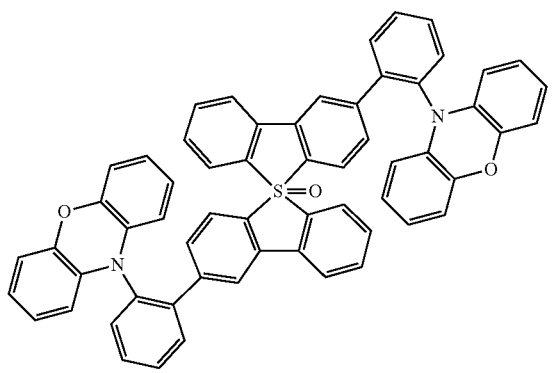

-continued
P075
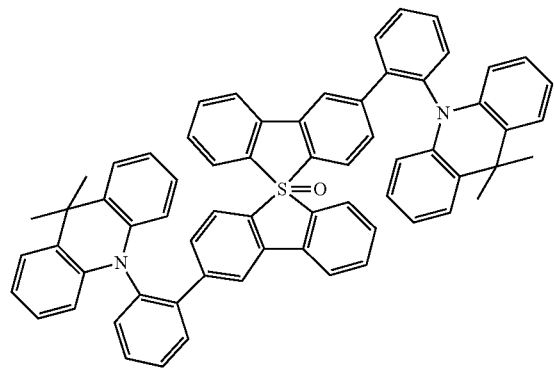
P076
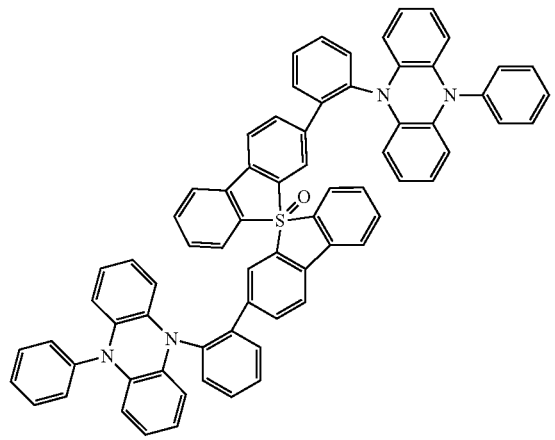
P077
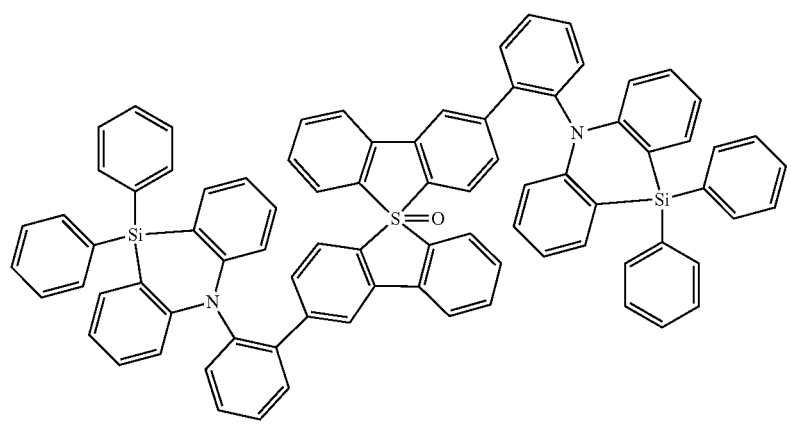
P078
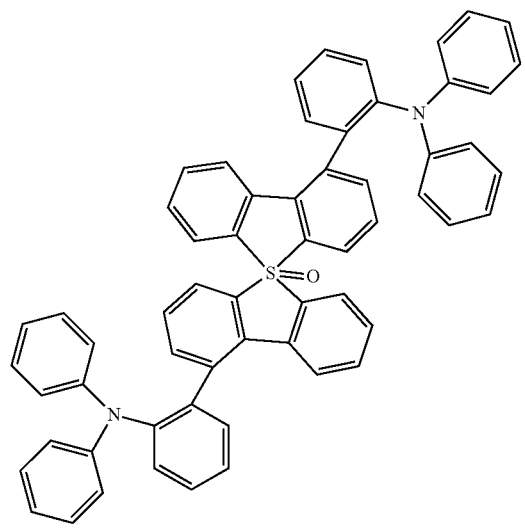

-continued
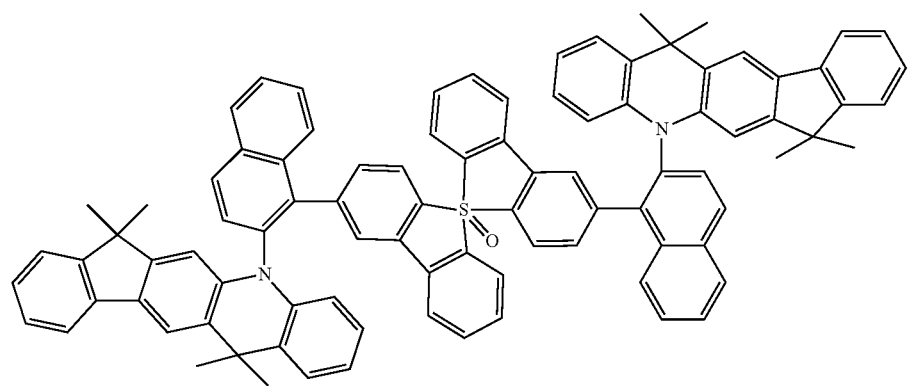
P079
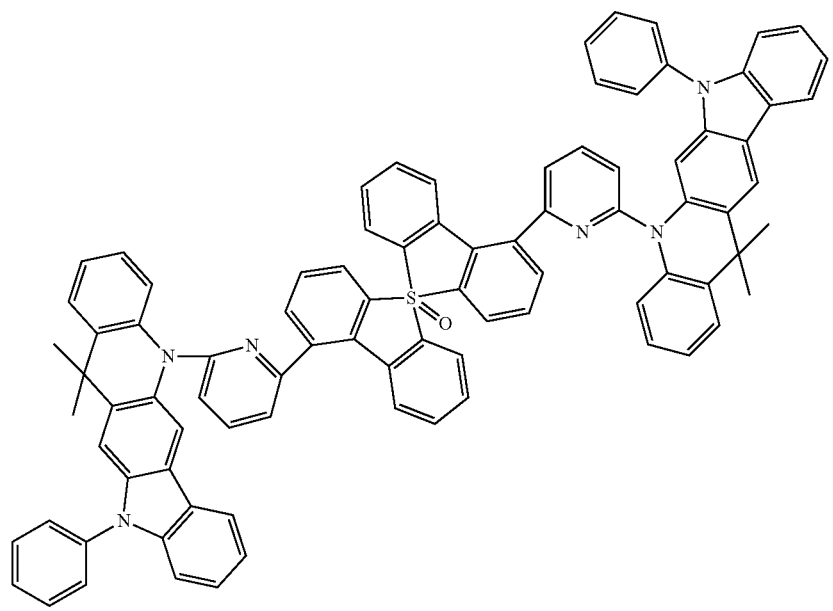
P080
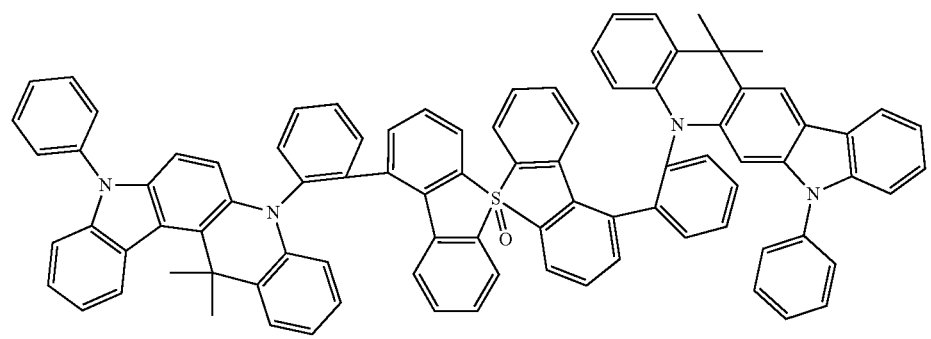
P081

-continued
P082
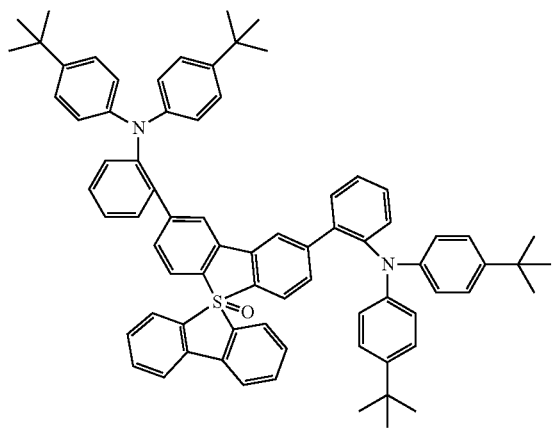
P083
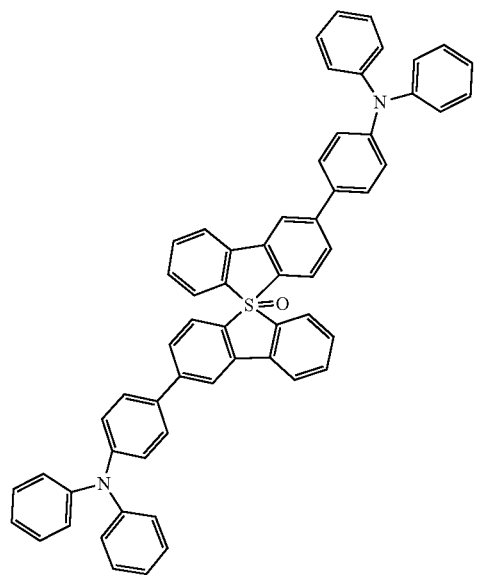
P084
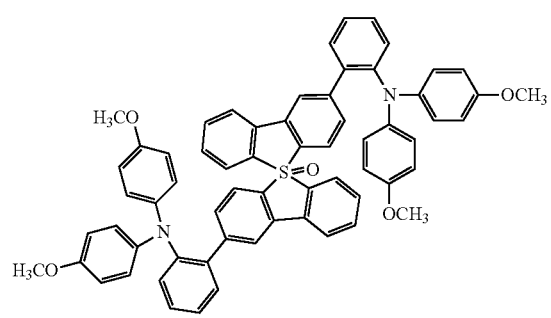
P085
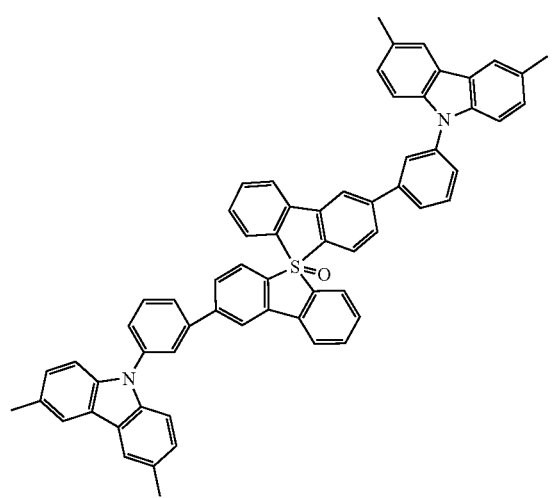

-continued
P086
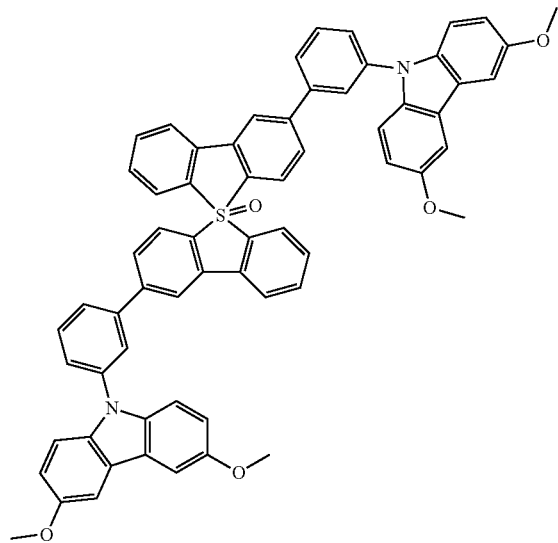
P087
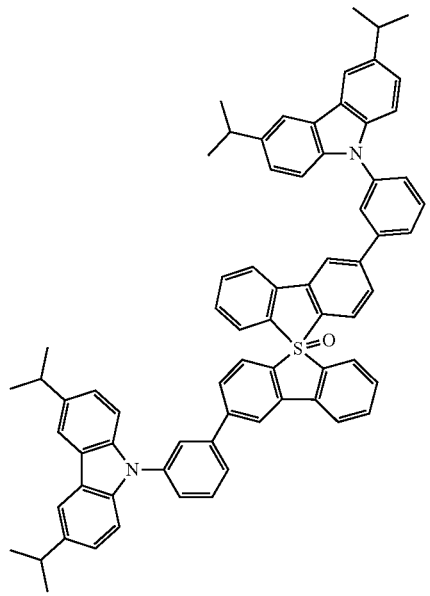
P088
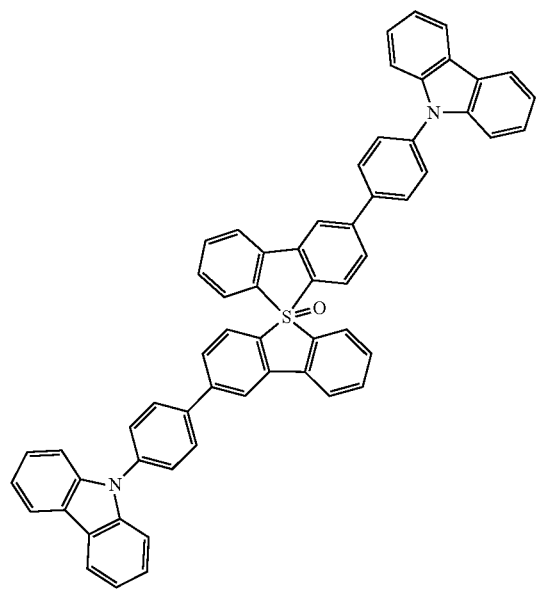

-continued
P089
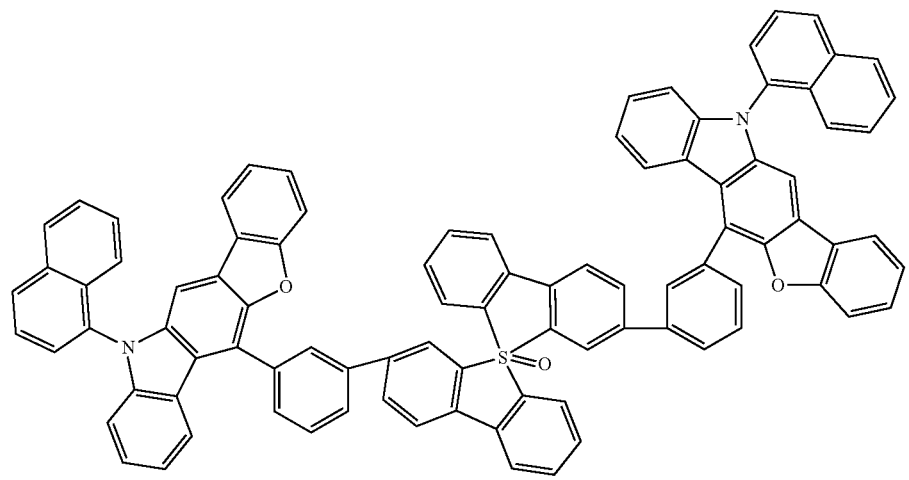
P090
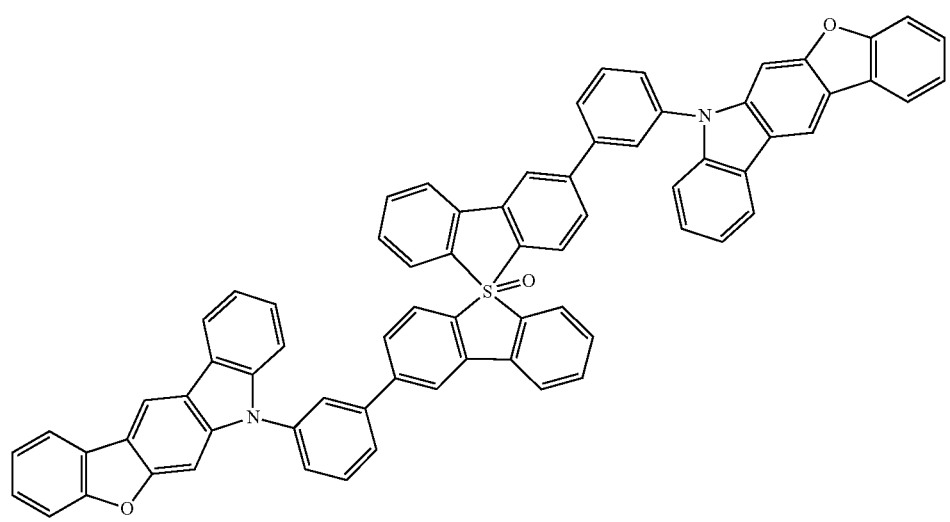
P091
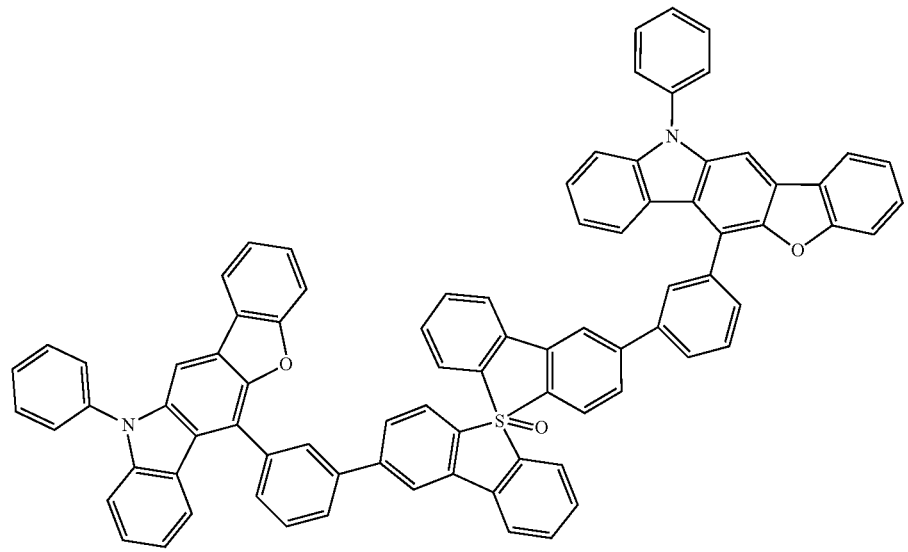

-continued
P092 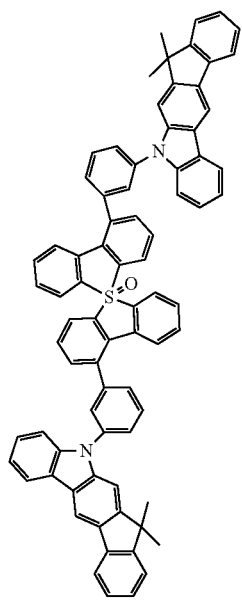
P093 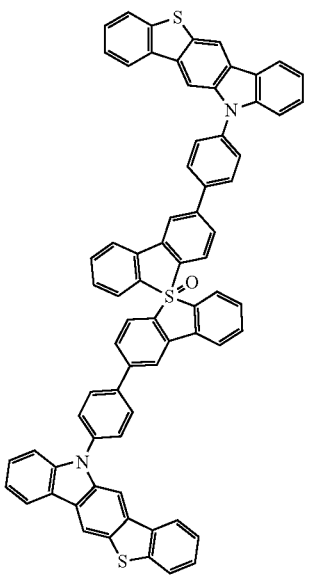
P094 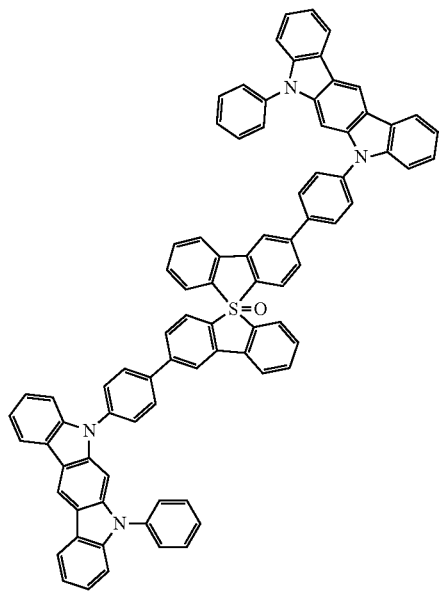
P095 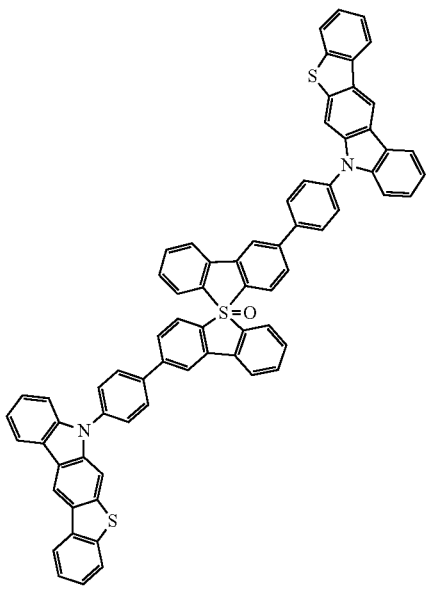

-continued
P096
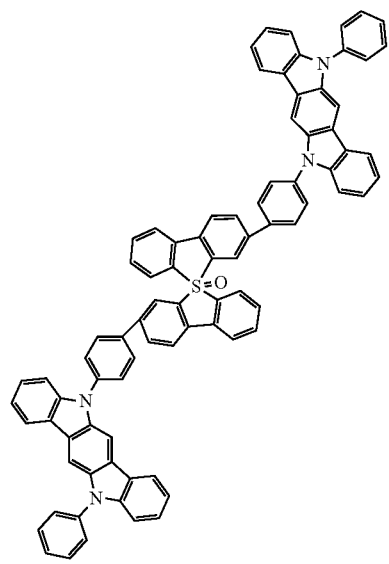
P097
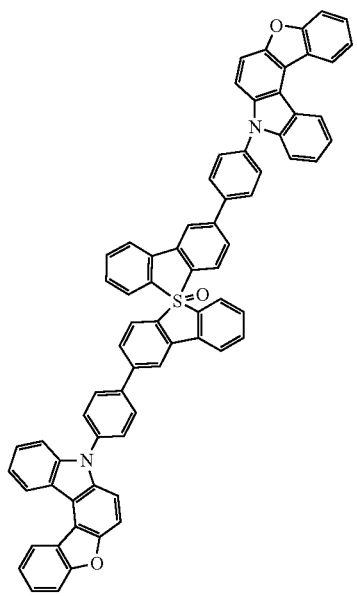
P098
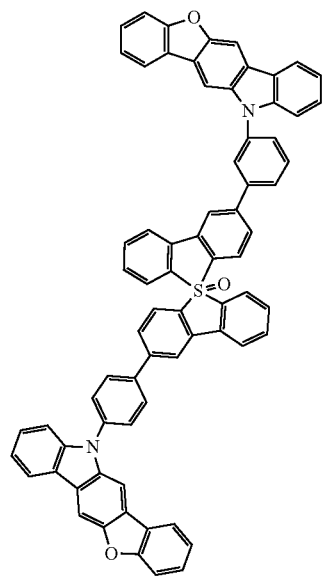
P099
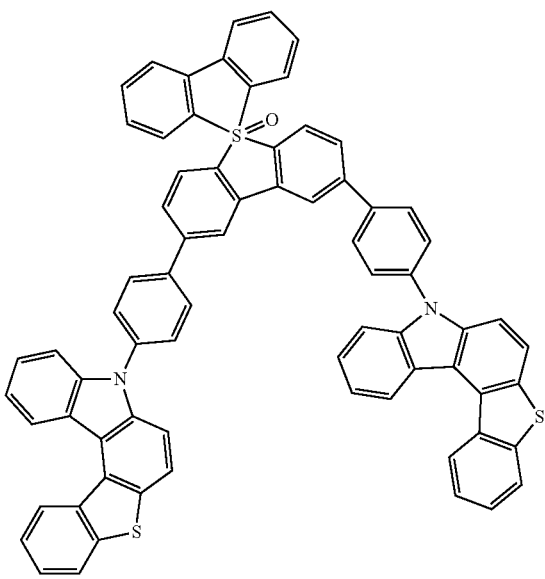

-continued
P100
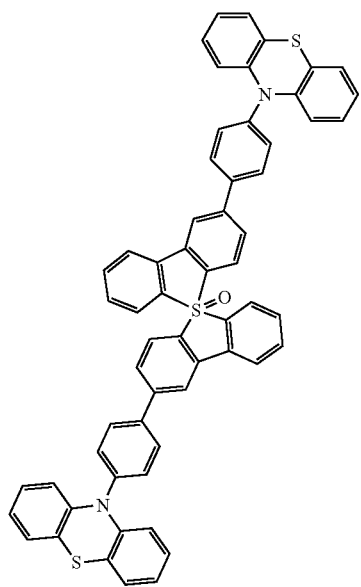
P101
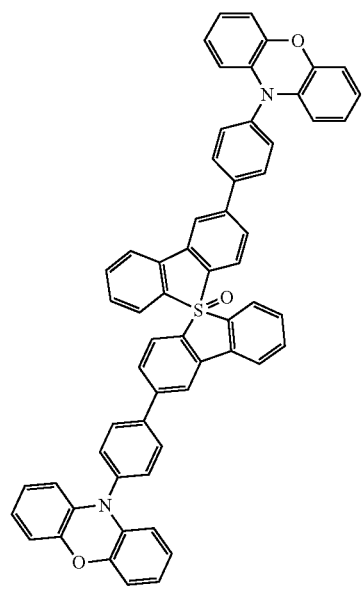
P102
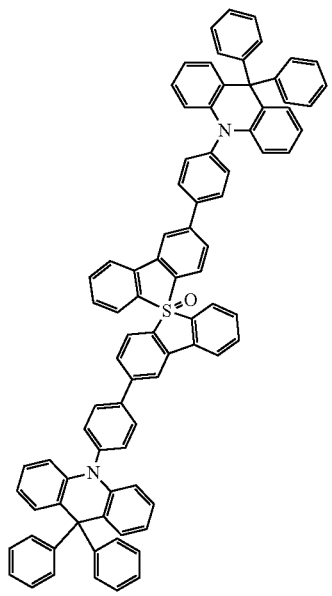

-continued
P103
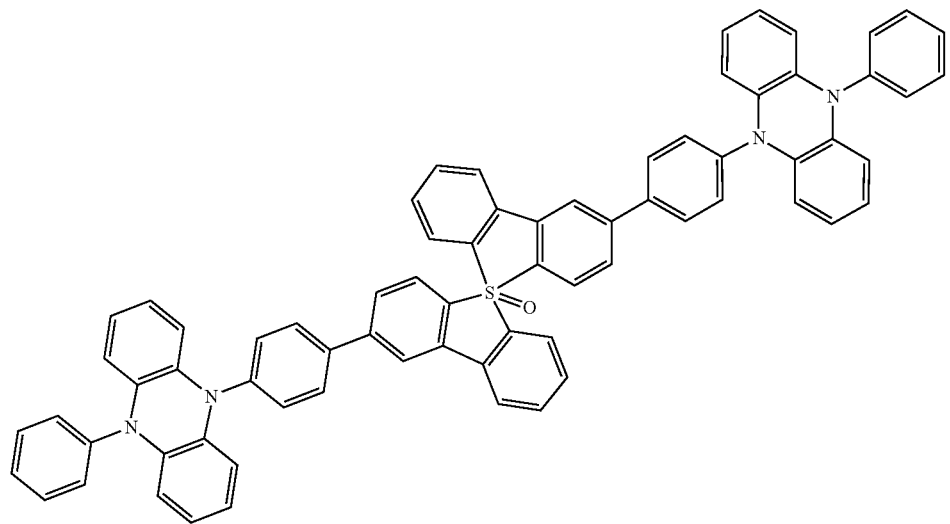
P104
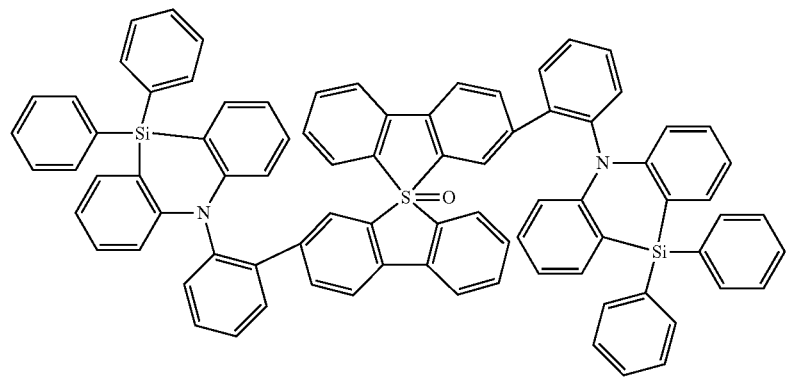
P105
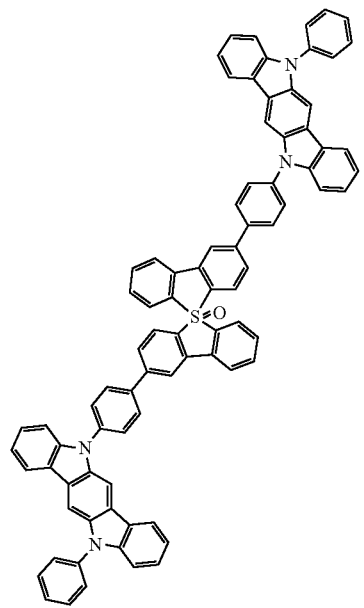
P106
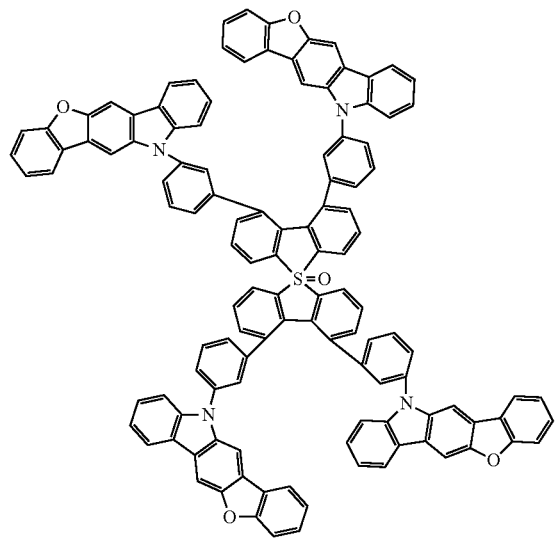

P107
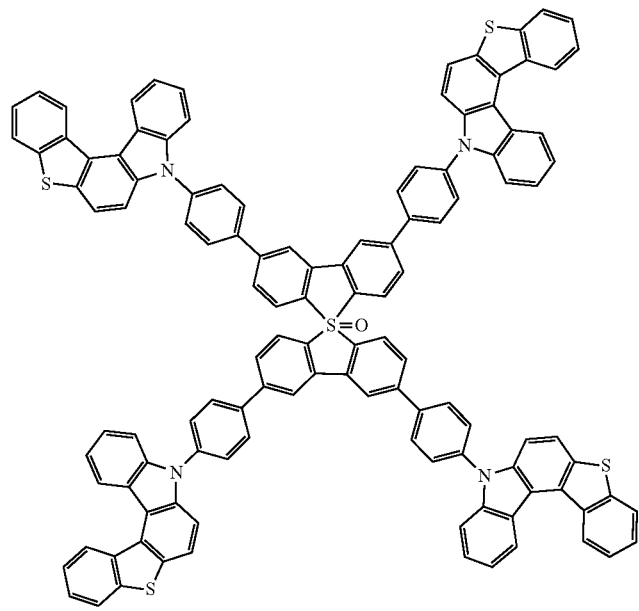
P108
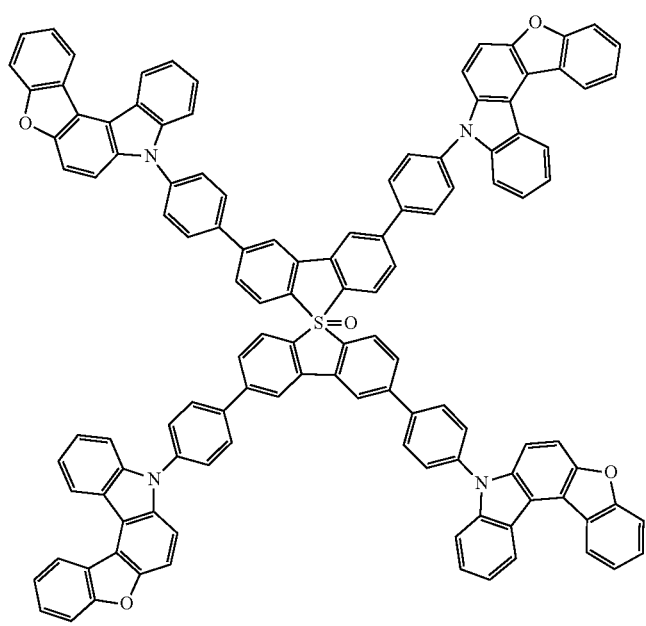

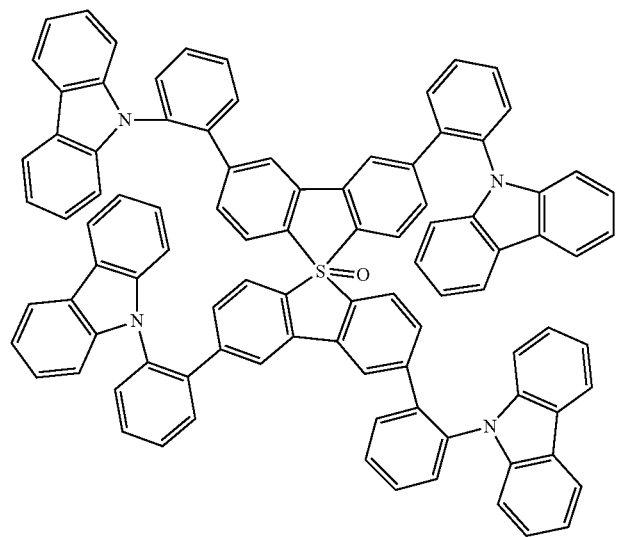
P109
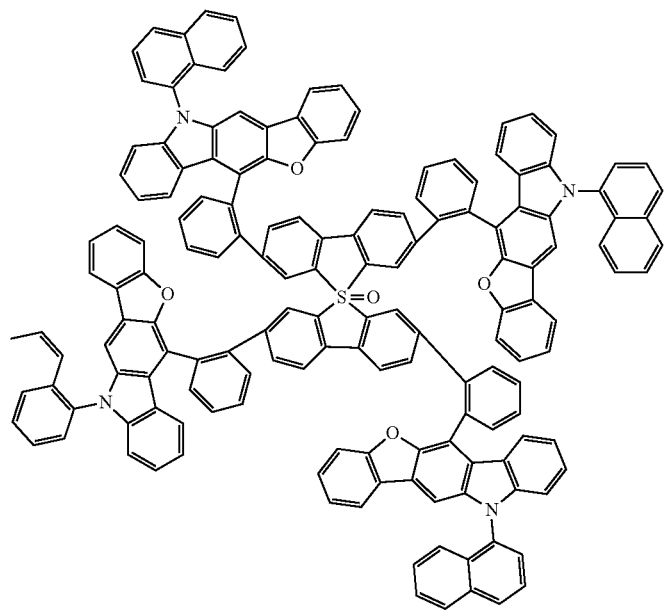
P110

-continued
P111
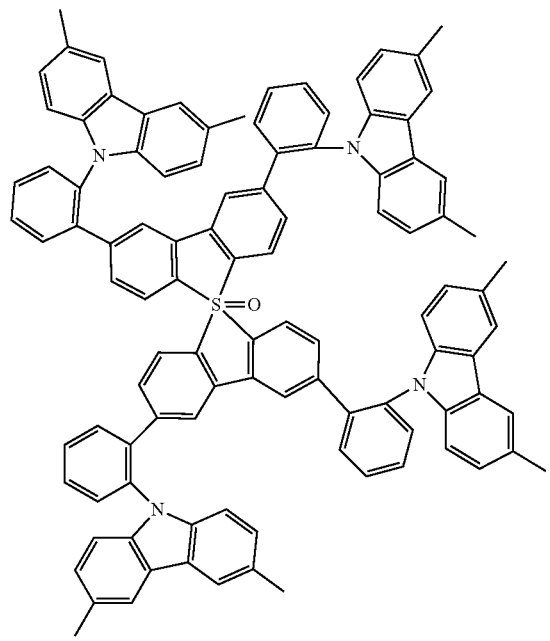
P112
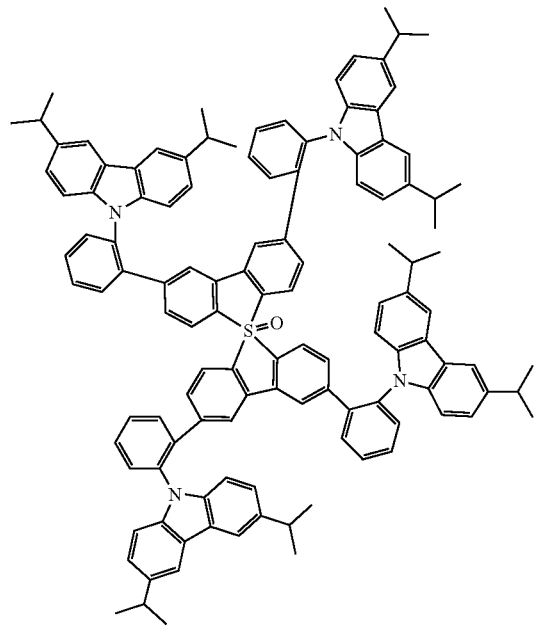
P113
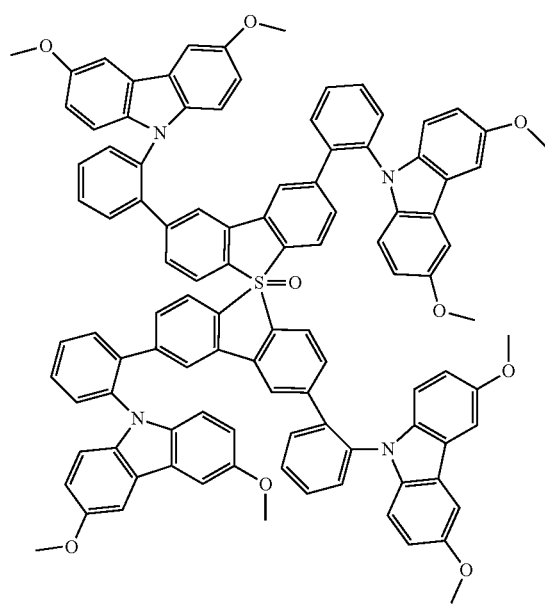
P114
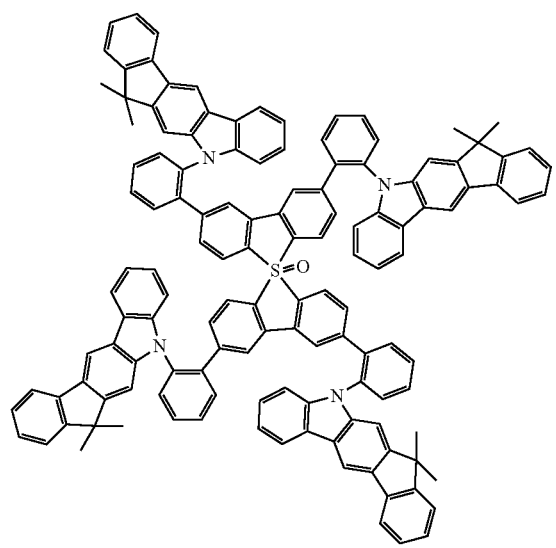

-continued
P115
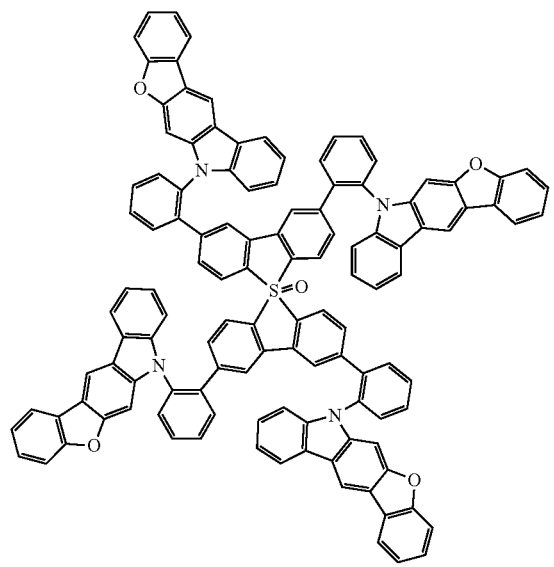
P116
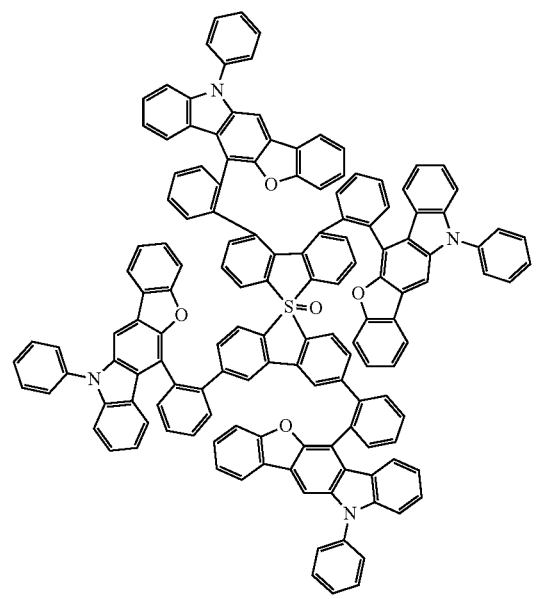
P117
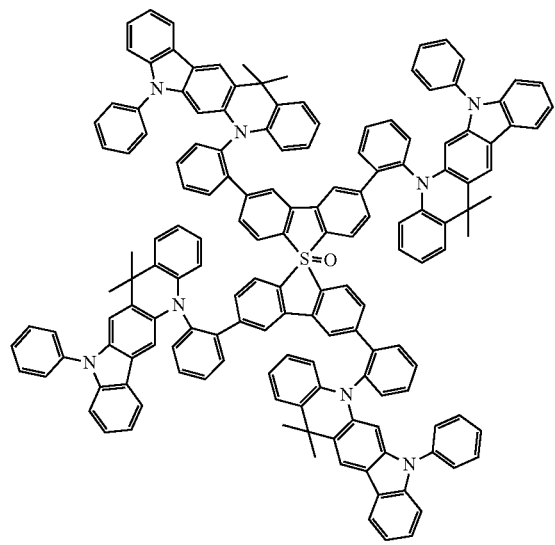
P118
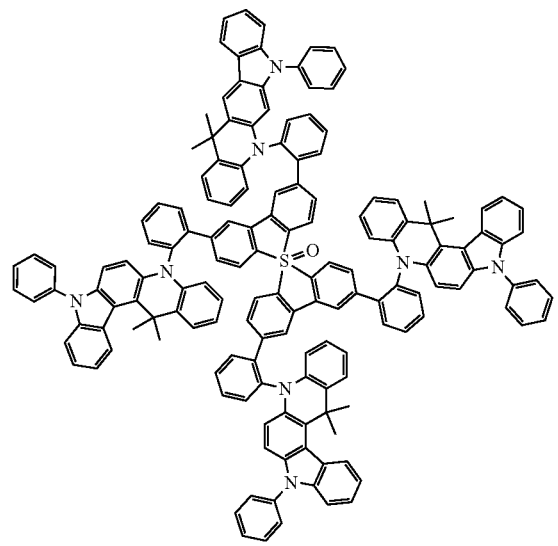

-continued
P119
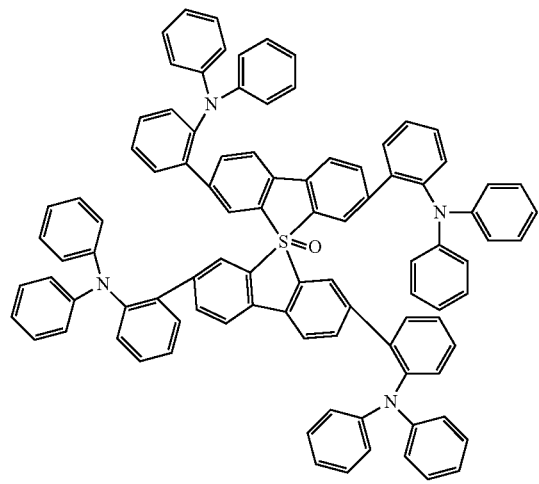
P120
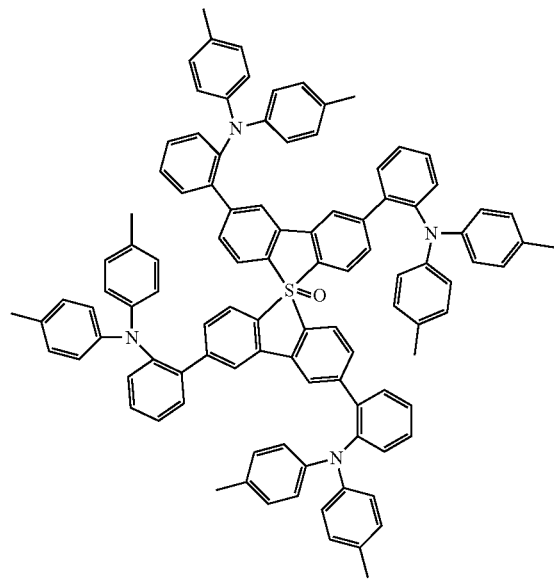
P121
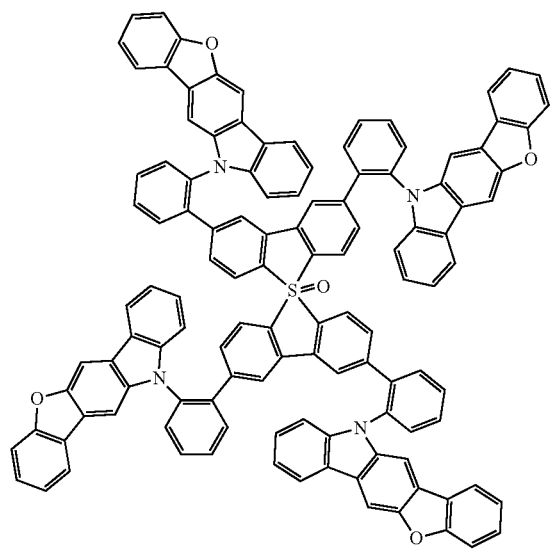
P122
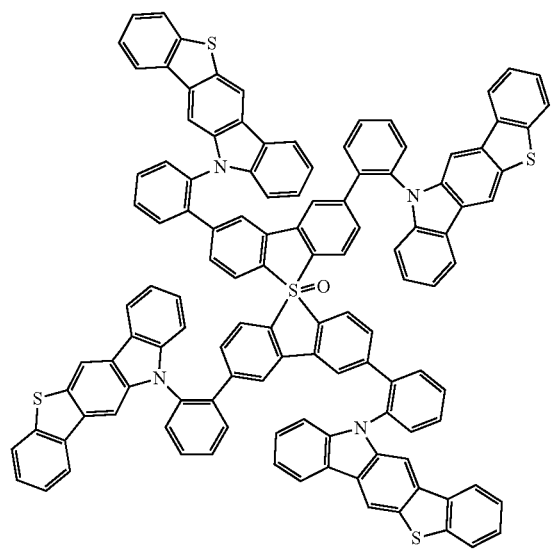

-continued
P123
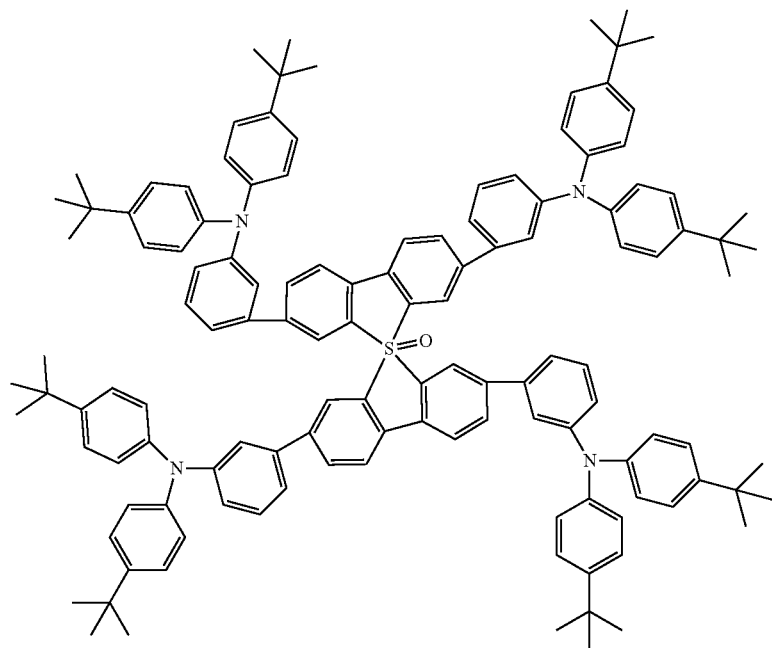
P124
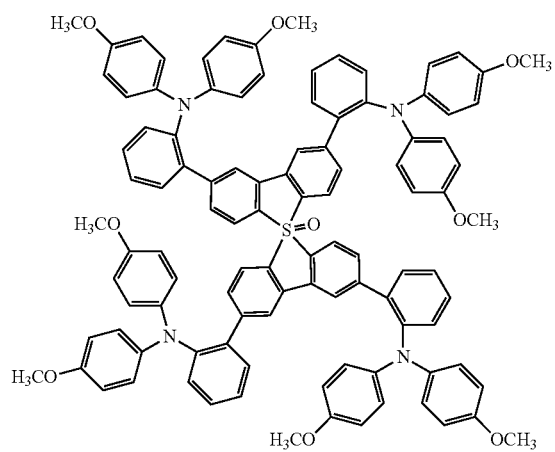
P125
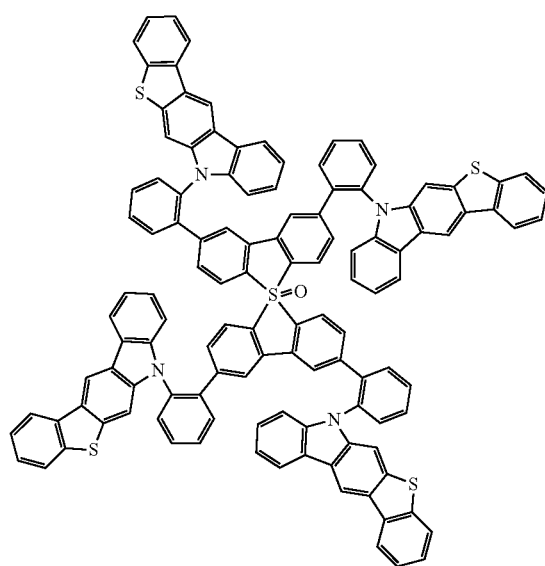

-continued
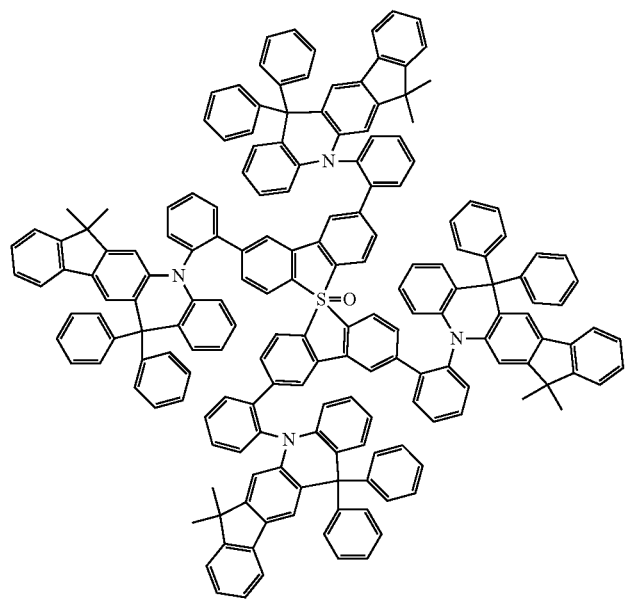
P126
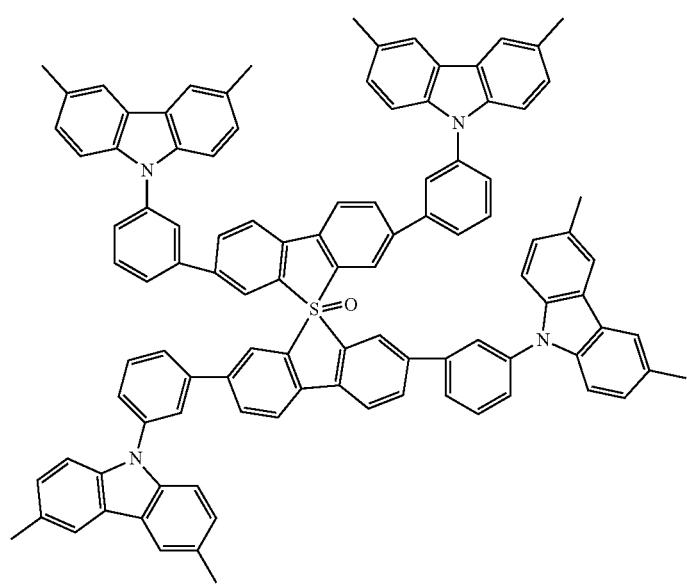
P127

-continued
211 P128
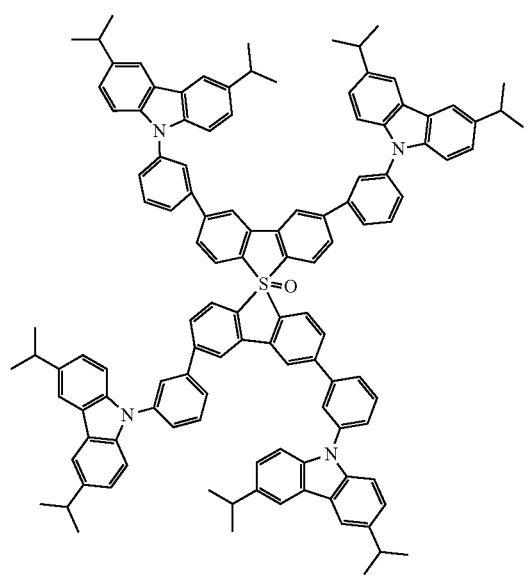
212 P129
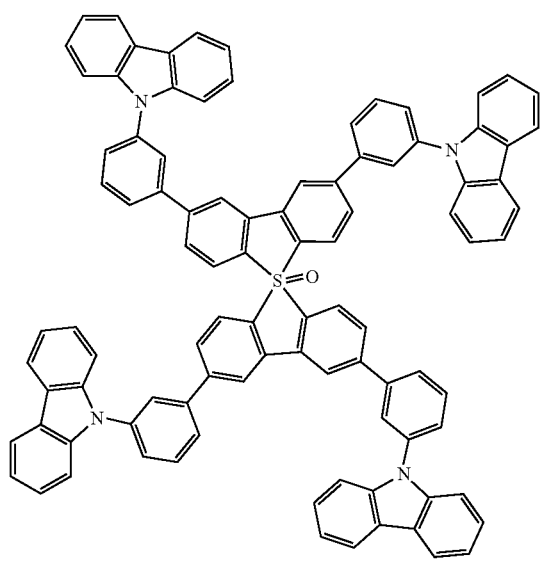
P130
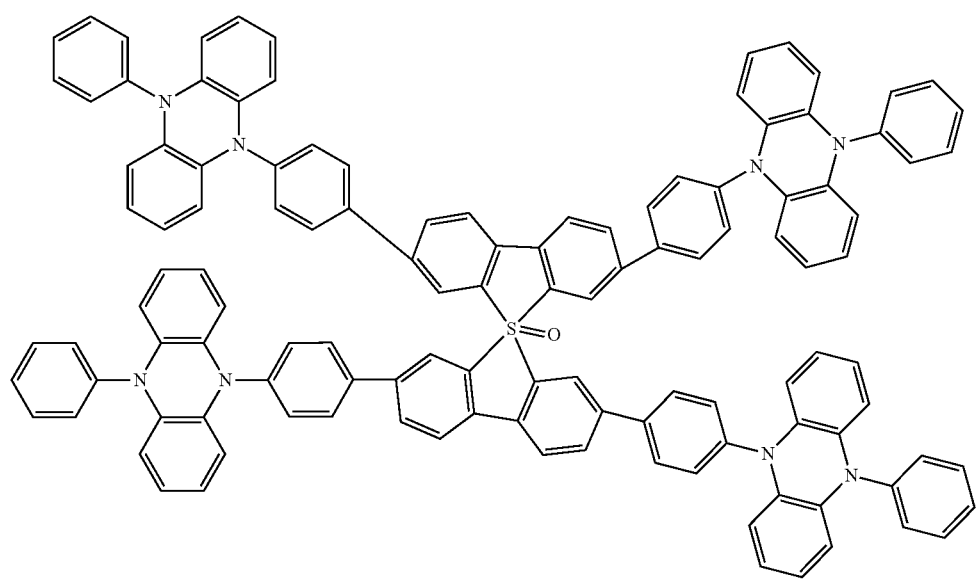

-continued
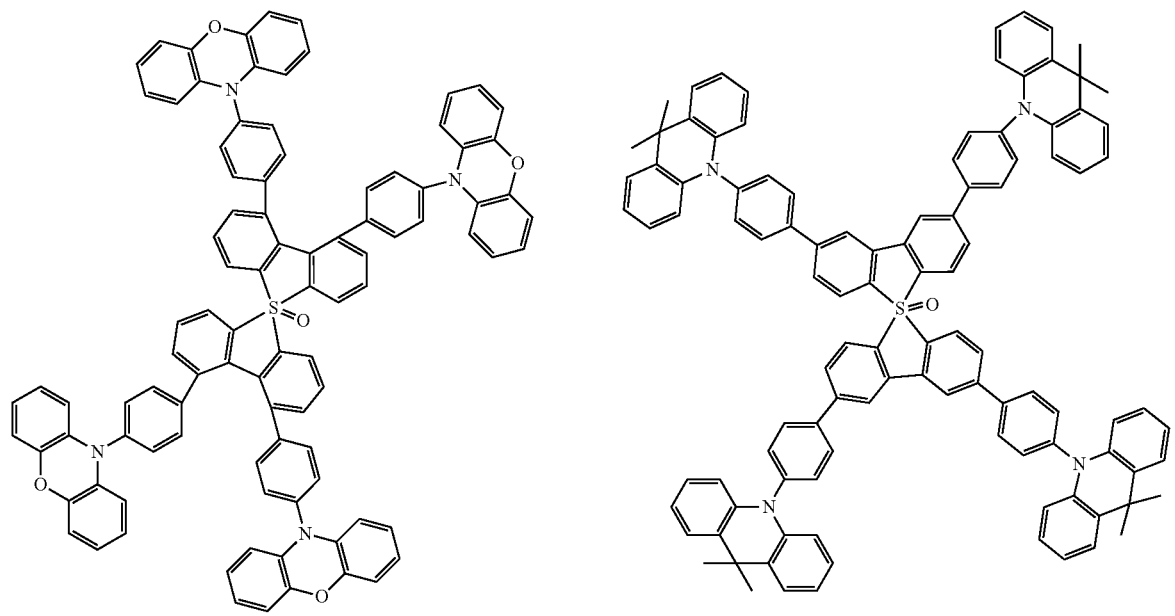
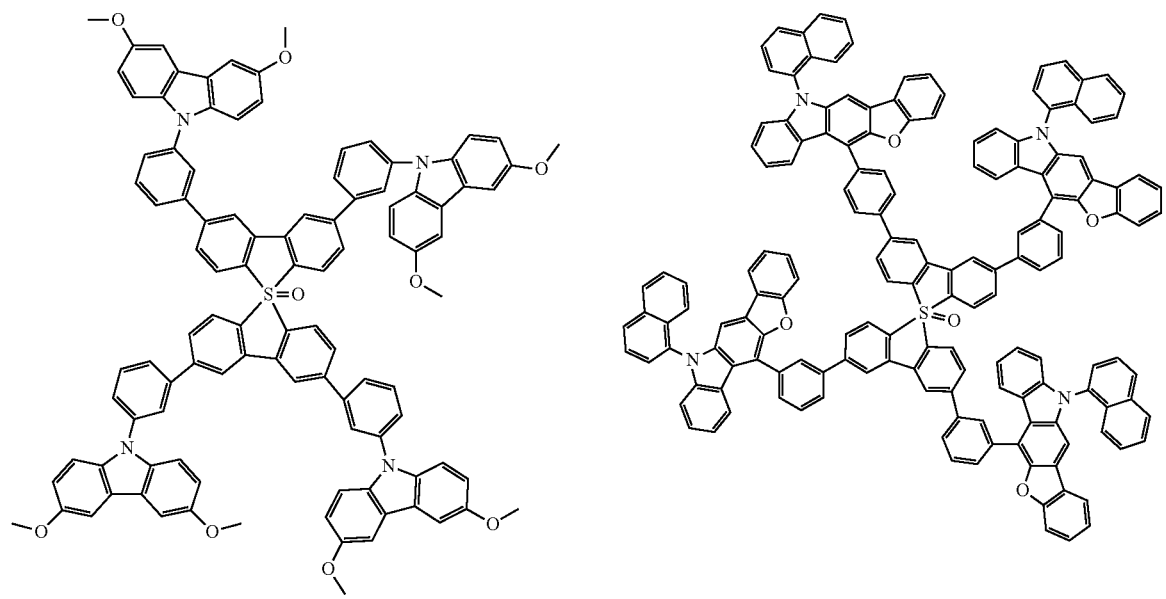

-continued
P135
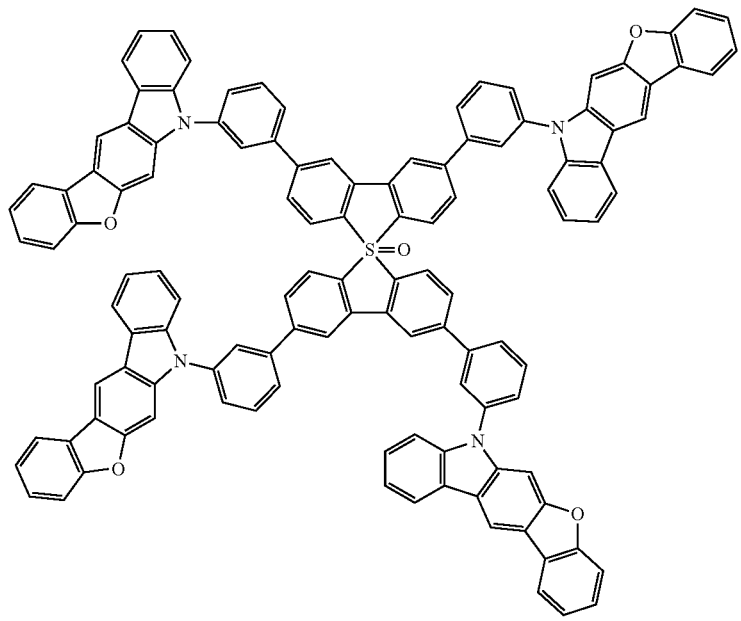
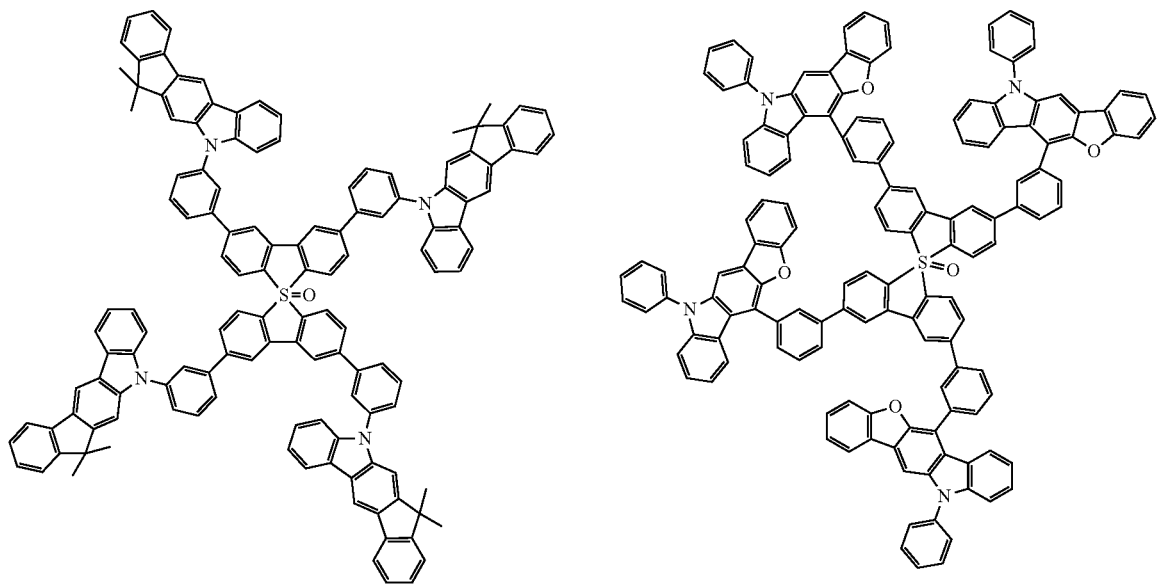

-continued
P138
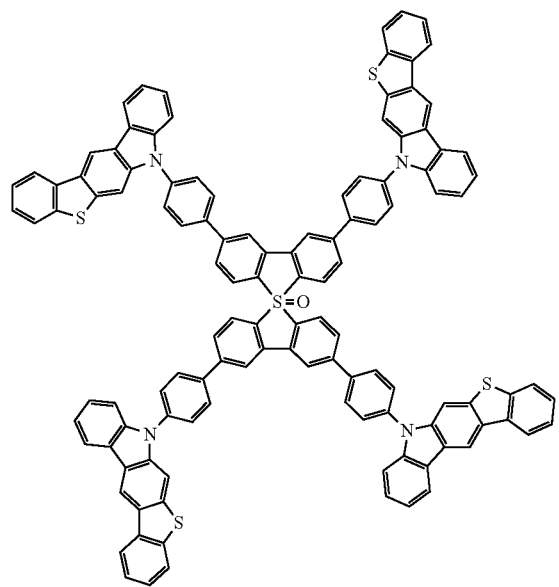
P139
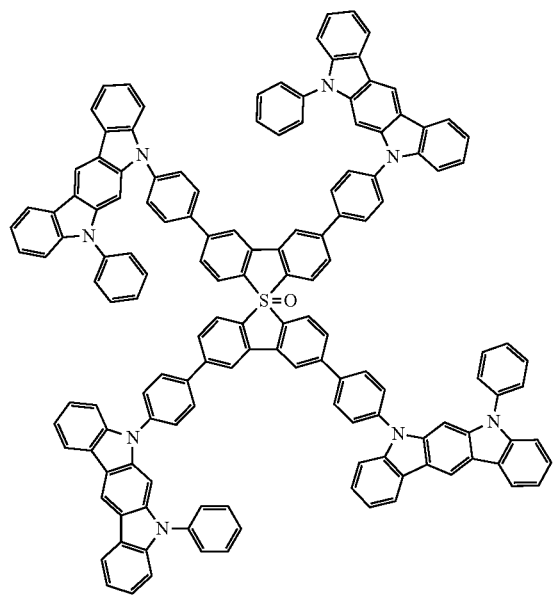
P140
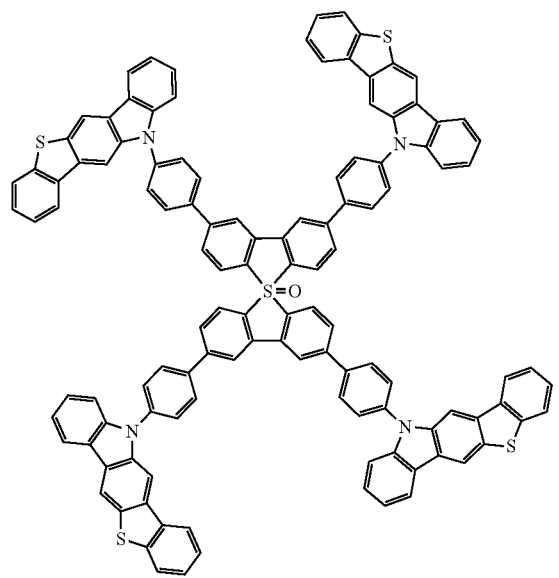
P141
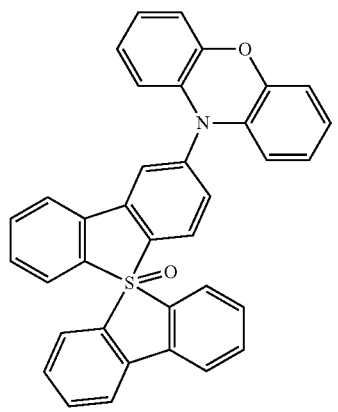

-continued
P142
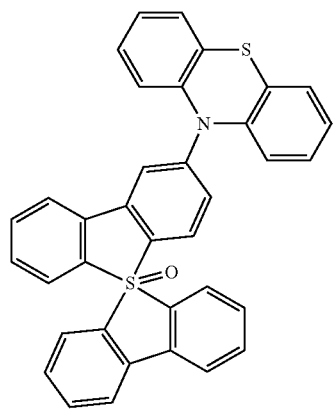
P143
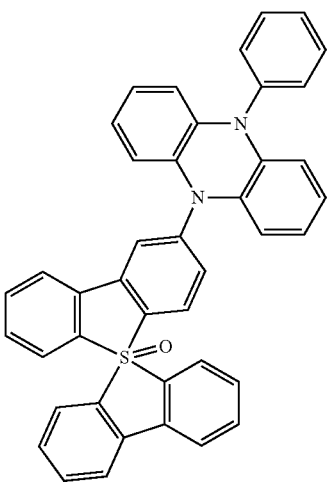
P144
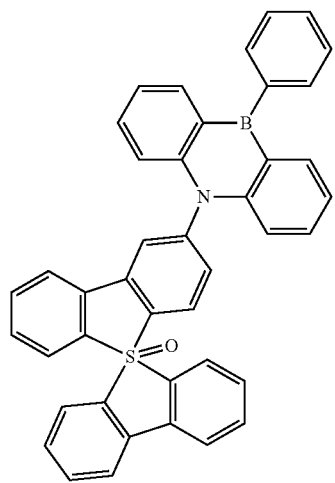
P145
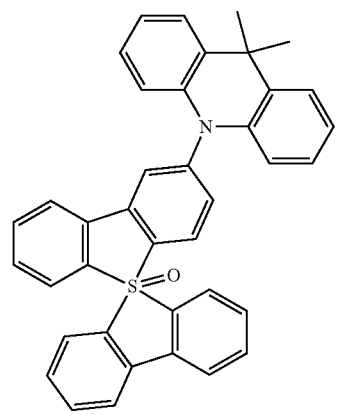
P146
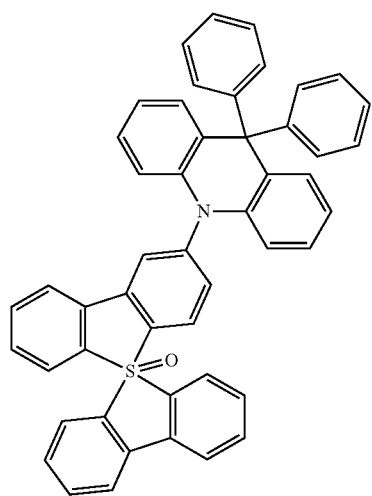
P147
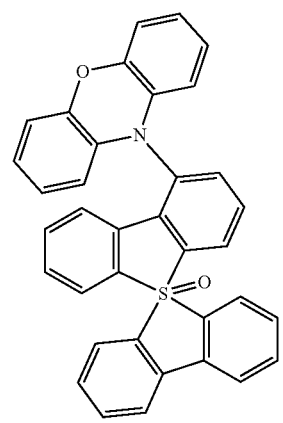

-continued
P148
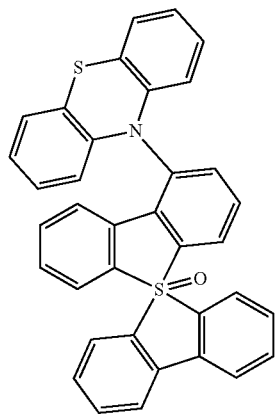
P149
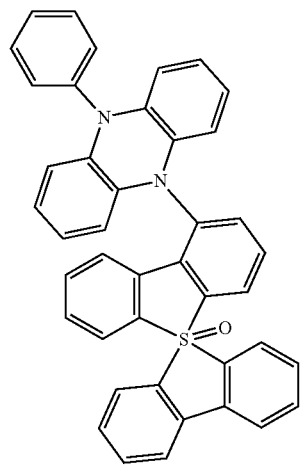
P150
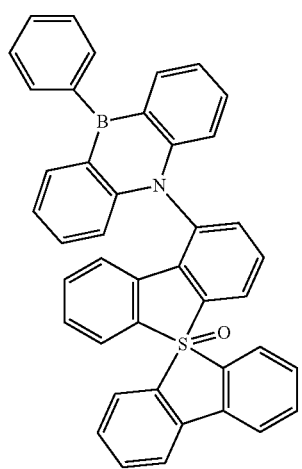
P151
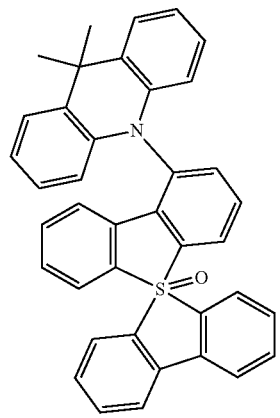
P152
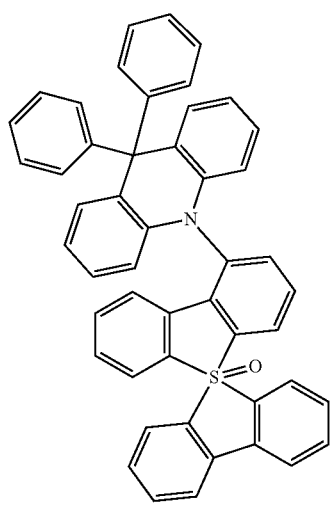
P153
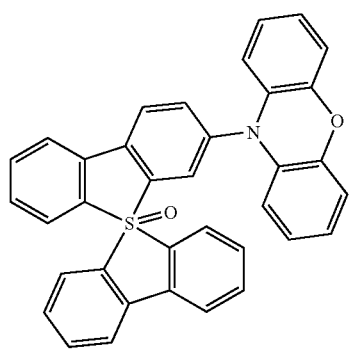

-continued
P154
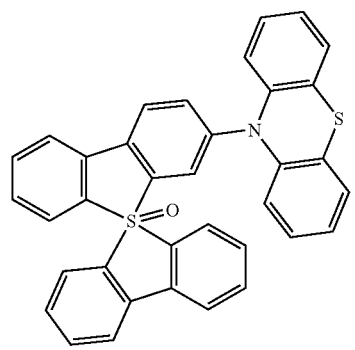
P155
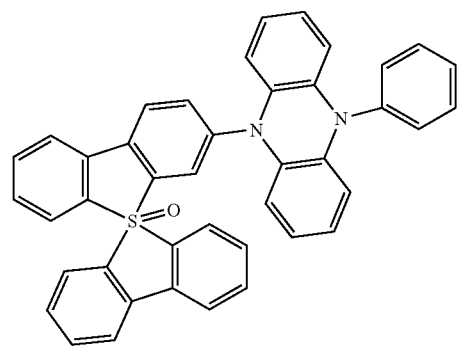
P156
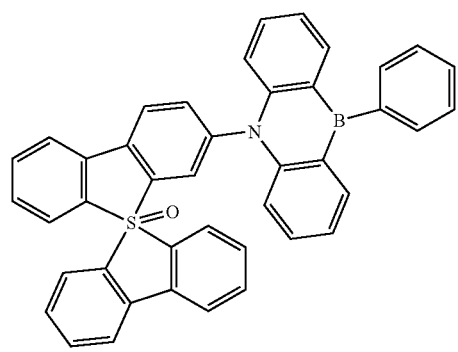
P157
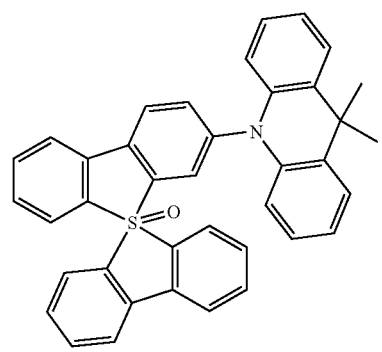
P158
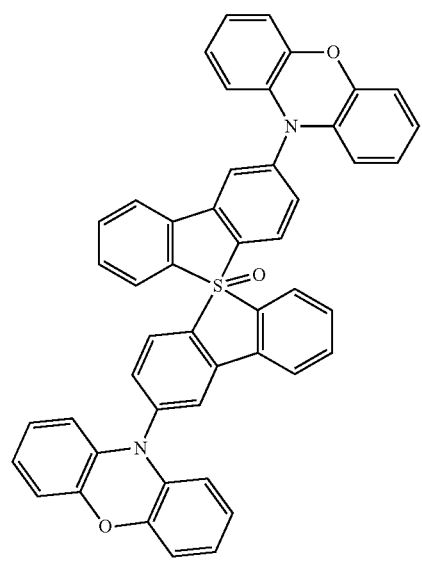
P159
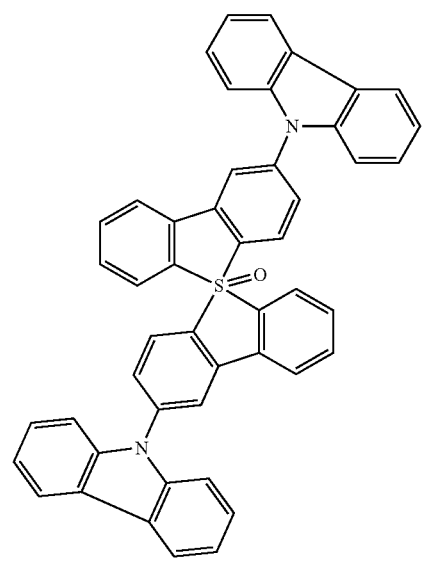

-continued
P160 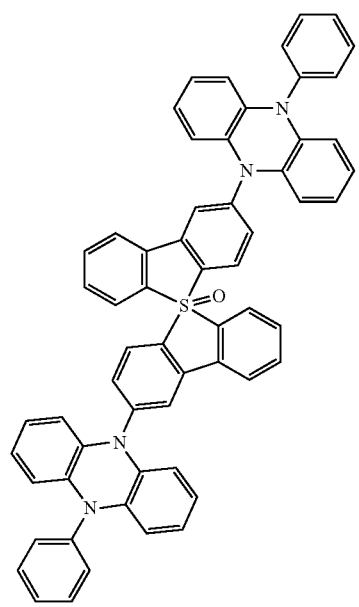
P161 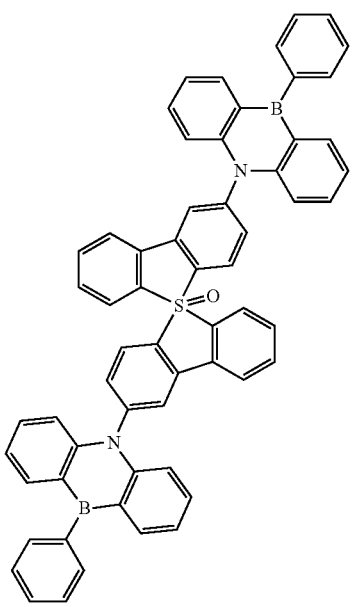
P162 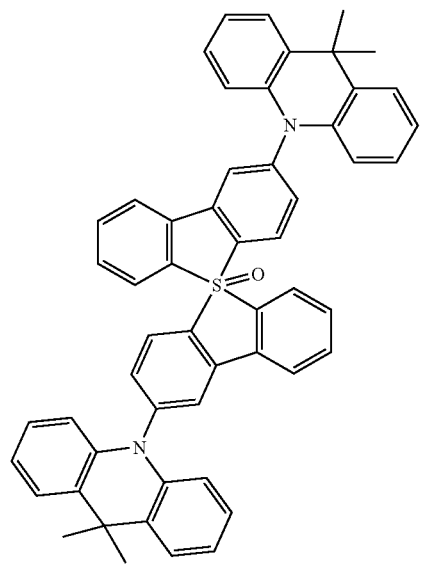
P163 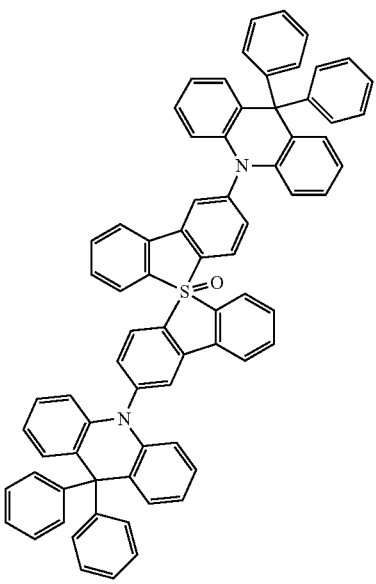

-continued
P164
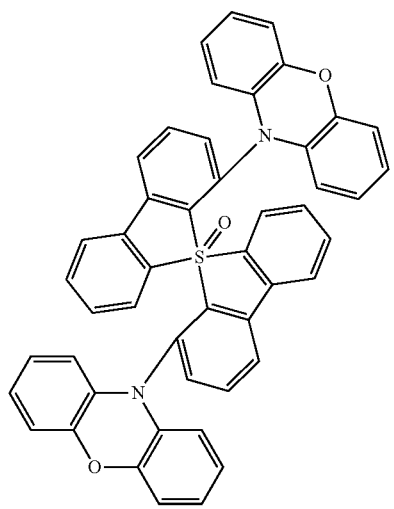
P165
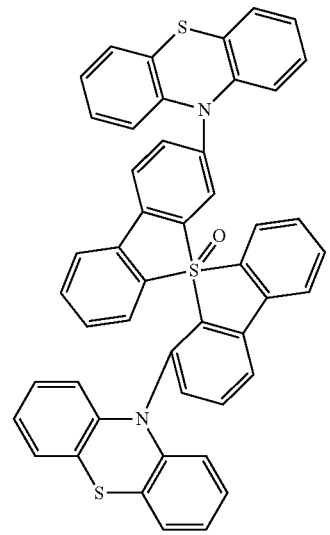
P166
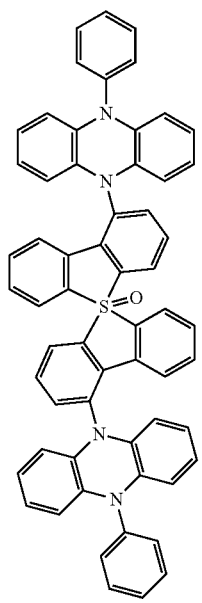
P167
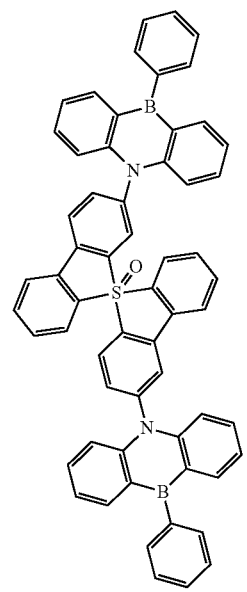
P168
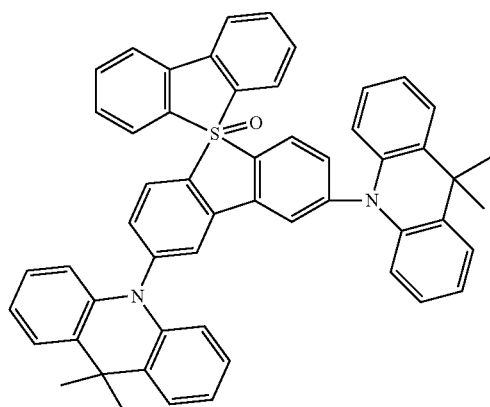
P169
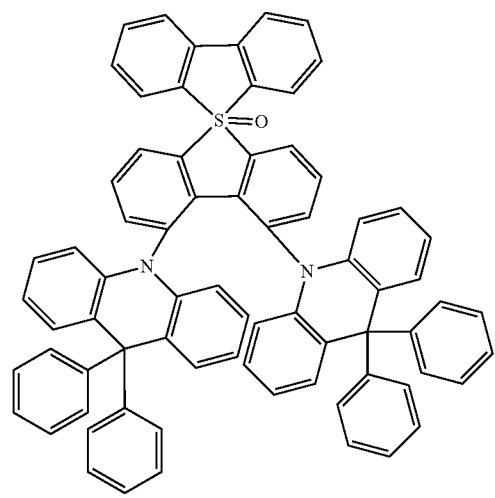

-continued
P170
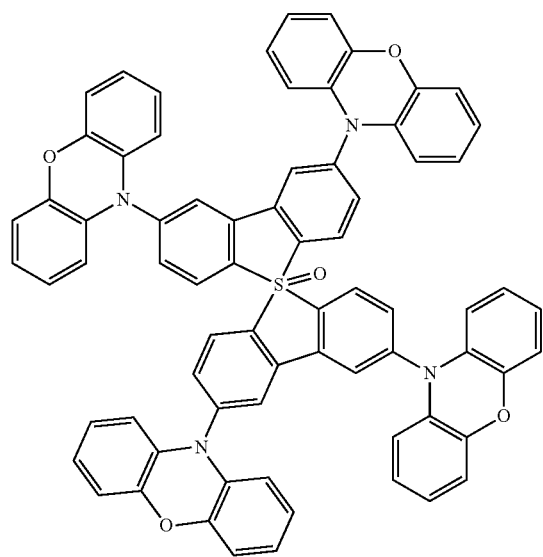
P171
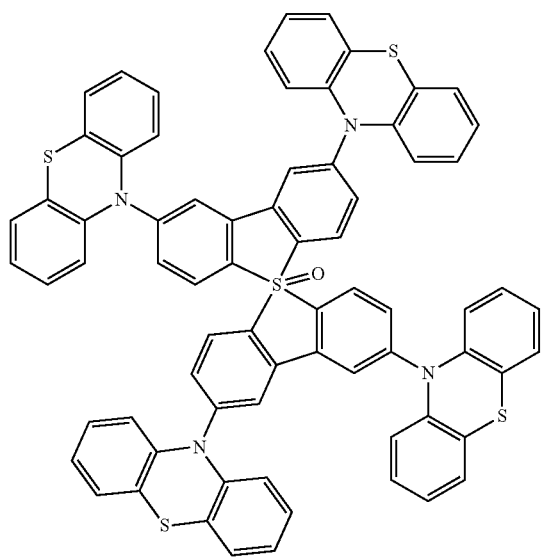
P172
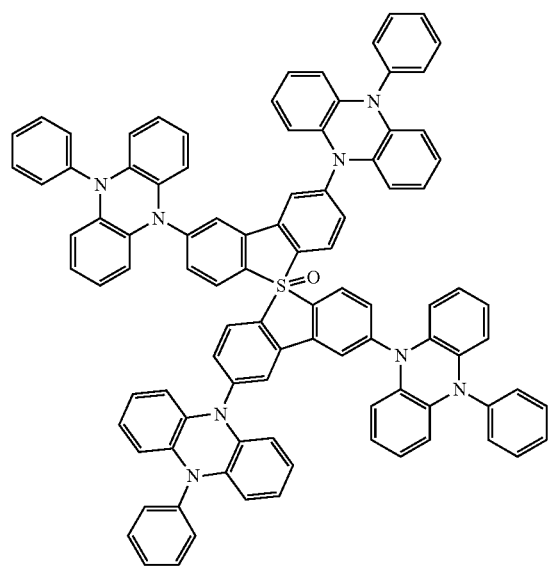
P173
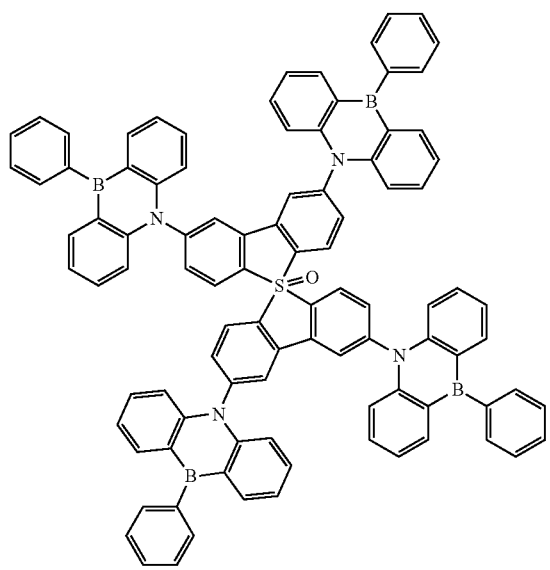

-continued
P174
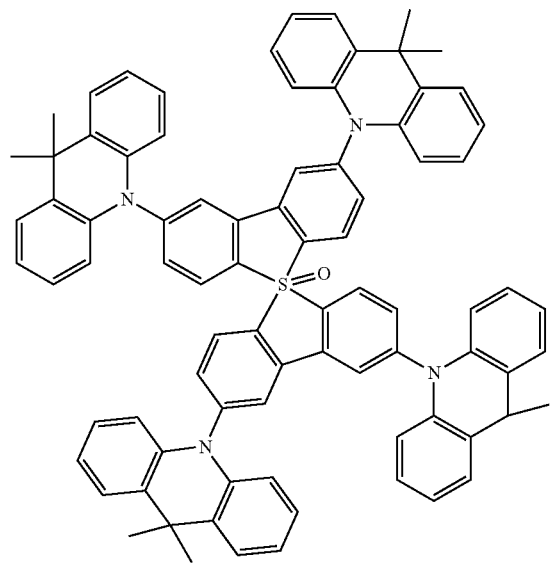
P175
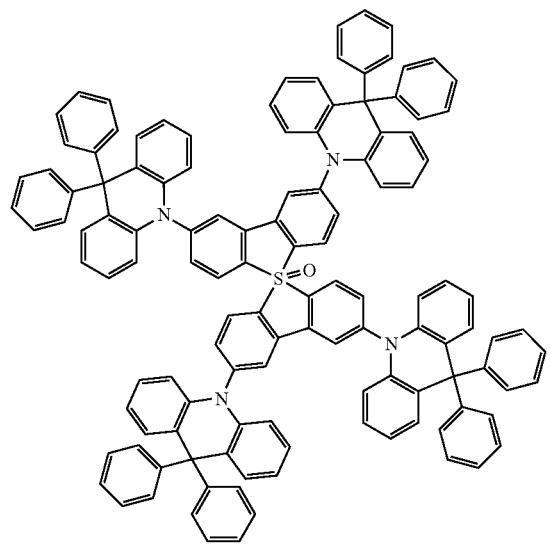
P176
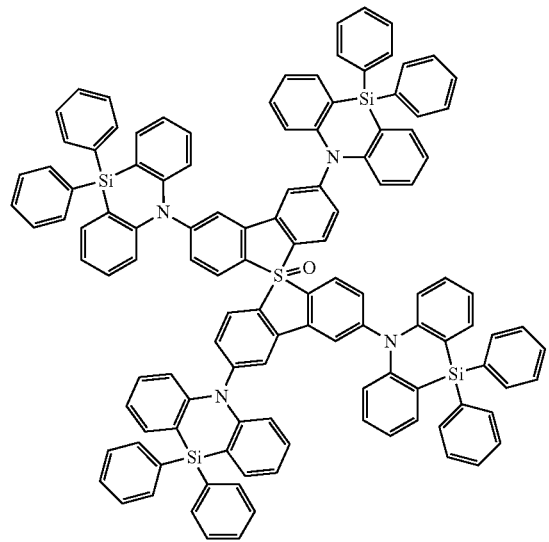
P177
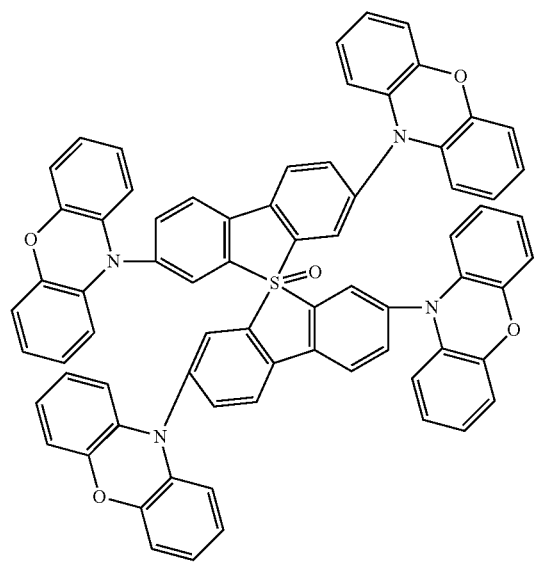

-continued
P178
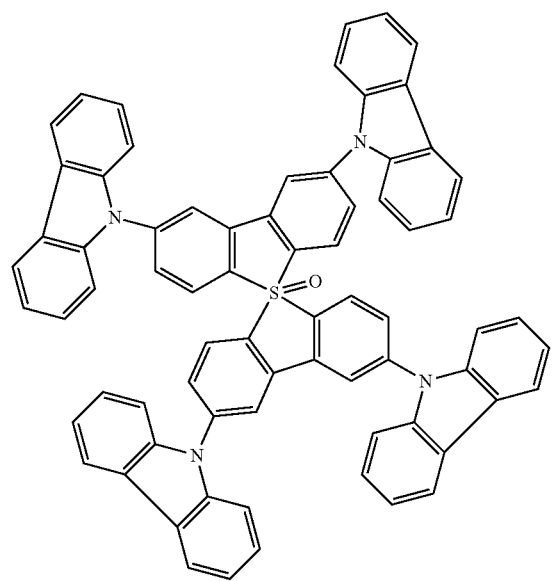
P179
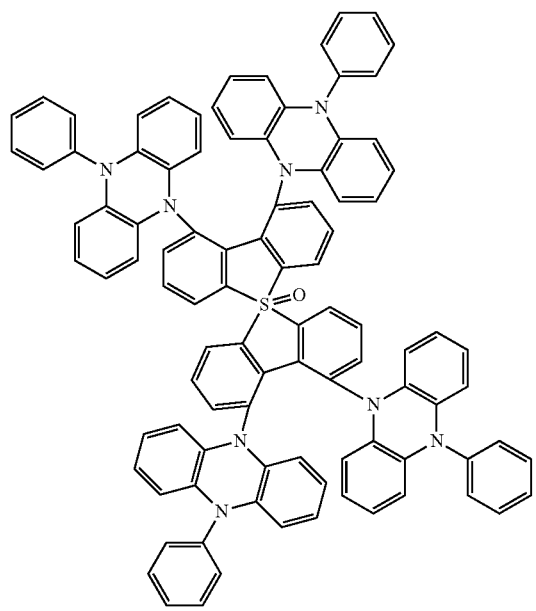
P180
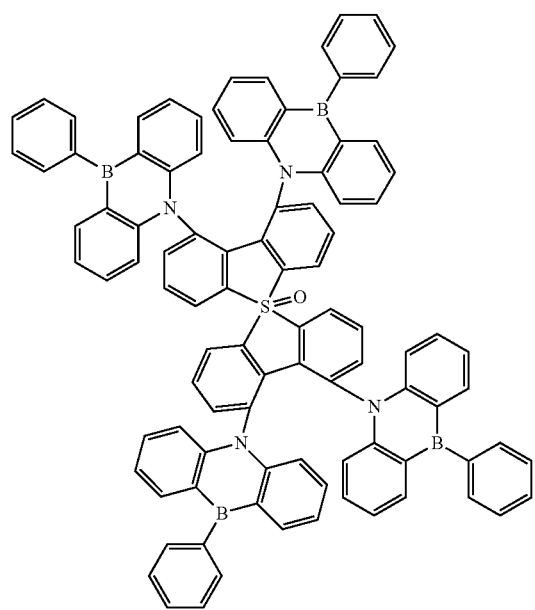
P181
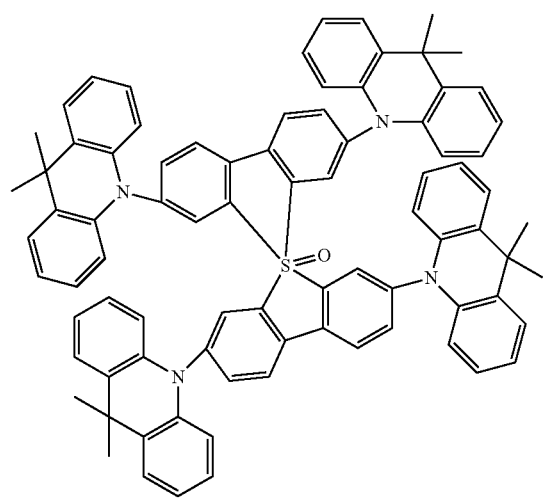

-continued
P182
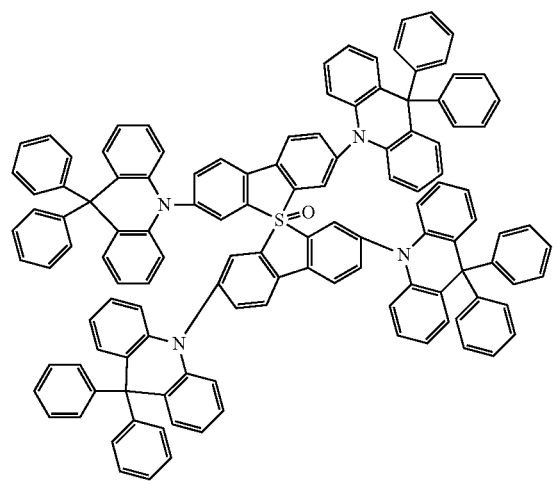
P183
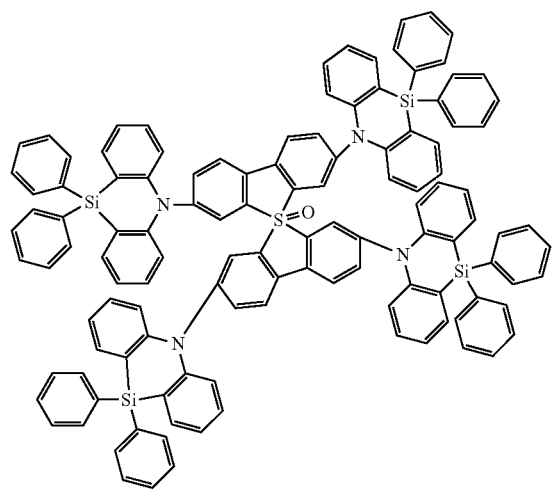
P184
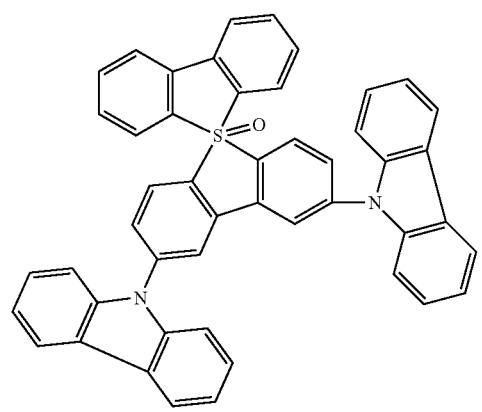
P185
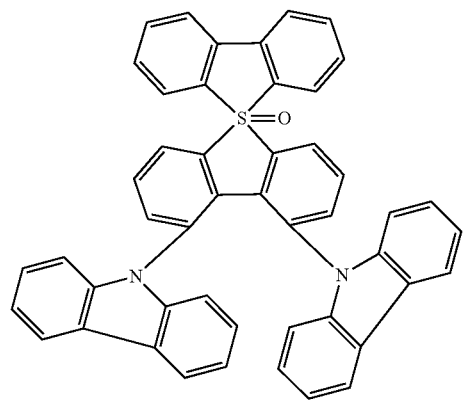
P186
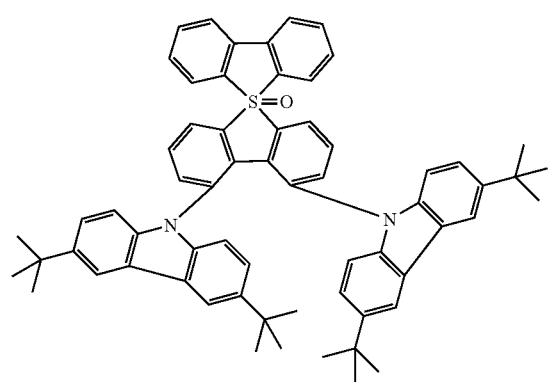
P187
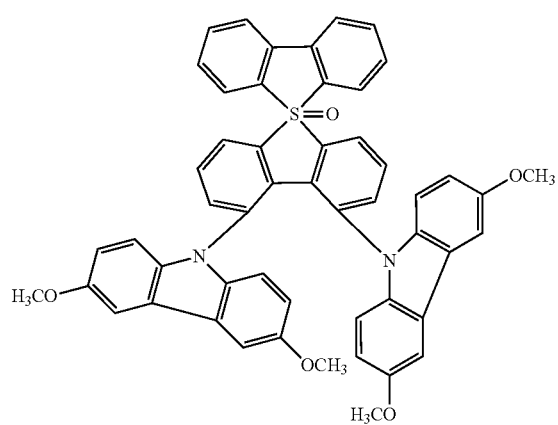

-continued
P188
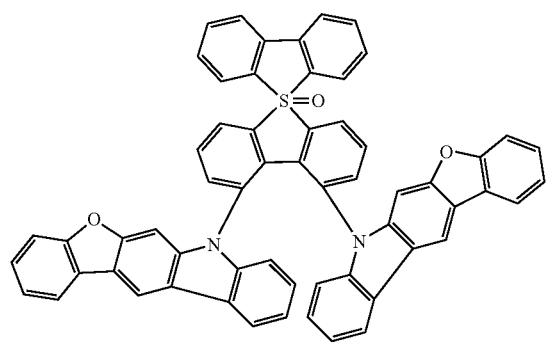
P189
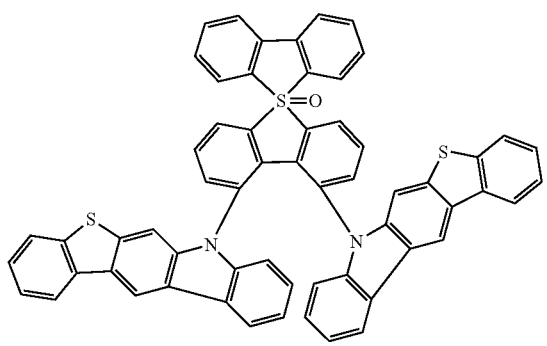
P190
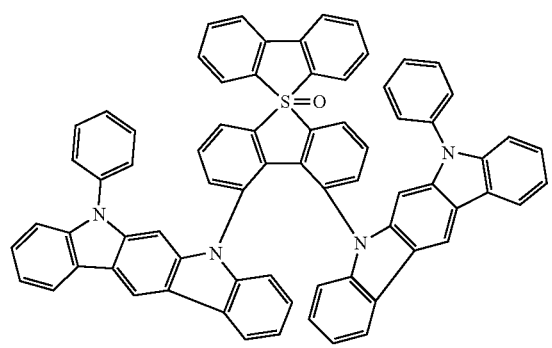
P191
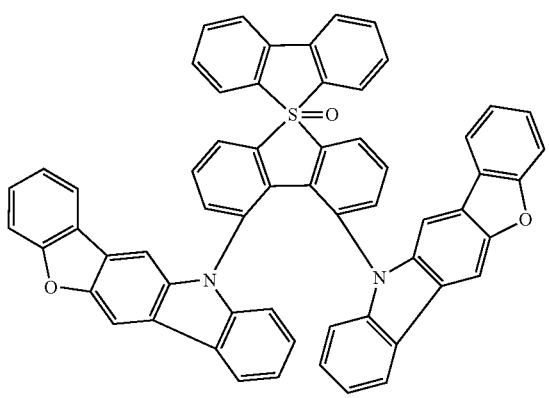
P192
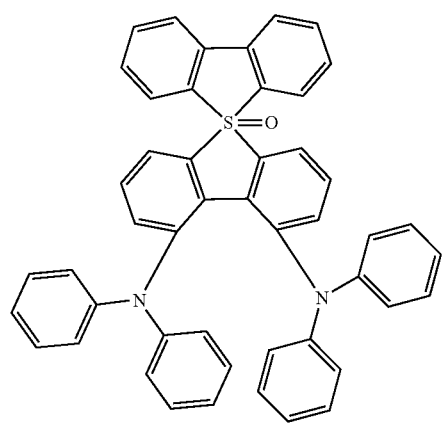
P193
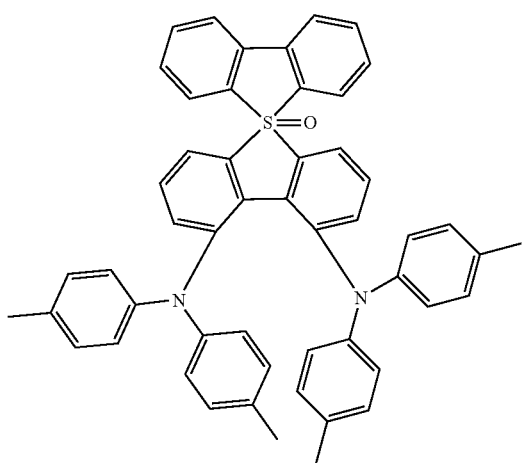

-continued

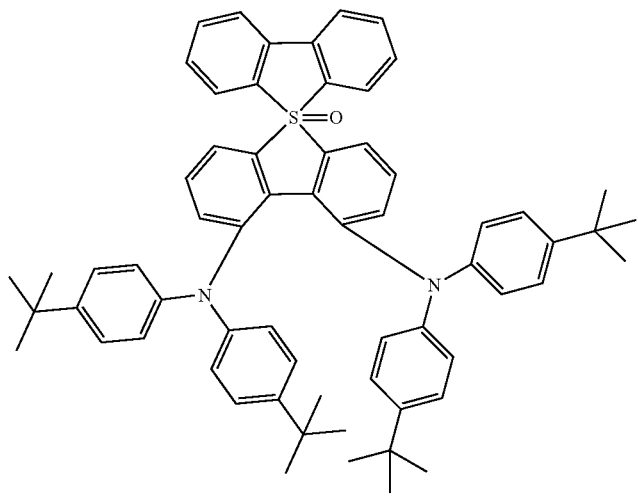
P194

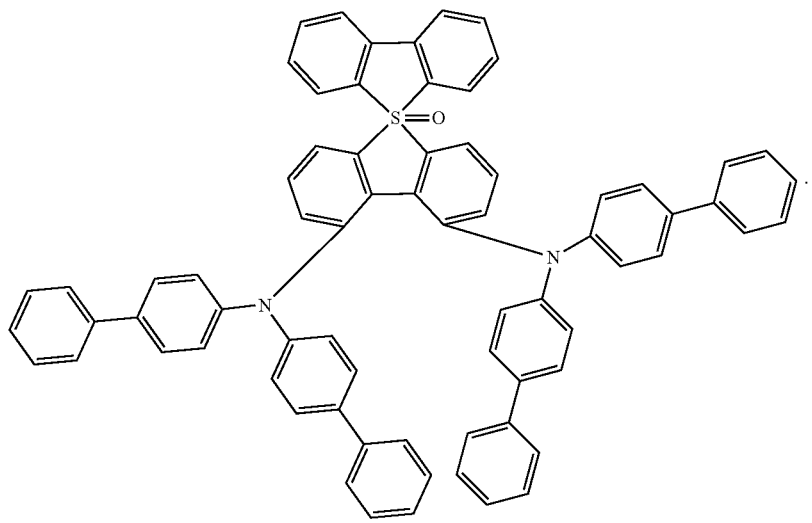
P195

12. The compound according to claim 1, wherein the compound satisfies $\Delta E_{ST} \leq 0.30$ eV.

13. A display panel, comprising an organic light-emitting device, wherein the organic light-emitting device comprises:
an anode;
a cathode; and
a light-emitting layer disposed between the anode and the cathode, wherein the light-emitting layer comprises one or more compounds having a structure represented by formula 1 and configured to emit light:

formula 1

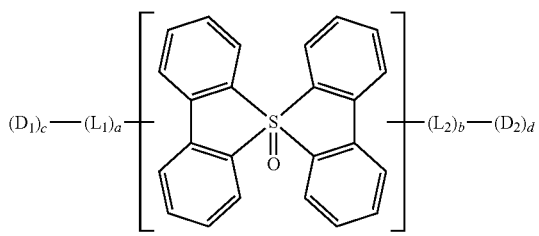

wherein $L_1$ and $L_2$ are each independently selected from the group consisting of a single bond, a substituted or unsubstituted C6-C30 aryl, and a C4-C30 heteroaryl; a and b are each independently selected from 0, 1, 2, 3, or 4;

$D_1$ and $D_2$ are each independently a nitrogen-containing electron donor unit selected from the group consisting of carbazolyl and derivative groups thereof, acridinyl and derivative groups thereof, diarylamino and derivative groups thereof, and triarylamino and derivative groups thereof; and
c and d are each independently selected from 0, 1, 2, 3, or 4, and c+d≥1.

14. The display panel according to claim 13, wherein a host material or a guest material of the light-emitting layer is at least one of the one or more compounds.

15. The display panel according to claim 13, wherein the light-emitting layer comprises a host material and a guest material, the host material is at least one of the one or more compounds, and the guest material is a red phosphorescent material and/or a green phosphorescent material.

16. The display panel according to claim 13, further comprising one or more of a hole injection layer, a hole transport layer, an electron blocking layer, a hole blocking layer, an electron transport layer, or an electron injection layer.

17. A display apparatus, comprising a display panel, wherein the display panel comprises an organic light-emitting device comprising:
an anode;
a cathode; and a light-emitting layer disposed between the anode and the cathode, wherein a light-emitting material of the light-emitting layer comprises one or more compounds having a structure represented by formula 1:

formula 1

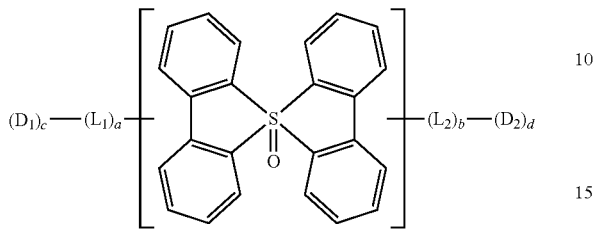

wherein $L_1$ and $L_2$ are each independently selected from the group consisting of a single bond, a substituted or unsubstituted C6-C30 aryl, and a C4-C30 heteroaryl; a and b are each independently selected from 0, 1, 2, 3, or 4;

$D_1$ and $D_2$ are each independently a nitrogen-containing electron donor unit selected from the group consisting of carbazolyl and derivative groups thereof, acridinyl and derivative groups thereof, diarylamino and derivative groups thereof, and triarylamino and derivative groups thereof; and c and d are each independently selected from 0, 1, 2, 3, or 4, and $c+d \geq 1$.

* * * * *